United States Patent
Wolf et al.

(10) Patent No.: US 10,943,682 B2
(45) Date of Patent: Mar. 9, 2021

(54) VIDEO USED TO AUTOMATICALLY POPULATE A POSTOPERATIVE REPORT

(71) Applicant: Theator Inc., San Mateo, CA (US)

(72) Inventors: Tamir Wolf, Palo Alto, CA (US); Dotan Asselmann, Holon (IL)

(73) Assignee: THEATOR INC., Palo Alto, CA (US)

( * ) Notice: Subject to any disclaimer, the term of this patent is extended or adjusted under 35 U.S.C. 154(b) by 0 days.

(21) Appl. No.: 16/796,325

(22) Filed: Feb. 20, 2020

(65) Prior Publication Data
US 2020/0273548 A1 Aug. 27, 2020

Related U.S. Application Data

(60) Provisional application No. 62/960,466, filed on Jan. 13, 2020, provisional application No. 62/838,066, (Continued)

(51) Int. Cl.
*G16H 10/60* (2018.01)
*F16H 15/00* (2006.01)
(Continued)

(52) U.S. Cl.
CPC .......... *G16H 10/60* (2018.01); *G06T 7/0012* (2013.01); *G16H 15/00* (2018.01); *G16H 50/20* (2018.01);
(Continued)

(58) Field of Classification Search
None
See application file for complete search history.

(56) References Cited

U.S. PATENT DOCUMENTS 9,836,654 B1 12/2017 Alvi et al.
10,387,720 B2 * 8/2019 Johnson .............. G06K 9/00369
(Continued)

FOREIGN PATENT DOCUMENTS

WO WO2015066565 A1 5/2015
WO WO 20191079430 A1 4/2019
WO WO2019226182 A1 11/2019

OTHER PUBLICATIONS

Münzer, Bernd et al., "EndoXplore: A Web-based Video Explorer for Endoscopic Videos"; 2017 IEEE; International Symposium on Multimedia (ISM); Dec. 11, 2017 (2 pp.).

(Continued)

*Primary Examiner* — Michael Tomaszewski
*Assistant Examiner* — Jay M. Patel
(74) *Attorney, Agent, or Firm* — Finnegan, Henderson, Farabow, Garrett & Dunner LLP

(57) ABSTRACT

Systems and methods for automatically populating a post-operative report of a surgical procedure are disclosed. A system may include at least one processor configured to implement a method including receiving an identifier of a patient, an identifier of a healthcare provider, and surgical footage of a surgical procedure performed on the patient. The method may include analyzing frames of the surgical footage to identify phases of the surgical procedure based on interactions between medical instruments and biological structures and, based on the interactions, associate a name with each phase. The method may include determining a beginning of each phase and associating a time marker with the beginning of each phase. The method may include populating a post-operative report with the patient identifier, the names of the phases, and time markers associated with the phases in a manner that enables the health care provider to alter the post-operative report.

20 Claims, 40 Drawing Sheets

Related U.S. Application Data filed on Apr. 24, 2019, provisional application No. 62/808,512, filed on Feb. 21, 2019, provisional application No. 62/808,500, filed on Feb. 21, 2019, provisional application No. 62/967,283, filed on Jan. 29, 2020.

(51) Int. Cl.
  *G06T 7/00* (2017.01)
  *G16H 50/20* (2018.01)
  *G16H 15/00* (2018.01)

(52) U.S. Cl.
  CPC .............. *G06T 2207/10016* (2013.01); *G06T 2207/30004* (2013.01)

(56) References Cited

U.S. PATENT DOCUMENTS

| | | |
|---|---|---|
| 2002/0172498 A1 | 11/2002 | Esenyan et al. |
| 2004/0062381 A1 | 4/2004 | Shambaugh et al. |
| 2004/0125121 A1 | 7/2004 | Pea et al. |
| 2006/0053249 A1* | 3/2006 | Yamaki ............... H04N 5/76 711/112 |
| 2007/0238981 A1 | 10/2007 | Zhu et al. |
| 2008/0243064 A1 | 10/2008 | Stahler et al. |
| 2009/0192823 A1 | 7/2009 | Hawkins et al. |
| 2010/0036676 A1* | 2/2010 | Safdi ................ G16H 15/00 705/2 |
| 2010/0097398 A1* | 4/2010 | Tsurumi ............ G11B 27/034 345/634 |
| 2010/0134609 A1* | 6/2010 | Johnson ............ G16H 10/60 348/77 |
| 2011/0046476 A1 | 2/2011 | Cinquin et al. |
| 2011/0225000 A1* | 9/2011 | Selim ................ G16H 15/00 705/2 |
| 2011/0264528 A1 | 10/2011 | Whale |
| 2011/0306985 A1 | 12/2011 | Inoue et al. |
| 2012/0035963 A1* | 2/2012 | Qian ................. G16H 30/20 705/3 |
| 2012/0177256 A1* | 7/2012 | Keefe ............... G16H 10/60 382/115 |
| 2014/0081659 A1 | 3/2014 | Nawana et al. |
| 2014/0270711 A1 | 9/2014 | Maser |
| 2014/0276940 A1 | 9/2014 | Seo |
| 2014/0297301 A1 | 10/2014 | Rock |
| 2016/0067007 A1 | 3/2016 | Piron et al. |
| 2016/0259888 A1* | 9/2016 | Liu ..................... G06F 16/71 |
| 2017/0046835 A1* | 2/2017 | Tajbakhsh ............ G06T 7/73 |
| 2017/0053543 A1 | 2/2017 | Agrawal et al. |
| 2017/0071679 A1 | 3/2017 | Weir et al. |
| 2017/0119258 A1 | 5/2017 | Kotanko et al. |
| 2017/0312031 A1* | 11/2017 | Amanatullah ........ G09B 23/30 |
| 2018/0122506 A1 | 5/2018 | Grantcharov et al. |
| 2018/0174311 A1* | 6/2018 | Kluckner ............ G06K 9/6259 |
| 2018/0174616 A1 | 6/2018 | Aguilar et al. |
| 2018/0197624 A1* | 7/2018 | Robaina ............. G16H 80/00 |
| 2018/0247024 A1* | 8/2018 | Divine .............. G06K 9/00671 |
| 2018/0303552 A1 | 10/2018 | Ryan et al. |
| 2018/0322949 A1* | 11/2018 | Mohr ................. G16H 40/63 |
| 2018/0366231 A1* | 12/2018 | Wolf .................. G06T 7/0012 |
| 2019/0125361 A1* | 5/2019 | Shelton, IV ...... A61B 17/07207 |
| 2019/0201136 A1* | 7/2019 | Shelton, IV .......... A61B 90/53 |
| 2019/0201141 A1* | 7/2019 | Shelton, IV .......... G16H 40/40 |
| 2019/0206565 A1* | 7/2019 | Shelton, IV .......... A61B 34/74 |
| 2019/0272917 A1 | 9/2019 | Couture et al. |
| 2019/0365252 A1 | 12/2019 | Fernald et al. |
| 2020/0082934 A1* | 3/2020 | Venkataraman ....... G16H 40/20 |

OTHER PUBLICATIONS

PCT Search Report, dated May 14, 2020, issued in corresponding PCT Application No. PCT/US2020/019050 (23 pp.).

"Video Analysis: An Approach for Use in Health Care"; Mackenzie et al.; Handbook of Human Factors and Ergonomics in Health Care and Patient Safety; Aug. 3, 2011 (Year: 2011).

\* cited by examiner

| Video Footage | Footage Location | Phase Tag | Event Location | Event Tag | Event Characteristic |
|---|---|---|---|---|---|
| LaparoscopicCholecystectomy_11_24_2019.mp4 | 0:39:02 – 1:04:36 | Calot's triangle dissection | 0:43:09 | Incision | Skill level: 8 |
| LaparoscopicCholecystectomy_11_24_2019.mp4 | 1:04:36 – 1:23:15 | Cutting of cystic duct | 1:08:39 | Incision | Skill level: 7 |
| CataractSurgery_03_11_2019.mp4 | 0:12:32 – 0:39:59 | Corneal incision | 0:22:56 | Incision | Skill level: 9 |
| ... | | | | | |

```
┌─────────────────────────────────────────────────────────────┐
│ ACCESS A REPOSITORY OF SURGICAL VIDEO FOOTAGE REFLECTING A  │
│ PLURALITY OF SURGICAL PROCEDURES PERFORMED ON DIFFERING     │
│                         PATIENTS                            │
│                          1210                               │
└─────────────────────────────────────────────────────────────┘
                              ↓
┌─────────────────────────────────────────────────────────────┐
│ ENABLE A SURGEON PREPARING FOR A CONTEMPLATED SURGICAL      │
│ PROCEDURE TO INPUT CASE-SPECIFIC INFORMATION CORRESPONDING  │
│         TO THE CONTEMPLATED SURGICAL PROCEDURE              │
│                          1220                               │
└─────────────────────────────────────────────────────────────┘
                              ↓
┌─────────────────────────────────────────────────────────────┐
│ COMPARE THE CASE-SPECIFIC INFORMATION WITH DATA ASSOCIATED  │
│ WITH THE SURGICAL VIDEO FOOTAGE TO IDENTIFY A GROUP OF      │
│ INTRAOPERATIVE EVENTS LIKELY TO BE ENCOUNTERED DURING THE   │
│              CONTEMPLATED SURGICAL PROCEDURE                │
│                          1230                               │
└─────────────────────────────────────────────────────────────┘
                              ↓
┌─────────────────────────────────────────────────────────────┐
│ USE THE CASE-SPECIFIC INFORMATION AND THE IDENTIFIED GROUP OF│
│ INTRAOPERATIVE EVENTS TO IDENTIFY SPECIFIC FRAMES IN THE    │
│ SURGICAL VIDEO FOOTAGE CORRESPONDING TO THE IDENTIFIED GROUP│
│                OF INTRAOPERATIVE EVENTS                     │
│                          1240                               │
└─────────────────────────────────────────────────────────────┘
                              ↓
┌─────────────────────────────────────────────────────────────┐
│ DETERMINE THAT A FIRST SET AND A SECOND SET OF VIDEO FOOTAGE│
│ FROM DIFFERING PATIENTS CONTAIN FRAMES ASSOCIATED WITH      │
│ INTRAOPERATIVE EVENTS SHARING A COMMON CHARACTERISTIC       │
│                          1250                               │
└─────────────────────────────────────────────────────────────┘
                              ↓
┌─────────────────────────────────────────────────────────────┐
│ OMIT AN INCLUSION OF THE SECOND SET FROM A COMPILATION TO BE│
│ PRESENTED TO THE SURGEON AND INCLUDING THE FIRST SET IN THE │
│       COMPILATION TO BE PRESENTED TO THE SURGEON            │
│                          1260                               │
└─────────────────────────────────────────────────────────────┘
                              ↓
┌─────────────────────────────────────────────────────────────┐
│ ENABLE THE SURGEON TO VIEW A PRESENTATION INCLUDING THE     │
│ COMPILATION AND INCLUDING FRAMES FROM THE DIFFERING SURGICAL│
│     PROCEDURES PERFORMED ON DIFFERING PATIENTS              │
│                          1270                               │
└─────────────────────────────────────────────────────────────┘
```

URGENCY

Surgery Type

Complications

Patient Profile:
Name          Contact
Address       Emergency Contact
Birthday

Medical History

Surgeon Team:
Name          Responsibilities

Add Next Member

| Record Number | Procedure | Age | Gender | Medical Considerations | Time | Other Data |
|---|---|---|---|---|---|---|
| 1 | Bypass Surgery | 65 | M | Renal Disease | 4 hours | |
| 2 | Bypass Surgery | 78 | F | None | 3 hours | |

1711 ... 1712A, 1712B, 1712C, 1712D

1713

| Record Number | Procedure | Surgeon Name |
|---|---|---|
| 1 | Bypass Surgery | Dr. Mac |
| 2 | Bypass Surgery | Dr. Doe |

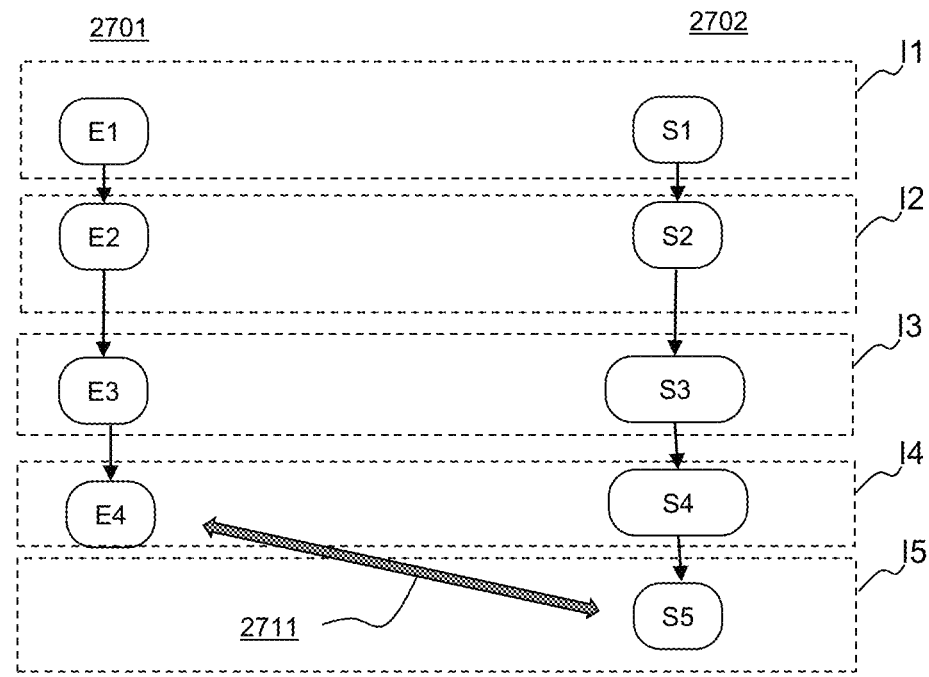
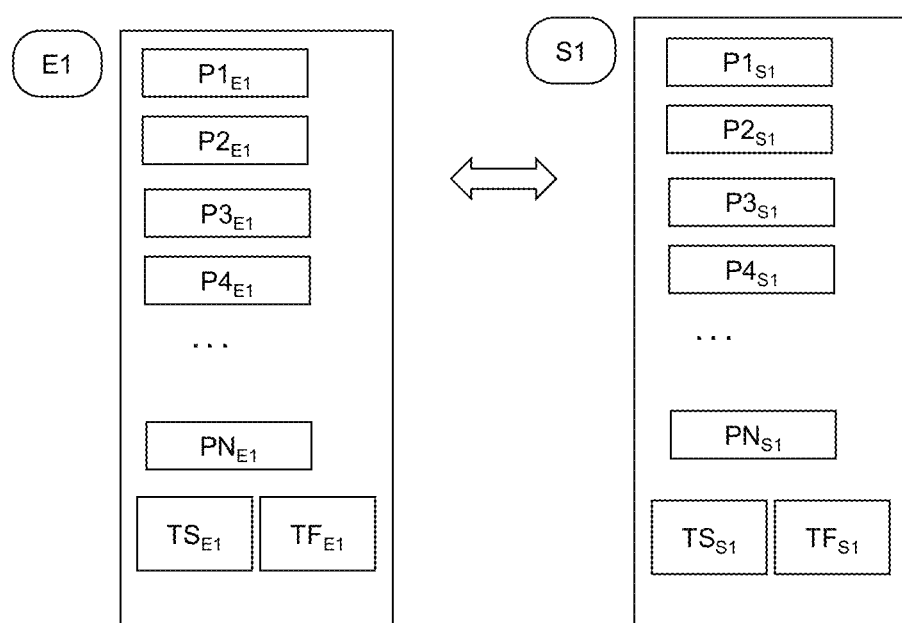
Fig. 27

2900

RECEIVE VIDEO FOOTAGE OF A SURGICAL PROCEDURE PERFORMED ON A PATIENT IN AN OPERATING ROOM
2902

ACCESS AT LEAST ONE DATA STRUCTURE INCLUDING IMAGE-RELATED DATA CHARACTERIZING SURGICAL PROCEDURES
2904

ANALYZING THE RECEIVED VIDEO FOOTAGE USING THE IMAGE-RELATED DATA TO DETERMINE, IN REAL TIME, AN EXISTENCE OF A SURGICAL DECISION MAKING JUNCTION
2906

ACCESS, IN THE AT LEAST ONE DATA STRUCTURE, A CORRELATION BETWEEN AN OUTCOME AND A SPECIFIC ACTION TAKEN AT THE DECISION MAKING JUNCTION
2908

OUTPUT A RECOMMENDATION TO THE SURGEON TO UNDERTAKE THE SPECIFIC ACTION OR TO AVOID THE SPECIFIC ACTION
2910

```
RECEIVE, FROM AT LEAST ONE IMAGE SENSOR IN AN OPERATING ROOM, IMAGE DATA
OF A SURGICAL PROCEDURE
3002
                              ↓
ANALYZE RECEIVED IMAGE DATA TO DETERMINE AN IDENTITY OF AN ANATOMICAL
STRUCTURE AND TO DETERMINE A CONDITION OF THE ANATOMICAL STRUCTURE AS
REFLECTED IN THE IMAGE DATA
3004
                              ↓
SELECT A CONTACT FORCE THRESHOLD ASSOCIATED WITH THE ANATOMICAL
STRUCTURE, THE SELECTED CONTACT FORCE THRESHOLD BEING BASED ON THE
DETERMINED CONDITION OF THE ANATOMICAL STRUCTURE
3006
                              ↓
RECEIVE AN INDICATION OF ACTUAL CONTACT FORCE ON THE ANATOMICAL
STRUCTURE
3008
                              ↓
COMPARING THE INDICATION OF ACTUAL CONTACT FORCE WITH THE SELECTED
CONTACT FORCE THRESHOLD
3010
                              ↓
OUTPUT A NOTIFICATION BASED ON A DETERMINATION THAT THE INDICATION OF
ACTUAL CONTACT FORCE EXCEEDS THE SELECTED CONTACT FORCE THRESHOLD
3012
```

RECEIVE, FROM AT LEAST ONE IMAGE SENSOR ARRANGED TO CAPTURE IMAGES OF A SURGICAL PROCEDURE, IMAGE DATA ASSOCIATED WITH A FIRST EVENT DURING THE SURGICAL PROCEDURE
3102

DETERMINE, BASED ON THE RECEIVED IMAGE DATA ASSOCIATED WITH THE FIRST EVENT, A PREDICTED OUTCOME ASSOCIATED WITH THE SURGICAL PROCEDURE
3104

RECEIVING, FROM AT LEAST ONE IMAGE SENSOR ARRANGED TO CAPTURE IMAGES OF A SURGICAL PROCEDURE, IMAGE DATA ASSOCIATED WITH A SECOND EVENT DURING THE SURGICAL PROCEDURE
3106

DETERMINE, BASED ON THE RECEIVED IMAGE DATA ASSOCIATED WITH THE SECOND EVENT, A CHANGE IN THE PREDICTED OUTCOME, CAUSING THE PREDICTED OUTCOME TO DROP BELOW A THRESHOLD
3108

ACCESSING A DATA STRUCTURE OF IMAGE-RELATED DATA BASED ON PRIOR SURGICAL PROCEDURES
3110

IDENTIFY, BASED ON THE ACCESSED IMAGE-RELATED DATA, A RECOMMENDED REMEDIAL ACTION
3112

OUTPUT RECOMMENDED REMEDIAL ACTION
3114

Fig. 31

VIDEO USED TO AUTOMATICALLY POPULATE A POSTOPERATIVE REPORT

CROSS REFERENCES TO RELATED APPLICATIONS

This application is based on and claims benefit of priority of U.S. Provisional Patent Application No. 62/808,500, filed Feb. 21, 2019, U.S. Provisional Patent Application No. 62/808,512, filed Feb. 21, 2019, U.S. Provisional Patent Application No. 62/838,066, filed Apr. 24, 2019, U.S. Provisional Patent Application No. 62/960,466, filed Jan. 13, 2020, and U.S. Provisional Patent Application No. 62/967,283, filed Jan. 29, 2020. The contents of the foregoing applications are incorporated herein by reference in their entireties.

BACKGROUND

Technical Field

The disclosed embodiments generally relate to systems and methods for analysis of videos of surgical procedures.

Background Information

When preparing for a surgical procedure, it may be beneficial for a surgeon to view video footage depicting certain surgical events, including events that may have certain characteristics. In addition, during a surgical procedure, it may be helpful to capture and analyze videos to provide various types of decision support to surgeons. Further, it may be helpful analyze surgical videos to facilitate postoperative activity.

Therefore, there is a need for unconventional approaches that efficiently and effectively analyze surgical videos to enable a surgeon to view surgical events, provide decision support, and/or facilitate postoperative activity.

SUMMARY

Embodiments consistent with the present disclosure provide systems and methods for analysis of surgical videos. The disclosed systems and methods may be implemented using a combination of conventional hardware and software as well as specialized hardware and software, such as a machine constructed and/or programmed specifically for performing functions associated with the disclosed method steps. Consistent with other disclosed embodiments, non-transitory computer-readable storage media may store program instructions, which are executable by at least one processing device and perform any of the steps and/or methods described herein.

Consistent with disclosed embodiments, systems, methods, and computer readable media related to reviewing surgical video are disclosed. The embodiments may include accessing at least one video of a surgical procedure and causing the at least one video to be output for display. The embodiments may further include overlaying, on the at least one video outputted for display, a surgical timeline. The surgical timeline may include markers identifying at least one of a surgical phase, an intraoperative surgical event, and a decision making junction. The surgical timeline may enable a surgeon, while viewing playback of the at least one video to select one or more markers on the surgical timeline, and thereby cause a display of the video to skip to a location associated with the selected marker.

In one embodiment, the one or more markers may include a decision making junction marker corresponding to a decision making junction of the surgical procedure. The selection of the decision making junction marker may enable the surgeon to view two or more alternative video clips from two or more corresponding other surgical procedures. Further, the two or more video clips may present differing conduct. In another embodiment, the selection of the decision making junction marker may cause a display of one or more alternative possible decisions related to the selected decision making junction marker.

Consistent with disclosed embodiments, systems, methods, and computer readable media related to video indexing are disclosed. The video indexing may include accessing video footage to be indexed, including footage of a particular surgical procedure, which may be analyzed to identify a video footage location associated with a surgical phase of the particular surgical procedure. A phase tag may be generated and may be associated with the video footage location. The video indexing may include analyzing the video footage to identify an event location of a particular intraoperative surgical event within the surgical phase and associating an event tag with the event location of the particular intraoperative surgical event. Further, an event characteristic associated with the particular intraoperative surgical event may be stored.

The video indexing may further include associating at least a portion of the video footage of the particular surgical procedure with the phase tag, the event tag, and the event characteristic in a data structure that contains additional video footage of other surgical procedures. The data structure may also include respective phase tags, respective event tags, and respective event characteristics associated with one or more of the other surgical procedures. A user may be enabled to access the data structure through selection of a selected phase tag, a selected event tag, and a selected event characteristic of video footage for display. Then, a lookup in the data structure of surgical video footage matching the at least one selected phase tag, selected event tag, and selected event characteristic may be performed to identify a matching subset of stored video footage. The matching subset of stored video footage may be displayed to the user, thereby enabling the user to view surgical footage of at least one intraoperative surgical event sharing the selected event characteristic, while omitting playback of video footage lacking the selected event characteristic.

Consistent with disclosed embodiments, systems, methods, and computer readable media related to generating surgical summary footage are disclosed. The embodiments may include accessing particular surgical footage containing a first group of frames associated with at least one intraoperative surgical event and a second group of frames not associated with surgical activity. The embodiments may further include accessing historical data associated with historical surgical footage of prior surgical procedures, wherein the historical data includes information that distinguishes portions of the historical surgical footage into frames associated with intraoperative surgical events and frames not associated with surgical activity. The first group of frames in the particular surgical footage may be distinguished from the second group of frames based on the information of the historical data. Upon request of a user, an aggregate of the first group of frames of the particular surgical footage may be presented to the user, whereas the second group of frames may be omitted from presentation to the user.

In some embodiments, the disclosed embodiments may further include analyzing the particular surgical footage to identify a surgical outcome and a respective cause of the surgical outcome. The identifying may be based on the historical outcome data and respective historical cause data. An outcome set of frames in the particular surgical footage may be detected based on the analyzing. The outcome set of frames may be within an outcome phase of the surgical procedure. Further, based on the analyzing, a cause set of frames in the particular surgical footage may be detected. The cause set of frames may be within a cause phase of the surgical procedure remote in time from the outcome phase, while an intermediate set of frames may be within an intermediate phase interposed between the cause set of frames and the outcome set of frames. A cause-effect summary of the surgical footage may then be generated, wherein the cause-effect summary includes the cause set of frames and the outcome set of frames and omits the intermediate set of frames. The aggregate of the first group of frames presented to the user may include the cause-effect summary.

Consistent with disclosed embodiments, systems, methods, and computer readable media related to surgical preparation are disclosed. The embodiments may include accessing a repository of a plurality of sets of surgical video footage reflecting a plurality of surgical procedures performed on differing patients and including intraoperative surgical events, surgical outcomes, patient characteristics, surgeon characteristics, and intraoperative surgical event characteristics. The methods may further include enabling a surgeon preparing for a contemplated surgical procedure to input case-specific information corresponding to the contemplated surgical procedure. The case-specific information may be compared with data associated with the plurality of sets of surgical video footage to identify a group of intraoperative events likely to be encountered during the contemplated surgical procedure. Further, the case-specific information and the identified group of intraoperative events likely to be encountered may be used to identify specific frames in specific sets of the plurality of sets of surgical video footage corresponding to the identified group of intraoperative events. The identified specific frames may include frames from the plurality of surgical procedures performed on differing patients.

The embodiments may further include determining that a first set and a second set of video footage from differing patients contain frames associated with intraoperative events sharing a common characteristic and omitting an inclusion of the second set from a compilation to be presented to the surgeon and including the first set in the compilation to be presented to the surgeon. Finally, the embodiments may include enabling the surgeon to view a presentation including the compilation containing frames from the differing surgical procedures performed on differing patients.

Consistent with disclosed embodiments, systems, methods, and computer readable media related to analyzing complexity of surgical footage are disclosed. The embodiments may include analyzing frames of the surgical footage to identify in a first set of frames an anatomical structure. The disclosed embodiments may further include accessing first historical data. The first historical data may be based on an analysis of first frame data captured from a first group of prior surgical procedures. The first set of frames may be analyzed using the first historical data and using the identified anatomical structure to determine a first surgical complexity level associated with the first set of frames.

Some embodiments may further include analyzing frames of the surgical footage to identify in a second set of frames a medical tool, the anatomical structure, and an interaction between the medical tool and the anatomical structure. The disclosed embodiments may include accessing second historical data, the second historical data being based on an analysis of a second frame data captured from a second group of prior surgical procedures. The second set of frames may be analyzed using the second historical data and using the identified interaction to determine a second surgical complexity level associated with the second set of frames.

The embodiments may further include tagging the first set of frames with the first surgical complexity level, tagging the second set of frames with the second surgical complexity level; and generating a data structure including the first set of frames with the first tag and the second set of frames with the second tag. The generated data structure may enable a surgeon to select the second surgical complexity level, and thereby cause the second set of frames to be displayed, while omitting a display of the first set of frames.

Consistent with disclosed embodiments, systems, methods, and computer-readable media for enabling adjustments of an operating room schedule are disclosed. Adjusting the operating room schedule may include receiving from an image sensor positioned in a surgical operating room, visual data tracking an ongoing surgical procedure, accessing a data structure containing historical surgical data, and analyzing the visual data of the ongoing surgical procedure and the historical surgical data to determine an estimated time of completion of the ongoing surgical procedure. Adjusting the operating room schedule may further include accessing a schedule for the surgical operating room. The schedule may include a scheduled time associated with completion of the ongoing surgical procedure. Further, adjusting the operating room schedule may include calculating, based on the estimated time of completion of the ongoing surgical procedure, whether an expected time of completion is likely to result in a variance from the scheduled time associated with the completion, and outputting a notification upon calculation of the variance, to thereby enable subsequent users of the surgical operating room to adjust their schedules accordingly.

Consistent with disclosed embodiments, systems, methods, and computer readable media for analyzing surgical images to determine insurance reimbursement are disclosed. The operations for analyzing surgical images to determine insurance reimbursement may include accessing video frames captured during a surgical procedure on a patient, analyzing the video frames captured during the surgical procedure to identify in the video frames at least one medical instrument, at least one anatomical structure, and at least one interaction between the at least one medical instrument and the at least one anatomical structure, and accessing a database of reimbursement codes correlated to medical instruments, anatomical structures, and interactions between medical instruments and anatomical structures. The operations may further include comparing the identified at least one interaction between the at least one medical instrument and the at least one anatomical structure with information in the database of reimbursement codes to determine at least one reimbursement code associated with the surgical procedure.

Consistent with disclosed embodiments, systems, methods, and computer readable media for populating a post-operative report of a surgical procedure are disclosed. The operations for populating a post-operative report of a surgical procedure may include receiving an input of a patient identifier, receiving an input of an identifier of a health care provider, and receiving an input of surgical footage of a surgical procedure performed on the patient by the health care provider. The operations may further include analyzing a plurality of frames of the surgical footage to derive image-based information for populating a post-operative report of the surgical procedure, and causing the derived image-based information to populate the post-operative report of the surgical procedure.

Consistent with disclosed embodiments, systems, methods, and computer readable media for enabling determination and notification of an omitted event in a surgical procedure are disclosed. The operations for enabling determination and notification of an omitted event may include accessing frames of video captured during a specific surgical procedure, accessing stored data identifying a recommended sequence of events for the surgical procedure, comparing the accessed frames with the recommended sequence of events to identify an indication of a deviation between the specific surgical procedure and the recommended sequence of events for the surgical procedure, determining a name of an intraoperative surgical event associated with the deviation, and providing a notification of the deviation including the name of the intraoperative surgical event associated with the deviation.

Some embodiments of this disclosure include systems, methods, and computer readable media for providing real-time decision support for surgical procedures. Some of such embodiments may involve at least one processor. Such embodiments may involve receiving video footage of a surgical procedure performed by a surgeon on a patient in an operating room and accessing at least one data structure including image-related data characterizing surgical procedures. Thereafter the received video footage may be analyzed using the image-related data to determine, in real time, an existence of a surgical decision making junction. At least one data structure may be accessed, and a correlation between an outcome and a specific action taken at the decision making junction. Based on the determined existence of the decision making junction and the accessed correlation, a recommendation may be output to the surgeon to undertake the specific action or to avoid the specific action.

Embodiments of this disclosure include systems, methods, and computer readable media for estimating contact force on an anatomical structure during a surgical procedure disclosed. Embodiments may involve receiving, from at least one image sensor in an operating room, image data of a surgical procedure, and analyzing the received image data to determine an identity of an anatomical structure and to determine a condition of the anatomical structure as reflected in the image data. A contact force threshold associated with the anatomical structure may be selected based on the determined condition of the anatomical structure. An actual contact force on the anatomical structure may be determined and compared with the selected contact force threshold. Thereafter, a notification may be output based on a determination that the indication of actual contact force exceeds the selected contact force threshold.

Some embodiments of this disclosure involve systems, methods and computer readable media for updating a predicted outcome during a surgical procedure. These embodiments may involve receiving, from at least one image sensor arranged to capture images of a surgical procedure, image data associated with a first event during the surgical procedure. The embodiments may determine, based on the received image data associated with the first event, a predicted outcome associated with the surgical procedure, and may receive, from at least one image sensor arranged to capture images of a surgical procedure, image data associated with a second event during the surgical procedure. The embodiments may then determine, based on the received image data associated with the second event, a change in the predicted outcome, causing the predicted outcome to drop below a threshold. A recommended remedial action may be identified and recommended based on image-related data on prior surgical procedures contained in a data structure.

Some embodiments of this disclosure involve systems methods, and computer readable media for enabling fluid leak detection during surgery. Embodiments may involve receiving, in real time, intracavitary video of a surgical procedure. The processor may be configured to analyze frames of the intracavitary video to determine an abnormal fluid leakage situation in the intracavitary video. The embodiments may institute a remedial action when the abnormal fluid leakage situation is determined.

Consistent with disclosed embodiments, systems, methods, and computer readable media for predicting post discharge risk are disclosed. The operations for predicting post discharge risk may include accessing frames of video captured during a specific surgical procedure on a patient, accessing stored historical data identifying intraoperative events and associated outcomes, analyzing the accessed frames, and based on information obtained from the historical data, identifying in the accessed frames at least one specific intraoperative event, determining, based on information obtained from the historical data and the identified at least one intraoperative event, a predicted outcome associated with the specific surgical procedure, and outputting the predicted outcome in a manner associating the predicted outcome with the patient.

The forgoing summary provides just a few examples of disclosed embodiments to provide a flavor for this disclosure and is not intended to summarize all aspects of the disclosed embodiments. Moreover, the following detailed description is exemplary and explanatory only and is not restrictive of the claims.

BRIEF DESCRIPTION OF THE DRAWINGS

The accompanying drawings, which are incorporated in and constitute a part of this disclosure, illustrate various disclosed embodiments. In the drawings:

FIG. 6 is a schematic illustration of an example data structure consistent with the disclosed embodiments.

FIG. 12 is a flowchart illustrating an exemplary process for surgical preparation, consistent with the disclosed embodiments.

FIG. 16 is an exemplary form for entering information for a schedule consistent with disclosed embodiments.

FIG. 27 shows an exemplary comparison of a sequence of events, consistent with disclosed embodiments.

FIG. 29 is a flowchart illustrating an exemplary process for decision support for surgical procedures, consistent with the disclosed embodiments.

FIG. 30 is a flowchart illustrating an exemplary process for estimating contact force on an anatomical structure during a surgical procedure, consistent with the disclosed embodiments FIG. 31 is a flowchart illustrating an exemplary process for updating a predicted outcome during a surgical procedure, consistent with the disclosed embodiments.

DETAILED DESCRIPTION

Figure 1:
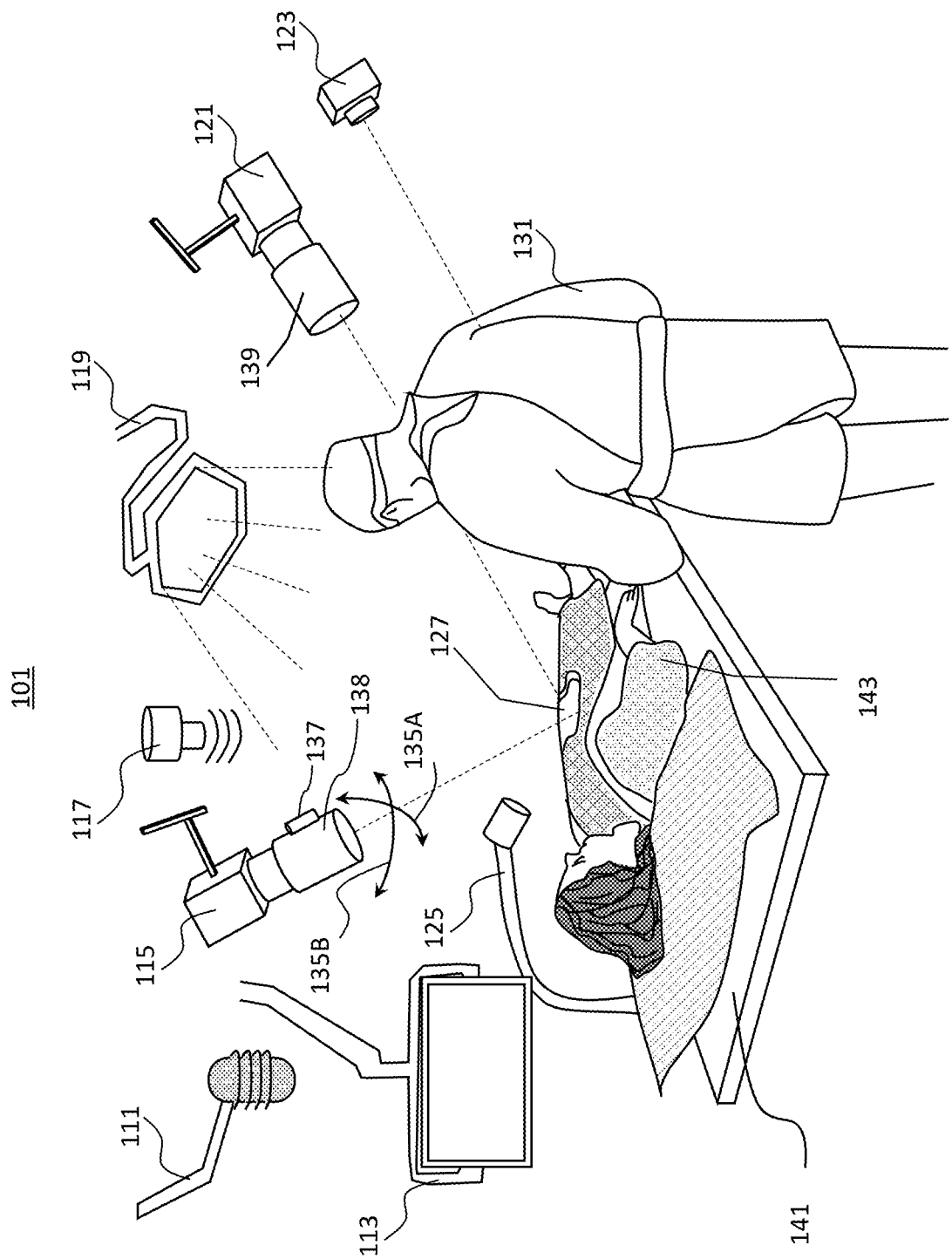
FIG. 1 is a perspective view of an example operating room, consistent with disclosed embodiments.

Unless specifically stated otherwise, as apparent from the following description, throughout the specification discussions utilizing terms such as "processing", "calculating", "computing", "determining", "generating", "setting", "configuring", "selecting", "defining", "applying", "obtaining", "monitoring", "providing", "identifying", "segmenting", "classifying", "analyzing", "associating", "extracting", "storing", "receiving", "transmitting", or the like, include actions and/or processes of a computer that manipulate and/or transform data into other data, the data represented as physical quantities, for example such as electronic quantities, and/or the data representing physical objects. The terms "computer", "processor", "controller", "processing unit", "computing unit", and "processing module" should be expansively construed to cover any kind of electronic device, component or unit with data processing capabilities, including, by way of non-limiting example, a personal computer, a wearable computer, smart glasses, a tablet, a smartphone, a server, a computing system, a cloud computing platform, a communication device, a processor (for example, digital signal processor (DSP), an image signal processor (ISR), a microcontroller, a field programmable gate array (FPGA), an application specific integrated circuit (ASIC), a central processing unit (CPA), a graphics processing unit (GPU), a visual processing unit (VPU), and so on), possibly with embedded memory, a single core processor, a multi core processor, a core within a processor, any other electronic computing device, or any combination of the above.

The operations in accordance with the teachings herein may be performed by a computer specially constructed or programmed to perform the described functions.

As used herein, the phrase "for example," "such as", "for instance" and variants thereof describe non-limiting embodiments of the presently disclosed subject matter. Reference in the specification to features of "embodiments" "one case", "some cases", "other cases" or variants thereof means that a particular feature, structure or characteristic described may be included in at least one embodiment of the presently disclosed subject matter. Thus the appearance of such terms does not necessarily refer to the same embodiment(s). As used herein, the term "and/or" includes any and all combinations of one or more of the associated listed items.

Features of the presently disclosed subject matter, are, for brevity, described in the context of particular embodiments. However, it is to be understood that features described in connection with one embodiment are also applicable to other embodiments. Likewise, features described in the context of a specific combination may be considered separate embodiments, either alone or in a context other than the specific combination.

In embodiments of the presently disclosed subject matter, one or more stages illustrated in the figures may be executed in a different order and/or one or more groups of stages may be executed simultaneously and vice versa. The figures illustrate a general schematic of the system architecture in accordance embodiments of the presently disclosed subject matter. Each module in the figures can be made up of any combination of software, hardware and/or firmware that performs the functions as defined and explained herein. The modules in the figures may be centralized in one location or dispersed over more than one location.

Examples of the presently disclosed subject matter are not limited in application to the details of construction and the arrangement of the components set forth in the following description or illustrated in the drawings. The subject matter may be practiced or carried out in various ways. Also, it is to be understood that the phraseology and terminology employed herein is for the purpose of description and should not be regarded as limiting.

In this document, an element of a drawing that is not described within the scope of the drawing and is labeled with a numeral that has been described in a previous drawing may have the same use and description as in the previous drawings.

The drawings in this document may not be to any scale. Different figures may use different scales and different scales can be used even within the same drawing, for example different scales for different views of the same object or different scales for the two adjacent objects.

Consistent with disclosed embodiments, "at least one processor" may constitute any physical device or group of devices having electric circuitry that performs a logic operation on an input or inputs. For example, the at least one processor may include one or more integrated circuits (IC), including application-specific integrated circuit (ASIC), microchips, microcontrollers, microprocessors, all or part of a central processing unit (CPU), graphics processing unit (GPU), digital signal processor (DSP), field-programmable gate array (FPGA), server, virtual server, or other circuits suitable for executing instructions or performing logic operations. The instructions executed by at least one processor may, for example, be pre-loaded into a memory integrated with or embedded into the controller or may be stored in a separate memory. The memory may include a Random Access Memory (RAM), a Read-Only Memory (ROM), a hard disk, an optical disk, a magnetic medium, a flash memory, other permanent, fixed, or volatile memory, or any other mechanism capable of storing instructions. In some embodiments, the at least one processor may include more than one processor. Each processor may have a similar construction or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically or by other means that permit them to interact.

Disclosed embodiments may include and/or access a data structure. A data structure consistent with the present disclosure may include any collection of data values and relationships among them. The data may be stored linearly, horizontally, hierarchically, relationally, non-relationally, uni-dimensionally, multidimensionally, operationally, in an ordered manner, in an unordered manner, in an object-oriented manner, in a centralized manner, in a decentralized manner, in a distributed manner, in a custom manner, or in any manner enabling data access. By way of non-limiting examples, data structures may include an array, an associative array, a linked list, a binary tree, a balanced tree, a heap, a stack, a queue, a set, a hash table, a record, a tagged union, ER model, and a graph. For example, a data structure may include an XML database, an RDBMS database, an SQL database or NoSQL alternatives for data storage/search such as, for example, MongoDB, Redis, Couchbase, Datastax Enterprise Graph, Elastic Search, Splunk, Solr, Cassandra, Amazon DynamoDB, Scylla, HBase, and Neo4J. A data structure may be a component of the disclosed system or a remote computing component (e.g., a cloud-based data structure). Data in the data structure may be stored in contiguous or non-contiguous memory. Moreover, a data structure, as used herein, does not require information to be co-located. It may be distributed across multiple servers, for example, that may be owned or operated by the same or different entities. Thus, the term "data structure" as used herein in the singular is inclusive of plural data structures.

In some embodiments, machine learning algorithms (also referred to as machine learning models in the present disclosure) may be trained using training examples, for example in the cases described below. Some non-limiting examples of such machine learning algorithms may include classification algorithms, data regressions algorithms, image segmentation algorithms, visual detection algorithms (such as object detectors, face detectors, person detectors, motion detectors, edge detectors, etc.), visual recognition algorithms (such as face recognition, person recognition, object recognition, etc.), speech recognition algorithms, mathematical embedding algorithms, natural language processing algorithms, support vector machines, random forests, nearest neighbors algorithms, deep learning algorithms, artificial neural network algorithms, convolutional neural network algorithms, recursive neural network algorithms, linear machine learning models, non-linear machine learning models, ensemble algorithms, and so forth. For example, a trained machine learning algorithm may comprise an inference model, such as a predictive model, a classification model, a regression model, a clustering model, a segmentation model, an artificial neural network (such as a deep neural network, a convolutional neural network, a recursive neural network, etc.), a random forest, a support vector machine, and so forth. In some examples, the training examples may include example inputs together with the desired outputs corresponding to the example inputs. Further, in some examples, training machine learning algorithms using the training examples may generate a trained machine learning algorithm, and the trained machine learning algorithm may be used to estimate outputs for inputs not included in the training examples. In some examples, engineers, scientists, processes and machines that train machine learning algorithms may further use validation examples and/or test examples. For example, validation examples and/or test examples may include example inputs together with the desired outputs corresponding to the example inputs, a trained machine learning algorithm and/or an intermediately trained machine learning algorithm may be used to estimate outputs for the example inputs of the validation examples and/or test examples, the estimated outputs may be compared to the corresponding desired outputs, and the trained machine learning algorithm and/or the intermediately trained machine learning algorithm may be evaluated based on a result of the comparison. In some examples, a machine learning algorithm may have parameters and hyper parameters, where the hyper parameters are set manually by a person or automatically by an process external to the machine learning algorithm (such as a hyper parameter search algorithm), and the parameters of the machine learning algorithm are set by the machine learning algorithm according to the training examples. In some implementations, the hyper-parameters are set according to the training examples and the validation examples, and the parameters are set according to the training examples and the selected hyper-parameters.

In some embodiments, trained machine learning algorithms (also referred to as trained machine learning models in the present disclosure) may be used to analyze inputs and generate outputs, for example in the cases described below. In some examples, a trained machine learning algorithm may be used as an inference model that when provided with an input generates an inferred output. For example, a trained machine learning algorithm may include a classification algorithm, the input may include a sample, and the inferred output may include a classification of the sample (such as an inferred label, an inferred tag, and so forth). In another example, a trained machine learning algorithm may include a regression model, the input may include a sample, and the inferred output may include an inferred value for the sample. In yet another example, a trained machine learning algorithm may include a clustering model, the input may include a sample, and the inferred output may include an assignment of the sample to at least one cluster. In an additional example, a trained machine learning algorithm may include a classification algorithm, the input may include an image, and the inferred output may include a classification of an item depicted in the image. In yet another example, a trained machine learning algorithm may include a regression model, the input may include an image, and the inferred output may include an inferred value for an item depicted in the image (such as an estimated property of the item, such as size, volume, age of a person depicted in the image, cost of a product depicted in the image, and so forth). In an additional example, a trained machine learning algorithm may include an image segmentation model, the input may include an image, and the inferred output may include a segmentation of the image. In yet another example, a trained machine learning algorithm may include an object detector, the input may include an image, and the inferred output may include one or more detected objects in the image and/or one or more locations of objects within the image. In some examples, the trained machine learning algorithm may include one or more formulas and/or one or more functions and/or one or more rules and/or one or more procedures, the input may be used as input to the formulas and/or functions and/or rules and/or procedures, and the inferred output may be based on the outputs of the formulas and/or functions and/or rules and/or procedures (for example, selecting one of the outputs of the formulas and/or functions and/or rules and/or procedures, using a statistical measure of the outputs of the formulas and/or functions and/or rules and/or procedures, and so forth).

In some embodiments, artificial neural networks may be configured to analyze inputs and generate corresponding outputs. Some non-limiting examples of such artificial neural networks may comprise shallow artificial neural networks, deep artificial neural networks, feedback artificial neural networks, feed forward artificial neural networks, autoencoder artificial neural networks, probabilistic artificial neural networks, time delay artificial neural networks, convolutional artificial neural networks, recurrent artificial neural networks, long short term memory artificial neural networks, and so forth. In some examples, an artificial neural network may be configured manually. For example, a structure of the artificial neural network may be selected manually, a type of an artificial neuron of the artificial neural network may be selected manually, a parameter of the artificial neural network (such as a parameter of an artificial neuron of the artificial neural network) may be selected manually, and so forth. In some examples, an artificial neural network may be configured using a machine learning algorithm. For example, a user may select hyper-parameters for the an artificial neural network and/or the machine learning algorithm, and the machine learning algorithm may use the hyper-parameters and training examples to determine the parameters of the artificial neural network, for example using back propagation, using gradient descent, using stochastic gradient descent, using mini-batch gradient descent, and so forth. In some examples, an artificial neural network may be created from two or more other artificial neural networks by combining the two or more other artificial neural networks into a single artificial neural network.

In some embodiments, analyzing image data (for example by the methods, steps and modules described herein) may comprise analyzing the image data to obtain a preprocessed image data, and subsequently analyzing the image data and/or the preprocessed image data to obtain the desired outcome. Some non-limiting examples of such image data may include one or more images, videos, frames, footages, 2D image data, 3D image data, and so forth. One of ordinary skill in the art will recognize that the followings are examples, and that the image data may be preprocessed using other kinds of preprocessing methods. In some examples, the image data may be preprocessed by transforming the image data using a transformation function to obtain a transformed image data, and the preprocessed image data may comprise the transformed image data. For example, the transformed image data may comprise one or more convolutions of the image data. For example, the transformation function may comprise one or more image filters, such as low-pass filters, high-pass filters, band-pass filters, all-pass filters, and so forth. In some examples, the transformation function may comprise a nonlinear function. In some examples, the image data may be preprocessed by smoothing at least parts of the image data, for example using Gaussian convolution, using a median filter, and so forth. In some examples, the image data may be preprocessed to obtain a different representation of the image data. For example, the preprocessed image data may comprise: a representation of at least part of the image data in a frequency domain; a Discrete Fourier Transform of at least part of the image data; a Discrete Wavelet Transform of at least part of the image data; a time/frequency representation of at least part of the image data; a representation of at least part of the image data in a lower dimension; a lossy representation of at least part of the image data; a lossless representation of at least part of the image data; a time ordered series of any of the above; any combination of the above; and so forth. In some examples, the image data may be preprocessed to extract edges, and the preprocessed image data may comprise information based on and/or related to the extracted edges. In some examples, the image data may be preprocessed to extract image features from the image data. Some non-limiting examples of such image features may comprise information based on and/or related to edges; corners; blobs; ridges; Scale Invariant Feature Transform (SIFT) features; temporal features; and so forth.

In some embodiments, analyzing image data (for example, by the methods, steps and modules described herein) may comprise analyzing the image data and/or the preprocessed image data using one or more rules, functions, procedures, artificial neural networks, object detection algorithms, face detection algorithms, visual event detection algorithms, action detection algorithms, motion detection algorithms, background subtraction algorithms, inference models, and so forth. Some non-limiting examples of such inference models may include: an inference model preprogrammed manually; a classification model; a regression model; a result of training algorithms, such as machine learning algorithms and/or deep learning algorithms, on training examples, where the training examples may include examples of data instances, and in some cases, a data instance may be labeled with a corresponding desired label and/or result; and so forth.

In some embodiments, analyzing image data (for example, by the methods, steps and modules described herein) may comprise analyzing pixels, voxels, point cloud, range data, etc. included in the image data.

FIG. 1 shows an example operating room 101, consistent with disclosed embodiments. A patient 143 is illustrated on an operating table 141. Room 101 may include audio sensors, video/image sensors, chemical sensors, and other sensors, as well as various light sources (e.g., light source 119 is shown in FIG. 1) for facilitating the capture of video and audio data, as well as data from other sensors, during the surgical procedure. For example, room 101 may include one or more microphones (e.g., audio sensor 111, as shown in FIG. 1), several cameras (e.g., overhead cameras 115, 121, and 123, and a tableside camera 125) for capturing video/image data during surgery. While some of the cameras (e.g., cameras 115, 123 and 125) may capture video/image data of operating table 141 (e.g., the cameras may capture the video/image data at a location 127 of a body of patient 143 on which a surgical procedure is performed), camera 121 may capture video/image data of other parts of operating room 101. For instance, camera 121 may capture video/image data of a surgeon 131 performing the surgery. In some cases, cameras may capture video/image data associated with surgical team personnel, such as an anesthesiologist, nurses, surgical tech and the like located in operating room 101. Additionally, operating room cameras may capture video/image data associated with medical equipment located in the room.

In various embodiments, one or more of cameras 115, 121, 123 and 125 may be movable. For example, as shown in FIG. 1, camera 115 may be rotated as indicated by arrows 135A showing a pitch direction, and arrows 135B showing a yaw direction for camera 115. In various embodiments, pitch and yaw angles of cameras (e.g., camera 115) may be electronically controlled such that camera 115 points at a region-of-interest (ROI), of which video/image data needs to be captured. For example, camera 115 may be configured to track a surgical instrument (also referred to as a surgical tool) within location 127, an anatomical structure, a hand of surgeon 131, an incision, a movement of anatomical structure, and the like. In various embodiments, camera 115 may be equipped with a laser 137 (e.g., an infrared laser) for precision tracking. In some cases, camera 115 may be tracked automatically via a computer-based camera control application that uses an image recognition algorithm for positioning the camera to capture video/image data of a ROI. For example, the camera control application may identify an anatomical structure, identify a surgical tool, hand of a surgeon, bleeding, motion, and the like at a particular location within the anatomical structure, and track that location with camera 115 by rotating camera 115 by appropriate yaw and pitch angles. In some embodiments, the camera control application may control positions (i.e., yaw and pitch angles) of various cameras 115, 121, 123 and 125 to capture video/image date from different ROIs during a surgical procedure. Additionally or alternatively, a human operator may control the position of various cameras 115, 121, 123 and 125, and/or the human operator may supervise the camera control application in controlling the position of the cameras.

Cameras 115, 121, 123 and 125 may further include zoom lenses for focusing in on and magnifying one or more ROIs. In an example embodiment, camera 115 may include a zoom lens 138 for zooming closely to a ROI (e.g., a surgical tool in the proximity of an anatomical structure). Camera 121 may include a zoom lens 139 for capturing video/image data from a larger area around the ROI. For example, camera 121 may capture video/image data for the entire location 127. In some embodiments, video/image data obtained from camera 121 may be analyzed to identify a ROI during the surgical procedure, and the camera control application may be configured to cause camera 115 to zoom towards the ROI identified by camera 121.

In various embodiments, the camera control application may be configured to coordinate the position, focus, and magnification of various cameras during a surgical procedure. For example, the camera control application may direct camera 115 to track an anatomical structure and may direct camera 121 and 125 to track a surgical instrument. Cameras 121 and 125 may track the same ROI (e.g., a surgical instrument) from different view angles. For example, video/image data obtained from different view angles may be used to determine the position of the surgical instrument relative to a surface of the anatomical structure, to determine a condition of an anatomical structure, to determine pressure applied to an anatomical structure, or to determine any other information where multiple viewing angles may be beneficial. By way of another example, bleeding may be detected by one camera, and one or more other cameras may be used to identify the source of the bleeding.

In various embodiments, control of position, orientation, settings, and/or zoom of cameras 115, 121, 123 and 125 may be rule-based and follow an algorithm developed for a given surgical procedure. For example, the camera control application may be configured to direct camera 115 to track a surgical instrument, to direct camera 121 to location 127, to direct camera 123 to track the motion of the surgeon's hands, and to direct camera 125 to an anatomical structure. The algorithm may include any suitable logical statements determining position, orientation, settings and/or zoom for cameras 115, 121, 123 and 125 depending on various events during the surgical procedure. For example, the algorithm may direct at least one camera to a region of an anatomical structure that develops bleeding during the procedure. Some non-limiting examples of settings of cameras 115, 121, 123 and 125 that may be controlled (for example by the camera control application) may include image pixel resolution, frame rate, image and/or color correction and/or enhancement algorithms, zoom, position, orientation, aspect ratio, shutter speed, aperture, focus, and so forth.

In various cases, when a camera (e.g., camera 115) tracks a moving or deforming object (e.g., when camera 115 tracks a moving surgical instrument, or a moving/pulsating anatomical structure), a camera control application may determine a maximum allowable zoom for camera 115, such that the moving or deforming object does not escape a field of view of the camera. In an example embodiment, the camera control application may initially select the first zoom for camera 115, evaluate whether the moving or deforming object escapes the field of view of the camera, and adjust the zoom of the camera as necessary to prevent the moving or deforming object from escaping the field of view of the camera. In various embodiments, the camera zoom may be readjusted based on a direction and a speed of the moving or deforming object.

Figure 2:
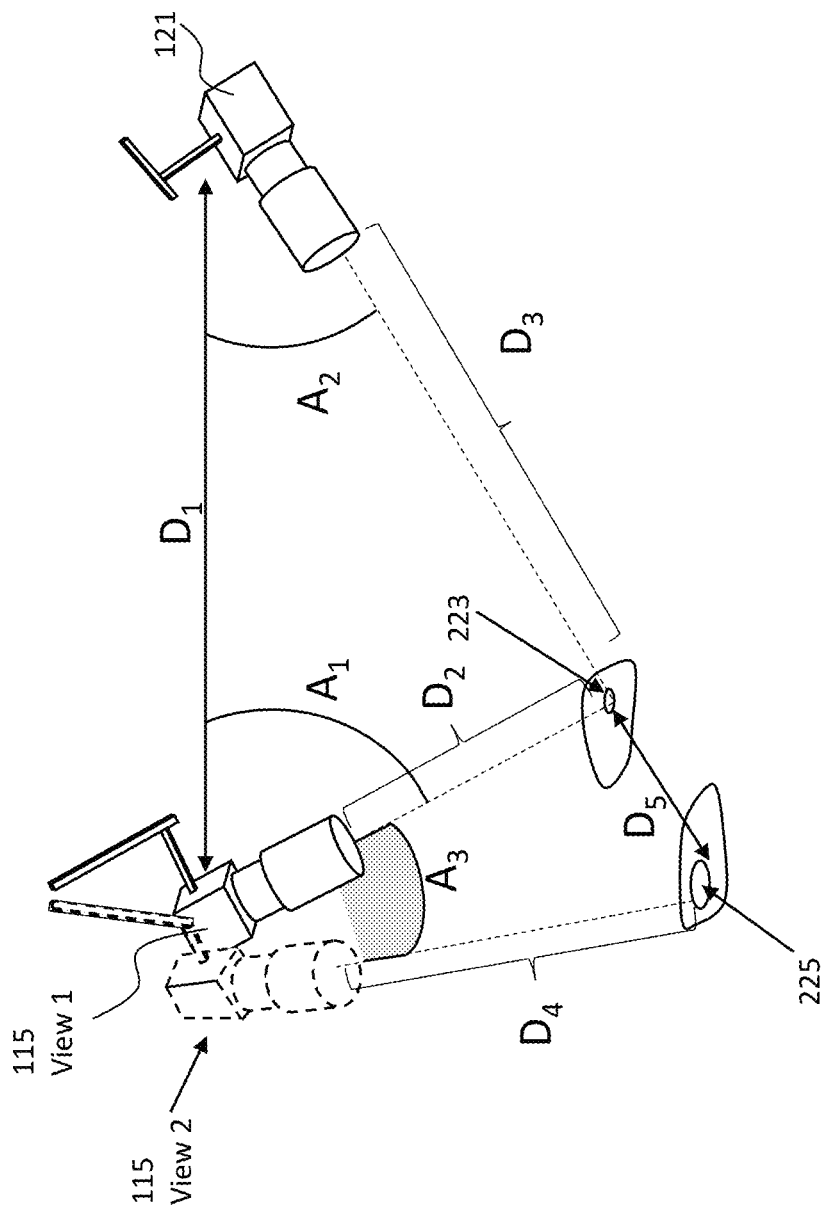
FIG. 2 is a perspective view of cameras, consistent with disclosed embodiments.

In various embodiments, one or more image sensors may include moving cameras 115, 121, 123 and 125. Cameras 115, 121, 123 and 125 may be used for determining sizes of anatomical structures and determining distances between different ROIs, for example using triangulation. For example, FIG. 2 shows exemplary cameras 115 (115 View 1, as shown in FIG. 2) and 121 supported by movable elements such that the distance between the two cameras is $D_1$, as shown in FIG. 2. Both cameras point at ROI 223. By knowing the positions of cameras 115 and 121 and the direction of an object relative to the cameras (e.g., by knowing angles $A_1$ and $A_2$, as shown in FIG. 2, for example based on correspondences between pixels depicting the same object or the same real-world point in the images captured by 115 and 121), distances $D_2$ and $D_3$ may be calculated using, for example, the law of sines and the known distance between the two cameras $D_1$. In an example embodiment, when camera 115 (115, View 2) rotates by a small angle $A_3$ (measured in radians), to point at ROI 225, the distance between ROI 223 and ROI 225 may be approximated (for small angles $A_3$) by $A_3 D_2$. More accuracy may be obtained using another triangulation process. Knowing distances between ROI 223 and 225 allows determining a length scale for an anatomical structure. Further, distances between various points of the anatomical structure, and distances from the various points to one or more cameras may be measured to determine a point-cloud representing a surface of the anatomical structure. Such a point-cloud may be used to reconstruct a three-dimensional model of the anatomical structure. Further, distances between one or more surgical instruments and different points of the anatomical structure may be measured to determine proper locations of the one or more surgical instruments in the proximity of the anatomical structure. In some other examples, one or more of cameras 115, 121, 123 and 125 may include a 3D camera (such as a stereo camera, an active stereo camera, a Time of Flight camera, a Light Detector and Ranging camera, etc.), and actual and/or relative locations and/or sizes of objects within operating room 101, and/or actual distances between objects, may be determined based on the 3D information captured by the 3D camera.

Returning to FIG. 1, light sources (e.g., light source 119) may also be movable to track one or more ROIs. In an example embodiment, light source 119 may be rotated by yaw and pitch angles, and in some cases, may extend towards to or away from a ROI (e.g., location 127). In some cases, light source 119 may include one or more optical elements (e.g., lenses, flat or curved mirrors, and the like) to focus light on the ROI. In some cases, light source 119 may be configured to control the color of the light (e.g., the color of the light may include different types of white light, a light with a selected spectrum, and the like). In an example embodiment, light 119 may be configured such that the spectrum and intensity of the light may vary over a surface of an anatomic structure illuminated by the light. For example, in some cases, light 119 may include infrared wavelengths which may result in warming of at least some portions of the surface of the anatomic structure.

In some embodiments, the operating room may include sensors embedded in various components depicted or not depicted in FIG. 1. Examples of such sensors may include: audio sensors; image sensors; motion sensors; positioning sensors; chemical sensors; temperature sensors; barometers; pressure sensors; proximity sensors; electrical impedance sensors; electrical voltage sensors; electrical current sensors; or any other detector capable of providing feedback on the environment or a surgical procedure, including, for example, any kind of medical or physiological sensor configured to monitor patient 143.

In some embodiments, audio sensor 111 may include one or more audio sensors configured to capture audio by converting sounds to digital information (e.g., audio sensors 121).

In various embodiments, temperature sensors may include infrared cameras (e.g., an infrared camera 117 is shown in FIG. 1) for thermal imaging. Infrared camera 117 may allow measurements of the surface temperature of an anatomic structure at different points of the structure. Similar to visible cameras D115, 121, 123 and 125, infrared camera 117 may be rotated using yaw or pitch angles. Additionally or alternatively, camera 117 may include an image sensor configured to capture image from any light spectrum, include infrared image sensor, hyper-spectral image sensors, and so forth.

FIG. 1 includes a display screen 113 that may show views from different cameras 115, 121, 123 and 125, as well as other information. For example, display screen 113 may show a zoomed-in image of a tip of a surgical instrument and a surrounding tissue of an anatomical structure in proximity to the surgical instrument.

Figure 3:
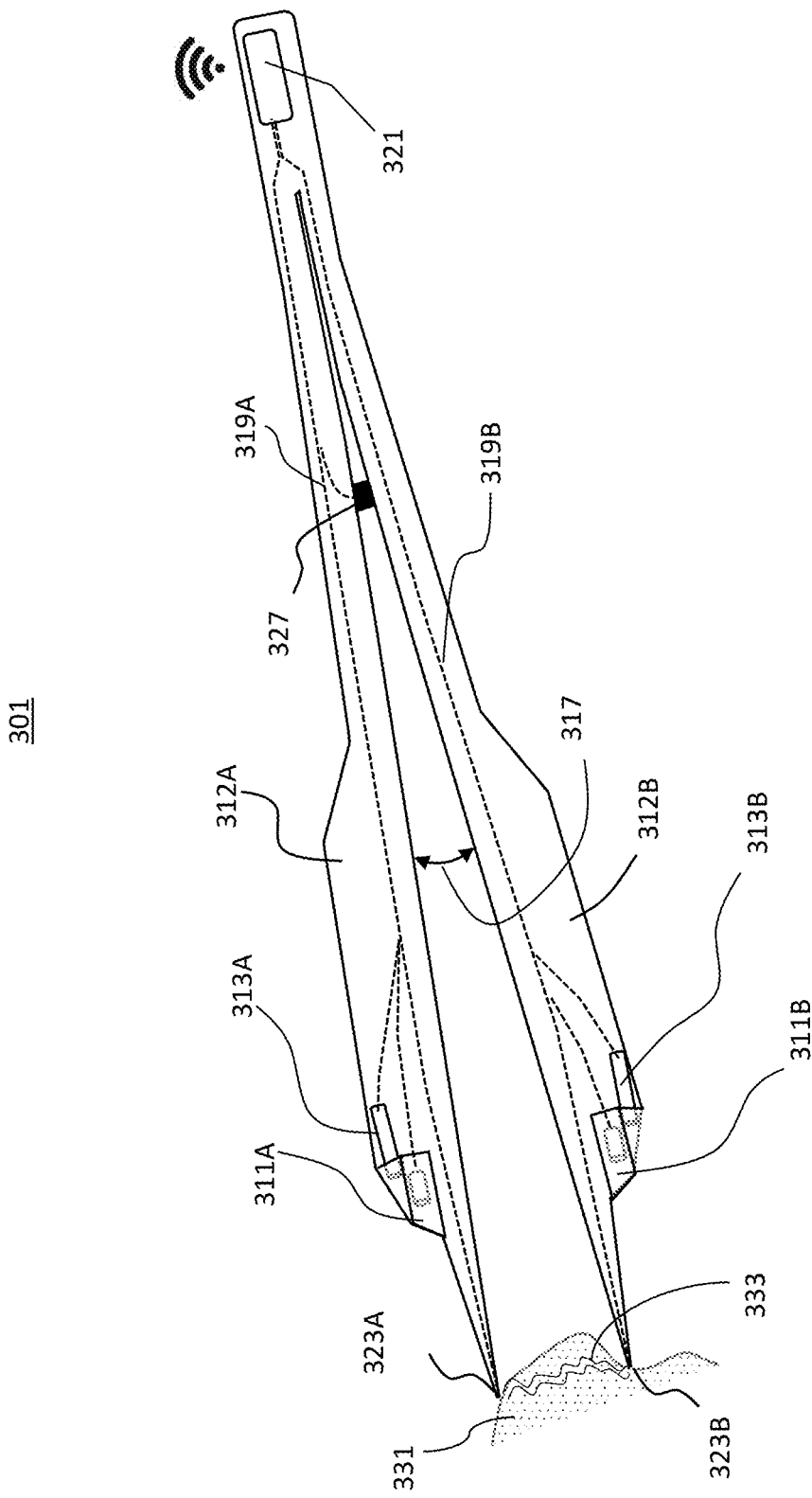
FIG. 3 is a perspective view of an example of a surgical instrument, consistent with disclosed embodiments.

FIG. 3 shows an example embodiment of a surgical instrument 301 that may include multiple sensors and light-emitting sources. Consistent with the present embodiments, a surgical instrument may refer to a medical device, a medical instrument, an electrical or mechanical tool, a surgical tool, a diagnostic tool, and/or any other instrumentality that may be used during a surgery. As shown, instrument 301 may include cameras 311A and 311B, light sources 313A and 313B as well as tips 323A and 323B for contacting tissue 331. Cameras 311A and 311B may be connected via data connection 319A and 319B to a data transmitting device 321. In an example embodiment, device 321 may transmit data to a data-receiving device using a wireless communication or using a wired communication. In an example embodiment, device 321 may use WiFi, Bluetooth, NFC communication, inductive communication, or any other suitable wireless communication for transmitting data to a data-receiving device. The data-receiving device may include any form of receiver capable of receiving data transmissions. Additionally or alternatively, device 321 may use optical signals to transmit data to the data-receiving device (e.g., device 321 may use optical signals transmitted through the air or via optical fiber). In some embodiments, device 301 may include local memory for storing at least some of the data received from sensors 311A and 311B.

Additionally, device 301 may include a processor for compressing video/image data before transmitting the data to the data-receiving device.

In various embodiments, for example when device 301 is wireless, it may include an internal power source (e.g., a battery, a rechargeable battery, and the like) and/or a port for recharging the battery, an indicator for indicating the amount of power remaining for the power source, and one or more input controls (e.g., buttons) for controlling the operation of device 301. In some embodiments, control of device 301 may be accomplished using an external device (e.g., a smartphone, tablet, smart glasses) communicating with device 301 via any suitable connection (e.g., WiFi, Bluetooth, and the like). In an example embodiment, input controls for device 301 may be used to control various parameters of sensors or light sources. For example, input controls may be used to dim/brighten light sources 313A and 313B, move the light sources for cases when the light sources may be moved (e.g., the light sources may be rotated using yaw and pitch angles), control the color of the light sources, control the focusing of the light sources, control the motion of cameras 311A and 311B for cases when the cameras may be moved (e.g., the cameras may be rotated using yaw and pitch angles), control the zoom and/or capturing parameters for cameras 311A and 311B, or change any other suitable parameters of cameras 311A-311B and light sources 313A-313B. It should be noted camera 311A may have a first set of parameters and camera 311B may have a second set of parameters that is different from the first set of parameters, and these parameters may be selected using appropriate input controls. Similarly, light source 313A may have a first set of parameters and light source 313B may have a second set of parameters that is different from the first set of parameters, and these parameters may be selected using appropriate input controls.

Additionally, instrument 301 may be configured to measure data related to various properties of tissue 331 via tips 323A and 323B and transmit the measured data to device 321. For example, tips 323A and 323B may be used to measure the electrical resistance and/or impedance of tissue 331, the temperature of tissue 331, mechanical properties of tissue 331 and the like. To determine elastic properties of tissue 331, for example, tips 323A and 323B may be first separated by an angle 317 and applied to tissue 331. The tips may be configured to move such as to reduce angle 317, and the motion of tips may result in pressure on tissue 331. Such pressure may be measured (e.g., via a piezoelectric element 327 that may be located between a first branch 312A and a second branch 312B of instrument 301), and based on the change in angle 317 (i.e., strain) and the measured pressure (i.e., stress), the elastic properties of tissue 331 may be measured. Furthermore, based on angle 317 distance between tips 323A and 323B may be measured, and this distance may be transmitted to device 321. Such distance measurements may be used as a length scale for various video/image data that may be captured by various cameras 115, 121, 123 and 125, as shown in FIG. 1.

Instrument 301 is only one example of possible surgical instrument, and other surgical instruments such as scalpels, graspers (e.g., forceps), clamps and occluders, needles, retractors, cutters, dilators, suction tips, and tubes, sealing devices, irrigation and injection needles, scopes and probes, and the like, may include any suitable sensors and light-emitting sources. In various cases, the type of sensors and light-emitting sources may depend on a type of surgical instrument used for a surgical procedure. In various cases, these other surgical instruments may include a device similar to device 301, as shown in FIG. 3, for collecting and transmitting data to any suitable data-receiving device.

When preparing for a surgical procedure, it may be beneficial for a surgeon to review video footage of surgical procedures having similar surgical events. It may be too time consuming, however, for a surgeon to view the entire video or to skip around to find relevant portions of the surgical footage. Therefore, there is a need for unconventional approaches that efficiently and effectively enable a surgeon to view a surgical video summary that aggregates footage of relevant surgical events while omitting other irrelevant footage.

Aspects of this disclosure may relate to reviewing surgical video, including methods, systems, devices, and computer readable media. An interface may allow a surgeon to review surgical video (of their own surgeries, other's surgeries, or compilations) with a surgical timeline simultaneously displayed. The timeline may include markers keyed to activities or events that occur during a surgical procedure. These markers may allow the surgeon to skip to particular activities to thereby streamline review of the surgical procedure. In some embodiments, key decision making junction points may be marked, and the surgeon may be permitted to view alternative actions taken at those decision making junction points.

For ease of discussion, a method is described below, with the understanding that aspects of the method apply equally to systems, devices, and computer readable media. For example, some aspects of such a method may occur electronically over a network that is either wired, wireless, or both. Other aspects of such a method may occur using non-electronic means. In a broadest sense, the method is not limited to particular physical and/or electronic instrumentalities, but rather may be accomplished using many differing instrumentalities.

Consistent with disclosed embodiments, a method may involve accessing at least one video of a surgical procedure. As described in greater detail above, video may include any form of recorded visual media including recorded images and/or sound. The video may be stored as a video file such as an Audio Video Interleave (AVI) file, a Flash Video Format (FLV) file, QuickTime File Format (MOV), MPEG (MPG, MP4, M4P, etc.), a Windows Media Video (WMV) file, a Material Exchange Format (MXF) file, or any other suitable video file formats, for example as described above.

A surgical procedure may include any medical procedure associated with or involving manual or operative procedures on a patient's body. Surgical procedures may include cutting, abrading, suturing, or other techniques that involve physically changing body tissues and organs. Examples of such surgical procedures are provided above. A video of a surgical procedure may include any series of still images that were captured during and are associated with the surgical procedure. In some embodiments, at least a portion of the surgical procedure may be depicted in one or more of the still images included in the video. For example, the video of the surgical procedure may be recorded by an image capture device, such as a camera, in an operating room or in a cavity of a patient. Accessing the video of the surgical procedure may include retrieving the video from a storage device (such as one or more memory units, a video server, a cloud storage platform, or any other storage platform), receiving the video from another device through a communication device, capturing the video using image sensors, or any other means for electronically accessing data or files.

Some aspects of the present disclosure may involve causing the at least one video to be output for display.

Outputting the at least one video may include any process by which the video is produced, delivered, or supplied using a computer or at least one processor. As used herein, "display" may refer to any manner in which a video may be presented to a user for playback. In some embodiments, outputting the video may include presenting the video using a display device, such as a screen (e.g., an OLED, QLED LCD, plasma, CRT, DLPT, electronic paper, or similar display technology), a light projector (e.g., a movie projector, a slide projector), a 3D display, screen of a mobile device, electronic glasses or any other form of visual and/or audio presentation. In other embodiments, outputting the video for display may include storing the video in a location that is accessible by one or more other computing devices. Such storage locations may include a local storage (such as a hard drive of flash memory), a network location (such as a server or database), a cloud computing platform, or any other accessible storage location. The video may be accessed from a separate computing device for display on the separate computing device. In some embodiments, outputting the video may include transmitting the video to an external device. For example, outputting the video for display may include transmitting the video through a network to a user device for playback on the user device.

Embodiments of the present disclosure may further include overlaying on the at least one video outputted for display a surgical timeline. As used herein, a "timeline" may refer to any depiction from which a sequence of events may be tracked or demarcated. In some embodiments, a timeline may be a graphical representation of events, for example, using an elongated bar or line representing time with markers or other indicators of events along the bar. A timeline may also be a text-based list of events arranged in chronological order. A surgical timeline may be a timeline representing events associated with a surgery. As one example, a surgical timeline may be a timeline of events or actions that occur during a surgical procedure, as described in detail above. In some embodiments, the surgical timeline may include textual information identifying portions of the surgical procedure. For example, the surgical timeline may be a list of descriptions of intraoperative surgical events or surgical phases within a surgical procedure. In other embodiments, by hovering over or otherwise actuating graphical markers on a timeline, a descriptor associated with the marker may appear.

Overlaying the surgical timeline on the at least one video may include any manner of displaying the surgical timeline such that it can be viewed simultaneously with the at least one video. In some embodiments, overlaying the video may include displaying the surgical timeline such that it at least partially overlaps the video. For example, the surgical timeline may be presented as a horizontal bar along a top or bottom of the video or a vertical bar along a side of the video. In other embodiments, overlaying may include presenting the surgical timeline alongside the video. For example, the video may be presented on a display with the surgical timeline presented above, below, and/or to the side of the video. The surgical timeline may be overlaid on the video while the video is being played. Thus, "overlaying" as used herein refers more generally to simultaneous display. The simultaneous display may or may not be constant. For example, the overlay may appear with the video output before the end of the surgical procedure depicted in the displayed video. Or, the overlay may appear during substantially all of the video procedure.

Figure 4:
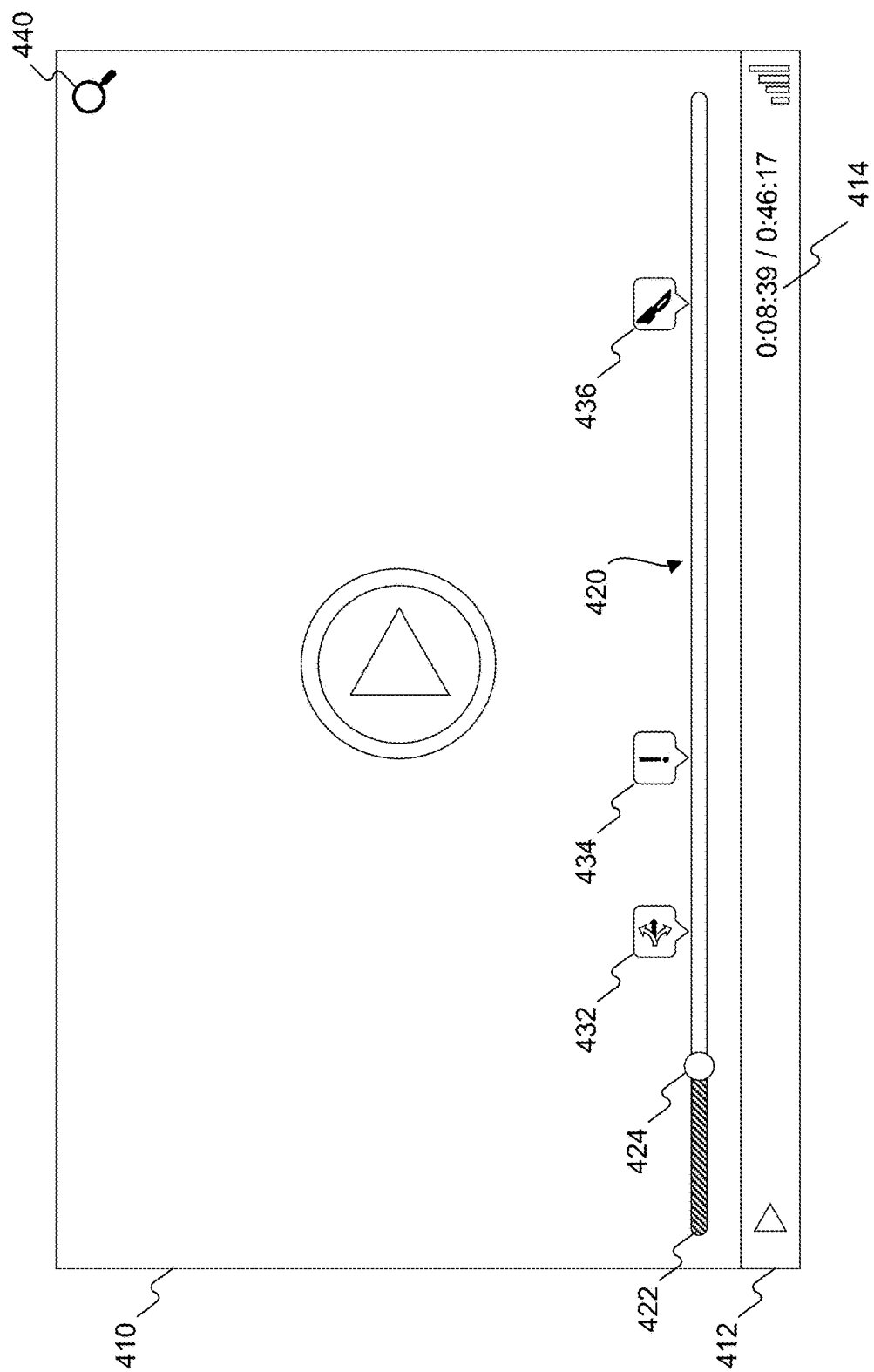
FIG. 4 illustrates an example timeline overlaid on a video of a surgical procedure consistent with the disclosed embodiments.

FIG. 4 illustrates an example timeline 420 overlaid on a video of a surgical procedure consistent with the disclosed embodiments. The video may be presented in a video playback region 410, which may sequentially display one or more frames of the video. In the example shown in FIG. 4, timeline 420 may be displayed as a horizontal bar representing time, with the leftmost portion of the bar representing a beginning time of the video and the rightmost portion of the bar representing an end time. Timeline 420 may include a position indicator 424 indicating the current playback position of the video relative to the timeline. Colored region 422 of timeline 420 may represent the progress within timeline 420 (e.g., corresponding to video that has already been viewed by the user, or to video coming before the currently presented frame). In some embodiments, position indicator 424 may be interactive, such that the user can move to different positions within the video by moving position indicator 424. In some embodiments, the surgical timeline may include markers identifying at least one of a surgical phase, an intraoperative surgical event, and a decision making junction. For example, timeline 420 may further include one or more markers 432, 434, and/or 436. Such markers are described in greater detail below.

In the example shown in FIG. 4, timeline 420 may be displayed such that it overlaps video playback region 410, either physically, temporally, or both. In some embodiments, timeline 420 may not be displayed at all times. As one example, timeline 420 may automatically switch to a collapsed or hidden view while a user is viewing the video and may return to the expanded view shown in FIG. 4 when the user takes an action to interact with timeline 420. For example, user may move a mouse pointer while viewing the video, move the mouse pointer over the collapsed timeline, move the mouse pointer to a particular region, click or tap the video playback region, or perform any other actions that may indicate an intent to interact with timeline 420. As discussed above, timeline 420 may be displayed in various other locations relative to video playback region 410, including on a top portion of video playback region 410, above or below video playback region 410, or within control bar 612. In some embodiments, timeline 420 may be displayed separately from a video progress bar. For example, a separate video progress bar, including position indicator 424 and colored region 422, may be displayed in control bar 412 and timeline 420 may be a separate timeline of events associated with a surgical procedure. In such embodiments, timeline 420 may not have the same scale or range of time as the video or the video progress bar. For example, the video progress bar may represent the time scale and range of the video, whereas timeline 420 may represent the timeframe of the surgical procedure, which may not be the same (e.g., where the video comprises a surgical summary, as discussed in detail above). In some embodiments, video playback region 410 may include a search icon 440, which may allow a user to search for video footage, for example, through user interface 700, as described above in reference to FIG. 7. The surgical timeline shown in FIG. 4 is provided by way of example only, and one skilled in the art would appreciate various other configurations that may be used.

Embodiments of the present disclosure may further include enabling a surgeon, while viewing playback of the at least one video to select one or more markers on the surgical timeline, and thereby cause a display of the video to skip to a location associated with the selected marker. As used herein, "playback" may include any presentation of a video in which one or more frames of the video are displayed to the user. Typically, playback will include sequentially displaying the images to reproduce moving images and/or sounds, however playback may also include the display of individual frames.

Consistent with the disclosed embodiments, a "marker" may include any visual indicator associated with location within the surgical timeline. As described above, the location may refer to any particular position within a video. For example, the location may be a particular frame or range of frames in the video, a particular timestamp, or any other indicator of position within the video. Markers may be represented on the timeline in various ways. In some embodiments, the markers may be icons or other graphic representations displayed along the timeline at various locations. The markers may be displayed as lines, bands, dots, geometric shapes (such as diamonds, squares, triangles, or any other shape), bubbles, or any other graphical or visual representation. In some embodiments, the markers may be text-based. For example, the markers may include textual information, such as a name, a description, a code, a timestamp, and so forth. In another example, the surgical timeline may be displayed as a list, as described above. Accordingly, the markers may include text-based titles or descriptions referring to a particular location of the video. Markers 432, 434, and 436 are shown by way of example in FIG. 4. The markers may be represented as callout bubbles, including an icon indicating the type of marker associated with the location. The markers may point to a particular point along timeline 420 indicating the location in the video.

Selection of the marker may include any action by a user directed towards a particular marker. In some embodiments, selecting the marker may include clicking on or tapping the marker through a user interface, touching the marker on a touch sensitive screen, glancing at the marker through smart glasses, indicating the marker through a voice interface, indicating the marker with a gesture, or undertaking any other action that causes the marker to be selected. Selection of the marker may thereby cause a display of the video to skip to a location associated with the selected marker. As used herein, skipping may include selectively displaying a particular frame within a video. This may include stopping display of a frame at a current location in the video (for example, if the video is currently playing) and displaying a frame at the location associated with the selected marker. For example, if a user clicks on or otherwise selects marker 432, as shown in FIG. 4, a frame at the location associated with marker 432 may be displayed in video playback region 410. In some embodiments, the video may continue playing from that location. Position indicator 424 may move to a position within timeline 420 associated with marker 432 and colored region 422 may be updated accordingly. While the present embodiment is described as enabling a surgeon to select the one or more markers, it is understood that this is an example only, and the present disclosure is not limited to any form of user. Various other users may view and interact with the overlaid timeline, including a surgical technician, a nurse, a physician's assistant, an anesthesiologist, a doctor, or any other healthcare professional, as well as a patient, an insurer, a medical student, and so forth. Other examples of users are provided herein.

In accordance with embodiments of the present disclosure, the markers may be automatically generated and included in the timeline based on information in the video at a given location. In some embodiments, computer analysis may be used to analyze frames of the video footage and identify markers to include at various locations in the timeline. Computer analysis may include any form of electronic analysis using a computing device. In some embodiments, computer analysis may include using one or more image recognition algorithms to identify features of one or more frames of the video footage. Computer analysis may be performed on individual frames, or may be performed across multiple frames, for example, to detect motion or other changes between frames. In some embodiments computer analysis may include object detection algorithms, such as Viola-Jones object detection, scale-invariant feature transform (SIFT), histogram of oriented gradients (HOG) features, convolutional neural networks (CNN), or any other forms of object detection algorithms. Other example algorithms may include video tracking algorithms, motion detection algorithms, feature detection algorithms, color-based detection algorithms, texture based detection algorithms, shape based detection algorithms, boosting based detection algorithms, face detection algorithms, or any other suitable algorithm for analyzing video frames. In one example, a machine learning model may be trained using training examples to generate markers for videos, and the trained machine learning model may be used to analyze the video and generate markers for that video. Such generated markers may include locations within the video for the marker, type of the marker, properties of the marker, and so forth. An example of such training example may include a video clip depicting at least part of a surgical procedure, together with a list of desired markers to be generated, possibly together with information for each desired marker, such as a location within the video for the marker, a type of the marker, properties of the marker, and so forth.

This computer analysis may be used to identify surgical phases, intraoperative events, event characteristics, and/or other features appearing in the video footage. For example, in some embodiments, computer analysis may be used to identify one or more medical instruments used in a surgical procedure, for example as described above. Based on identification of the medical instrument, a particular intraoperative event may be identified at a location in the video footage associated with the medical instrument. For example, a scalpel or other instrument may indicate that an incision is being made and a marker identifying the incision may be included in the timeline at this location. In some embodiments, anatomical structures may be identified in the video footage using the computer analysis, for example as described above. For example, the disclosed methods may include identifying organs, tissues, fluids or other structures of the patient to determine markers to include in the timeline and their respective locations. In some embodiments, locations for video markers may be determined based on an interaction between a medical instrument and the anatomical structure, which may indicate a particular intraoperative event, type of surgical procedure, event characteristic, or other information useful in identifying marker locations. For example, visual action recognition algorithms may be used to analyze the video and detect the interactions between the medical instrument and the anatomical structure. Other examples of features that may be detected in video footage for placing markers may include, motions of a surgeon or other medical professional, patient characteristics, surgeon characteristics or characteristics of other medical professionals, sequences of operations being performed, timings of operations or events, characteristics of anatomical structures, medical conditions, or any other information that may be used to identify particular surgical procedures, surgical phases, intraoperative events, and/or event characteristics appearing in the video footage.

In some embodiments, marker locations may be identified using a trained machine learning model. For example, a machine learning model may be trained using training examples, each training example may include video footage known to be associated with surgical procedures, surgical phases, intraoperative events, and/or event characteristics, together with labels indicating locations within the video footage. Using the trained machine learning model, similar phases and events may be identified in other video footage for the determining marker locations. Various machine learning models may be used, including a logistic regression model, a linear regression model, a regression model, a random forest model, a K-Nearest Neighbor (KNN) model, a K-Means model, a decision tree, a cox proportional hazards regression model, a Naïve Bayes model, a Support Vector Machines (SVM) model, a gradient boosting algorithm, artificial neural networks (such as deep neural networks, convolutional neural networks, etc.) or any other form of machine learning model or algorithm.

In some embodiments, video markers may be identified in conjunction with the video indexing techniques discussed above. As described above, video footage may be indexed based on surgical phases, intraoperative events, and/or event characteristics identified in the video footage. This information may be stored in a data structure, such as data structure 600, as described in reference to FIG. 6. The data structure may include footage locations and/or event locations associated with phases and events within the video footage. In some embodiments, the markers displayed in the timeline may correspond to these locations in the video. Accordingly any of the techniques or processes described above for indexing video footage may similarly apply to determining marker locations for presenting in a timeline.

According to various exemplary embodiments of the present disclosure, the markers may be coded by at least one of a color or a criticality level. The coding of a marker may be any indicator of a type, property, or characteristic of the marker. The coding may be useful for a user in visually determining which locations of the video may be of interest. Where the marker is coded by color, the color of the marker displayed on the surgical timeline may indicate the property or characteristic of the marker based on a predefined color scheme. For example, the marker may have a different color depending on what type of intraoperative surgical event the marker represents. In some example embodiments, markers associated with an incision, an excision, a resection, a ligation, a graft, or various other events may each be displayed with a different color. In other embodiments, intraoperative adverse events may be associated with one color (e.g., red), where planned events may be associated with another color (e.g., green). In some embodiments, color scales may be used. For example, the severity of an adverse event may be represented by on a color scale ranging from yellow to red, or other suitable color scales.

In some embodiments, the location and/or size of the marker may be associated with a criticality level. The criticality level may represent the relative importance of an event, action, technique, phase or other occurrence identified by the marker. Accordingly, as used herein, the term "criticality level" refers to any measure of an immediate need for an action to prevent hazardous result within a surgical procedure. For example, criticality level may include a numerical measure (such as "1.12", "3.84", "7", "-4.01", etc.), for example within a particular range of values. In another example, criticality level may include finite number of discrete levels (such as "Level 0", "Level 1", "Level 2", "High Criticality", "Low Criticality", "Non Critical", etc.).

While color is provided as one example for distinguishing marker appearance to represent information, various other techniques may be used. For example, markers may have varying sizes, shapes, positions, orientations, font size, font types, font colors, marker animations, or other visual properties. In some embodiments, markers may be associated with different icons depending on the type of event, action, or phase with which they are associated. For example, as shown in FIG. 4, marker 432, which may be associated with a decision junction, may have a different icon than marker 434, which may be associated with another type of event, such as a complication. The icon may represent the type of intraoperative event associated with that location. For example, marker 436 may indicate that an incision occurs at this location in the video. The icons (or other visual properties) may be used to distinguish between unplanned events and planned events, types of errors (e.g., miscommunication errors, judgment errors, or other forms of errors), specific adverse events that occurred, types of techniques being performed, the surgical phase being performed, locations of intraoperative surgical events (e.g., in the abdominal wall, etc.), a surgeon performing the procedure, an outcome of the surgical procedure, or various other information.

In some exemplary embodiments, the one or more markers may include a decision making junction marker corresponding to a decision making junction of the surgical procedure. In some embodiments, such decision making junction markers maybe visually distinct from other forms or types of markers. As an illustrative example, the decision making junction marker may have an icon indicating the location is associated with a decision making junction, as shown in FIG. 4 by marker 432. As used herein, a decision making junction may refer to any part of a procedure in which a decision is made, or in which a decision of a selected type of decisions or of a plurality of selected types of decisions is made. For example, the decision making junction marker may indicate a location of a video depicting a surgical procedure where multiple courses of action are possible, and a surgeon opts to follow one course over another. For example, the surgeon may decide whether to depart from a planned surgical procedure, to take a preventative action, to remove an organ or tissue, to use a particular instrument, to use a particular surgical technique, or any other intraoperative decisions a surgeon may encounter. In one example, a decision making junction may refer to a part of a procedure in which a decision that has significant effect on an outcome of the procedure is made. In another example, decision making junction may refer to a part of a procedure in which a decision that has no clear decision making guidelines has to be made. In yet another example, a decision making junction may refer to a part of a procedure in which a surgeon is faced with two or more viable alternatives, and where choosing the better alternative of the two or more viable alternatives (for example, the alternative that is predicted to reduce a particular risk, the alternative that is predicted to improve outcome, the alternative that is predicted to reduce cost, etc.) is based on at least a particular number of factors (for example, is based on at least two factors, on at least five factors, on at least ten factors, on at least one hundred factors, and so forth). In an additional example, decision making junction may refer to a part of a procedure in which a surgeon is faced with a decision of a particular type, and where the particular type is included in a group of selected decision types.

The decision making junction may be detected using the computer analysis described above. In some embodiments, video footage may be analyzed to identify particular actions or sequences of actions performed by a surgeon that may indicate a decision has been made. For example, if the surgeon pauses during a procedure, begins to use a different medical device, or changes to a different course of action, this may indicate a decision has been made. In some embodiments, the decision making junction may be identified based on a surgical phase or intraoperative event identified in the video footage at that location. For example, an adverse event, such as a bleed, may be detected which may indicate a decision must be made on how to address the adverse event. As another example, a particular phase of a surgical procedure may be associated with multiple possible courses of action. Accordingly, detecting this surgical phase in the video footage may indicate a decision making junction. In some embodiments, a trained machine learning model may be used to identify the decision making junction. For example, a machine learning model may be trained using training examples to detect decision making junctions in videos, and the trained machine learning model may be used to analyze the video and detect the decision making junction. An example of such training example may include a video clip, together with a label indicating locations of decision making junctions within the video clip, or together with a label indicating an absent of decision making junctions in the video clip.

The selection of the decision making junction marker may enable the surgeon to view two or more alternative video clips from two or more corresponding other surgical procedures, thereby enabling the viewer to compare alternative approaches. Alternative video clips may be any video clips illustrating a procedure other than one currently being displayed to the user. Such an alternative may be drawn from other video footage not included in the current video being output for display. Alternatively, if the current video footage includes a compilation of differing procedures, the alternative footage may be drawn from a differing location of the current video footage being displayed. The other surgical procedures may be any surgical procedure other than the specific procedure depicted in the current video being output for display. In some embodiments, the other surgical procedures may be the same type of surgical procedure depicted in the video being output for display, but performed at different times, on different patients, and/or by different surgeons. In some embodiments, the other surgical procedures may not be the same type of procedure but may share the same or similar decision making junctions as the one identified by the decision making junction marker. In some embodiments, the two or more video clips may present differing conduct. For example, the two or more video clips may represent an alternate choice of action than the one taken in the current video, as represented by the decision making junction marker.

The alternative video clips may be presented in various ways. In some embodiments, selecting the decision making junction marker may automatically cause display of the two or more alternative video clips. For example, one or more of the alternative video clips may be displayed in video playback region 410. In some embodiments, the video playback region may be split or divided to show one or more of the alternative video clips and/or the current video. In some embodiments, the alternative video clips may be displayed in another region, such as above, below, or to the side of video playback region 410. In some embodiments, the alternative video clips may be displayed in a second window, on another screen, or in any other space other than playback region 410. According to other embodiments, selecting the decision marker may open a menu or otherwise display options for viewing the alternative video clips. For example, selecting the decision naming marker may pop up an alternative video menu containing depictions of the conduct in the associated alternative video clips. The alternative video clips may be presented as thumbnails, text-based descriptions, video previews (e.g., playing a smaller resolution version or shortened clip), or the like. The menu may be overlaid on the video, may be displayed in conjunction with the video, or may be displayed in a separate area.

In accordance with embodiments of the present disclosure, the selection of the decision making junction marker may cause a display of one or more alternative possible decisions related to the selected decision making junction marker. Similar to the alternative videos, the alternative possible decisions may be overlaid on the timeline and/or video, or may be displayed in a separate region, such as above, below and/or to the side of the video, in a separate window, on a separate screen, or in any other suitable manner. The alternative possible decisions may be a list of alternative decisions the surgeon could have made at the decision making junction. The list may also include images (e.g., depicting alternative actions), flow diagrams, statistics (e.g., success rates, failure rates, usage rates, or other statistical information), detailed descriptions, hyperlinks, or other information associated with the alternative possible decisions that may be relevant to the surgeon viewing the playback. Such a list may be interactive, enabling the viewer to select an alternative course of action from the list and thereby cause video footage of the alternative course of action to be displayed.

Further, in some embodiments, one or more estimated outcomes associated with the one or more alternative possible decisions may be displayed in conjunction with the display of the one or more alternative possible decisions. For example, the list of alternative possible decisions may include estimated outcomes of each of the alternative possible decisions. The estimated outcomes may include an outcome that is predicted to occur were the surgeon to have taken the alternative possible decision. Such information may be helpful for training purposes. For example, the surgeon may be able to determine that a more appropriate action could have been taken than the one in the video and may plan future procedures accordingly. In some embodiments, each of the alternative possible decisions may be associated with multiple estimated outcomes and a probability of each may be provided. The one or more estimated outcomes may be determined in various ways. In some embodiments, the estimated outcomes may be based on known probabilities associated with the alternative possible decisions. For example, aggregated data from previous surgical procedures with similar decision making junctions may be used to predict the outcome of the alternative possible decisions associated with the marker. In some embodiments, the probabilities and/or data may be tailored to one or more characteristics or properties of the current surgical procedure. For example, patient characteristics (such as a patient's medical condition, age, weight, medical history, or other characteristics), surgeon skill level, difficulty of the procedure, type of procedure, or other factors may be considered in determining the estimated outcomes. Other characteristics may also be analyzed, including the event characteristics described above with respect to video indexing.

In accordance with the present disclosure, the decision making junction of the surgical procedure may be associated with a first patient, and the respective similar decision making junctions may be selected from past surgical procedures associated with patients with similar characteristics to the first patient. The past surgical procedures may be preselected or automatically selected based on similar estimated outcomes as the respective similar decision making junctions, or because of similarities between the patient in the current video with the patient's in the past surgical procedures. These similarities or characteristics may include a patient's gender, age, weight, height, physical fitness, heart rate, blood pressure, temperature, whether the patient exhibits a particular medical condition or disease, medical treatment history, or any other traits or conditions that may be relevant.

Similarly, in some embodiments, the decision making junction of the surgical procedure may be associated with a first medical professional, and the respective similar past decision making junctions may be selected from past surgical procedures associated with medical professionals with similar characteristics to the first medical professional. These characteristics may include, but are not limited to, the medical professional's age, medical background, experience level (e.g., the number of times the surgeon has performed this or similar surgical procedures, the total number of surgical procedures the surgeon has performed, etc.), skill level, training history, success rate for this or other surgical procedures, or other characteristics that may be relevant.

In some exemplary embodiments, the decision making junction of the surgical procedure is associated with a first prior event in the surgical procedure, and the similar past decision making junctions are selected from past surgical procedures including prior events similar to the first prior event. In one example, prior events may be determined to be similar to the first prior event based on, for example, the type of the prior events, characteristics of the prior events, and so forth. For example, a prior event may be determined as similar to the first prior event when a similarity measure between the two is above a selected threshold. Some non-limiting examples of such similarity measures are described above. The occurrence and/or characteristics of the prior event may be relevant for determining estimated outcomes for the alternative possible decisions. For example, if the surgeon runs into complications with a patient, the complications may at least partially be determinative of the most appropriate outcome, whereas a different outcome may be appropriate in absence of the complications. The first prior event may include, but is not limited to, any of the intraoperative events described in detail above. Some non-limiting characteristics of the first prior may include any of the event characteristics described above. For example, the first prior event may include an adverse event or complication, such as bleeding, mesenteric emphysema, injury, conversion to unplanned open, incision significantly larger than planned, hypertension, hypotension, bradycardia, hypoxemia, adhesions, hernias, atypical anatomy, dural tears, periorator injury, arterial occlusions, and so forth. The first prior event may also include positive or planned events, such as a successful incision, administration of a drug, usage of a surgical instrument, an excision, a resection, a ligation, a graft, suturing, stitching, or any other event.

In accordance with the present disclosure, the decision making junction of the surgical procedure may be associated with a medical condition, and the respective similar decision making junctions may be selected from past surgical procedures associated with patients with similar medical conditions. The medical conditions may include any condition of the patient related to the patient's health or well-being. In some embodiments, the medical condition may be the condition being treated by the surgical procedure. In other embodiments, the medical condition may be a separate medical condition. The medical condition may be determined in various ways. In some embodiments, the medical condition may be determined based on data associated with the plurality of videos. For example, the video may be tagged with information including the medical condition. In other embodiments, the medical condition may be determined by an analysis of the at least one video and may be based on an appearance of an anatomical structure appearing in the at least one video. For example, the color of a tissue, the relative color of one tissue with respect to the color of another tissue, size of an organ, relative size of one organ with respect to a size of another organ, appearance of a gallbladder or other organ, presence of lacerations or other marks, or any other visual indicators associated with an anatomical structure, may be analyzed to determine the medical condition. In one example, a machine learning model may be trained using training examples to determine medical conditions from videos, and the trained machine learning model may be used to analyze the at least one video footage and determine the medical condition. An example of such training example may include a video clip of a surgical procedure, together with a label indicating one or more medical conditions.

In some aspects of the present disclosure, information related to a distribution of past decisions made in respective similar past decision making junctions may be displayed in conjunction with the display of the alternative possible decisions. For example, as described above, a particular decision making junction may be associated with multiple possible decisions for a course of action. The past decisions may include decisions that were made by surgeons in previous surgical procedures when faced with the same or similar decision making junction. For example, each of the past decisions may correspond to one of the alternate possible decisions described above. Accordingly, as used herein, respective similar past decision making junctions refers to the decision making junction that occurred in the past surgical procedure when the past decision was made. In some embodiments, the respective similar past decision making junctions may be the same as the decision making junction identified by the marker. For example, if the decision making junction is an adverse event, such as a bleed, the past decisions may correspond to how other surgeons have addressed the bleed in previous surgical procedures. In other embodiments, the decision making junction may not be identical, but may be similar. For example, the possible decisions made by surgeons encountering a dural tear may be similar to other forms of tears and, accordingly, a distribution of past decisions associated with a dural tear may be relevant to the other forms of tears. The past decisions may be identified by analyzing video footage, for example, using the computer analysis techniques described above. In some embodiments, the past decisions may be indexed using the video indexing techniques described above, such that they can be readily accessed for displaying a distribution of past decisions. In one example, the distribution may include a conditional distribution, for example presenting a distribution of past decisions made in respective similar past decision making junctions that has a common property. In another example, the distribution may include an unconditional distribution, for example presenting a distribution of past decisions made in all respective similar past decision making junctions.

The displayed distribution may indicate how common each of the possible decisions were among the other alternative possible decisions associated with the respective similar past decision making junctions. In some embodiments, the displayed distribution may include a number of times each of the decisions was made. For example, a particular decision making junction may have three alternative possible decisions: decision A, decision B, and decision C. Based on the past decisions made in similar decision making junctions, the number of times each of these alternative possible decisions has been performed may be determined. For example, decision A may have been performed 167 times, decision B may have been performed 47 times, and decision C may have been performed 13 times. The distribution may be displayed as a list of each of the alternative possible decisions, along with the number of times they have been performed. The displayed distribution may also indicate the relative frequency of each of the decisions, for example, by displaying ratios, percentages, or other statistical information. For example, the distribution may indicate that decisions A, B and C have been performed in 73.6%, 20.7% and 5.7% of past decisions, respectively. In some embodiments, the distribution may be displayed as a graphical representation of the distribution, such as a bar graph, a histogram, a pie chart, a distribution curve, or any other graphical representation that may be used to show distribution.

In some embodiments, only a subset of the decisions may be displayed. For example, only the most common decisions may be displayed based on the number of times the decision was made (e.g., exceeding a threshold number of times, etc.). Various methods described above for identifying the similar past decision making junctions may be used, including identifying surgical procedures associated with similar medical conditions, patient characteristics, medical professional characteristics, and/or prior events.

In some embodiments, the one or more estimated outcomes may be a result of an analysis of a plurality of videos of past surgical procedures including respective similar decision making junctions. For example, a repository of video footage may be analyzed using various computer analysis techniques, such as the object and/or motion detection algorithms described above, to identify videos including decision making junctions that are the same as or share similar characteristics with the decision making junction identified by the marker. This may include identifying other video footage having the same or similar surgical phases, intraoperative surgical events, and/or event characteristics as those that were used to identify the decision making junction in the video presented in the timeline. The outcomes of the alternative possible decisions may be estimated based on the outcomes in the past surgical procedures. For example, if a particular method of performing a suture consistently results in a full recovery by the patient, this outcome may be estimated for this possible decision and may be displayed on the timeline.

In some exemplary embodiments, the analysis may include usage of an implementation of a computer vision algorithm. The computer vision algorithm may be the same as or similar to any of the computer vision algorithms described above. One example of such computer algorithm may include the object detection and tracking algorithms described above. Another example of such computer vision algorithm may include usage of a trained machine learning model. Other non-limiting examples of such computer vision algorithm are described above. For example, if the decision making junction marker was identified based on a particular adverse event occurring in the video, other video footage having the same or similar adverse events may be identified. The video footage may further be analyzed to determine an outcome of the decision made in past surgical video. This may include the same or similar computer analysis techniques described above. In some embodiments, this may include analyzing the video to identify the result of the decision. For example, if the decision making junction is associated with an adverse event associated with an anatomical structure, such as a tear, the anatomical structure may be assessed at various frames after the decision to determine whether the adverse event was remediated, how quickly it was remediated, whether additional adverse events occurred, whether the patient survived, or other indicators of the outcome.

In some embodiments, additional information may also be used to determine the outcome. For example, the analysis may be based on one or more electronic medical records associated with the plurality of videos of past surgical procedures. For example, determining the outcome may include referencing an electronic medical record associated with the video in which a particular decision was made to determine whether the patient recovered, how quickly the patient recovered, whether there were additional complications, or the like. Such information may be useful in predicting the outcome that may result at a later time, outside of the scope of the video footage. For example, the outcome may be several days, weeks, or months after the surgical procedure. In some embodiments, the additional information may be used to inform the analysis of which videos to include in the analysis. For example, using information gleaned from the medical records, videos sharing similar patient medical history, disease type, diagnosis type, treatment history (including past surgical procedures), healthcare professional identities, healthcare professional skill levels, or any other relevant data may be identified. Videos sharing these or other characteristics may provide a more accurate idea of what outcome can be expected for each alternative possible decision.

The similar decision making junctions may be identified based on how closely they correlate to the current decision making junction. In some embodiments, the respective similar decision making junctions may be similar to the decision making junction of the surgical procedure according to a similarity metric. The metric may be any value, classification, or other indicator of how closely the decision making junctions are related. Such a metric may be determined based on the computer vision analysis in order to determine how closely the procedures or techniques match. The metric may also be determined based on the number of characteristics the decision making junctions have in common and the degree to which the characteristics match. For example, two decision making junctions with patients having similar medical conditions and physical characteristics may be assigned a higher similarity based on the similarity metric than two more distinctive patients. Various other characteristics and/or considerations may also be used. Additionally or alternatively, the similarity metric may be based on any similarity measure, such as the similarity measures described above. For example, the similarity metric may be identical to the similarity measure, may be a function of the similarity measure, and so forth.

Various other marker types may be used in addition to or instead of decision making junction markers. In some embodiments, the markers may include intraoperative surgical event markers, which may be associated with locations in the video associated with the occurrence of an interoperative event. Examples of various intraoperative surgical events that may be identified by the markers are provided throughout the present disclosure, including in relation to the video indexing described above. In some embodiments, the intraoperative surgical event markers may be generic markers, indicating that an intraoperative surgical event occurred at that location. In other embodiments, the intraoperative surgical event markers may identify a property of the intraoperative surgical event, including the type of the event, whether the event was an adverse event, or any other characteristic. Example markers are shown in FIG. 4. As an illustrative example, the icon shown for marker 434 may be used to represent a generic intraoperative surgical event marker. Marker 436 on the other hand, may represent a more specific intraoperative surgical event marker, such as identifying that an incision occurred at that location. The markers shown in FIG. 4 are provided by way of example, and various other forms of markers may be used.

These intraoperative surgical event markers may be identified automatically, as described above. Using the computer analysis methods described above, medical instruments, anatomical structures, surgeon characteristics, patient characteristics, event characteristics, or other features may be identified in the video footage. For example, the interaction between an identified medical instrument and an anatomical structure may indicate that an incision, a suturing, or other intraoperative event is being performed. In some embodiments, the intraoperative surgical event markers may be identified based on information provided in a data structure, such as data structure 600 described above in reference to FIG. 6.

Consistent with the disclosed embodiments, selection of an intraoperative surgical event marker may enable the surgeon to view alternative video clips from differing surgical procedures. In some embodiments, the alternative video clips may present differing ways in which a selected intraoperative surgical event was handled. For example, in the current video the surgeon may perform an incision or other action according to one technique. Selecting the intraoperative surgical event markers may allow the surgeon to view alternative techniques that may be used to perform the incision or other action. In another example, the intraoperative surgical event may be an adverse event, such as a bleed, and the alternative video clips may depict other ways surgeons have handled the adverse event. In some embodiments, where the markers relate to intraoperative surgical events, the selection of an intraoperative surgical event marker may enable the surgeon to view alternative video clips from differing surgical procedures. For example, the differing surgical procedures may be of a different type (such as a laparoscopic surgery versus thoracoscopic surgery) but may still include the same or similar intraoperative surgical events. The surgical procedures may also differ in other ways, including differing medical conditions, differing patient characteristics, differing medical professionals, or other distinctions. Selecting the intraoperative surgical event marker may allow the surgeon to view alternative video clips from the differing surgical procedures.

The alternative video clips may be displayed in various ways, similar to other embodiments described herein. For example, selecting the intraoperative surgical event markers may cause a menu to be displayed, from which the surgeon may select the alternative video clips. The menu may include descriptions of the differing ways in which the selected intraoperative surgical event was handled, thumbnails of the video clips, previews of the video clips, and/or other information associated with the video clips, such as the dates they were recorded, the type of surgical procedure, a name or identity of a surgeon performing the surgical procedure, or any other relevant information.

In accordance with some embodiments of the present disclosure, the at least one video may include a compilation of footage from a plurality of surgical procedures, arranged in procedural chronological order. Procedural chronological order may refer to the order events occur relative to a surgical procedure. Accordingly, arranging a compilation of footage in procedural chronological order may include arranging the different events from differing patients in the order in which they would have occurred if the procedure had been conducted on a single patient. In other words, although compiled from various surgeries on differing patients, playback of the compilation will display the footage in the order the footage would appear within the surgical procedure. In some embodiments, the compilation of footage may depict complications from the plurality of surgical procedures. In such embodiments, the one or more markers may be associated with the plurality of surgical procedures and may be displayed on a common timeline. Thus, although a viewer interacts with a single timeline, the video footage presented along the timeline may be derived from differing procedures and/or differing patients. Example complications that may be displayed are described above with respect to video indexing.

Figure 5:
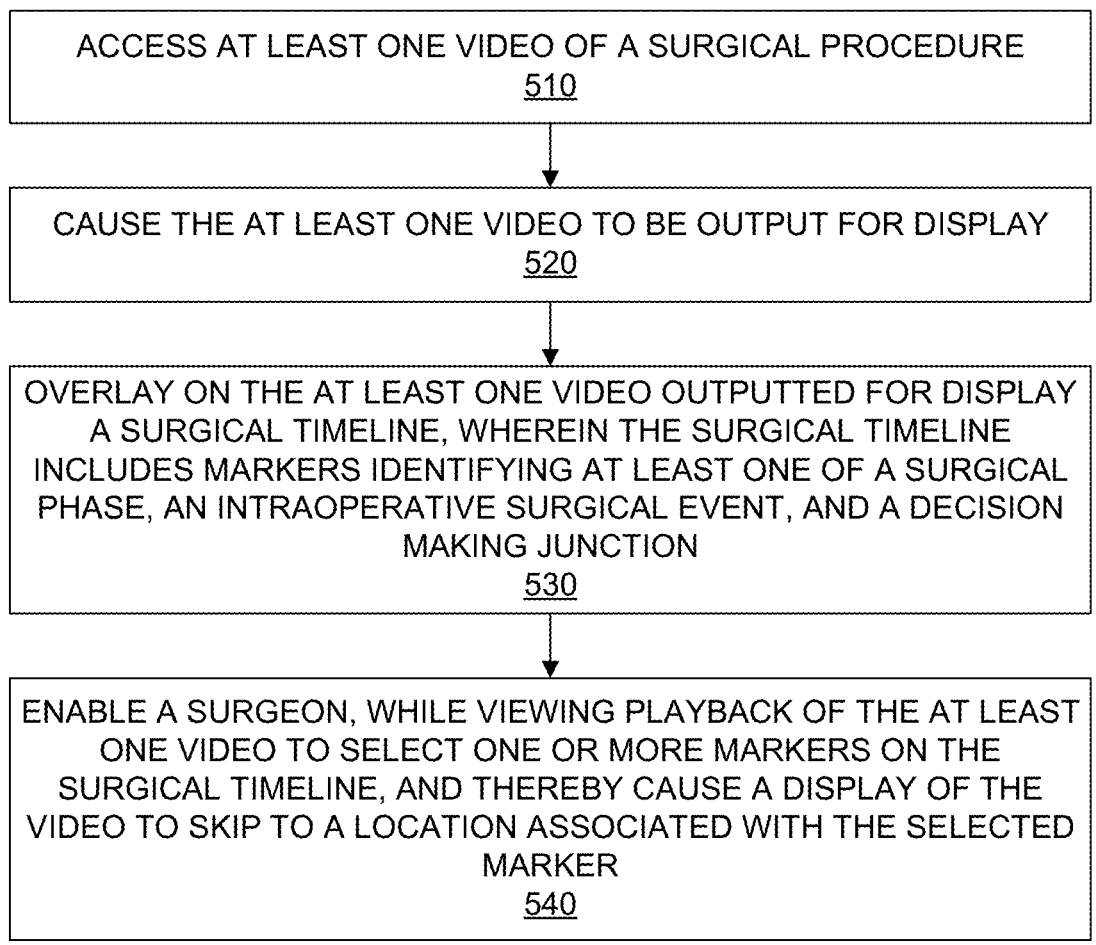
FIG. 5 is a flowchart illustrating an example process for reviewing surgical video, consistent with the disclosed embodiments.

FIG. 5 is a flowchart illustrating an example process 500 for reviewing surgical videos, consistent with the disclosed embodiments. Process 500 may be performed by at least one processor, such as one or more microprocessors. In some embodiments, process 500 is not necessarily limited to the steps illustrated, and any of the various embodiments described herein may also be included in process 500. At step 510, process 500 may include accessing at least one video of a surgical procedure, for example as described above. The at least one video may include video footage from a single surgical procedure or may be a compilation of footage from a plurality of procedures, as previously discussed. Process 500 may include causing the at least one video to be output for display in step 520. As described above, causing the at least one video to be output for display may include sending a signal for causing display of the at least one video on a screen or other display device, storing the at least one video in a location accessible to another computing device, transmitting the at least one video, or any other process or steps that may cause the video to be displayed.

At step 530, process 500 may include overlaying on the at least one video outputted for display a surgical timeline, wherein the surgical timeline includes markers identifying at least one of a surgical phase, an intraoperative surgical event, and a decision making junction. In some embodiments, the surgical timeline may be represented as a horizontal bar displayed along with the video. The markers may be represented as shapes, icons, or other graphical representations along the timeline. FIG. 4 provides an example of such an embodiment. In other embodiments, the timeline may be a text-based list of phases, events, and/or decision making junctions in chronological order. The markers may similarly be text-based and may be included in the list.

Step 540 may include enabling a surgeon, while viewing playback of the at least one video, to select one or more markers on the surgical timeline, and thereby cause a display of the video to skip to a location associated with the selected marker. In some embodiments, the surgeon may be able to view additional information about the event or occurrence associated with the marker, which may include information from past surgical procedures. For example, the markers may be associated with an intraoperative surgical event and selecting the marker may enable the surgeon to view alternative video clips of past surgical procedures associated with the intraoperative surgical event. For example, the surgeon may be enabled to view clips from other surgeries where a similar intraoperative surgical event was handled differently, where a different technique was used, or where an outcome varied. In some embodiments, the marker may be a decision making junction marker, representing a decision that was made during the surgical procedure. Selecting the decision making junction marker may enable the surgeon to view information about the decision, including alternative decisions. Such information may include videos of past surgical procedures including similar decision making junctions, a list or distribution of alternate possible decisions, estimated outcomes of the alternate possible decisions, or any other relevant information. Based on the steps described in process 500, the surgeon or other users may be able to more effectively and more efficiently review surgical videos using the timeline interface.

In preparing for a surgical procedure, it is often beneficial for surgeons to review videos of similar surgical procedures that have been performed. It may be too cumbersome and time consuming, however, for a surgeon to identify relevant videos or portions of videos in preparing for a surgical procedure. Therefore, there is a need for unconventional approaches that efficiently, effectively index surgical video footage based on contents of the footage such that it may be easily accessed and reviewed by a surgeon or other medical professional.

Aspects of this disclosure may relate to video indexing, including methods, systems, devices, and computer readable media. For example, surgical events within surgical phases may be automatically detected in surgical footage. Viewers may be enabled to skip directly to an event, to view only events with specified characteristics, and so forth. In some embodiments, a user may specify within a surgical phase (e.g., a dissection) an event (e.g., inadvertent injury to an organ) having a characteristic (e.g., a particular complication), so that the user may be presented with video clips of one or more events sharing that characteristic.

For ease of discussion, a method is described below, with the understanding that aspects of the method apply equally to systems, devices, and computer readable media. For example, some aspects of such a method may occur electronically over a network that is either wired, wireless, or both. Other aspects of such a method may occur using non-electronic means. In a broadest sense, the method is not limited to particular physical and/or electronic instrumentalities, but rather may be accomplished using many differing instrumentalities.

Consistent with disclosed embodiments, a method may involve accessing video footage to be indexed, the video footage to be indexed including footage of a particular surgical procedure. As used herein, video may include any form of recorded visual media including recorded images and/or sound. For example, a video may include a sequence of one or more images captured by an image capture device, such as cameras 115, 121, 123, and/or 125, as described above in connection with FIG. 1. The images may be stored as individual files or may be stored in a combined format, such as a video file, which may include corresponding audio data. In some embodiments, video may be stored as raw data and/or images output from an image capture device. In other embodiments the video may be processed. For example, video files may include Audio Video Interleave (AVI), Flash Video Format (FLV), QuickTime File Format (MOV), MPEG (MPG, MP4, M4P, etc.), Windows Media Video (WMV), Material Exchange Format (MXF), uncompressed format, lossy compressed format, lossless compressed format, or any other suitable video file formats.

Video footage may refer to a length of video that has been captured by an image capture device. In some embodiments, video footage may refer to a length of video that includes a sequence of images in the order they were originally captured in. For example, video footage may include video that has not been edited to form a video compilation. In other embodiments, video footage may be edited in one or more ways, such as to remove frames associated with inactivity, or to otherwise compile frames not originally captured sequentially. Accessing the video footage may include retrieving video footage from a storage location, such as a memory device. The video footage may be accessed from a local memory, such as a local hard drive, or may be accessed from a remote source, for example, through a network connection. Consistent with the present disclosure, indexing may refer to a process for storing data such that it may be retrieved more efficiently and/or effectively. Indexing video footage may include associating one or more properties or indicators with the video footage such that the video footage may be identified based on the properties or indicators.

A surgical procedure may include any medical procedure associated with or involving manual or operative procedures on a patient's body. Surgical procedures may include cutting, abrading, suturing, or other techniques that involve physically changing body tissues and organs. Some examples of such surgical procedures may include a laparoscopic surgery, a thoracoscopic procedure, a bronchoscopic procedure, a microscopic procedure, an open surgery, a robotic surgery, an appendectomy, a carotid endarterectomy, a carpal tunnel release, a cataract surgery, a cesarean section, a cholecystectomy, a colectomy (such as a partial colectomy, a total colectomy, etc.), a coronary angioplasty, a coronary artery bypass, a debridement (for example of a wound, a burn, an infection, etc.), a free skin graft, a hemorrhoidectomy, a hip replacement, a hysterectomy, a hysteroscopy, an inguinal hernia repair, a knee arthroscopy, a knee replacement, a mastectomy (such as a partial mastectomy, a total mastectomy, a modified radical mastectomy, etc.), a prostate resection, a prostate removal, a shoulder arthroscopy, a spine surgery (such as a spinal fusion, a laminectomy, a foraminotomy, a discectomy, a disk replacement, an interlaminar implant, etc.), a tonsillectomy, a cochlear implant procedure, brain tumor (for example meningioma, etc.) resection, interventional procedures such as percutaneous transluminal coronary angioplasty, transcatheter aortic valve replacement, minimally Invasive surgery for intracerebral hemorrhage evacuation, or any other medical procedure involving some form of incision. While the present disclosure is described in reference to surgical procedures, it is to be understood that it may also apply to other forms of medical procedures, or procedures generally.

In some exemplary embodiments, the accessed video footage may include video footage captured via at least one image sensor located in at least one of a position above an operating table, in a surgical cavity of a patient, within an organ of a patient or within vasculature of a patient. An image sensor may be any sensor capable of recording video. An image sensor located in a position above an operating table may include any image sensor placed external to a patient configured to capture images from above the patient. For example, the image sensor may include cameras 115 and/or 121, as shown in FIG. 1. In other embodiments, the image sensor may be placed internal to the patient, such as, for example, in a cavity. As used herein, a cavity may include any relatively empty space within an object. Accordingly, a surgical cavity may refer to a space within the body of a patient where a surgical procedure or operation is being performed, or where surgical tools are present and/or used. It is understood that the surgical cavity may not be completely empty but may include tissue, organs, blood or other fluids present within the body. An organ may refer to any self-contained region or part of an organism. Some examples of organs in a human patient may include a heart or liver. A vasculature may refer to a system or grouping of blood vessels within an organism. An image sensor located in a surgical cavity, an organ, and/or a vasculature may include a camera included on a surgical tool inserted into the patient.

Aspects of this disclosure may include analyzing the video footage to identify a video footage location associated with a surgical phase of the particular surgical procedure. As used herein with respect to video footages, a location may refer any particular position or range within the video footage. In some embodiments the location may include a particular frame or range of frames of a video. Accordingly, video footage locations may be represented as one or more frame numbers or other identifiers of a video footage file. In other embodiments, the location may refer to a particular time associated with the video footage. For example, a video footage location may refer to a time index or timestamp, a time range, a particular starting time and/or ending time, or any other indicator of position within the video footage. In other embodiments, the location may refer to at least one particular position within at least one frame. Accordingly, video footage locations may be represented as one or more pixels, voxels, bounding boxes, bounding polygons, bounding shapes, coordinates, and so forth.

For the purposes of the present disclosure, a phase may refer to a particular period or stage of a process or series of events. Accordingly, a surgical phase may refer to a particular period or stage of a surgical procedure, as described above. For example, surgical phases of a laparoscopic cholecystectomy surgery may include trocar placement, preparation, calot's triangle dissection, clipping and cutting of cystic duct and artery, gallbladder dissection, gallbladder packaging, cleaning and coagulation of liver bed, gallbladder retraction, and so forth. In another example, surgical phases of a cataract surgery may include preparation, povidone-iodine injection, corneal incision, capsulorhexis, phaco-emulsification, cortical aspiration, intraocular lens implantation, intraocular-lens adjustment, wound sealing, and so forth. In yet another example, surgical phases of a pituitary surgery may include preparation, nasal incision, nose retractor installation, access to the tumor, tumor removal, column of nose replacement, suturing, nose compress installation, and so forth. Some other examples of surgical phases may include preparation, incision, laparoscope positioning, suturing, and so forth.

In some embodiments, identifying the video footage location may be based on user input. User input may include any information provided by a user. As used with respect to video indexing, the user input may include information relevant to identifying the video footage location. For example, a user may input a particular frame number, timestamp, range of times, start times and/or stop times, or any other information that may identify a video footage location. Alternatively, the user input might include entry or selection of a phase, event, procedure, or device used, which input may be associated with particular video footage (e.g., for example through a lookup table or other data structure). The user input may be received through a user interface of a user device, such as a desktop computer, a laptop, a table, a mobile phone, a wearable device, an internet of things (IoT) device, or any other means for receiving input from a user. The interface may include, for example, one or more drop down menus with one or more pick lists of phase names; a data entry field that permits the user to enter the phase name and/or that suggests phase names once a few letters are entered; a pick list from which phase names may be chosen; a group of selectable icons each associated with a differing phase, or any other mechanism that allows users to identify or select a phase. For example, a user may input the phase name through a user interface similar to user interface 700, as described in greater detail below with respect to FIG. 7. In another example, the user input may be received through voice commands and/or voice inputs, and the user input may be processed using speech recognition algorithms. In yet another example, the user input may be received through gestures (such as hand gestures), and the user input may be processed using gesture recognition algorithms.

In some embodiments, identifying the video footage location may include using computer analysis to analyze frames of the video footage. Computer analysis may include any form of electronic analysis using a computing device. In some embodiments, computer analysis may include using one or more image recognition algorithms to identify features of one or more frames of the video footage. Computer analysis may be performed on individual frames, or may be performed across multiple frames, for example, to detect motion or other changes between frames. In some embodiments computer analysis may include object detection algorithms, such as Viola-Jones object detection, scale-invariant feature transform (SIFT), histogram of oriented gradients (HOG) features, convolutional neural networks (CNN), or any other forms of object detection algorithms. Other example algorithms may include video tracking algorithms, motion detection algorithms, feature detection algorithms, color-based detection algorithms, texture based detection algorithms, shape based detection algorithms, boosting based detection algorithms, face detection algorithms, or any other suitable algorithm for analyzing video frames. In one example, a machine learning model may be trained using training examples to identify particular locations within videos, and the trained machine learning model may be used to analyze the video footage and identify the video footage location. An example of such training example may include a video clip together with a label indicating a location within a video clip, or together with a label indicating that no corresponding location is included within the video clip.

In some embodiments, the computer image analysis may include using a neural network model trained using example video frames including previously-identified surgical phases to thereby identify at least one of a video footage location or a phase tag. In other words, frames of one or more videos that are known to be associated with a particular surgical phase may be used to train a neural network model, for example using a machine learning algorithm, using back propagation, using gradient descent optimization, and so forth. The trained neural network model may therefore be used to identify whether one or more video frames are also associated with the surgical phase. Some non-limiting examples of such artificial neural networks may comprise shallow artificial neural networks, deep artificial neural networks, feedback artificial neural networks, feed forward artificial neural networks, autoencoder artificial neural networks, probabilistic artificial neural networks, time delay artificial neural networks, convolutional artificial neural networks, recurrent artificial neural networks, long short term memory artificial neural networks, and so forth. In some embodiments, the disclosed methods may further include updating the trained neural network model based on at least one of the analyzed frames.

In some aspects of the present disclosure, analyzing the video footage to identify the video footage location associated with at least one of the surgical event or the surgical phase may include performing computer image analysis on the video footage to identify at least one of a beginning location of the surgical phase for playback or a beginning of a surgical event for playback. In other words, using the computer analysis techniques discussed above, the disclosed methods may include identifying a location within the video footage where a surgical phase or event begins. For example, the beginning of a surgical event, such as an incision, may be detected using the object and/or motion detection algorithms described above. In other embodiments, the beginning of the incision may be detected based on machine learning techniques. For example, a machine learning model may be trained using video footage and corresponding label indicating known beginning points of an incision or other surgical events and/or procedures. The trained model may be used to identify similar procedure and/or event beginning locations within other surgical video footage.

Some aspects of this disclosure may include generating a phase tag associated with the surgical phase. As used herein, a "tag" may refer to any process or marker by which information is associated with or linked to a set of data. In some embodiments, a tag may be a property of a data file, such as a video file. Accordingly, generating the tag may include writing or overwriting properties within a video file. In some embodiments, generating a tag may include writing information to a file other than the video file itself, for example, by associating the video file with the tag in a separate database. The tag may be expressed as textual information, a numerical identifier, or any other suitable means for tagging. A phase tag may be a tag that identifies a phase of a surgical phase, as described above. In one embodiment, a phase tag may be a marker indicating a location in video where a surgical phase begins, a marker indicating a location in video where a surgical phase ends, a marker indicating a location in video in the middle of a surgical phase, or indicating a range of video encompassing the surgical phase. The tag may be a pointer in the video data itself or may be located in a data structure to permit a lookup of a phase location. The phase tag may include computer readable information for causing display of the phase and may also include human-readable information for identifying the phase to a user. For example, generating a phase tag associated with the surgical phase may include generating a tag including text such as "laparoscope positioning" to indicate the tagged data is associated with that phase of the surgical procedure. In another example, generating a phase tag associated with the surgical phase may include generating a tag including binary encoding of a surgical phase identifier. In some embodiments, generating the phase tag may be based on a computer analysis of video footage depicting the surgical phase. For example, the disclosed methods may include analyzing footage of the surgical phase using the object and motion detection analysis methods described above to determine the phase tag. For example, if it is known that a phase begins or ends using a particular type of medical device or other instrumentality used in a unique way or in a unique order, image recognition may be performed on the video footage to identify a particular phase through image recognition performed to identify the unique use of the instrumentality to identify a particular phase. Generating the phase tag may also include using a trained machine learning model or a neural network model (such as deep neural network, convolutional neural networks, etc.), which may be trained to associate one or more video frames with one or more phase tags. For example, training examples may be fed to a machine learning algorithm to develop a model configured to associate other video footage data with one or more phase tags. An example of such training example may include a video footage together with a label indicating the desired tags or the absent of desired tags corresponding to the video footage. Such label may include an indication of one or more locations within the video footage corresponding to the surgical phase, an indication of a type of the surgical phase, an indication of properties of the surgical phase, and so forth.

A method in accordance with the present disclosure may include associating the phase tag with the video footage location. Any suitable means may be used to associate the phase tag with the video footage location. Such tag may include an indication of one or more locations within the video footage corresponding to the surgical phase, an indication of a type of the surgical phase, an indication of properties of the surgical phase, and so forth. In some embodiments, the video footage location may be included in the tag. For example, the tag may include a timestamp, time range, frame number, or other means for associating the phase tag to the video footage location. In other embodiments, the tag may be associated with the video footage location in a database. For example, the database may include information linking the phase tag to the video footage and to the particular video footage location. The database may include a data structure, as described in further detail below.

Embodiments of the present disclosure may further include analyzing the video footage to identify an event location of a particular intraoperative surgical event within the surgical phase. An intraoperative surgical event may be any event or action that occurs during a surgical procedure or phase. In some embodiments, an intraoperative surgical event may include an action that is performed as part of a surgical procedure, such as an action performed by a surgeon, a surgical technician, a nurse, a physician's assistant, an anesthesiologist, a doctor, or any other healthcare professional. The intraoperative surgical event may be a planned event, such as an incision, administration of a drug, usage of a surgical instrument, an excision, a resection, a ligation, a graft, suturing, stitching, or any other planned event associated with a surgical procedure or phase. In some embodiments, the intraoperative surgical event may include an adverse event or a complication. Some examples of intraoperative adverse events may include bleeding, mesenteric emphysema, injury, conversion to unplanned open surgery (for example, abdominal wall incision), incision significantly larger than planned, and so forth. Some examples of intraoperative complications may include hypertension, hypotension, bradycardia, hypoxemia, adhesions, hernias, atypical anatomy, dural tears, periorator injury, arterial occlusions, and so forth. The intraoperative event may include other errors, including technical errors, communication errors, management errors, judgment errors, decision making errors, errors related to medical equipment utilization, miscommunication, and so forth.

The event location may be a location or range within the video footage associated with the intraoperative surgical event. Similar to the phase location described above, the event location may be expressed in terms of particular frames of the video footage (e.g., a frame number or a range of frame numbers) or based on time information (e.g., a timestamp, a time range, or beginning and end times), or any other means for identifying a location within the video footage. In some embodiments, analyzing the video footage to identify the event location may include using computer analysis to analyze frames of the video footage. The computer analysis may include any of the techniques or algorithms described above. As with phase identification, event identification may be based on a detection of actions and instrumentalities used in a way that uniquely identifies an event. For example, image recognition may identify when a particular organ is incised, to enable marking of that incision event. In another example, image recognition may be used to note the severance of a vessel or nerve, to enable marking of that adverse event. Image recognition may also be used to mark events by detection of bleeding or other fluid loss. In some embodiments, analyzing the video footage to identify the event location may include using a neural network model (such as a deep neural network, a convolutional neural network, etc.) trained using example video frames including previously-identified surgical events to thereby identify the event location. In one example, a machine learning model may be trained using training examples to identify locations of intraoperative surgical events in portions of videos, and the trained machine learning model may be used to analyze the video footage (or a portion of the video footage corresponding to the surgical phase) and identify the event location of the particular intraoperative surgical event within the surgical phase. An example of such training example may include a video clip together with a label indicating a location of a particular event within the video clip, or an absence of such event.

Some aspects of the present disclosure may involve associating an event tag with the event location of the particular intraoperative surgical event. As discussed above, a tag may include any means for associating information with data or a portion of data. An event tag may be used to associate data or portions of data with an event, such as an intraoperative surgical event. Similar to the phase tag, associating the event tag with the event location may include writing data to a video file, for example, to the properties of the video file. In other embodiments, associating the event tag with the event location may include writing data to a file or database associating the event tag with the video footage and/or the event location. Alternatively, associating an event tag with an event location may include recording a marker in a data structure, where the data structure correlates a tag with a particular location or range of locations in video footage. In some embodiments, the same file or database may be used to associate the phase tag to the video footage as the event tag. In other embodiments, a separate file or database may be used.

Consistent with the present disclosure, the disclosed methods may include storing an event characteristic associated with the particular intraoperative surgical event. The event characteristic may be any trait or feature of the event. For example, the event characteristic may include properties of the patient or surgeon, properties or characteristics of the surgical event or surgical phase, or various other traits. Examples of features may include, excessive fatty tissue, an enlarged organ, tissue decay, a broken bone, a displaced disc, or any other physical characteristic associated with the event. Some characteristics may be discernable by computer vision, and others may be discernable by human input. In the latter example, the age or age range of a patient may be stored as an event characteristic. Similarly, aspects of a patient's prior medical history may be stored as an event characteristic (e.g., patient with diabetes). In some embodiments, the stored event characteristic may be used to distinguish intraoperative surgical events from other similar events. For example, a medical practitioner may be permitted to search video footage to identify one or more coronary artery bypass surgeries performed on males over the age of 70 with arrhythmia. Various other examples of stored event characteristics that may be used are provided below.

The stored event characteristic may be determined in various ways. Some aspects of the disclosed methods may involve determining the stored event characteristic based on user input. For example, a user may input the event characteristic to be stored via a user interface similar to what was described above in connection with the selection of a phase or an event. In another example, a user may input the event characteristic to be stored via voice commands. Various examples of such uses are provided below. Other aspects of the disclosed methods may involve determining the stored event characteristic based on a computer analysis of video footage depicting the particular intraoperative surgical event. For example, the disclosed methods may include using various image and/or video analysis techniques as described above to recognize event characteristics based on the video footage. As an illustrative example, the video footage may include a representation of one or more anatomical structures of a patient and an event characteristic identifying the anatomical structures may be determined based on detecting the anatomical structure in the video footage, or based on detecting the interaction between a medical instrument and the anatomical structure. In another example, a machine learning model may be trained using training examples to determine event characteristics from videos, and the trained machine learning model may be used to analyze the video footage and determine the stored event characteristic. An example of such training example may include a video clip depicting an intraoperative surgical event together with a label indicating a characteristic of the event.

Some aspects of the present disclosure may include associating at least a portion of the video footage of the particular surgical procedure with the phase tag, the event tag, and the event characteristic in a data structure that contains additional video footage of other surgical procedures, wherein the data structure also includes respective phase tags, respective event tags, and respective event characteristics associated with one or more of the other surgical procedures. A data structure consistent with this disclosure may include any collection of data values and relationships among them. The data may be stored linearly, horizontally, hierarchically, relationally, non-relationally, uni-dimensionally, multidimensionally, operationally, in an ordered manner, in an unordered manner, in an object-oriented manner, in a centralized manner, in a decentralized manner, in a distributed manner, in a custom manner, in a searchable repository, in a sorted repository, in an indexed repository, or in any manner enabling data access. By way of non-limiting examples, data structures may include an array, an associative array, a linked list, a binary tree, a balanced tree, a heap, a stack, a queue, a set, a hash table, a record, a tagged union, ER model, and a graph. For example, a data structure may include an XML database, an RDBMS database, an SQL database or NoSQL alternatives for data storage/search such as, for example, MongoDB, Redis, Couchbase, Datastax Enterprise Graph, Elastic Search, Splunk, Solr, Cassandra, Amazon DynamoDB, Scylla, HBase, and Neo4J. A data structure may be a component of the disclosed system or a remote computing component (e.g., a cloud-based data structure). Data in the data structure may be stored in contiguous or non-contiguous memory. Moreover, a data structure, as used herein, does not require information to be co-located. It may be distributed across multiple servers, for example, that may be owned or operated by the same or different entities. Thus, for example, a data structure may include any data format that may be used to associate video footage with phase tags, event tags, and/or event characteristics.

FIG. 6 illustrates an example data structure 600 consistent with the disclosed embodiments. As shown in FIG. 6, data structure 600 may comprise a table including video footage 610 and video footage 620 pertaining to different surgical procedures. For example, video footage 610 may include footage of a laparoscopic cholecystectomy, while video footage 620 may include footage of a cataract surgery. Video footage 620 may be associated with footage location 621, which may correspond to a particular surgical phase of the cataract surgery. Phase tag 622 may identify the phase (in this instance a corneal incision) associated with footage location 621, as discussed above. Video footage 620 may also be associated with event tag 624, which may identify an intraoperative surgical event (in this instance an incision) within the surgical phase occurring at event location 623. Video footage 620 may further be associated with event characteristic 625, which may describe one or more characteristics of the intraoperative surgical event, such as surgeon skill level, as described in detail above. Each video footage identified in the data structure may be associated with more than one footage location, phase tag, event location, event tag and/or event characteristic. For example, video footage 610 may be associated with phase tags corresponding to more than one surgical phase (e.g., "Calot's triangle dissection" and "cutting of cystic duct"). Further, each surgical phase of a particular video footage may be associated with more than one event, and accordingly may be associated with more than one event location, event tag, and/or event characteristic. It is understood, however, that in some embodiments, a particular video footage may be associated with a single surgical phase and/or event. It is also understood that in some embodiments, an event may be associated with any number of event characteristics, including no event characteristics, a single event characteristic, two event characteristics, more than two event characteristics, and so forth. Some non-limiting examples of such event characteristics may include skill level associated with the event (such as minimal skill level required, skill level demonstrated, skill level of a medical care giver involved in the event, etc.), time associated with the event (such as start time, end time, etc.), type of the event, information related to medical instruments involved in the event, information related to anatomical structures involved in the event, information related to medical outcome associated with the event, one or more amounts (such as an amount of leak, amount of medication, amount of fluids, etc.), one or more dimensions (such as dimensions of anatomical structures, dimensions of incision, etc.), and so forth. Further, it is to be understood that data structure 600 is provided by way of example and various other data structures may be used.

Embodiments of the present disclosure may further include enabling a user to access the data structure through selection of a selected phase tag, a selected event tag, and a selected event characteristic of video footage for display. The user may be any individual or entity that may be provided access to data stored in the data structure. In some embodiments, the user may be a surgeon or other healthcare professional. For example, a surgeon may access the data structure and/or video footage associated with the data structure for review or training purposes. In some embodiments, the user may be an administrator, such as a hospital administrator, a manager, a lead surgeon, or other individual that may require access to video footage. In some embodiments the user may be a patient, who may be provided access to video footage of his or her surgery. Similarly, the user may be a relative, a guardian, a primary care physician, an insurance agent, or another representative of the patient. The user may include various other entities, which may include, but are not limited to, an insurance company, a regulatory authority, a police or investigative authority, a medical association, or any other entity that may be provided access to video footage. Selection by the user may include any means for identifying a particular phase tag, event tag, and/or event characteristic. In some embodiments, selection by the user may occur through a graphical user interface, such as on a display of a computing device. In another example, the selection by the user may occur through a touch screen. In an additional example, the selection by the user may occur through voice input, and the voice input may be processed using a speech recognition algorithm. In yet another example, the selection by the user may occur through gestures (such as hand gestures), and the gestures may be analyzed using gesture recognition algorithms. In some embodiments, the user may not select all three of the selected phase tag, the selected event tag, or the selected event characteristic, but may select a subset of these. For example, the user may just select an event characteristic and the user may be allowed access to information associated with the data structure based on the selected event characteristic.

Figure 7:
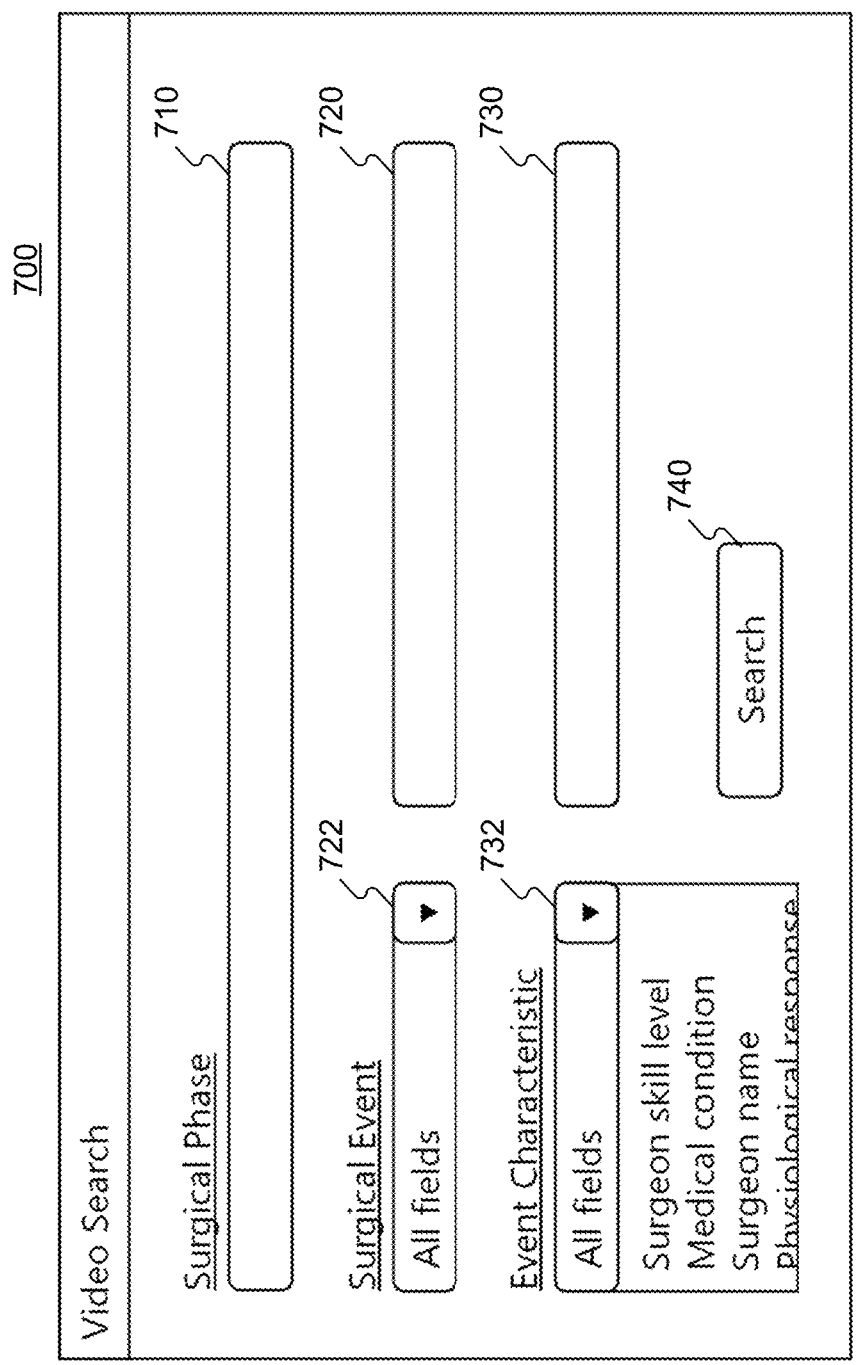
FIG. 7 is a schematic illustration of an example user interface for selecting indexed video footage for display consistent with the disclosed embodiments.

FIG. 7 is an illustration of exemplary user interface 700 for selecting indexed video footage for display consistent with the disclosed embodiments. User interface 700 may include one or more search boxes 710, 720, and 730 for selecting video footage. Search box 710 may allow the user to select one or more surgical phases to be displayed. In some embodiments, user interface 700 may provide suggested surgical phases based on the phase tags include in data structure 600. For example, as a user starts typing in search box 710, user interface 700 may suggest phase tag descriptions to search for based on the characters the user has entered. In other embodiments, the user may select the phase tag using radio buttons, checkboxes, a dropdown list, touch interface, or any other suitable user interface feature. Similar to with the phase tags, a user may select video footage based on event tags and event characteristics using search boxes 720 and 730, respectively. User interface 700 may also include dropdown buttons 722 and 732 to access dropdown lists and further filter the results. As shown in FIG. 7, selecting dropdown button 732 may allow the user to select an event characteristic based on subcategories of event characteristics. For example, a user may select "Surgeon skill level" in the dropdown list associated with dropdown button 732, which may allow the user to search based on a skill level of the surgeon in search box 730. While "Surgeon skill level," and various other event characteristic subcategories are provided by way of example, it is understood that a user may select any characteristic or property of the surgical procedure. For example, the user may refine the surgeon skill level based on the surgeon, qualifications, years of experience, and/or any indications of surgical skill level, as discussed in greater detail below. A user may be enabled to access the data structure by clicking, tapping, or otherwise selecting search button 740.

Display of video footage may include any process by which one or more frames of video footage or a portion thereof are presented to the user. In some embodiments, displaying may include electronically transmitting at least a portion of the video footage for viewing by the user. For example, displaying the video footage may comprise transmitting at least a portion of the video footage over a network. In other embodiments, displaying the video footage may include making the video footage available to the user by storing the video footage in a location accessible to the user or a device being used by the user. In some embodiments, displaying the video footage may comprise causing the video footage to be played on a visual display device, such as a computer or video screen. For example, displaying may include sequentially presenting frames associated with the video footage and may further include presenting audio associated with the video footage.

Some aspects of the present disclosure may include performing a lookup in the data structure of surgical video footage matching the at least one selected phase tag, selected event tag, and selected event characteristic to identify a matching subset of stored video footage. Performing the lookup may include any process for retrieving data from a data structure. For example, based on the at least one selected phase tag, event tag, and selected event characteristic, a corresponding video footage or portion of video footage may be identified from the data structure. A subset of stored video footage may include a single identified video footage or multiple identified video footages associated with selections of the user. For example, the subset of stored video footage may include surgical video footage having the at least one of a phase tag exactly identical to the selected phase tag, event tag exactly identical to the selected event tag, and event characteristic exactly identical to the selected event characteristic. In another example, the subset of stored video footage may include surgical video footage having the at least one of a phase tag similar (e.g., according to a selected similarity measure) to the selected phase tag, an event tag similar (e.g., according to a selected similarity measure) to the selected event tag, and/or an event characteristic similar (e.g., according to a selected similarity measure) to the selected event characteristic. In some embodiments, performing the lookup may be triggered by selection of search button 740, as shown in FIG. 7.

In some exemplary embodiments, identifying a matching subset of stored video footage includes using computer analysis to determine a degree of similarity between the matching subset of stored video and the selected event characteristic. Accordingly, "matching" may refer to an exact match or may refer to an approximate or closest match. In one example, the event characteristic may comprise a numerical value (such as an amount, a dimension, a length, an area, a volume, etc., for example as described above), and the degree of similarity may be based on a comparison of a numerical value included in the selected event characteristic and a corresponding numerical value of a stored video. In one example, any similarity function (including but not limited to affinity functions, correlation functions, polynomial similarity functions, exponential similarity functions, similarity functions based on distance, linear functions, non-linear functions, and so forth) may be used to calculate the degree of similarity. In one example, graph matching algorithms or hypergraph matching algorithms (such as exact matching algorithms, inexact matching algorithms) may be used to determine the degree of similarity. As another illustrative example, video footage associated with a "preparation" phase tag may also be retrieved for phase tags including terms "prep," "preparing," "preparatory," "pre-procedure," or other similar but not exact matches that may refer to a "preparation" phase tag. The degree of similarity may refer to any measure of how closely the subset of stored video matches the selected event characteristic. The degree of similarity may be expressed as a similarity ranking (e.g., on scale of 1-10, 1-100, etc.), as a percentage match, or through any other means of expressing how closely there is a match. Using computer analysis may include using a computer algorithm to determine a degree of similarity between the selected event characteristic and the event characteristic of one or more surgical procedures included in the data structure. In one example, k-Nearest-Neighbors algorithms may be used to identify the most similar entries in the data structure. In one example, the entries of the data structures, as well as the user inputted event characteristics, may be embedded in a mathematical space (for example, using any dimensionality reduction or data embedding algorithms), distance between the embedding of an entry and the user inputted characteristics may be used to calculate the degree of similarity between the two. Further, in some examples, the entries nearest to the user inputted characteristics in the embedded mathematical space may be selected as the most similar entries to the user inputted data in the data structure.

Some aspects of the invention may involve causing the matching subset of stored video footage to be displayed to the user, to thereby enable the user to view surgical footage of at least one intraoperative surgical event sharing the selected event characteristic, while omitting playback of video footage lacking the selected event characteristic. Surgical footage may refer to any video or video footage, as described in greater detail above, capturing a surgical procedure. In some embodiments, causing the matching subset of stored video footage to be displayed may comprise executing instructions for playing the video. For example, a processing device performing the methods described herein may access the matching subset of video footage and may be configured to present the stored video footage to the user on a screen or other display. For example, the stored video footage may be displayed in a video player user interface, such as in video playback region 410, as discussed in further detail below with respect to FIG. 4. In some embodiments, causing the matching subset of stored video footage to be displayed to the user may include transmitting the stored video footage for display, as described above. For example, the matching subset of video footage may be transmitted through a network to a computing device associated with the user, such as a desktop computer, a laptop computer, a mobile phone, a tablet, smart glasses, heads up display, a training device, or any other device capable of displaying video footage.

Omitting playback may include any process resulting in the video lacking the selected event characteristic from being presented to the user. For example, omitting playback may include designating footage as not to be displayed and not displaying that footage. In embodiments where the matching subset of video footage is transmitted, omitting playback may include preventing transmission of video footage lacking the selected event characteristic. This may occur by selectively transmitting only those portions of footage related to the matching subset; by selectively transmitting markers associated with portions of footage related to the matching subset; and/or by skipping over portions of footage unrelated to the matching subset. In other embodiments, the video footage lacking the selected event characteristic may be transmitted but may be associated with one or more instructions not to present the video footage lacking the selected event characteristic.

According to various exemplary embodiments of the present disclosure, enabling the user to view surgical footage of at least one intraoperative surgical event that has the selected event characteristic, while omitting playback of portions of selected surgical events lacking the selected event characteristic, may include sequentially presenting to the user portions of surgical footage of a plurality of intraoperative surgical events sharing the selected event characteristic, while omitting playback of portions of selected surgical events lacking the selected event characteristic. In other words, one or more portions of video footage may be identified, for example through a lookup function in the data structure, as being associated with the selected event characteristic. Enabling the user to view surgical footage of the at least one intraoperative surgical event that has the selected event characteristic may include sequentially presenting one or more of the identified portions to the user. Any portions of video footage that are not identified may not be presented. In some embodiments, video footage may be selected based on the selected event tag and the selected phase tag. Accordingly, in embodiments consistent with the present disclosure, enabling the user to view surgical footage of at least one intraoperative surgical event that has the selected event characteristic, while omitting playback of portions of selected surgical events lacking the selected event characteristic, may include sequentially presenting to the user portions of surgical footage of a plurality of intraoperative surgical events sharing the selected event characteristic and associated with the selected event tag and the selected phase tag, while omitting playback of portions of selected surgical events lacking the selected event characteristic or not associated the at least one of selected event tag and the selected phase tag.

As mentioned above, the stored event characteristic may include a wide variety of characteristics relating to a surgical procedure. In some example embodiments, the stored event characteristic may include an adverse outcome of the surgical event. For example, the stored event characteristic may identify whether the event is an adverse event, or whether it was associated with a complication, including the examples described in greater detail above. Accordingly, causing the matching subset to be displayed may include enabling the user to view surgical footage of a selected adverse outcome while omitting playback of surgical events lacking the selected adverse outcome. By way of example, in response to a user's desire to see how a surgeon dealt with a vascular injury during a laparoscopic procedure, rather than displaying to the user the entire procedure, the user might select the vascular injury event, after which the system might display only a portion of the video footage where the event occurred. The stored event characteristic may similarly identify outcomes, including desired and/or expected outcomes. Examples of such outcomes may include full recovery by the patient, whether a leak occurred, an amount of leak that occurred, whether the amount of leak was within a selected range, whether the patient was readmitted after discharge, a length of hospitalization after surgery, or any other outcomes that may be associated with the surgical procedure. In this way, a user may be able to ascertain at the time of viewing, the long-term impact of a particular technique. Accordingly, in some embodiments, the stored event characteristic may include these or other outcomes, and causing the matching subset to be displayed may include enabling the user to view surgical footage of the selected outcome while omitting playback of surgical events lacking the selected outcome.

In some embodiments, the stored event characteristic may include a surgical technique. Accordingly, the stored event characteristic may identify whether a particular technique is performed. For example, there may be multiple techniques that may be applied at a particular stage of surgery and the event characteristic may identify which technique is being applied. In this way, a user interested in learning a particular technique might be able to filter video results so that only procedures using the specified technique are displayed. Causing the matching subset to be displayed may include enabling the user to view surgical footage of a selected surgical technique while omitting playback of surgical footage not associated with the selected surgical technique. For example, the user may be enabled to view in sequence, non-sequential portions of video captured from either the same surgery or from different surgeries. In some embodiments, the stored event characteristic may include an identity of a specific surgeon. For example, the event characteristic may include an identity of a particular surgeon performing the surgical procedure. The surgeon may be identified based on his or her name, an identification number (e.g., employee number, medical registration number, etc.) or any other form of identity. In some embodiments, the surgeon may be identified based on recognizing representations of the surgeon in the captured video. For example, various facial and/or voice recognition techniques may be used, as discussed above. In this way, if a user wishes to study a technique of a particular surgeon, the user may be enabled to do so. For example, causing the matching subset to be displayed may include enabling the user to view footage exhibiting an activity by a selected surgeon while omitting playback of footage lacking activity by the selected surgeon. Thus for example, if multiple surgeons participate in the same surgical procedure, a user may choose to view only the activities of a subset of the team.

In some embodiments, the event characteristic may also be associated with other healthcare providers or healthcare professionals who may be involved in the surgery. In some examples, a characteristic associated with a healthcare provider may include any characteristic of a healthcare provider involved in the surgical procedure. Some non-limiting examples of such healthcare providers may include the title of any member of the surgical team, such as surgeons, anesthesiologists, nurses, Certified Registered Nurse Anesthetist (CRNA), surgical tech, residents, medical students, physician assistants, and so forth. Additional non-limiting examples of such characteristics may include certification, level of experience (such as years of experience, past experience in similar surgical procedures, past success rate in similar surgical procedures, etc.), demographic characteristics (such as age), and so forth.

In other embodiments, the stored event characteristic may include a time associated with the particular surgical procedure, surgical phase, or portion thereof. For example, the stored event characteristic may include a duration of the event. Causing the matching subset to be displayed may include enabling the user to view footage exhibiting events of selected durations while omitting playback of footage of events of different durations. In this way, for example, a user who might wish to view a particular procedure completed more quickly than the norm, might set a time threshold to view specified procedures completed within that threshold. In another example, a user who might wish to view more complex events may set a time threshold to view procedures including events lasting longer than a selected threshold, or the procedures including events that lasted the longest of a selected group of events. In other embodiments, the stored event characteristic may include a starting time of the event, an ending time of the event, or any other time indicators.

Causing the matching subset to be displayed may include enabling the user to view footage exhibiting events from selected times within the particular surgical procedure, within the phase associated with the event, or within the selected portion of the particular surgical procedure, while omitting playback of footage of events associated with different times.

In another example, the stored event characteristic may include a patient characteristic. The term "patient characteristic" refers to any physical, sociological, economical, demographical or behavioral characteristics of the patient, and to characteristics of the medical history of the patient. Some non-limiting examples of such patient characteristics may include age, gender, weight, height, Body Mass Index (BMI), menopausal status, typical blood pressure, characteristics of the patient genome, educational status, level of education, socio-economic status, level of income, occupation, type of insurance, health status, self-rated health, functional status, functional impairment, duration of disease, severity of disease, number of illnesses, illness characteristics (such as type of illness, size of tumor, histology grade, number of infiltrated lymph nodes, etc.), utilization of health care, number of medical care visits, medical care visit intervals, regular source of medical care, family situation, marital status, number of children, family support, ethnicity, race, acculturation, religious, type of religion, native language, characteristics of past medical test performed on the patient (such as type of test, time of test, results of test, etc.), characteristics of past medical treatments performed on the patient (such as type of treatment, time of treatment, results of treatment, etc.), and so forth. Some non-limiting examples of such medical tests may include blood tests, urine tests, stool tests, medical imaging (such as ultrasonography, angiography, Magnetic Resonance Imaging (MRI), Computed Tomography (CT), X-ray, electromyography, Positron Emission Tomography (PET), etc.), physical examination, electrocardiography, amniocentesis, pap test, skin allergy tests, endoscopy, biopsy, pathology, blood pressure measurements, oxygen saturation test, pulmonary function test, and so forth. Some non-limiting examples of such medical treatments may include medication, dietary treatment, surgery, radiotherapy, chemotherapy, physical therapy, psychological therapy, blood transfusion, infusion, and so forth. Accordingly, causing the matching subset to be displayed may include enabling the user to view footage of patients exhibiting a selected patient characteristic while omitting playback of footage of patients lacking the selected patient characteristic.

In some embodiments, the selected physical patient characteristic may include a type of anatomical structure. As used herein, an anatomical structure may be any particular part of a living organism. For example, an anatomical structure may include any particular organ, tissue, cell, or other structures of the patient. In this way, if for example, a user wishes to observe video relating to surgery on a pleura sack in a lung, that portion of footage may be presented while other non-related portions may be omitted. The stored event characteristic may include various other patient characteristics, such as the patient's demographics, medical condition, medical history, previous treatments, or any other relevant patient descriptor. This can enable a viewer to view surgical procedures on patients matching very particular characteristics (e.g., 70-75 year old Caucasian, with coronary heart disease who previously had bypass surgery. In this way, video of one or more patients matching those specific criteria might be selectively presented to the user.

In yet another example, the stored event characteristic may include a physiological response. As used herein, the term "physiological response" refers to any physiological change that may have occurred in reaction to an event within a surgical procedure. Some non-limiting examples of such physiological changes may include change in blood pressure, change in oxygen saturation, change in pulmonary functions, change in respiration rate, change in blood composition (count chemistry, etc.), bleeding, leakage, change in blood flow to a tissue, changing in a condition of a tissue (such as change in color, shape, structural condition, functional condition, etc.), change in body temperature, a change in brain activity, a change in perspiration, or any other physical change in response to the surgical procedure. In this way, a user might be able to prepare for eventualities that might occur during a surgical procedure by selectively viewing those eventualities (and omitting playback of non-matching eventualities).

In some examples, the event characteristic may include a surgeon skill level. The skill level may include any indication of the surgeon's relative abilities. In some embodiments, the skill level may include a score reflecting the surgeon's experience or proficiency in performing the surgical procedure or specific techniques within the surgical procedure. In this way, a user can compare, by selecting different skill levels how surgeons of varying experience handle the same procedure. In some embodiments the skill level may be determined based on the identity of a surgeon, either determined via data entry (manually inputting the surgeon's ID) or by machine vision. For example, the disclosed methods may include analysis of the video footage to determine an identity of the surgeon through biometric analysis (e.g., face, voice, etc.) and identify a predetermined skill level associated with that surgeon. The predetermined skill level may be obtained by accessing a database storing skill levels associated with particular surgeons. The skill level may be based on past performances of the surgeon, a type and/or level of training or education of the surgeon, a number of surgeries the surgeon has performed, types of surgeries surgeon has performed, qualifications of the surgeon, a level of experience of the surgeon, ratings of the surgeon from patients or other healthcare professionals, past surgical outcomes, past surgical outcomes and complications, or any other information relevant to assessing the skill level of a healthcare professional. In some embodiments, the skill level may be determined automatically based on computer analysis of the video footage. For example, the disclosed embodiments, may include analyzing video footage capturing performance of a procedure, performance of a particular technique, a decision made by the surgeon, or similar events. The skill level of the surgeon may then be determined based on how well the surgeon performs during the event, which may be based on timeliness, effectiveness, adherence to a preferred technique, the lack of injury or adverse effects, or any other indicator of skill that may be gleaned from analyzing the footage.

In some embodiments, the skill level may be a global skill level assigned to each surgeon or may be in reference to specific events. For example, a surgeon may have a first skill level with regard to a first technique or procedure and may have a second skill level with regard to a different technique or procedure. The skill level of the surgeon may also vary throughout an event, technique and/or procedure. For example, a surgeon may act at a first skill level within a first portion of the footage but may act at a second skill level at a second portion of the footage. Accordingly, the skill level may be a skill level associated with a particular location of the footage. The skill level also may be a plurality of skill levels during an event or may be an aggregation of the plurality of skill levels during the event, such as an average value, a rolling average, or other forms of aggregation. In some embodiments, the skill level may be a general required skill level for performing the surgical procedure, the surgical phase, and/or the intraoperative surgical event and may not be tied to a particular surgeon or other healthcare professional. The skill level may be expressed in various ways, including as a numerical scale (e.g., 1-10, 1-100, etc.), as a percentage, as a scale of text-based indicators (e.g., "highly skilled," "moderately skilled," "unskilled," etc.) or any other suitable format for expressing the skill of a surgeon. While the skill level is described herein as the skill level of a surgeon, in some embodiments the skill level may be associated with another healthcare professional, such as a surgical technician, a nurse, a physician's assistant, an anesthesiologist, a doctor, or any other healthcare professional.

Embodiments of the present disclosure may further include accessing aggregate data related to a plurality of surgical procedures similar to the particular surgical procedure. Aggregate data may refer to data collected and/or combined from multiple sources. The aggregate data may be compiled from multiple surgical procedures having some relation to the particular surgical procedure. For example, a surgical procedure may be considered similar to the particular surgical procedure if it includes the same or similar surgical phases, includes the same or similar intraoperative events, or is associated with the same or similar tags or properties (e.g., event tags, phase tags, event characteristics, or other tags).

The present disclosure may further include presenting to the user statistical information associated with the selected event characteristic. Statistical information may refer to any information that may be useful to analyze multiple surgical procedures together. Statistical information may include, but is not limited to, average values, data trends, standard deviations, variances, correlations, causal relations, test statistics (including t statistics, chi-squared statistics, f statistics, or other forms of test statistics), order statistics (including sample maximum and minimum), graphical representations (e.g., charts, graphs, plots, or other visual or graphical representations), or similar data. As an illustrative example, in embodiments where the user selects an event characteristic including the identity of a particular surgeon, the statistical information may include the average duration in which the surgeon performs the surgical operation (or phase or event of the surgical operation), the rate of adverse or other outcomes the surgeon, the average skill level at which the surgeon performs an intraoperative event, or similar statistical information. A person of ordinary skill in the art would appreciate other forms of statistical information that may be presented according to the disclosed embodiments.

Figure 8A:
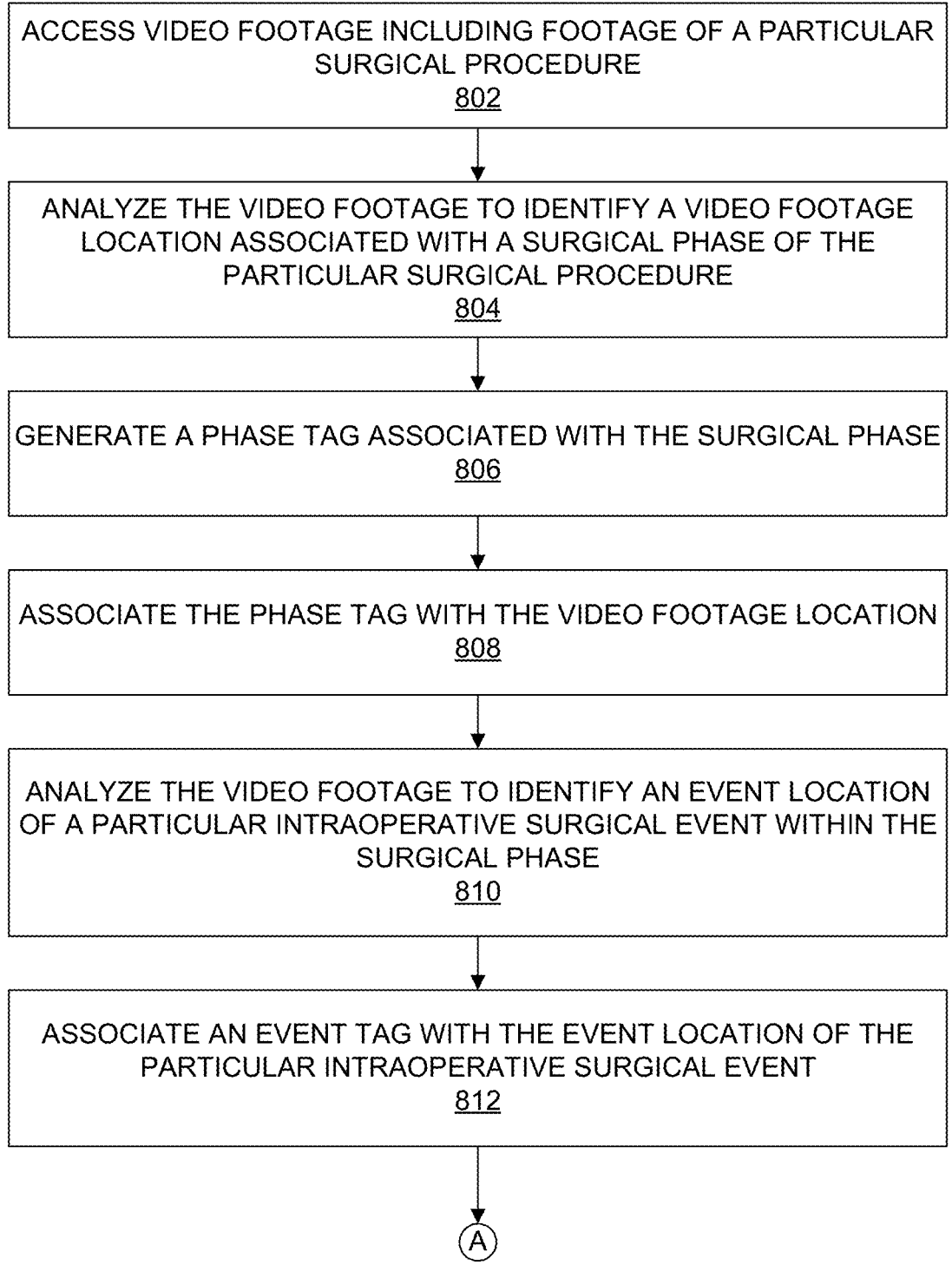
FIGS. 8A and 8B are flowcharts illustrating an example process for video indexing consistent with the disclosed embodiments.
Figure 8B:
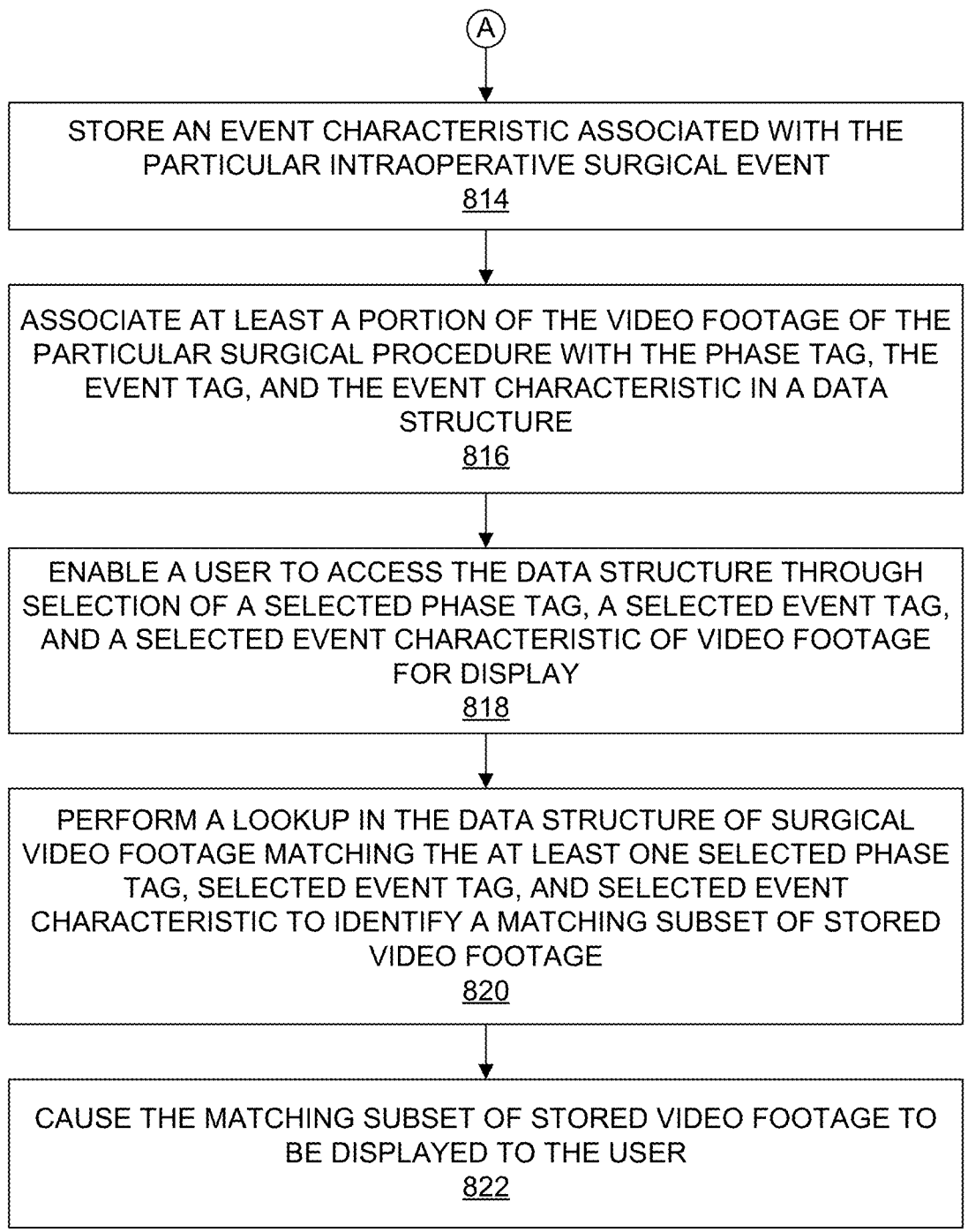

FIGS. 8A and 8B are flowcharts illustrating an example process 800 for video indexing consistent with the disclosed embodiments. Process 800 may be performed by a processing device, such as at least one processor. For example, the at least one processor may include one or more integrated circuits (IC), including application-specific integrated circuit (ASIC), microchips, microcontrollers, microprocessors, all or part of a central processing unit (CPU), graphics processing unit (GPU), digital signal processor (DSP), field-programmable gate array (FPGA), server, virtual server, or other circuits suitable for executing instructions or performing logic operations. The instructions executed by at least one processor may, for example, be pre-loaded into a memory integrated with or embedded into the controller or may be stored in a separate memory. The memory may include a Random Access Memory (RAM), a Read-Only Memory (ROM), a hard disk, an optical disk, a magnetic medium, a flash memory, other permanent, fixed, or volatile memory, or any other mechanism capable of storing instructions. In some embodiments, the at least one processor may include more than one processor. Each processor may have a similar construction or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically or by other means that permit them to interact.

In some embodiments, a non-transitory computer readable medium may contain instructions that when executed by a processor cause the processor to perform process 800. At step 802, process 800 may include accessing video footage to be indexed, the video footage to be indexed including footage of a particular surgical procedure. The video footage may be accessed from a local memory, such as a local hard drive, or may be accessed from a remote source, for example, through a network connection. In another example, the video footage may be captured using one or more image sensors, or generated by another process. At step 804, process 800 may include analyzing the video footage to identify a video footage location associated with a surgical phase of the particular surgical procedure. As discussed above, the location may be associated with a particular frame, a range of frames, a time index, a time range, or any other location identifier.

Process 800 may include generating a phase tag associated with the surgical phase, as shown in step 806. This may occur, for example, through video content analysis (VCA), using techniques such as one or more of video motion detection, video tracking, shape recognition, object detection, fluid flow detection, equipment identification, behavior analysis, or other forms of computer aided situational awareness. When learned characteristics associated with a phase are identified in the video, a tag may be generated demarcating that phase. The tag may include, for example, a predefined name for the phase. At step 808, process 800 may include associating the phase tag with the video footage location. The phase tag may indicate, for example, that the identified video footage location is associated with the surgical phase of the particular surgical procedure. At step 810, process 800 may include analyzing the video footage using one or more of the VCA techniques described above, to identify an event location of a particular intraoperative surgical event within the surgical phase. Process 800 may include associating an event tag with the event location of the particular intraoperative surgical event, as shown at step 812. The event tag may indicate, for example, that the video footage is associated with the surgical event at the event location. As with the phase tag, the event tag may include a predefined name for the event. At step 814, in FIG. 8B, process 800 may include storing an event characteristic associated with the particular intraoperative surgical event. As discussed in greater detail above, the event characteristic may include an adverse outcome of the surgical event, a surgical technique, a surgeon skill level, a patient characteristic, an identity of a specific surgeon, a physiological response, a duration of the event, or any other characteristic or property associated with the event. The event characteristic may be manually determined (for example, inputted by a viewer), or may be determined automatically through artificial intelligence applied to machine vision, for example as described above. In one example, the event characteristic may include skill level (such as minimal skill level required, skill level demonstrated during the event, etc.), a machine learning model may be trained using training example to determine such skill levels from videos, and the trained machine learning model may be used to analyze the video footage to determine the skill level. An example of such training example may include a video clip depicting an event together with a label indicating the corresponding skill level. In another example, the event characteristic may include time related characteristics of the event (such as start time, end time, duration, etc.), and such time related characteristics may be calculated by analyzing the interval in the video footage corresponding to the event. In yet another example, the event characteristic may include an event type, a machine learning model may be trained using training examples to determine event types from videos, and the trained machine learning model may be used to analyze the video footage and determine the event type. An example of such training example may include a video clip depicting an event together with a label indicating the event type. In an additional example, the event characteristic may include information related to a medical instrument involved in the event (such as type of medical instrument, usage of the medical instrument, etc.), a machine learning model may be trained using training examples to identify such information related to medical instruments from videos, and the trained machine learning model may be used to analyze the video footage and determine the information related to a medical instrument involved in the event. An example of such training example may include video clip depicting an event including a usage of a medical instrument, together with a label indicative of the information related to the medical instrument. In yet another example, the event characteristic may include information related to an anatomical structure involved in the event (such as type of the anatomical structure, condition of the anatomical structure, change occurred to the anatomical structure in relation to the event, etc.), a machine learning model may be trained using training example to identify such information related to anatomical structures from videos, and the trained machine learning model may be used to analyze the video footage and determine the information related to the anatomical structure involved in the event. An example of such training example may include a video clip depicting an event involving an anatomical structure, together with a label indicative of information related to the anatomical structure. In an additional example, the event characteristic may include information related to a medical outcome associated with the event, a machine learning model may be trained using training example to identify such information related to medical outcomes from videos, and the trained machine learning model may be used to analyze the video footage and determine the information related to the medical outcome associated with the event. An example of such training example may include a video clip depicting a medical outcome, together with a label indicative of the medical outcome.

At step 816, process 800 may include associating at least a portion of the video footage of the particular surgical procedure with at least one of the phase tag, the event tag, and the event characteristic in a data structure. In this step, the various tags are associated with the video footage to permit the tags to be used to access the footage. As previously described, various data structures may be used to store related data in an associated manner.

At step 818, process 800 may include enabling a user to access the data structure through selection of at least one of a selected phase tag, a selected event tag, and a selected event characteristic of video footage for display. In some embodiments, the user may select the selected phase tag, selected event tag, and selected event characteristic through a user interface of a computing device, such as user interface 700 shown in FIG. 7. For example, data entry fields, drop down menus, icons, or other selectable items may be provided to enable a user to select a surgical procedure, the phase of the procedure, an event within a procedure and a characteristic of the procedure and patient. At step 820, process 800 may include performing a lookup in the data structure of surgical video footage matching the at least one selected phase tag, selected event tag, and selected event characteristic to identify a matching subset of stored video footage. At step 822, process 800 may include causing the matching subset of stored video footage to be displayed to the user, to thereby enable the user to view surgical footage of at least one intraoperative surgical event sharing the selected event characteristic, while omitting playback of video footage lacking the selected event characteristic. Through this filtering, the user may be able to quickly view only those video segments corresponding to the user's interest, while omitting playback of large volumes of video data unrelated to the user's interest.

When preparing for a surgical procedure, it may be beneficial for a surgeon to review video footage of surgical procedures having similar surgical events. It may be too time consuming, however, for a surgeon to view the entire video or to skip around to find relevant portions of the surgical footage. Therefore, there is a need for unconventional approaches that efficiently and effectively enable a surgeon to view a surgical video summary that aggregates footage of relevant surgical events while omitting other irrelevant footage.

Aspects of this disclosure may relate to generating surgical summary footage, including methods, systems, devices, and computer readable media. For example, footage of one surgical procedure may be compared with that of previously analyzed procedures to identify and tag relevant intraoperative surgical events. A surgeon may be enabled to watch a summary of a surgery that aggregates the intraoperative surgical events, while omitting much of the other irrelevant footage. For ease of discussion, a method is described below, with the understanding that aspects of the method apply equally to systems, devices, and computer readable media. For example, some aspects of such a method may occur electronically over a network that is either wired, wireless, or both. Other aspects of such a method may occur using non-electronic means. In a broadest sense, the method is not limited to particular physical and/or electronic instrumentalities, but rather may be accomplished using many differing instrumentalities.

Consistent with disclosed embodiments, a method may involve accessing particular surgical footage containing a first group of frames associated with at least one intraoperative surgical event. Surgical footage may refer to any video, group of video frames, or video footage including representations of a surgical procedure. For example, the surgical footage may include one or more video frames captured during a surgical operation. Accessing the surgical footage may include retrieving video from a storage location, such as a memory device. The surgical footage may be accessed from a local memory, such as a local hard drive, or may be accessed from a remote source, for example, through a network connection. As described in greater detail above, video may include any form of recorded visual media including recorded images and/or sound. The video may be stored as a video file such as an Audio Video Interleave (AVI) file, a Flash Video Format (FLV) file, QuickTime File Format (MOV), MPEG (MPG, MP4, M4P, etc.), a Windows Media Video (WMV) file, a Material Exchange Format (MXF) file, or any other suitable video file formats. Additionally or alternatively, in some examples accessing particular surgical footage may include capturing the particular surgical footage using one or more image sensors.

As described above, the intraoperative surgical event may be any event or action that is associated with a surgical procedure or phase. A frame may refer to one of a plurality of still images which compose a video. The first group of frames may include frames that were captured during the interoperative surgical event. For example, the particular surgical footage may depict a surgical procedure performed on a patient and captured by at least one image sensor in an operating room. The image sensors may include, for example, cameras 115, 121, and 123, and/or 125 located in operating room 101. In some embodiments, the at least one image sensor may be at least one of above an operating table in the operating room or within the patient. For example, the image sensor may be located above the patient, or may be located within a surgical cavity, organ, or vasculature of the patient, as described above. The first group of frames may include representations of the intraoperative surgical event, including anatomical structures, surgical tools, healthcare professionals performing the intraoperative surgical event, or other visual representations of the intraoperative surgical event. In some embodiments, however, some or all of the frames may not contain representations of the intraoperative surgical event, but may be otherwise associated with the event (e.g., captured while the event was being performed, etc.).

Consistent with the present disclosure, the particular surgical footage may contain a second group of frames not associated with surgical activity. For example, surgical procedures may involve extensive periods of downtime, where significant surgical activity is not taking place and where there would be no material reason for review of the footage. Surgical activity may refer to any activities that are performed in relation to a surgical procedure. In some embodiments, surgical activity may broadly refer to any activities associated with the surgical procedure, including preoperative activity, perioperative activity, intraoperative activity, and/or postoperative activity. Accordingly, the second group of frames may include frames not associated with any such activities. In other embodiments, surgical activity may refer to a narrower set of activity, such as physical manipulation of organs or tissues of the patient being performed by the surgeon. Accordingly, the second group of frames may include various activities associated with preparation, providing anesthesia, monitoring vital signs, gathering or preparing surgical tools, discussion between healthcare professionals, or other activities that may not be considered surgical activity.

In accordance with the present disclosure, the methods may include accessing historical data based on historical surgical footage of prior surgical procedures. Historical data may refer to data of any format that was recorded and/or stored previously. In some embodiments, the historical data may be one or more video files including the historical surgical footage. For example, the historical data may include a series of frames captured during the prior surgical procedures. This historical data is not limited to video files, however. For example, the historical data may include information stored as text representing at least one aspect of the historical surgical footage. For example, the historical data may include a database of information summarizing or otherwise referring to historical surgical footage. In another example, the historical data may include information stored as numerical values representing at least one aspect of the historical surgical footage. In an additional example, the historical data may include statistical information and/or statistical model based on an analysis of the historical surgical footage. In yet another example, the historical data may include a machine learning model trained using training examples, and the training examples may be based on the historical surgical footage. Accessing the historical data may include receiving the historical data through an electronic transmission, retrieving the historical data from storage (e.g., a memory device), or any other process for accessing data. In some embodiments, the historical data may be accessed from the same resource as the particular surgical footage discussed above. In other embodiments, the historical data may be accessed from a separate resource. Additionally or alternatively, accessing the historical data may include generating the historical data, for example by analyzing the historical surgical footage of prior surgical procedures or by analyzing data based on the historical surgical footage of prior surgical procedures.

In accordance with embodiments of the present disclosure, the historical data may include information that distinguishes portions of surgical footage into frames associated with intraoperative surgical events and frames not associated with surgical activity. The information may distinguish the portions of surgical footage in various ways. For example, in connection with historical surgical footage, frames associated with surgical and non-surgical activity may already have been distinguished. This may have previously occurred, for example, through manual flagging of surgical activity or through training of an artificial intelligence engine to distinguish between surgical and non-surgical activity. The historical information may identify, for example, a set of frames (e.g., using a starting frame number, a number of frames, an end frame number, etc.) of the surgical footage. The information may also include time information, such as a begin timestamp, an end timestamp, a duration, a timestamp range, or other information related to timing of the surgical footage. In one example, the historical data may include various indicators and/or rules that distinguish the surgical activity from non-surgical activity. Some non-limiting examples of such indicators and/or rules are discussed below. In another example, the historical data may include a machine learning model trained to identify portions of videos corresponding to surgical activity and/or portions of videos corresponding to non-surgical activity, for example based on the historical surgical footage.

Various indicators may be used to distinguish the surgical activity from non-surgical activity—either manually, semi-manually, of automatically (for example, via machine learning). For example, in some embodiments, the information that distinguishes portions of the historical surgical footage into frames associated with an intraoperative surgical event may include an indicator of at least one of a presence or a movement of a surgical tool. A surgical tool may be any instrument or device that may be used during a surgical procedure, which may include, but is not limited to, cutting instruments (such as scalpels, scissors, saws, etc.), grasping and/or holding instruments (such as Billroth's clamps, hemostatic "mosquito" forceps, atraumatic hemostatic forceps, Deschamp's needle, Hopfner's hemostatic forceps, etc.), retractors (such as Farabef's Cshaped laminar hook, blunt-toothed hook, sharp-toothed hook, grooved probe, tamp forceps, etc.), tissue unifying instruments and/or materials (such as needle holders, surgical needles, staplers, clips, adhesive tapes, mesh, etc.), protective equipment (such as facial and/or respiratory protective equipment, headwear, footwear, gloves, etc.), laparoscopes, endoscopes, patient monitoring devices, and so forth. A video or image analysis algorithm, such as those described above with respect to video indexing, may be used to detect the presence and/or motion of the surgical tool within the footage. In some examples, a measure of motion of the surgical tool may be calculated, and the calculated measure of motion may be compared with a selected threshold to distinguish the surgical activity from non-surgical activity. For example, the threshold may be selected based on a type of surgical procedure, based on time of or within the surgical procedure, based on a phase of the surgical procedure, based on parameters determined by analyzing video footage of the surgical procedure, based on parameters determined by analyzing the historical data, and so forth. In some examples, signal processing algorithms may be used to analyze calculated measures of motion for various times within the video footage of the surgical procedure to distinguish the surgical activity from non-surgical activity. Some non-limiting examples of such signal processing algorithms may include machine learning based signal processing algorithms trained using training examples to distinguish the surgical activity from non-surgical activity, artificial neural networks (such as recursive neural networks, long short-term memory neural networks, deep neural networks, etc.) configured to distinguish the surgical activity from non-surgical activity, Markov models, Viterbi models, and so forth.

In some exemplary embodiments, the information that distinguishes portions of the historical surgical footage into frames associated with an intraoperative surgical event may include detected tools and anatomical features in associated frames. For example, the disclosed methods may include using an image and/or video analysis algorithm to detect tools and anatomical features. The tools may include surgical tools, as described above, or other nonsurgical tools. The anatomical features may include anatomical structures (as defined in greater detail above) or other parts of a living organism. The presence of both a surgical tool and an anatomical structure detected in one or more associated frames, may serve as an indicator of surgical activity, since surgical activity typically involves surgical tools interacting with anatomical structures. For example, in response to a detection of a first tool in a group of frames, the group of frames may be determined to be associated with an intraoperative surgical event, while in response to no detection of the first tool in the group of frames, the group of frames may be identified as not associated with the intraoperative surgical event. In another example, in response to a detection of a first anatomical feature in a group of frames, the group of frames may be determined to be associated with an intraoperative surgical event, while in response to no detection of the first anatomical feature in the group of frames, the group of frames may be identified as not associated with the intraoperative surgical event. In some examples, video footage may be further analyzed to detect interaction between the detected tools and anatomical features, and distinguishing the surgical activity from non-surgical activity may be based on the detected interaction. For example, in response to a detection of a first interaction in a group of frames, the group of frames may be determined to be associated with an intraoperative surgical event, while in response to no detection of the first interaction in the group of frames, the group of frames may be identified as not associated with the intraoperative surgical event. In some examples, video footage may be further analyzed to detect actions performed by the detected tools, and distinguishing the surgical activity from non-surgical activity may be based on the detected actions. For example, in response to a detection of a first action in a group of frames, the group of frames may be determined to be associated with an intraoperative surgical event, while in response to no detection of the first action in the group of frames, the group of frames may be identified as not associated with the intraoperative surgical event. In some examples, video footage may be further analyzed to detect changes in the condition of anatomical features, and distinguishing the surgical activity from non-surgical activity may be based on the detected changes. For example, in response to a detection of a first change in a group of frames, the group of frames may be determined to be associated with an intraoperative surgical event, while in response to no detection of the first change in the group of frames, the group of frames may be identified as not associated with the intraoperative surgical event.

Some aspects of the invention may involve distinguishing in the particular surgical footage the first group of frames from the second group of frames based on the information of the historical data. For example, the information may provide context that is useful in determining which frames of the particular surgical footage are associated with intraoperative events and/or surgical activity. In some embodiments, distinguishing in the particular surgical footage the first group of frames from the second group of frames may involve the use of a machine learning algorithm. For example, a machine learning model may be trained to identify intraoperative events and/or surgical activity using training examples based on the information of the historical data.

Figure 9:
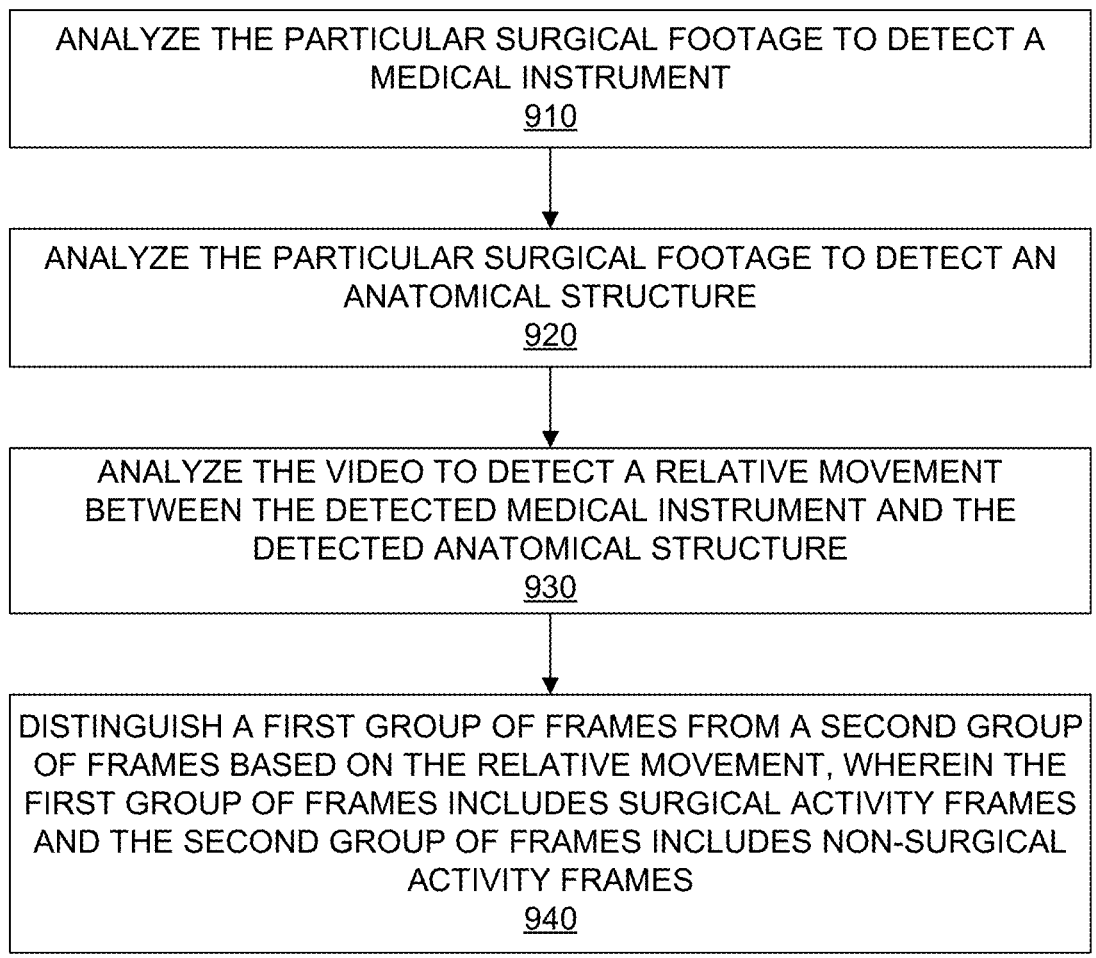
FIG. 9 is a flowchart illustrating an example process for distinguishing a first group of frames from a second group of frames, consistent with the disclosed embodiments.

In accordance with the present disclosure, the first and second group of frames may be distinguished by analyzing the surgical footage to identify information similar to the information of the historical data. FIG. 9 is a flowchart illustrating an example process 900 for distinguishing the first group of frames from the second group of frames. It is to be understood that process 900 is provided by way of example. A person of ordinary skill would appreciate various other processes for distinguishing the first group of frames from the second group, consistent with this disclosure. At step 910, process 900 may include analyzing the particular surgical footage to detect a medical instrument. A medical instrument may refer to any tool or device used for treatment of a patient, including surgical tools, as described above. In addition to the surgical tools listed above, medical instruments may include, but are not limited to stethoscopes, gauze sponges, catheters, cannulas, defibrillators, needles, trays, lights, thermometers, pipettes or droppers, oxygen masks and tubes, or any other medical utensils. For example, a machine learning model may be trained using training examples to detect medical instruments in images and/or videos, and the trained machine learning model may be used to analyze the particular surgical footage and detect the medical instrument. An example of such training example may include a video and/or an image of a surgical procedure, together with a label indicating the presence of one or more particular medical instruments in the video and/or in the image, or together with a label indicating an absence of particular medical instruments in the video and/or in the image.

At step 920, process 900 may include analyzing the particular surgical footage to detect an anatomical structure. The anatomical structure may be any organ, part of an organ, or other part of a living organism, as discussed above. One or more video and/or image recognition algorithms, as described above, may be used to detect the medical instrument and/or anatomical structure. For example, a machine learning model may be trained using training examples to detect anatomical structures in images and/or videos, and the trained machine learning model may be used to analyze the particular surgical footage and detect the anatomical structure. An example of such training example may include a video and/or an image of a surgical procedure, together with a label indicating the presence of one or more particular anatomical structures in the video and/or in the image, or together with a label indicating an absence of particular anatomical structures in the video and/or in the image.

At step 930, process 900 may include analyzing the video to detect a relative movement between the detected medical instrument and the detected anatomical structure. Relative movement may be detected using a motion detection algorithm, for example, based on changes in pixels between frames, optical flow, or other forms of motion detection algorithms. For example, motion detection algorithms may be used to estimate the motion of the medical instrument in the video and to estimate the motion of the anatomical structure in the video, and the estimated motion of the medical instrument may be compared with the estimated motion of the anatomical structure to determine the relative movement. At step 940, process 900 may include distinguishing the first group of frames from the second group of frames based on the relative movement, wherein the first group of frames includes surgical activity frames and the second group of frames includes non surgical activity frames. For example, in response to a first relative movement pattern in a group of frames, it may be determined that the group of frames includes surgical activity, while in response to a detection of a second relative movement pattern in the group of frames, the group of frames may be identified as not including non surgical activity frames. Accordingly, presenting an aggregate of the first group of frames may thereby enable a surgeon preparing for surgery to omit the non-surgical activity frames during a video review of the abridged presentation. In some embodiments, omitting the non-surgical activity frames may include omitting a majority of frames that capture non-surgical activity. For example, not all frames that capture non-surgical activity may be omitted, such as frames that immediately precede or follow intraoperative surgical events, frames capturing non-surgical activity that provides context to intraoperative surgical events, or any other frames that may be relevant to a user.

In some exemplary embodiments of the present disclosure, distinguishing the first group of frames from the second group of frames may further be based on a detected relative position between the medical instrument and the anatomical structure. The relative position may refer to a distance between the medical instrument and the anatomical structure, an orientation of the medical instrument relative to the anatomical structure, or the location of the medical instrument relative to the anatomical structure. For example, the relative position may be estimated based on a relative position of the detected medical instrument and anatomical structure within one or more frames of the surgical footage. For example, the relative position may include a distance (for example, in pixels, in real world measurements, etc.), a direction, a vector, and so forth. In one example, object detection algorithms may be used to determine a position of the medical instrument, and to determine a position of the anatomical structure, and the two determined positions may be compared to determine the relative position. In one example, in response to a first relative position in a group of frames, it may be determined that the group of frames includes surgical activity, while in response to a detection of a second relative position in the group of frames, the group of frames may be identified as non surgical activity frames. In another example, the distance between the medical instrument and the anatomical structure may be compared with a selected threshold, and distinguishing the first group of frames from the second group of frames may further be based on a result of the comparison. For example, the threshold may be selected based on the type of the medical instrument, the type of the anatomical structure, the type of the surgical procedure, and so forth. In other embodiments, distinguishing the first group of frames from the second group of frames may further be based on a detected interaction between the medical instrument and the anatomical structure. An interaction may include any action by the medical instrument that may influence the anatomical structure, or vice versa. For example, the interaction may include a contact between the medical instrument and the anatomical structure, an action by the medical instrument on the anatomical structure (such as cutting, clamping, applying pressure, scraping, etc.), a reaction by the anatomical structure (such as a reflex action), or any other form of interaction. For example, a machine learning model may be trained using training examples to detect interactions between medical instruments and anatomical structures from videos, and the trained machine learning model may be used to analyze the video footage and detect the interaction between the medical instrument and the anatomical structure. An example of such training example may include a video clip of a surgical procedure, together with a label indicating the presence of particular interactions between medical instruments and anatomical structures in the video clip, or together with a label indicating the absence of particular interactions between medical instruments and anatomical structures in the video clip.

Some aspects of the present disclosure may involve, upon request of a user, presenting to the user an aggregate of the first group of frames of the particular surgical footage, while omitting presentation to the user of the second group of frames. The aggregate of the first group of frames may be presented in various forms. In some embodiments, the aggregate of the first group of frames may include a video file. The video file may be a compilation of video clips including the first group of frames. In some embodiments the user may be presented each of the video clips separately, or may be presented a single compiled video. In some embodiments a separate video file may be generated for the aggregate of the first group of frames. In other embodiments, the aggregate of the first group of frames my include instructions for identifying frames to be included for presentation, and frames to be omitted. Execution of the instructions may appear to the user as if a continuous video has been generated. Various other formats may also be used, including presenting the first group of frames as still images.

Presenting may include any process for delivering the aggregate to the user. In some embodiments, this may include causing the aggregate to be played on a display, such as a computer screen or monitor, a projector, a mobile phone display, a tablet, a smart device, or any device capable of displaying images and/or audio. Presenting may also include transmitting the aggregate of the first group of frames to the user or otherwise making it accessible to the user. For example, the aggregate of the first group of frames may be transmitted through a network to a computing device of the user. As another example, the location of the aggregate of the first group of frames may be shared with the user. The second group of frames may be omitted by not including the second group of frames in the aggregate. For example, if the aggregate is presented as a video, video clips comprising the second group of frames may not be included in the video file. The first group of frames may be presented in any order, including chronological order. In some instances, it may be logical to present at least some of the first group of frames in non-chronological order. In some embodiments, the aggregate of the first group of frames may be associated with more than one intraoperative surgical event. For example, a user may request to view a plurality of intraoperative surgical events in the particular surgical footage. Presenting to the user an aggregate of the first group of frames may include displaying the first group frames in chronological order with chronological frames of the second group omitted.

The user may be any individual or entity that may require access to surgical summary footage. In some embodiments, the user may be a surgeon or other healthcare professional. For example, a surgeon may request surgical summary footage for review or training purposes. In some embodiments the user may be an administrator, a manager, a lead surgeon, insurance company personnel, a regulatory authority, a police or investigative authority, or any other entity that may require access to surgical footage. Various other examples of users are provided above in reference to video indexing techniques. The user may submit the request through a computer device, such as a laptop, a desktop computer, a mobile phone, a tablet, smart glasses or any other form of computing device capable of submitting requests. In some embodiments, the request may be received electronically through a network and the aggregate may be presented based on receipt of the request.

In some exemplary embodiments, the request of the user may include an indication of at least one type of intraoperative surgical event of interest and the first group of frames may depict at least one intraoperative surgical event of the at least one type of intraoperative surgical event of interest. The type of the intraoperative surgical event may be any category in which the intraoperative surgical event may be classified. For example, the type may include the type of procedure being performed, the phase of the procedure, whether or not the intraoperative surgical event is adverse, whether the intraoperative surgical event is part of the planned procedure, the identity of a surgeon performing the intraoperative surgical event, a purpose of the intraoperative surgical event, a medical condition associated with the intraoperative surgical event, or any other category or classification.

Embodiments of the present disclosure may further include exporting the first group of frames for storage in a medical record of the patient. As described above, the particular surgical footage may depict a surgical procedure performed on a patient. Using the disclosed methods, the first group of frames associated with the at least one interoperative surgical event may be associated with the patients medical record. As used herein, a medical record may include any form of documentation of information relating to a patient's health, including diagnoses, treatment, and/or care. The medical record may be stored in a digital format, such as an electronic medical record (EMR). Exporting the first group of frames may include transmitting or otherwise making the first group of frames available for storage in the medical record or in a manner otherwise associating the first group of frames with the medical record. This may include, for example, transmitting the first group of frames (or copies of the first group of frames) to an external device, such as a database. In some embodiments, the disclosed methods may include associating the first group of frames with a unique patient identifier and updating a medical record including the unique patient identifier. The unique patient identifier may be any indicator, such as an alphanumerical string, that uniquely identifies the patient. The alphanumeric string may anonymize the patient, which may be required for privacy purposes. In instances where privacy may not be an issue, the unique patient identifier may include a name and/or social security number of the patient.

In some exemplary embodiments, the disclosed methods may further comprise generating an index of the at least one intraoperative surgical event. As described above, an index may refer to a form of data storage that enables retrieval of the associated video frames. Indexing may expedite retrieval in a manner more efficient and/or effective than if not indexed. The index may include a list or other itemization of intraoperative surgical events depicted in or otherwise associated with the first group of frames. Exporting the first group of frames may include generating a compilation of the first group of frames, the compilation including the index and being configured to enable viewing of the at least one intraoperative surgical event based on a selection of one or more index items. For example, by selecting "incision" through the index, the user may be presented with a compilation of surgical footage depicting incisions. Various other intraoperative surgical events may be included on the index. In some embodiments, the compilation may contain a series of frames of differing intraoperative events stored as a continuous video. For example, the user may select multiple intraoperative events through the index, and frames associated with the selected intraoperative events may be compiled into a single video.

Embodiments of the present disclosure may further include generating a cause effect summary. The cause-effect summary may allow a user to view clips or images associated with a cause phase of a surgical procedure and clips or images of associated outcome phase, without having to view intermediate clips or images. As used herein "cause" refers to trigger or action that gives rise to a particular result, phenomenon or condition. The "outcome" refers to the phenomenon or condition that can be attributed to the cause. In some embodiments, the outcome may be an adverse outcome. For example, the outcome may include a bleed, mesenteric emphysema, injury, conversion to unplanned open surgery (for example, abdominal wall incision), an incision that is significantly larger than planned, and so forth. The cause may an action, such as an error by the surgeon, that results in or can be attributed to the adverse outcome. For example, the error may include a technical error, a communication error, a management error, a judgment error, a decision-making error, an error related to medical equipment utilization, or other forms of errors that may occur. The outcome may also include a positive or expected outcome, such as a successful operation, procedure, or phase.

In embodiments where a cause-effect summary is generated, the historical data may further include historical surgical outcome data and respective historical cause data. The historical surgical outcome data may indicate portions of the historical surgical footage associated with an outcome and the historical cause data may indicate portions of the historical surgical footage associated with a respective cause of the outcome. In such embodiments, the first group of frames may include a cause set of frames and an outcome set of frames, whereas the second group of frames may include an intermediate set of frames.

Figure 10:
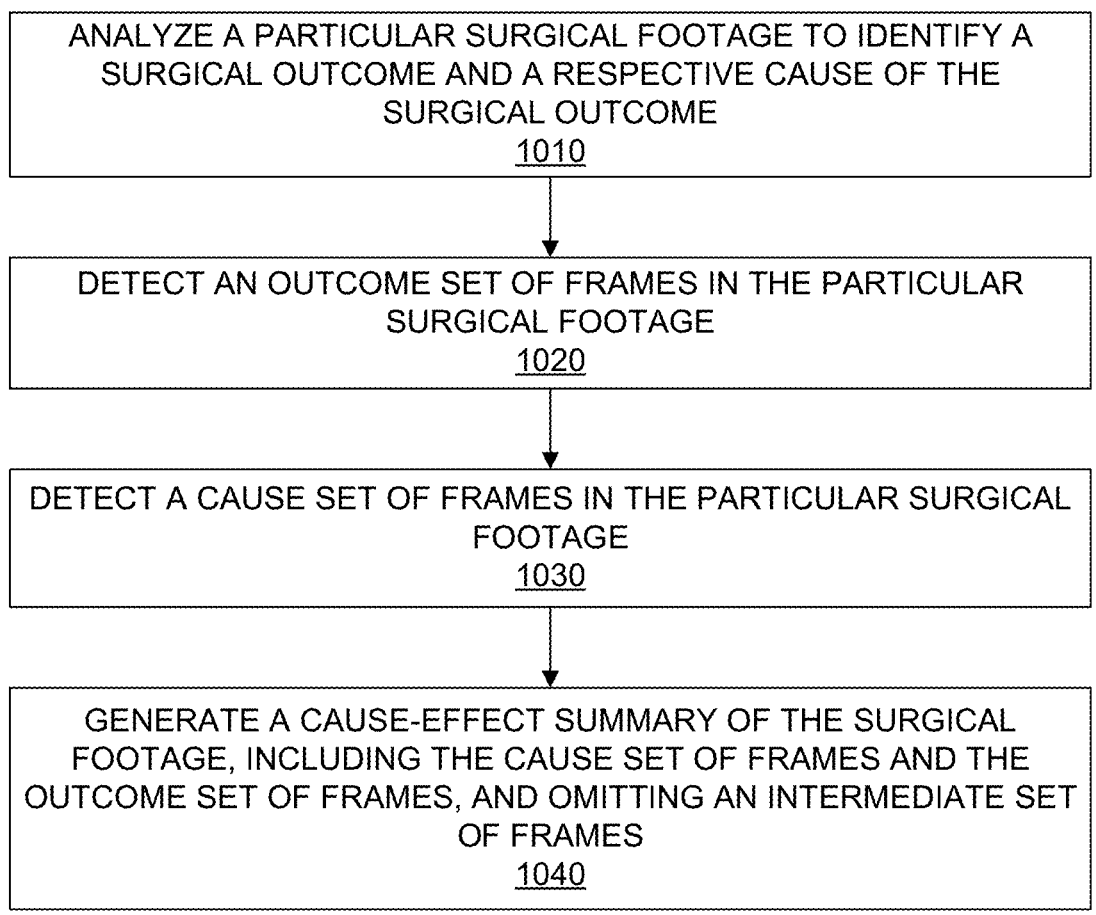
FIG. 10 is a flowchart illustrating an example process for generating a cause-effect summary, consistent with the disclosed embodiments.

FIG. 10 is a flowchart illustrating an exemplary process 1000 for generating a cause-effect summary, consistent with the disclosed embodiments. Process 1000 is provided by way of example, and a person of ordinary skill would appreciate various other processes for generating a cause-effect summary consistent with this disclosure. At step 1010, process 1000 may include analyzing the particular surgical footage to identify a surgical outcome and a respective cause of the surgical outcome, the identifying being based on the historical outcome data and respective historical cause data. The analysis may be performed using image and/or video processing algorithms, as discussed above. In some embodiments, step 1010 may include using a machine learning model trained to identify surgical outcomes and respective causes of the surgical outcomes using the historical data to analyze the particular surgical footage. For example, the machine learning model may be trained based on historical data with known or predetermined surgical outcomes and respective causes. The trained model may then be used to identify surgical outcomes and respective causes in other footage, such as the particular surgical footage. An example of a training examples used to train such machine learning model may include a video clip of a surgical procedure, together with a label indicating a surgical outcome corresponding to the video clip, and possibly a respective cause of the surgical outcome. Such training example may be based on the historical data, for example including a video clip from the historical data, including an outcome determined based on the historical data, and so forth.

At step 1020, process 1000 may include detecting, based on the analyzing, the outcome set of frames in the particular surgical footage, the outcome set of frames being within an outcome phase of the surgical procedure. The outcome phase may be a timespan or portion of a surgical procedure that is associated with an outcome as described above. At step 1030, process 1000 may include detecting, based on the analyzing, a cause set of frames in the particular surgical footage, the cause set of frames being within a cause phase of the surgical procedure remote in time from the outcome phase. In some embodiments, the outcome phase may include a surgical phase in which the outcome is observable, and the outcome set of frames may be a subset of frames in the outcome phase. The cause phase may be a timespan or portion of the surgical procedure that is associated with a cause of the outcome in the outcome phase. In some embodiments, the cause phase may include a surgical phase in which the cause occurred, and the cause set of frames may be a subset of the frames in the cause phase. The intermediate set of frames may be within an intermediate phase interposed between the cause set of frames and the outcome set of frames. At step 1040, process 1000 may include generating a cause-effect summary of the surgical footage, wherein the cause-effect summary includes the cause set of frames and the outcome set of frames and omits the intermediate set of frames. In some embodiments, the cause-effect summary may be similar to the aggregate of the first group of frames, as described above. Accordingly, the cause-effect summary may include a compilation of video clips associated with the cause set of frames and outcome set of frames. The aggregate of the first group of frames presented to the user, as described above, may include the cause effect summary.

Figure 11:
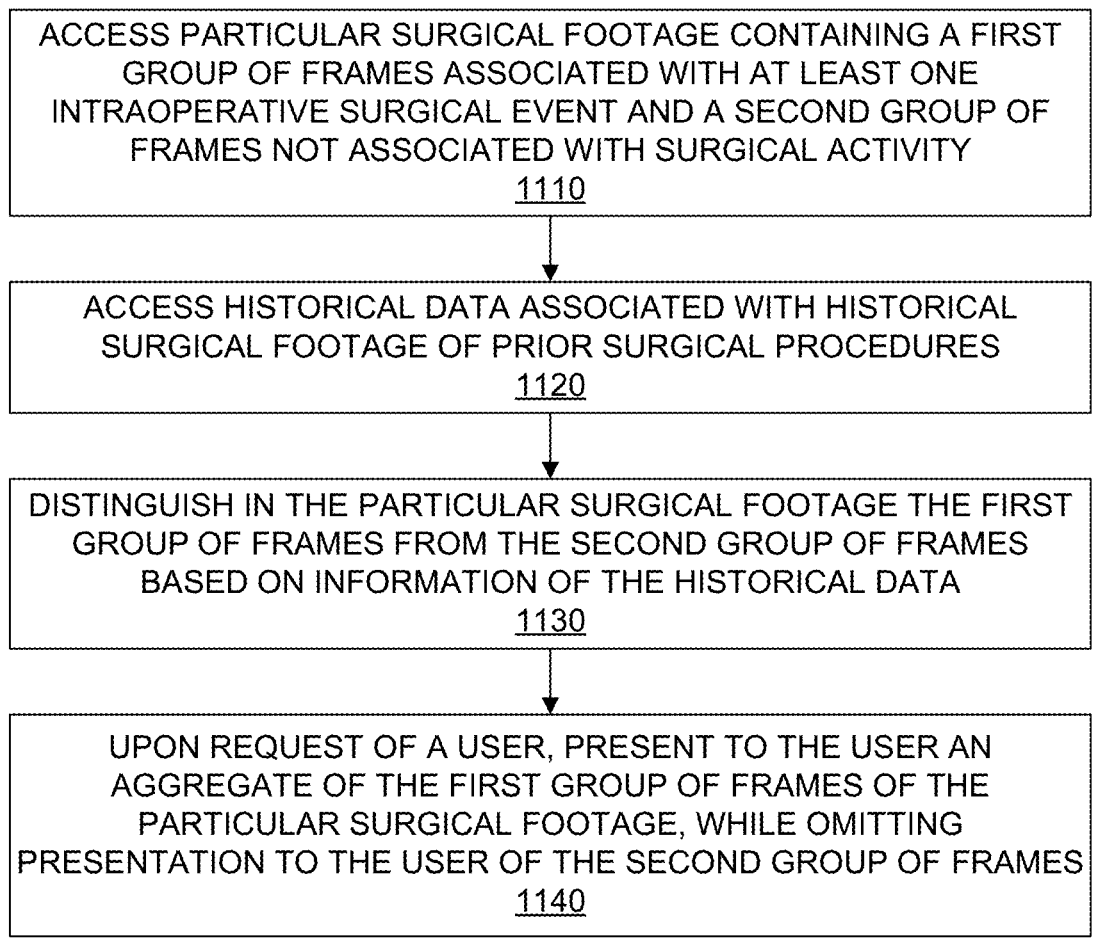
FIG. 11 is a flowchart illustrating an example process for generating surgical summary footage, consistent with the disclosed embodiments.

FIG. 11 is a flowchart illustrating an example process 1100 for generating surgical summary footage, consistent with the disclosed embodiments. Process 1100 may be performed by a processing device. In some embodiments, a non-transitory computer readable medium may contain instructions that when executed by a processor cause the processor to perform process 1100. At step 1110, process 1100 may include accessing particular surgical footage containing a first group of frames associated with at least one intraoperative surgical event and a second group of frames not associated with surgical activity. As discussed in further detail above, the first group of frames may be associated with multiple intraoperative surgical events and may not necessarily be consecutive frames. Further, in some embodiments, the first group of frames may include a cause set of frames and an outcome set of frames, and the second group of frames may include an intermediate set of frames, as discussed above with respect to process 1000.

At step 1120, process 1100 may include accessing historical data based on historical surgical footage of prior surgical procedures, wherein the historical data includes information that distinguishes portions of surgical footage into frames associated with intraoperative surgical events and frames not associated with surgical activity. In some embodiments, the information that distinguishes portions of the historical surgical footage into frames associated with an intraoperative surgical event may include an indicator of at least one of a presence or a movement of a surgical tool and/or an anatomical feature. At step 1130, process 1100 may include distinguishing in the particular surgical footage the first group of frames from the second group of frames based on the information of the historical data.

At step 1140, process 1100 may include, upon request of a user, presenting to the user an aggregate of the first group of frames of the particular surgical footage, while omitting presentation to the user of the second group of frames. The request of the user may be received from a computing device which may include a user interface enabling the user to make the request. In some embodiments, the user may further request frames associated with a particular type or category of intraoperative events. Based on the steps described in process 1100, the user may be presented a summary including frames associated with intraoperative events and omitting frames not associated with surgical activity. The summary may be used, for example, by a surgeon as a training video that aggregates the intraoperative surgical events, while omitting much of the other irrelevant footage.

When preparing for a surgical procedure, it may be beneficial for a surgeon to review video footage of several surgical procedures having similar surgical events. Conventional approaches may not allow a surgeon to easily access video footage of surgical procedures having similar surgical events. Further, even if the footage is accessed, it may be too time consuming to watch the entire video or to find relevant portions of the videos. Therefore, there is a need for unconventional approaches that efficiently and effectively enable a surgeon to view a video compiling footage of surgical events from surgeries performed on different patients.

Aspects of this disclosure may relate to surgical preparation, including methods, systems, devices, and computer readable media. In particular, a compilation video of differing events in surgeries performed on different patients may be presented to a surgeon or other user. The compilation may include excerpts of surgical video of differing intraoperative events from similar surgical procedures, which may be automatically aggregated in a composite form. A surgeon may be enabled to input case-specific information, to retrieve the compilation of video segments selected from similar surgeries on different patients. The compilation may include one intraoperative event from one surgery and other different intraoperative events from one or more second surgeries. For example, different complications that occur when operating on different patients may all be included in one compilation video. In situations where videos of multiple surgical procedures contain the same event with a shared characteristic (e.g., a similar technique employed), the system may omit footage from one or more surgical procedures to avoid redundancy.

For ease of discussion, a method is described below, with the understanding that aspects of the method apply equally to systems, devices, and computer readable media. For example, some aspects of such a method may occur electronically over a network that is either wired, wireless, or both. Other aspects of such a method may occur using non-electronic means. In a broadest sense, the method is not limited to particular physical and/or electronic instrumentalities, but rather may be accomplished using many differing instrumentalities.

Consistent with disclosed embodiments, a method may involve accessing a repository of a plurality of sets of surgical video footage. As used herein, a repository may refer to any storage location or set of storage locations where video footage may be stored electronically. For example, the repository may include a memory device, such as a hard drive and/or flash drive. In some embodiments, the repository may be a network location such as a server, a cloud storage location, a shared network drive, or any other form of storage accessible over a network. The repository may include a database of surgical video footage captured at various times and/or locations. In some embodiments, the repository may store additional data besides the surgical video footage.

As described above, surgical video footage may refer to any video, group of video frames, or video footage including representations of a surgical procedure. For example, the surgical footage may include one or more video frames captured during a surgical operation. A set of surgical video footage may refer to a grouping of one or more surgical videos or surgical video clips. The video footage may be stored in the same location or may be selected from a plurality of storage locations. Although not necessarily so, videos within a set may be related in some way. For example, video footage within a set may include videos, recorded by the same capture device, recorded at the same facility, recorded at the same time or within the same timeframe, depicting surgical procedures performed on the same patient or group of patients, depicting the same or similar surgical procedures, depicting surgical procedures sharing a common characteristic (such as similar complexity level, including similar events, including usages of similar techniques, including usages of similar medical instruments, etc.), or sharing any other properties or characteristics.

The plurality of sets of surgical video footage may reflect a plurality of surgical procedures performed on differing patients. For example, a number of different individuals who underwent the same or similar surgical procedure, or who underwent surgical procedures where a similar technique was employed may be included within a common set or a plurality of sets. Alternatively or in addition, one or more sets may include surgical footage captured from a single patient but at different times. The plurality of surgical procedures may be of the same type, for example, all including appendectomies, or may be of different types. In some embodiments, the plurality of surgical procedures may share common characteristics, such as the same or similar phases or intraoperative events.

The plurality of sets of surgical video footage may further include intraoperative surgical events, surgical outcomes, patient characteristics, surgeon characteristics, and intraoperative surgical event characteristics. Examples of such events, outcomes, and characteristics are described throughout the present disclosure. A surgical outcome may include outcomes of the surgical procedure as a whole (e.g., whether the patient recovered or recovered fully, whether patient was readmitted after discharge, whether the surgery was successful), or outcomes of individual phases or events within the surgical procedure (e.g., whether a complication occurred or whether a technique was successful).

Some aspects of the present disclosure may involve enabling a surgeon preparing for a contemplated surgical procedure to input case-specific information corresponding to the contemplated surgical procedure. A contemplated surgical procedure may include any surgical procedure that has not already been performed. In some embodiments, the surgical procedure may be a planned surgical procedure that the surgeon intends to perform on a patient. In other embodiments the contemplated surgical procedure may be a hypothetical procedure and may not necessarily be associated with a specific patient. In some embodiments, the contemplated surgical procedure may be experimental and may not be in widespread practice. The case-specific information may include any characteristics or properties of the contemplated surgical procedure or of a contemplated or hypothetical patient. For example, the case-specific information may include, but is not limited to, characteristics of the patient the procedure will be performed on, characteristics of the surgeon performing the procedure, characteristics of other healthcare professionals involved in the procedure, the type of procedure being performed, unique details or aspects of the procedure, the type of equipment or tools involved, types of technology involved, complicating factors of the procedure, a location of the procedure, the type of medical condition being treated or certain aspects thereof, a surgical outcome, an intraoperative event outcome, or any other information that may define or describe the contemplated surgical procedure. For example, the case-specific information may include a patient's age, weight, medical condition, vital signs, other physical characteristics, past medical history, family medical history, or any other type of patient-related information that might have some direct or indirect bearing on a potential outcome. The case-specific information may also include an indicator of the performing surgeon's skill level, a surgical technique employed, a complication encountered, or any other information about the surgeon, the procedure, the tools used, or the facility.

The case-specific information may be input in various ways. In some embodiments, the surgeon may input the case-specific information through a graphical user interface. The user interface may include one or more text fields, prompts, drop-down lists, checkboxes or other fields or mechanisms for inputting the information. In some embodiments, the graphical user interface may be associated with the computing device or processor performing the disclosed methods. In other embodiments, the graphical user interface may be associated with an external computing device, such as a mobile phone, a tablet, a laptop, a desktop computer, a computer terminal, a wearable device (including smart watches, smart glasses, smart jewelry, head-mounted displays, etc.), or any other electronic device capable of receiving a user input. In some embodiments, the case-specific information may be input at an earlier time or over a period of time (e.g., several days, several months, several years, or longer). Some or all of the case-specific information may be extracted from a hospital or other medical facility database, an electronic medical record, or any other location that may store patient data and/or other medical data. In some embodiments, the case-specific information corresponding to the contemplated surgical procedure may be received from an external device. For example, the case-specific information may be retrieved or otherwise received from an external computing device, a server, a cloud-computing service, a network device, or any other device external to the system performing the disclosed methods. In one example, at least part of the case-specific information corresponding to the contemplated surgical procedure may be received from an Electronic Health Record (EMR) or from a system handling the EMR (for example, an EMR of a particular patient the procedure will be performed on, an EMR associated with the contemplated surgical procedure, etc.), from a scheduling system, from electronic records corresponding to a medical professional associated with the contemplated surgical procedure or from a system handling the electronic record, and so forth.

In some exemplary embodiments, the case-specific information may include a characteristic of a patient associated with the contemplated procedure. For example, as mentioned earlier, the case-specific information may include characteristics of a contemplated patient. Patient characteristics may include, but are not limited to, a patient's gender, age, weight, height, physical fitness, heart rate, blood pressure, temperature, medical condition or disease, medical history, previous treatments, or any other relevant characteristic. Other exemplary patient characteristics are described throughout the present disclosure. In some embodiments, a characteristic of the patient may be entered directly by the surgeon. For example, a patient characteristic may be entered through a graphical user interface, as described above. In other embodiments, the characteristic of the patient may be retrieved from a database or other electronic storage location. In some embodiments, the characteristic of the patient may be received from a medical record of the patient. For example, a patient characteristic may be retrieved from the medical record or other information source based on an identifier or other information input by the surgeon. For example, the surgeon may enter a patient identifier and the medical record of the patient and/or the patient characteristic may be retrieved using the patient identifier. As describe herein, the patient identifier may be anonymous (e.g., an alphanumeric code or machine readable code) or it may identify the patient in a discernable way (e.g., patient name or social security number). In some examples, the case-specific information may include characteristics of two or more patients associated with the contemplated procedure (for example, for contemplated surgical procedures that involves two or more patients, such as transplants)

In accordance with the present disclosure, the case-specific information may include information relating to a surgical tool. The surgical tool may be any device or instrument used as part of a surgery. Some exemplary surgical tools are described throughout the present disclosure. In some embodiments, the information relating to the surgical tool may include at least one of a tool type or a tool model. A tool type may refer to any classification of the tool. For example, the tool type may refer to the kind of instrument being used (e.g., "scalpel," "scissors," "forceps," "retractor," or other kinds of instruments). Tool type may include various other classifications, such as whether the tool is electronic, whether the tool is used for a minimally invasive surgery, the materials the tool is constructed of, a size of the tool, or any other distinguishing properties. The tool model may refer to the specific make and/or manufacturer of the instrument (e.g., "15921 Halsted Mosquito Forceps").

Embodiments of the present disclosure may further include comparing the case-specific information with data associated with the plurality of sets of surgical video footage to identify a group of intraoperative events likely to be encountered during the contemplated surgical procedure. Data associated with the plurality of sets of surgical videos may include any stored information regarding the surgical video footage. The data may include information identifying intraoperative surgical events, surgical phases, or surgical event characteristics depicted in or associated with the surgical video footage. The data may include other information such as patient or surgeon characteristics, properties of the video (e.g., capture date, file size, information about the capture device, capture location, etc.) or any other information pertaining to the surgical video footage. The data may be stored as tags or other data within the video files. In other embodiments, the data may be stored in a separate file. In some embodiments the surgical video footage may be indexed to associate the data with the video footage. Accordingly, the data may be stored in a data structure, such as data structure 600, described above. In one example, comparing the case-specific information with data associated one or more surgical video footage (for example, with the plurality of sets of surgical video footage) may include calculating one or more similarity measures between the case-specific information and the data associated one or more surgical video footage, for example using one or more similarity functions. Further, in one example, the calculated similarity measures may be compared with selected threshold to determine if an event that occurred in the one or more surgical video footage is likely to occur in the contemplated surgical procedure, for example using a k-Nearest Neighbors algorithm to predict that events commonly occurring the k most similar surgical video footage are likely to be encountered during the contemplated surgical procedure. In some examples, a machine learning model may be trained using training examples to identify intraoperative events likely to be encountered during specific surgical procedures from information related to the specific surgical procedures, and the trained machine learning model may be used to analyze the case-specific information of the contemplated surgical procedure and identify the group of intraoperative events likely to be encountered during the contemplated surgical procedure. An example of such training example may include information related to a particular surgical procedure, together with a label indicating intraoperative events likely to be encountered during the particular surgical procedure.

The group of intraoperative events likely to be encountered during the contemplated surgical procedure may be determined based on the data. For example, the case-specific information may be compared to the data associated with the plurality of sets of surgical video footage. This may include comparing characteristics of the contemplated surgical procedure (as represented in the case-specific information) to identify surgical video footage associated with surgical procedures having the same or similar characteristics. For example, if the case-specific information includes a medical condition of a patient associated with the contemplated procedure, sets of surgical video footage associated with surgical procedures on patients with the same or similar medical conditions may be identified. By way of another example, a surgeon preparing to perform a catheterization on a 73 year old male with diabetes, high cholesterol, high blood pressure, and a family history of heart disease, may enter that case-specific information in order to draw video footage for review of patients sharing similar characteristics (or patients predicted to present similarly to the specific patient). The group of intraoperative events likely to be encountered during the contemplated surgical procedure may include intraoperative surgical events that were encountered during the surgical procedures associated with the identified surgical video footage. In some embodiments, multiple factors may be considered in identifying the surgical video footage and/or the group of intraoperative events likely to be encountered.

Whether an intraoperative event is considered likely to be encountered during the contemplated surgical procedure may depend on how frequently the intraoperative event occurs in surgical procedures similar to the contemplated surgical procedure. For example, the intraoperative event may be identified based on the number of times it occurs in similar procedures, the percentage of times it occurs in similar procedures, or other statistical information based on the plurality of sets of surgical video footage. In some embodiments, intraoperative events may be identified based on comparing the likelihood to a threshold. For example, an intraoperative event may be identified if it occurs in more than 50% of similar surgical procedures, or any other percentage. In some embodiments, the group of intraoperative events may include tiers of intraoperative events based on their likelihood of occurrence. For example, group may include a tier of intraoperative events with a high likelihood of occurrence and one or more tiers of intraoperative events with a lower likelihood of occurrence.

In accordance with some embodiments of the present disclosure, machine learning or other artificial intelligence techniques may be used to identify the group of intraoperative events. Accordingly, comparing the case-specific information with data associated with the plurality of sets of surgical video footage may include using an artificial neural network to identify the group of intraoperative events likely to be encountered during the contemplated surgical procedure. In one example, the artificial neural network may be configured manually, may be generated from a combination of two or more other artificial neural networks, and so forth. In one example, the artificial neural network may be fed training data correlating various case-specific information with intraoperative events likely to be encountered. In some embodiments, the training data may include one or more sets of surgical video footage included in the repository and data associated with the surgical footage. The training data may also include non-video related data, such as patient characteristics or past medical history. Using an artificial neural network, a trained model may be generated based on the training data. Accordingly, using the artificial neural network may include providing the case-specific information to the artificial neural network as an input. As an output of the model, the group of intraoperative events likely to be encountered during the contemplated surgical procedure may be identified. Various other machine learning algorithms may be used, including a logistic regression, a linear regression, a regression, a random forest, a K-Nearest Neighbor (KNN) model (for example as described above), a K-Means model, a decision tree, a cox proportional hazards regression model, a Naïve Bayes model, a Support Vector Machines (SVM) model, a gradient boosting algorithm, or any other form of machine learning model or algorithm.

Some aspects of the present disclosure may further include using the case-specific information and the identified group of intraoperative events likely to be encountered to identify specific frames in specific sets of the plurality of sets of surgical video footage corresponding to the identified group of intraoperative events. The specific frames in specific sets of the plurality of sets of surgical video footage may be locations in the video footage where the intraoperative events occur. For example, if the group of intraoperative events includes a complication, the specific frames may include video footage depicting the complication or otherwise associated with the complication. In some embodiments, the specific frames may include some surgical video footage before or after occurrence of the intraoperative event, for example, to provide context for the intraoperative event. Further, the specific frames may not necessarily be consecutive. For example, if the intraoperative event is an adverse event or outcome, the specific frames may include frames corresponding to the adverse outcome and a cause of the adverse outcome, which may not be consecutive. The specific frames may be identified based on frame numbers (e.g., a frame number, a beginning frame number and an ending frame number, a beginning frame number and a number of subsequent frames, etc.), based on time information (e.g., a start time and stop time, a duration, etc.), or any other manner for identifying specific frames of video footage.

In some embodiments, the specific frames may be identified based on indexing of the plurality of surgical video footage. For example, as described above, video footage may be indexed to correlate footage locations to phase tags, event tags, and or event characteristics. Accordingly, identifying the specific frames in specific sets of the plurality of sets of surgical video footage may include performing a lookup or search for the intraoperative events using a data structure, such as data structure 600 as described in relation to FIG. 6.

In accordance with the present disclosure, the identified specific frames may include frames from the plurality of surgical procedures performed on differing patients. Accordingly, the identified specific frames may form a compilation of footage associated with intraoperative events from surgical procedures performed on different patients, which may be used for surgical preparation. For example, the best video clip examples (in terms of video quality, clarity, representativeness, compatibility with the contemplated surgical procedure, etc.) may be chosen from differing procedures performed on differing patients, and associated with each other so that a preparing surgeon can view the best of a group of video clips, for example without having to separately review video of each case, one by one.

Embodiments of the present disclosure may further include omitting portions of the identified specific frames, for example, to avoid redundancy, to shorten the resulting compilation, to remove less relevant or less informative portions, and so forth. Accordingly, some embodiments may include determining that a first set and a second set of video footage from differing patients contain frames associated with intraoperative events sharing a common characteristic. The first set and second set of video footage may comprise frames of the identified specific frames corresponding to the identified group of intraoperative events. The common characteristic may be any characteristic of the intraoperative events that is relevant to determining whether frames from the first set and the second set should both be included. The common characteristic may be used to determine whether the first set and the second set are redundant. For example, the intraoperative event may be a complication that occurs during the surgical procedure and the common characteristic may be a type of complication. If the complications in first and seconds sets of frames are of the same type, it may not be efficient or beneficial for a surgeon preparing for surgery to view both the first set and second set of frames. Thus, only one set may be chosen for presentation to the surgeon, with the other set being omitted. In some embodiments of the present disclosure, the common characteristic may include a characteristic of the differing patients. For example, the common characteristic may include a patient's age, weight, height, or other demographics, may include patient condition, and so forth. Various other patient characteristics described throughout the present disclosure may also be shared. In other embodiments, the common characteristic may include an intraoperative surgical event characteristic of the contemplated surgical procedure. The intraoperative surgical event characteristic may include any trait or property of the intraoperative event. For example, an adverse outcome of the surgical event, a surgical technique, a surgeon skill level, an identity of a specific surgeon, a physiological response, duration of the event, or any other characteristic or property associated with the event.

According to various exemplary embodiments of the present disclosure, determining that a first set and a second set of video footage from differing patients contain frames associated with intraoperative events sharing a common characteristic may include using an implementation of a machine learning model to identify the common characteristic. In one example, a machine learning model may be trained using training examples to identify frames of video footage having particular characteristics, and the trained machine learning model may be used to analyze the first set and the second set of video footage from differing patients to identify the frames associated with intraoperative events sharing a common characteristic. An example of such training example may include a video clip together with a label indicating particular characteristics of particular frames of the video clip. Various machine learning models are described above and may include a logistic regression model, a linear regression model, a regression model, a random forest model, a K-Nearest Neighbor (KNN) model, a K-Means model, a decision tree, a cox proportional hazards regression model, a Naïve Bayes model, a Support Vector Machines (SVM) model, a gradient boosting algorithm, a deep learning model, or any other form of machine learning model or algorithm. Some embodiments of the present disclosure may further include using example video footage to train the machine learning model to determine whether two sets of video footage share the common characteristic, and wherein implementing the machine learning model includes implementing the trained machine learning model. In one example, the example video footage may be training footage, which may include pairs of sets of video footage known to share the common characteristic. The trained machine learning model may be configured to determine whether two sets of video footage share the common characteristic.

The disclosed embodiments may further include omitting an inclusion of the second set from a compilation to be presented to the surgeon and including the first set in the compilation to be presented to the surgeon. As used herein, a compilation may include a series of frames that may be presented for continuous and/or consecutive playback. In some embodiment, the compilation may be stored as a separate video file. In other embodiments, the compilation may be stored as instructions to present the series of frames from their respective surgical video footage, for example, stored in the repository. The compilation may include additional frames besides those included in the first set, including other frames from the identified specific frames.

Some aspects of the present disclosure may further include enabling the surgeon to view a presentation including the compilation containing frames from the differing surgical procedures performed on differing patients. The presentation may be any form of visual display including the compilation of frames. In some embodiments the presentation may be a compilation video. The presentation may include other elements, such as menus, controls, indices, timelines, or other content in addition to the compilation. In some embodiments, enabling the surgeon to view the presentation may include outputting data for displaying the presentation using a display device, such as a screen (e.g., an OLED, QLED LCD, plasma, CRT, DLPT, electronic paper, or similar display technology), a light projector (e.g., a movie projector, a slide projector), a 3D display, smart glasses, or any other visual presentation mechanism, with or without audio presentation. In other embodiments, enabling the surgeon to view the presentation may include storing the presentation in a location that is accessible by one or more other computing devices. Such storage locations may include a local storage (such as a hard drive of flash memory), a network location (such as a server or database), a cloud computing platform, or any other accessible storage location. Accordingly, the presentation may be accessed from an external device to be displayed on the external device. In some embodiments, outputting the video may include transmitting the video to an external device. For example, enabling the surgeon to view the presentation may include transmitting the presentation through a network to a user device or other external device for playback on the external device.

The presentation may stitch together disparate clips from differing procedures, presenting them to the surgeon in the chronological order in which they might occur during surgery. The clips may be presented to play continuously, or may be presented in a manner requiring the surgeon to affirmatively act in order for a succeeding clip to play. In some instances where it may be beneficial for the surgeon to view multiple alternative techniques or to view differing responses to adverse events, multiple alternative clips from differing surgical procedures may be presented sequentially.

Some embodiments of the present disclosure may further include enabling a display of a common surgical timeline including one or more chronological markers corresponding to one or more of the identified specific frames along the presentation. For example, the common surgical timeline may be overlaid on the presentation, as discussed above. An example surgical timeline 420 including chronological markers is shown in FIG. 4. The chronological markers may correspond to markers 432, 434, and/or 436. Accordingly, the chronological markers may correspond to a surgical phase, an intraoperative surgical event, a decision making junction, or other notable occurrences the identified specific frames along the presentation. The markers may be represented as shapes, icons, or other graphical representations along the timeline, as described in further detail above. The timeline may be presented together with frames associated with a surgery performed on a single patient, or may be presented together with a compilation of video clips from surgeries performed on a plurality of patients.

In accordance with some embodiments of the present disclosure, enabling the surgeon to view the presentation may include sequentially displaying discrete sets of video footage of the differing surgical procedures performed on differing patients. Each discrete set of video footage may correspond to a different surgical procedure performed on a different patient. In some embodiments, sequentially displaying the discrete sets of video footage may appear to the surgeon or another user as a continuous video. In other embodiments playback may stop or pause between the discrete sets of video footage. The surgeon or other user may manually start the next set of video footage in the sequence.

In accordance with some embodiments of the present disclosure, the presentation may include a display of a simulated surgical procedure based on the identified group of intraoperative events likely to be encountered and/or the identified specific frames in specific sets of the plurality of sets of surgical video footage corresponding to the identified group of intraoperative events. For example, a machine learning algorithm (such as a Generative Adversarial Network) may be used to train a machine learning model (such as an artificial neural network, a deep learning model, a convolutional neural network, etc.) using training examples to generate simulations of surgical procedures based on groups of intraoperative events and/or frames of surgical video footage, and the trained machine learning model may be used to analyze the identified group of intraoperative events likely to be encountered and/or the identified specific frames in specific sets of the plurality of sets of surgical video footage corresponding to the identified group of intraoperative events and generate the simulated surgical procedure.

In some embodiments, sequentially displaying discrete sets of video footage may include displaying an index of the discrete sets of video footage enabling the surgeon or other user to select one or more of the discrete sets of video footage. The index may be a text-based index, for example, listing intraoperative events, surgical phases, or other indicators of the different discrete sets of video footage. In other embodiments, the index may be a graphical display, such as a timeline as described above, or a combination of graphical and textual information. For example, the index may include a timeline parsing the discrete sets into corresponding surgical phases and textual phase indicators. In such embodiments, the discrete sets may correspond to different surgical phases of the surgical procedure. The discrete sets may be displayed using different colors, with different shading, with bounding boxes or separators, or other visual indicators to distinguish the discrete sets. The textual phase indicators may describe or otherwise identify the corresponding surgical phase. The textual phase indicators may be displayed within the timeline, above the timeline, below the timeline or in any location such that they identify the discrete sets. In some embodiments, the timeline may be displayed in a list format and the textual phase indicators may be included within the list.

In accordance with the present disclosure, the timeline may include an intraoperative surgical event marker corresponding to an intraoperative surgical event. The intraoperative surgical event marker may correspond to an intraoperative surgical event associated with a location in the surgical video footage. The surgeon may be enabled to click on the intraoperative surgical event marker to display at least one frame depicting the corresponding intraoperative surgical event. For example, clicking on the intraoperative surgical event may cause a display of the compilation video to skip to a location associated with the selected marker. In some embodiments, the surgeon may be able to view additional information about the event or occurrence associated with the marker, which may include information summarizing aspects of the procedure or information derived from past surgical procedures, as described in greater detail above. Any of the features or functionality described above with respect to timeline overlay on surgical video may also apply to the compilation videos described herein.

Embodiments of the present disclosure may further include training a machine learning model to generate an index of the repository based on the intraoperative surgical events, the surgical outcomes, the patient characteristics, the surgeon characteristics, and the intraoperative surgical event characteristics and generating the index of the repository. Comparing the case-specific information with data associated with the plurality of sets may include searching the index. The various machine learning models described above, including a logistic regression model, a linear regression model, a regression model, a random forest model, a K-Nearest Neighbor (KNN) model, a K-Means model, a decision tree, a cox proportional hazards regression model, a Naïve Bayes model, a Support Vector Machines (SVM) model, a gradient boosting algorithm, a deep learning model, or any other form of machine learning model or algorithm may be used. A training data set of surgical video footage with known intraoperative surgical events, surgical outcomes, patient characteristics, surgeon characteristics, and intraoperative surgical event characteristics may be used to train the model. The trained model may be configured to determine intraoperative surgical events, surgical outcomes, patient characteristics, surgeon characteristics, and intraoperative surgical event characteristics based on additional surgical video footage not included in the training set. When applied to surgical video footage in the repository, the video footage may be tagged based on the identified properties. For example, the video footage may be associated with a footage location, phase tag, event location, and/or event tag as described above with respect to video indexing. Accordingly, the repository may be stored as a data structure, such as data structure 600, described above.

FIG. 12 is a flowchart illustrating an example process 1200 for surgical preparation, consistent with the disclosed embodiments. Process 1200 may be performed by a processing device, such as one or more collocated or dispersed processors as described herein. In some embodiments, a non-transitory computer readable medium may contain instructions that when executed by a processor cause the processor to perform process 1200. Process 1200 is not necessarily limited to the steps shown in FIG. 1200 and any steps or processes of the various embodiments described throughout the present disclosure may also be included in process 1200. At step 1210, process 1200 may include accessing a repository of a plurality of sets of surgical video footage reflecting a plurality of surgical procedures performed on differing patients. The plurality of sets of surgical video footage may include intraoperative surgical events, surgical outcomes, patient characteristics, surgeon characteristics, and intraoperative surgical event characteristics. In some embodiments, the repository may be indexed, for example using process 800, to facilitate retrieval and identification of the plurality of sets of surgical video footage.

At step 1220, process 1200 may include enabling a surgeon preparing for a contemplated surgical procedure to input case-specific information corresponding to the contemplated surgical procedure. As described above, the contemplated surgical procedure may be a planned procedure, a hypothetical procedure, an experimental procedure, or another procedure that has not yet occurred. The case-specific information may be manually input by the surgeon, for example through a user interface. In some embodiments, some or all of the case-specific information may be received from a medical record of the patient. The case-specific information may include a characteristic of a patient associated with the contemplated procedure, information includes information relating to a surgical tool (e.g., a tool type, a tool model, a tool manufacturer, etc.), or any other information that may be used to identify relevant surgical video footage.

At step 1230, process 1200 may include comparing the case-specific information with data associated with the plurality of sets of surgical video footage to identify a group of intraoperative events likely to be encountered during the contemplated surgical procedure. The group of intraoperative events likely to be encountered may be determined, for example, based on machine learning analyses performed on historical video footage, historical data other than video data, or any other form of data from which a prediction may be derived. At step 1240, process 1200 may include using the case-specific information and the identified group of intraoperative events likely to be encountered to identify specific frames in specific sets of the plurality of sets of surgical video footage corresponding to the identified group of intraoperative events. The identified specific frames may include frames from the plurality of surgical procedures performed on differing patients, as described earlier.

At step 1250, process 1200 may include determining that a first set and a second set of video footage from differing patients contain frames associated with intraoperative events sharing a common characteristic, as described earlier. At step 1260, process 1200 may include omitting an inclusion of the second set from a compilation to be presented to the surgeon and including the first set in the compilation to be presented to the surgeon, as described earlier.

At step 1270, process 1200 may include enabling the surgeon to view a presentation including the compilation containing frames from the differing surgical procedures performed on differing patients. As described above, enabling the surgeon to view the presentation may include outputting data to enable displaying the presentation on a screen or other display device, storing the presentation in a location accessible to another computing device, transmitting the presentation, or any other process or method that may cause the enable the presentation and/or compilation to be viewed.

When preparing for a surgical procedure, it may be beneficial for a surgeon to review video footage of past surgical procedures. However, in some instances, only particularly complex portions of the surgical procedures may be relevant to the surgeon. Using conventional approaches, it may be too difficult and time consuming for a surgeon to identify portions of a surgical video based on the complexity of the procedure. Therefore, there is a need for unconventional approaches for efficiently and effectively analyzing complexity of surgical footage and enabling a surgeon to quickly review relevant portions of a surgical video.

Aspects of this disclosure may relate to surgical preparation, including methods, systems, devices, and computer readable media. In particular, when preparing for a surgical procedure, surgeons may wish to view portions of surgical videos that have particular complexity levels. For example, within a generally routine surgical video, a highly skilled surgeon may wish to view only a single event that was unusually complex. Finding the appropriate video and the appropriate location in the video, however, can be time consuming for the surgeon. Accordingly, in some embodiments, methods and systems for analyzing complexity of surgical footage are provided. For example, the process of viewing surgical video clips based on complexity may be accelerated by automatically tagging portions of surgical video with a complexity score, thereby permitting a surgeon to quickly find the frames of interest based on complexity.

For ease of discussion, a method is described below, with the understanding that aspects of the method apply equally to systems, devices, and computer readable media. For example, some aspects of such a method may occur electronically over a network that is either wired, wireless, or both. Other aspects of such a method may occur using non-electronic means. In a broadest sense, the method is not limited to particular physical and/or electronic instrumentalities, but rather may be accomplished using many differing instrumentalities.

Consistent with disclosed embodiments, a method may involve analyzing frames of the surgical footage to identify in a first set of frames an anatomical structure. As described above, surgical footage may refer to any video, group of video frames, or video footage including representations of a surgical procedure. For example, the surgical footage may include one or more video frames captured during a surgical operation. The first set of frames may be a grouping of one or more frames included within the surgical footage. In some embodiments, the first set of frames may be consecutive frames, however, this is not necessarily true. For example, the first set of frames may include a plurality of groups of consecutive frames.

As discussed above, an anatomical structure may be any particular part of a living organism, including, for example organs, tissues, ducts, arteries, cells, or other anatomical parts. The first set of frames may be analyzed to identify the anatomical structure using various techniques, for example as described above. In some embodiments, the frames of the surgical footage may be analyzed using object detection algorithms, as described above. For example, the object detection algorithms may be detected objects based on one or more of appearance, image features, templates, and so forth. In some embodiments, identifying the anatomical structure in a first set of frames includes using a machine learning model trained to detect anatomical structures, for example as described above. For example, images and/or videos along with identifications of anatomical structures known to be depicted in the images and/or videos may be input into a machine learning model as training data. As a result, the trained model may be used to analyze the surgical footage to identify in the first set of frames, an anatomical structure. For example, an artificial neural network configured to identify anatomical structures in images and/or videos may be used to analyze the surgical footage to identify in the first set of frames an anatomical structure. Various other machine learning algorithms may be used, including a logistic regression, a linear regression, a regression, a random forest, a K-Nearest Neighbor (KNN) model, a K-Means model, a decision tree, a cox proportional hazards regression model, a Naïve Bayes model, a Support Vector Machines (SVM) model, a gradient boosting algorithm, a deep learning model, or any other form of machine learning model or algorithm.

Some aspects of the present disclosure may further include accessing first historical data, the first historical data being based on an analysis of first frame data captured from a first group of prior surgical procedures. Generally, frame data may include any image or video data depicting surgical procedures as described herein. The first historical data and/or the first frame data may be stored on one or more storage locations. Accordingly, accessing the first historical data may include retrieving the historical data from a storage location. In other embodiments, accessing the first historical data may include receiving the first historical data and/or the first frame data, for example, from an image capture device or a computing device. Consistent with embodiments of the present disclosure, accessing the first historical data may include retrieving or receiving the first frame data and analyzing the first frame data to identify the first historical data.

Historical data may be any information pertaining to prior surgical procedures. Some non-limiting examples of such historical data are described above. In some embodiments, the first historical data may include complexity information associated with the first group of prior surgical procedures. The complexity information may include any data indicating a complexity level of the surgery, as discussed further below. The first historical data may include any other information pertaining to the first group of surgical procedures that may be gleaned from the first frame data. For example, the first frame data may include or indicate information associated with the prior surgical procedures, including anatomical structures involved, medical tools used, types of surgical procedures performed, intraoperative events (including adverse events) occurring in the procedures, medical conditions exhibited by the patient, patient characteristics, surgeon characteristics, skill levels of surgeons or other healthcare professionals involved, timing information (e.g., duration of interactions between medical tools and anatomical structures, duration of a surgical phase or intraoperative event, time between appearance of a medical tool and a first interaction between the medical tool and an anatomical structure, or other relevant duration or timing information), a condition of an anatomical structure, a number of surgeons or other healthcare professionals involved, or any other information associated with the prior surgical procedures.

In embodiments where the first historical data includes complexity information, such information may be indicative of or associated with the complexity of a surgical procedure or a portion thereof. For example, the first historical data may include an indication of a statistical relation between a particular anatomical structure and a particular surgical complexity level. The statistical relation may be any information that may indicate some correlation between the particular surgical complexity level and the particular anatomical structure. For example, when a particular vessel is exposed in a surgical procedure, a particular portion of an organ is lacerated, or a particular amount of blood is detected, such events may statistically correlate to a surgical complexity level. Similarly, detection of a high volume of fat or a poor condition of an organ may also correlate to a complexity level. These are just examples, any condition or event that correlates to surgical complexity may serve as an indication of surgical complexity In some embodiments, the first historical data may be identified from the first frame data using one or more image or video analysis algorithms, including object detection algorithms and/or motion detection algorithms. In other embodiments, the first historical data may be identified from the first frame data using a machine learning model trained to identify historical data based on frame data. For example, a machine learning model may be trained using training examples to identify historical data (as described above) from frame data, and the trained machine learning model may be used to analyze the first frame data to determine the first historical data. An example of such training example may include an image and/or a video depicting a surgical procedure or a portion of a surgical procedure, together with a label indicating the complexity level of the surgical procedure or of the portion of a surgical procedure. For example, such label may be generated manually, may be generated by a different process, may be read from memory, and so forth.

Embodiments of the present disclosure may involve analyzing the first set of frames using the first historical data and using the identified anatomical structure, to determine a first surgical complexity level associated with the first set of frames. As used herein, a complexity level may be a value or other classifier indicating a relative complexity of a surgical procedure or portion of a surgical procedure. For example, the complexity may be based on a difficulty of the surgical procedure relative to other surgical procedures. The difficulty may be based on the surgeon skill level required to perform one or more techniques involved in the surgical procedure, a likelihood of occurrence of an adverse event (such as tear, a bleed, an injury, or other adverse events), a success rate of the surgical procedure, or any other indicator of difficulty of the procedure. Surgical procedures with higher relative difficulty levels may be associated with higher complexity levels.

As another illustrative example, the complexity level may be based on a duration or time requirement for completing the surgical procedure or portions thereof. For example, procedures or techniques requiring longer performance times may be considered more complex and may be associated with a higher complexity level. As another example, the complexity level may be based on the number of steps required to perform the surgical procedure or portions thereof. For example, procedures or techniques requiring more steps may be considered more complex and may be associated with a higher complexity level. In some embodiments, the complexity level may be based on the type of surgical techniques or procedures being performed. Certain techniques or procedures may have a predetermined complexity and the complexity level may be based on the complexity of the techniques or procedures involved. For example, a cholecystectomy may be considered more complex than an omentectomy and, accordingly, surgical procedures involving the cholecystectomy may be assigned a higher complexity level. Other factors that may be relevant to a complexity level may include information relating to disease severity, complicating factors, anatomical structures involved, types of medical tools used, types of surgical procedures performed, intraoperative events (including adverse events) occurring in the procedures, a physiological response of the patient, a medical condition exhibited by the patient, patient characteristics, surgeon characteristics, a skill level of a surgeon or other healthcare provider involved, timing information (e.g., duration of interactions between medical tools and anatomical structures, a duration of a surgical phase or intraoperative event, time between appearance of a medical tool and a first interaction between the medical tool and an anatomical structure, or other relevant duration or timing information), a condition of an anatomical structure, a number of surgeons or other healthcare professionals involved, or any other information associated with the prior surgical procedures. A surgical complexity level may not be limited to any of the examples above and may be based on a combination of factors, including the examples provided above.

The surgical complexity level may be represented in various manners. In some embodiments, the complexity level may be represented as a value. For example, the surgical complexity level may be a value within a range of values corresponding to a scale of complexity (e.g., 0-5, 0-10, 0-100, or any other suitable scale). A percentage or other score may also be used. Generally, a higher value may indicate a higher complexity level, however, in some embodiments, the surgical complexity may be an inverse of the value. For example, a complexity level of 1 may indicate a higher complexity than a complexity level of 7. In other embodiments, the complexity level may be represented as a text-based indicator of complexity. For example, the first set of frames may be assigned a complexity level of "high complexity," "moderate complexity," "low complexity," or various other classifiers. In some embodiments, the surgical complexity level may correspond to a standardized scale or index used to represent surgical complexities. The surgical complexity level may be specific to a particular type of surgical procedure (or a subset of surgical procedure types), or may be a universal complexity level applicable to any surgical procedure.

As mentioned above, the first surgical complexity level may be determined by analyzing the first set of frames using historical data. Analyzing the first set of frames may include any process for determining the complexity level based on information included in the first set of frames. Examples of analysis for determining surgical complexity levels are provided in greater detail below.

Further, the first surgical complexity level may be determined using the identified anatomical structure. In some embodiments, a type of anatomical structure involved in the procedure may be at least partially indicative of the surgical complexity level. For example, procedures performed on certain anatomical structures (e.g., anatomical structures associated with the brain or heart of a patient) may be considered more complex. In some embodiments, the condition of the anatomical structure may also be relevant to determining the complexity level, as discussed in more detail below.

Some aspects of the present disclosure may involve analyzing frames of the surgical footage to identify in a second set of frames a medical tool, the anatomical structure, and an interaction between the medical tool and the anatomical structure. For example, the second set of frames may indicate a portion of the surgical footage in which a surgical operation is being performed on the anatomical structure. A medical tool may include any apparatus or equipment used as part of a medical procedure. In some embodiments, the medical tool may be a surgical tool, as discussed above. For example, the medical tool may include, but is not limited to, cutting instruments, grasping and/or holding instruments, retractors, tissue unifying instruments and/or materials, protective equipment, laparoscopes, endoscopes, patient monitoring devices, patient imaging devices, or similar tools. As discussed above, the interaction may include any action by the medical instrument that may influence the anatomical structure, or vice versa. For example, the interaction may include a contact between the medical instrument and the anatomical structure, an action by the medical instrument on the anatomical structure (such as cutting, clamping, grasping, applying pressure, scraping, etc.), a physiological response by the anatomical structure, or any other form of interaction.

As with the first set of frames, the second set of frames may be a grouping of one or more frames included within the surgical footage. The second set of frames may be consecutive frames, or may include a plurality of groups of consecutive frames. In some embodiments, the first set of frames and the second set of frames may be completely distinct. In other embodiments, the first set of frames and the second set of frames may include at least one common frame appearing in both the first set of frames and the second set of frames. As with the first set of frames, the second set of frames may be analyzed to identify the medical tool, the anatomical structure, and the interaction between the medical tool and the anatomical structure using various techniques. In some embodiments, the frames of the surgical footage may be analyzed using object detection algorithms (e.g. appearance-based detection algorithms, image feature based detection algorithms, template based detection algorithms, etc.) and/or motion detection algorithms. In some embodiments, identifying the medical tool, the anatomical structure, and the interaction between the medical tool and the anatomical structure in the second set of frames may include using a machine learning model trained to detect medical tools, anatomical structures, and interactions between medical tools and anatomical structures. For example, a machine learning model may be trained using training examples to detect medical tools and/or anatomical structures and/or interactions between medical tools and anatomical structures from images and/or videos, and the trained machine learning model may be used to analyze the second set of frames to detect the medical tools and/or the anatomical structures and/or the interactions between medical tools and anatomical structures. An example of such training example may include an image and/or a video clip of a surgical procedure, together with a label indicating at least one of a medical tool depicted in the image and/or in the video clip, an anatomical structure depicted in the image and/or in the video clip, and an interaction between a medical tool and an anatomical structure depicted in the image and/or in the video clip.

In some exemplary embodiments, identifying the anatomical structure in the first set of frames may be based on an identification of a medical tool and a first interaction between the medical tool and the anatomical structure. In some embodiments, the medical tool identified in the first set of frames may be the same tool as the medical tool identified in the second set of frames. Accordingly, the interaction between the medical tool and the anatomical structure in the second set of frames may be a later interaction between the medical tool and the anatomical structure. This may be helpful, for example, in determining a time between the first interaction and the later interaction, which may be at least partially indicative of a surgical complexity level.

Embodiments of the present disclosure may further include accessing second historical data, the second historical data being based on an analysis of second frame data captured from a second group of prior surgical procedures. In some embodiments, the first group of prior surgical procedures and the second group of prior surgical procedures may be of a same type. For example, first historical data and second historical data may relate to a first group of appendectomies and a second group of appendectomies, respectively. A first group and second group may differ according to a characteristic. By way of one non-limiting example, the first group may involve patients exhibiting peritonitis, and the second group may include patients who did not exhibit peritonitis.

In some embodiments, first frame data and second frame data may be identical (i.e., the first historical data and the second historical data may be based on the same frame data). For example, first historical data and second historical data may be based on different analysis of the same frame data. As an illustrative example, first frame data may include estimates of surgical contact force not included in second frame data, consistent with the present embodiments. In some embodiments, first historical data and second historical data may be based on different subsets of the same frame data (e.g., different surgical phases and/or different surgical procedures).

In some embodiments, the first frame data and the second frame data may be different (i.e., accessed or stored in different data structures). For example, different frames of the same surgical procedures may be analyzed to generate the first historical data than the second historical data.

In other embodiments the first group of prior surgical procedures and the second group of prior surgical procedures may be different in at least one aspect. For example, the first and second group may include appendectomies but may differ in that the first group includes appendectomies in which an abnormal fluid leakage event was detected while no abnormal fluid leakage events were detected in the second group. In some embodiments, the first group of prior surgical procedures and the second group of prior surgical procedures may have at least one surgical procedure in common (e.g., both groups may include an incision). In other embodiments, however, the first group of prior surgical procedures and the second group of prior surgical procedures may have no surgical procedures in common.

In some embodiments, a method may include tagging a first set of frames with a first complexity level, tagging a second set of frames with the second complexity level, and storing first set of frames with the first tag and the second set of frames with the second tag in a data structure. This may enable a surgeon to select the second complexity level, and thereby cause the second set of frames to be displayed, while omitting a display of the first set of frames. In some embodiments, a method may include receiving a selection of a complexity level (e.g., receiving a selection based on user input to an interface). Further, a method may include accessing a data structure to retrieve selected frames. A method may include displaying frames tagged with the selected complexity level while omitting frames tagged without the selected complexity level.

Similar to the first historical data and frame data, the second historical data and frame data may be stored in one or more storage locations. In some embodiments, the second historical data may be stored in the same storage location as the first historical data. In other embodiments, the first and second historical data may be stored in separate locations. Consistent with other embodiments, accessing the first historical data may include receiving the second historical data and/or the second frame data, for example from an image capture device or a computing device. Further as with the first historical data, accessing the second historical data may include retrieving or receiving the second frame data and analyzing the second frame data to identify the second historical data. In some embodiments, the first historical data and the second historical data may be identical. In other embodiments, the first historical data and the second historical data may be different. The second historical data may include information pertaining to the second frame data, similar to the first historical data, as discussed above. The second historical data may include any of the information described above with respect to the first historical data, such as medical tool information, anatomical structure information, and/or associated complexity information. In embodiments where the second historical data includes complexity information, such information may be indicative of or associated with the complexity information. For example, the second historical data may include an indication of a statistical relation between a particular anatomical structure and a particular surgical complexity level.

Some aspects of the present disclosure may involve analyzing the second set of frames using the second historical data and using the identified interaction to determine a second surgical complexity level associated with the second set of frames. The second surgical complexity level may be similar to the first surgical complexity level and thus may be based on one or more of the example factors provided above with respect to the first surgical complexity level. In some embodiments, the second surgical complexity level may be represented in the same form as the first surgical complexity level (e.g., as a value within the same scale, etc.), however, a different form of representation may be used in some embodiments.

Consistent with embodiments of the present disclosure, the first and second surgical complexity levels may be determined according to various methods. In some embodiments, the disclosed embodiments may include using a machine learning model trained to identify surgical complexity levels using frame data captured from prior surgical procedures to determine at least one of the first surgical complexity level or the second surgical complexity level. For example, a machine learning model may be developed using a machine learning algorithm. Training data, which may include frame data captured from prior surgical procedures and labels indicating surgical complexity levels known to correspond to the frame data, may be supplied to a machine learning algorithm to develop the trained model. The machine learning algorithm may include a logistic regression, a linear regression, a regression, a random forest, a K-Nearest Neighbor (KNN) model, a K-Means model, a decision tree, a cox proportional hazards regression model, a Naïve Bayes model, a Support Vector Machines (SVM) model, an artificial neural network, a gradient boosting algorithm, or any other form of machine learning model or algorithm. Accordingly, the first historical data may include a machine learning model trained using the first frame data captured from the first group of prior surgical procedures. Similarly, the second historical data may comprise a machine learning model trained using the second frame data captured from the second group of prior surgical procedures. As a result, the trained model, when provided the first set of frames and the second set of frames, may be configured to determine the first and second surgical complexity levels, respectively.

In some exemplary embodiments, at least one of determining the first complexity level or second complexity level may be based on a physiological response. As discussed above, the physiological response may include any physical or anatomical condition or reaction of the patient resulting, either directly or indirectly, from the surgical procedure. For example, the physiological response may include, a change in heart rate, a physical movement, a failure or decrease in function of one or more organs, a change in body temperature, a spoken reaction of the patient, a change in brain activity, a change in respiratory rate, a change in perspiration, a change in blood oxygen level, a change in heart function, activation of the sympathetic nervous system, an endocrine response, cytokine production, acute phase reaction, neutrophil leukocytosis, lymphocyte proliferation, or any other physical change in response to the surgical procedure. In some embodiments, the physiological response may be indicative of the surgical complexity level. For example, surgical procedures that trigger a certain physiological response may be considered more complex and thus may have a higher complexity level rating. For example, a machine learning model may be trained using training examples to identify physiological responses from images and/or videos, the trained machine learning model may be used to analyze the first set of frames to identify a first physiological response and/or to analyze the second set of frames to identify a second physiological response, and the first surgical complexity level may be determined based on the identified first physiological response and/or the second surgical complexity level may be determined based on the identified second physiological response. An example of such training example may include an image and/or a video clip of a surgical procedure, together with a label indicating a physiological response depicted in the image and/or the video clip.

In some exemplary embodiments, determining at least one of the first surgical complexity level or the second surgical complexity level may be based on a condition of the anatomical structure, as mentioned above. By way of example, the condition may involve a detected deterioration of the anatomical structure, a tear, bleeding, swelling, discoloration, distortion, or any properties of the anatomical structure reflective of its current state. In some embodiments, the condition of the anatomical structure may include a medical condition affecting the anatomical structure. This medical condition may indicate the purpose or type of surgical procedure being performed and thus may indicate an associated complexity level. For example, if a gallbladder exhibits large polyps, this may indicate that a cholecystectomy is involved in the surgical procedure, which may be useful for determining the complexity level. In other embodiments, the medical condition may indicate one or more complicating factors associated with the surgical procedure. For example, hemorrhaging occurring at the anatomical structure may indicate complications that have arisen during the surgical procedure, which may affect the surgical complexity level. Alternatively, or additionally, the medical condition itself may be associated with a certain complexity level. In some embodiments, the condition of the anatomical structure may be a state of the anatomical structure based on the current stage or phase of the surgical procedure. For example, an incision made in the anatomical structure may impact the condition of the anatomical structure and thus change a complexity level as compared to a complexity level before the incision. For example, a machine learning model may be trained using training examples to identify condition of anatomical structures from images and/or videos, the trained machine learning model may be used to analyze the first set of frames to identify a first condition of a first anatomical structure and/or to analyze the second set of frames to identify a second condition of a second anatomical structure (while may be the same as the first anatomical structure or a different anatomical structure), and the first surgical complexity level may be determined based on the identified first condition and/or the second surgical complexity level may be determined based on the identified second condition. An example of such training example may include an image and/or a video clip of an anatomical structure, together with a label indicating a condition of the anatomical structure.

In some embodiments of the present disclosure, determining at least one of the first surgical complexity level or the second surgical complexity level may be based on a patient characteristic. Patient characteristics may include, but are not limited to, age, gender, weight, height, Body Mass Index (BMI), menopausal status, typical blood pressure, characteristics of the patient genome, educational status, level of education, economical status, level of income, level of occupation, type of insurance, health status, self-rated health, functional status, functional impairment, duration of disease, severity of disease, number of illnesses, illness characteristics (such as type of illness, size of tumor, histology grade, number of infiltrated lymph nodes, etc.), utilization of health care, number of medical care visits, medical care visit intervals, regular source of medical care, family situation, marital status, number of children, family support, ethnicity, race, acculturation, religious, type of religion, native language, characteristics of past medical test performed on the patient (such as type of test, time of test, results of test, etc.), characteristics of past medical treatments performed on the patient (such as type of treatment, time of treatment, results of treatment, etc.), or any other relevant characteristic. Other example patient characteristics are described throughout the present disclosure. These characteristics may be correlated with certain levels of surgical complexity. For example, an older and/or overweight patient may be associated with surgical procedures having higher complexities than patients that are younger or in better physical shape.

In accordance with some embodiments, determining at least one of the first surgical complexity level or the second surgical complexity level may be based on a skill level of a surgeon associated with the surgical footage. For example, if a surgeon depicted in surgical footage has a low skill level, then a procedure that might ordinarily be considered as having a low complexity may be made more complex as the result of the reduced performance skill. Thus, as discussed above, the skill level may be an indication of the surgeon's ability to perform the surgical procedure or specific techniques within the surgical procedure. In some embodiments, the skill level may relate to past performances of the surgeon, a type and/or level of training or education the surgeon has received, a number of surgeries the surgeon has performed, types of surgeries surgeon has performed, qualifications of the surgeon, years of experience of the surgeon, ratings of the surgeon from patients or other healthcare professionals, past surgical outcomes, past surgical complications, or any other information relevant to assessing the skill level of a surgeon. Alternatively or additionally, the skill level of the surgeon may be determined through computer analysis of video footage. For example, artificial intelligence can be used to classify a surgeon's skill level, as discussed in greater detail below. While the skill level is described herein as the skill level of a surgeon, in some embodiments the skill level may be associated with another healthcare professional, such as anesthesiologists, nurses, Certified Registered Nurse Anesthetist (CRNA), surgical technicians, residents, medical students, physician assistants, or any other healthcare professional. Thus, reference to a surgeon as used throughout this disclosure is a shorthand for any relevant medical professional.

Some embodiments of the present disclosure may further include determining a level of skill demonstrated by a healthcare provider in the surgical footage. At least one of determining the first complexity level or second complexity level may be based on the determined level of skill demonstrated by the healthcare provider. The skill level of the healthcare provider may be determined based on analysis of the first or second set of frames using image and/or video analysis algorithms, such as object and/or motion detection algorithms. For example, the healthcare provider may perform one or more techniques in a manner that demonstrates a certain level of skill. In one example, a machine learning model may be trained using training examples to determine skill levels of healthcare providers from images and/or videos, and the trained machine learning model may be used to analyze the surgical footage and determine the level of skill demonstrated by the healthcare provided in the surgical footage. An example of such training example may include a video clip depicting a portion of a surgical procedure, together with a label indicating the level of skill demonstrated in the video clip. In other embodiments, the skill level may be determined based on an identity of the healthcare provider in the surgical footage. For example, based on the identity of a surgeon, an associated skill level may be determined from an external source, such as a database including skill level information for various surgeons. Accordingly, one or more facial recognition algorithms may be used to identify the healthcare provider, and the identity of the healthcare provider may be used to determine the healthcare provider skill level.

In some exemplary embodiments, determining at least one of the first surgical complexity level or the second surgical complexity level may be based on an analysis of an electronic medical record. In some embodiments, information regarding a medical history of the patient, which may be included in the electronic medical record, may be relevant to the complexity level of a surgical procedure being performed on the patient. For example, the electronic medical record may include surgical history (such a list of surgeries performed on the patient, operative reports, etc.), obstetric history (such as a list of pregnancies, possibly together with details associated with the pregnancies, such as complications, outcomes, etc.), allergies, past and present medications, immunization history, growth chart and/or development history, notes from past medical encounters (for example, such note may include details about the complaints, physical examinations, medical assessment, diagnosis, etc.), test results, medical images (such as X-ray images, Computed Tomography images, Magnetic Resonance Imaging images, Positron Emission Tomography images, Single-Photon Emission Computed Tomography images, Ultra-Sound images, Electro-Cardio-Graphy images, Electro-Encephalo-Graphy images, Electro-Myo-Graphy images, Magneto-Encephalo-Graphy images, etc.) and/or information based on medical images, medical videos and/or information based on medical videos, orders, prescriptions, medical history of the patient's family, and so forth.

In accordance with embodiments of the present disclosure, determining the first surgical complexity level may further include identifying in the first set of frames a medical tool. In some embodiments, the medical tool identified in the first set of frames may correspond to the medical tool identified in the second set of frames. For example, the same tool may be identified in both sets of frames. In other embodiments, the medical tool identified in the first set of frames may differ from the medical tool identified in the second set of frames. Determining the first surgical complexity level may be based on a type of the medical tool. The type of tool appearing in the first set of frames may be indicative of the type and/or complexity of procedure being performed. For example, if the medical tool is a specialized tool, used only for certain procedures or types of procedures, the complexity level may be determined at least in part based on the complexity associated with those procedures or types of procedures.

In some exemplary embodiments, determining the first surgical complexity level may be based on an event that occurred after the first set of frames. For example a surgical event such as a leak that occurs in frames after a first set of frames depicting suturing, may inform the complexity level associated with the first set of frames. (e.g., the suturing procedure that might otherwise be associated with a lower complexity level based on the first set of frames alone, may be elevated to a higher complexity level when from the footage it was determined that the leak likely occurred as the result of improper suturing. The later event may include any event related to the surgical procedure that has an impact on a surgical complexity of the footage, including the various examples of intraoperative surgical events described throughout the present disclosure. By way of another example, the event that occurred after the first set of frames may be an adverse event, such as a bleed, that occurs after the first set of frames. The occurrence of the event may provide context for determining the first surgical complexity level. In some embodiments, the event occurring after the first set of frames may be identified based on analysis of additional frames. For example, the event may occur before the second set of frames and may be identified based on analyzing frames between the first set of frames and the second set of frames. In other embodiments, the occurrence of the event between the first and second set of frames may be inferred based on the second set of frames, without analyzing additional frames. Further, in some embodiments the event may occur after the second set of frames.

Similarly, in some embodiments, determining the second surgical complexity level may be based on an event that occurred between the first set of frames and the second set of frames. The event may occur at other times, including at the first set of frames, before the first set of frames, or after the second set of frames. In some embodiments, the first and/or second surgical complexity level may be determined based on occurrence of the event based on a machine learning model trained to correlate events and/or event timings with various complexity levels. As an illustrative example, determining the second surgical complexity level may be based on an indication that an additional surgeon was called after the first set of frames. The indication that an additional surgeon was called may include, for example, the presence of a surgeon in the second set of frames but in first set of frames. Calling of the additional surgeon may indicate that the surgeon performing the surgery needed assistance and/or guidance, which may be relevant to determining the surgical complexity level. In another example, determining the second surgical complexity level may be based on an indication that a particular medicine was administered after the first set of frames. For example, the medicine may include an anesthesia (e.g., local, regional, and/or general anesthesia), a barbiturate, a benzodiazepine, a sedative, a coagulant, or various other medications that may be administered during a surgical procedure. Administration of the medicine may be relevant to determining the surgical complexity level. In some embodiments, administration of the medicine may be indicative of one or more complications that may have occurred, which may also be relevant determining the surgical complexity level.

In accordance with the embodiments of the present disclosure determining the second surgical complexity level may be based on time elapsed from the first set of frames to the second set of frames. For example, the time elapsed from the first set of frames to the second set of frames may represent a time between when an anatomical structure first appears in the surgical footage and the first time a medical tool interacts with the anatomical structure. As another example, the elapsed time may indicate the time between two surgical phases and/or intraoperative surgical events. For example, in embodiments where determining the first surgical complexity level further includes identifying in the first set of frames a medical tool, the first set of frames may indicate one surgical phase, such as an incision, and the second set of frames may indicate a second surgical phase, such as a suturing. The elapsed time between the two phases or events may be at least partially indicative of a surgical complexity level. (E.g., an elapsed time greater than normal for a particular procedure may indicate that the procedure was more complex than normal.) Other time durations within the surgical procedure may also be indicative of the surgical complexity level, such as a duration of an action, a duration of an event, a duration of a surgical phase, a duration between an action and a corresponding physiological response, and so forth. The surgical footage may be analyzed to measure such time durations, and the determination of the surgical complexity levels may be based on the determined time durations.

Embodiments of the present disclosure may further include comparing the first and/or second surgical complexity levels to a selected threshold. In some embodiments, the selected threshold may be used to select which frames should be selected for display and/or inclusion in a data structure. For example, the disclosed methods may include determining that the first surgical complexity level is less than a selected threshold and determining that the second surgical complexity level exceeds the selected threshold. This may indicate that the second set of frames are associated with a complexity level meeting a minimum complexity level, while the first set of frames are not. Accordingly, the disclosed methods may further include, in response to the determination that the first surgical complexity level is less than the selected threshold and the determination that the second surgical complexity level exceeds the selected threshold, storing the second set of frames in a data structure while omitting the first set of frames from the data structure. The data structure may be used by a surgeon or other user for selecting video for display meeting a minimum complexity level requirement.

Some embodiments of the present disclosure may further include tagging the first set of frames with the first surgical complexity level; tagging the second set of frames with the second surgical complexity level; and generating a data structure including the first set of frames with the first tag and the second set of frames with the second tag. The data structure may associate the first and second set of frames, as well as other frames of the surgical video footage, with the corresponding complexity level such that it is indexed for easy retrieval. Such indexing may correspond to the video indexing discussed in detail above. For example, the surgical complexity level may be an event characteristic as described above and as illustrated in data structure 600, shown in FIG. 6. Accordingly, generating the data structure may enable a surgeon to select the second surgical complexity level, and thereby cause the second set of frames to be displayed, while omitting a display of the first set of frames. For example, video may be selected for playback based on process 800 described above with respect to FIGS. 8A and 8B.

Figure 13:
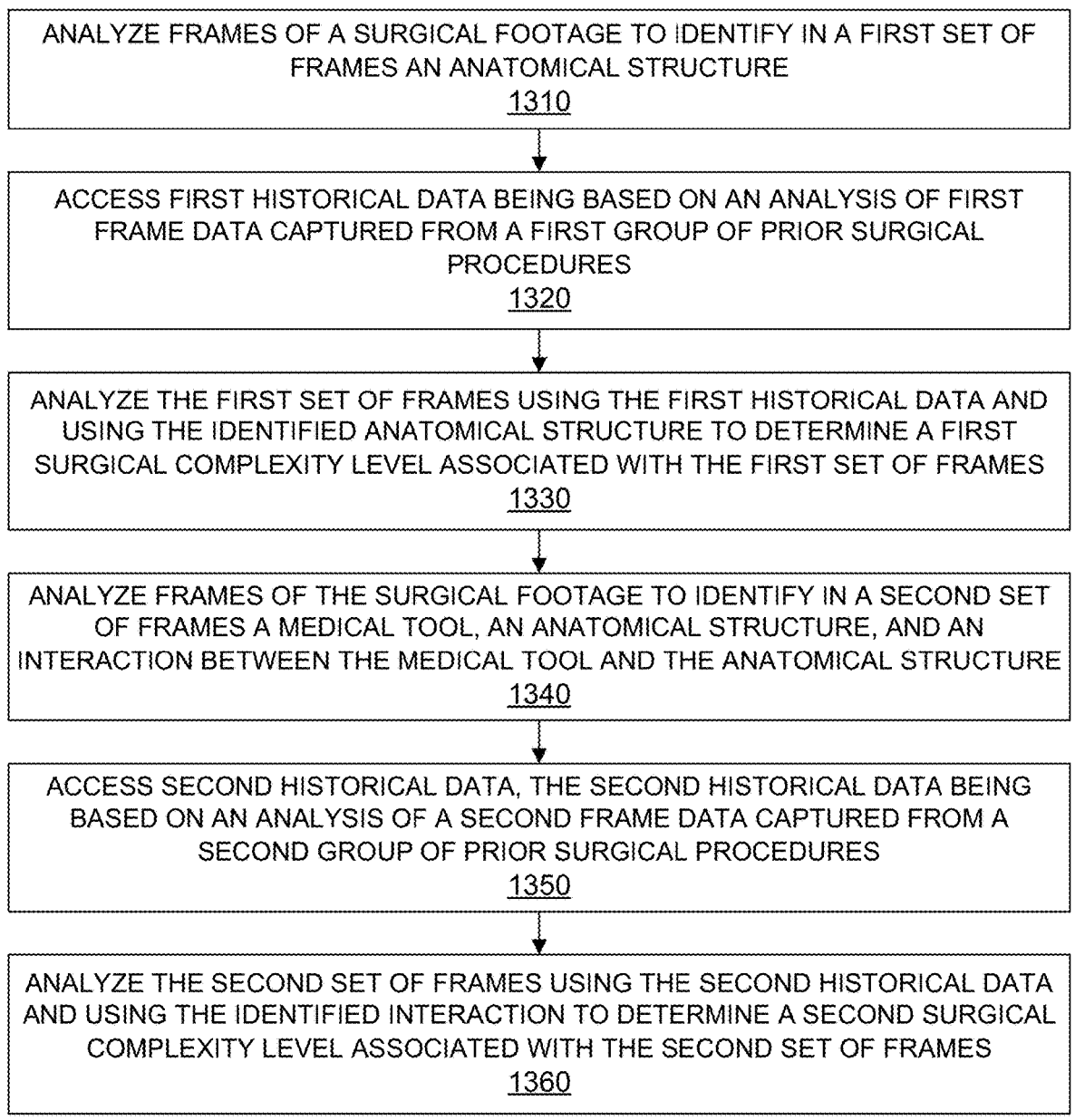
FIG. 13 is a flowchart illustrating an exemplary process for analyzing complexity of surgical footage, consistent with the disclosed embodiments.
Figure 14:
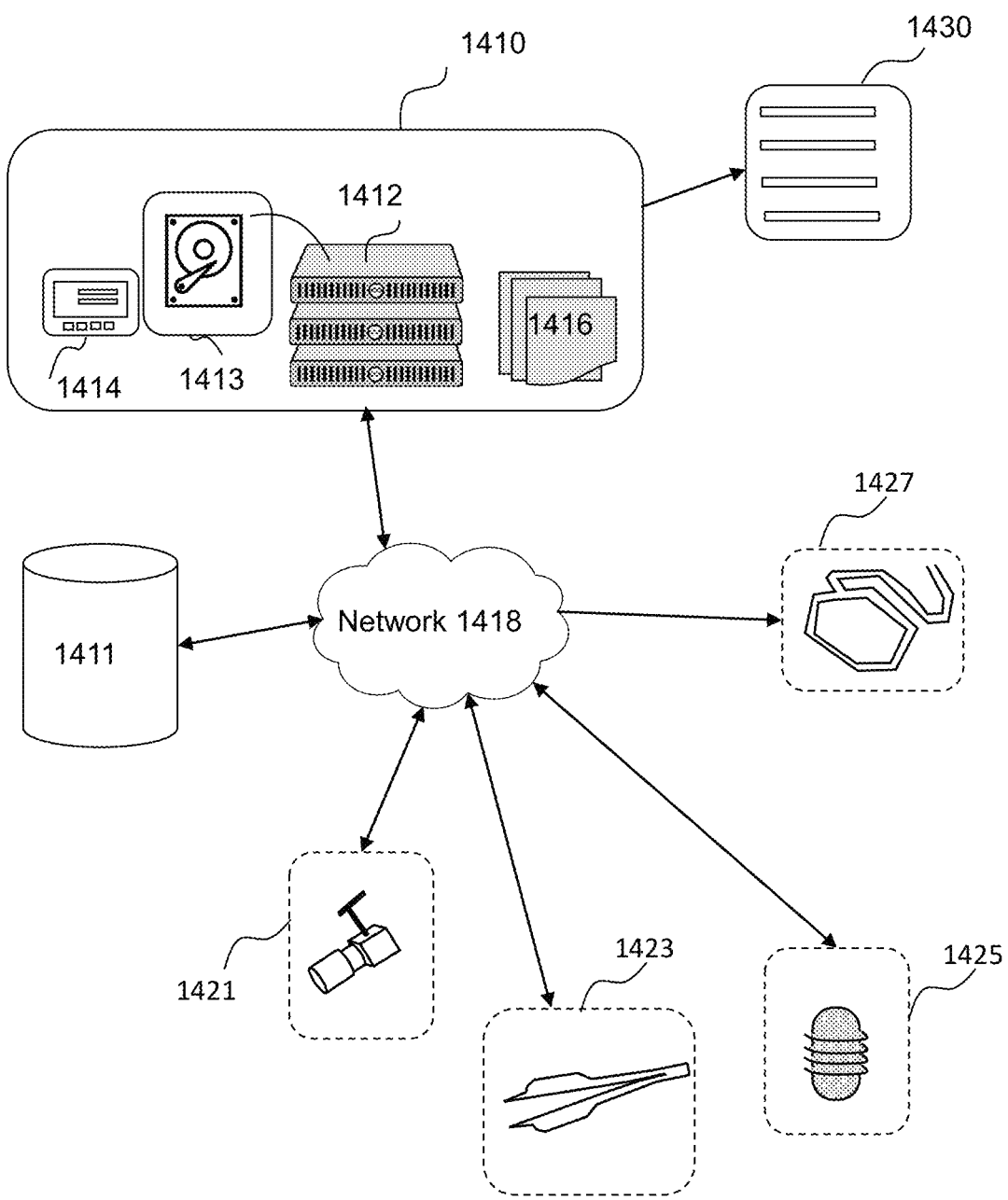
FIG. 14 is a schematic illustration of an exemplary system for managing various data collected during a surgical procedure, and for controlling various sensors consistent with disclosed embodiments.

FIG. 13 is a flowchart illustrating an example process 1300 for analyzing complexity of surgical footage, consistent with the disclosed embodiments. Process 1300 may be performed by at least one processing device, such as processor, as described herein. By way of one example a processor may include processors 1412 as illustrated in FIG. 14. Throughout this disclosure, the term "processor" is used as a shorthand for "at least one processor." In other words, a processor may include one or more structures that perform logic operations whether such structures are collocated, connected, or disbursed. In some embodiments, a non-transitory computer readable medium may contain instructions that when executed by a processor cause the processor to perform process 1300. Process 1300 is not necessarily limited to the steps shown in FIG. 1300, and any steps or processes of the various embodiments described throughout the present disclosure may also be included in process 1300. At step 1310, process 1300 may include analyzing frames of the surgical footage to identify in a first set of frames an anatomical structure, as discussed previously. In some embodiments, the anatomical structure may be identified using an image and/or video analysis algorithm, such as an object or motion detection algorithm, as previously discussed. In other embodiments, the anatomical structure may be identified using a machine learning model trained to detect anatomical structures, as described earlier.

At step 1320, process 1300 may include accessing first historical data, the first historical data being based on an analysis of first frame data captured from a first group of prior surgical procedures. In some embodiments, the first historical data may include a machine learning model trained using the first frame data captured from the first group of prior surgical procedures, as described previously. At step 1330, process 1300 may include analyzing the first set of frames using the first historical data and using the identified anatomical structure to determine a first surgical complexity level associated with the first set of frames. For example, a machine learning model may be trained using training data (for example, training data based on the historical data based on an analysis of frame data captured from prior surgical procedures) to identify surgical complexity level associated with a set of frames, and the trained machine learning model may be used to analyze the first set of frames to determine a first surgical complexity level associated with the first set of frames.

At step 1340, process 1300 may include analyzing frames of the surgical footage to identify in a second set of frames a medical tool, the anatomical structure, and an interaction between the medical tool and the anatomical structure, as described in greater detail previously. For example, object detection algorithms and/or action detection algorithms may be used to analyze the second set of frames to detect the medical tool and/or the anatomical structure and/or the interaction between the medical tool and the anatomical structure. In another example, a machine learning model trained using training examples to detect medical tools and/or anatomical structures and/or the interaction between the medical tools and the anatomical structures in images and/or videos may be used. At step 1350, process 1300 may include accessing second historical data, the second historical data being based on an analysis of second frame data captured from a second group of prior surgical procedures. In some embodiments, the first historical data and the second historical data may be identical. In other embodiments, the first historical data and the second historical data may be different. At step 1360, process 1300 may include analyzing the second set of frames using the second historical data and using the identified interaction to determine a second surgical complexity level associated with the second set of frames, as previously described.

An operating room schedule may need to be adjusted based on delays associated with surgical Disclosed systems and methods may involve analyzing surgical footage to identify features of surgery, patient conditions, and other features to determine adjustments to an operating room schedule. procedures conducted in the operating room. Conversely, the schedule may need to be adjusted if a surgical procedure is completed ahead of a scheduled time. Therefore, there is a need for adjusting an operating room schedule in an effective and efficient manner using information obtained from surgical footage during a surgical procedure Aspects of this disclosure may relate to adjusting an operating room schedule, including methods, systems, devices, and computer-readable media. The operating room schedule may include a scheduled time associated with completion of the ongoing surgical procedure, as well as scheduled times for starting and finishing future surgical procedures.

Both a method for enabling adjustments of an operating room schedule and a system is described below, with the understanding that aspects of the method or the system may occur electronically over a network that is either wired, wireless, or both. Other aspects of such a method or system may occur using non-electronic means. In the broadest sense, the method or the system is not limited to a particular physical and/or electronic instrumentality, but rather may be accomplished using many differing instrumentalities. For ease of discussion, a method is described first below, with the understanding that aspects of the method apply equally to systems, devices, and computer-readable media.

Disclosed embodiments may involve receiving from an image sensor positioned in a surgical operating room, visual data tracking an ongoing surgical procedure. As used herein, the visual data may include any form of recorded visual media, including recorded images, one or more frames or images or clips, and/or data directly or indirectly derived from the foregoing. Additionally, the video data may include sound. For example, the visual data may include a sequence of one or more images captured by image sensors, such as cameras 115, 121, 123, and/or 125, as described above in connection with FIG. 1. Some of the cameras (e.g., cameras 115, 121 and 125) may capture video/image data of operating table 141, camera 121 may capture video/image data of a surgeon 131 performing the surgery. In some cases, cameras may capture video/image data associated with surgical team personnel, such as anesthesiologists, nurses, surgical technicians, or other healthcare professionals located in operating room 101.

In various embodiments, image sensors may be configured to capture visual data by converting visible light, x-ray light (e.g., via fluoroscopy), infrared light, or ultraviolet light to images, sequence of images, videos, and any other form of representations. The image/video data may be stored as computer files using any suitable format such as JPEG, PNG, TIFF, Audio Video Interleave (AVI), Flash Video Format (FLV), QuickTime File Format (MOV), MPEG (MPG, MP4, M4P, etc.), Windows Media Video (WMV), Material Exchange Format (MXF), uncompressed formats, lossless compressed formats, lossy compressed formats, or other audio or video format.

An image sensor may be any sensor capable of capturing image or video data. A single sensor may be used, or multiple image sensors may be positioned in a surgical operating room (e.g., the sensors may be positioned throughout the operating room). In an illustrative embodiment, an example image sensor may be positioned above a patient. The example image sensor may be above an operating table, next to the operating table, next to devices located in the operating room, or anywhere else capable of detecting information about a surgery. As shown in FIG. 1, the image sensor may include cameras 115-125. In some cases, image sensors may be wearable devices (e.g., head mounted cameras, body mounted cameras, or any sensor capable of being associated with a person). Additionally or alternatively, an example image sensor may be positioned on a surgical tool (i.e., be a part of a surgical instrument). For example, an image sensor may be a part of a bronchoscope tube, a laparoscope, an endoscope, or any other medical instrument configured for location inside or outside a patient (e.g., for procedures such as gastroscopy, colonoscopy, hysteroscopy, cystoscopy, flexible sigmoidoscopy, wireless capsule endoscopy, and the like).

Image sensors, particularly when being part of surgical instruments, may include one or more light emitting sources for emitting light of suitable wavelength such as visible light, infrared light, and/or ultraviolet light. The light emitting sources may include any suitable sources (e.g., light emitting diodes (LEDs) emitting visible light, fluorescent light sources, incandescent light sources, infrared LEDs, ultraviolet LEDs, and/or other type of light source). Image sensors may not be limited to capturing light, but may be configured to process other signals for producing visual data related to the captured signals. For example, image sensors may be configured to capture ultrasound, changes in an electromagnetic field, or any other suitable signals (e.g., distribution of a force over a surface), and the like to produce visual data related to the captured signals.

A surgical procedure may include any medical procedure associated with or involving manual or operative procedures on a patient's body. Surgical procedures may include cutting, abrading, suturing, and/or other techniques that involve measuring, treating or physically changing body tissues and/or organs. Some non-limiting examples of such surgical procedures may include a laparoscopic surgery, a thoracoscopic procedure, a bronchoscopic procedure, a microscopic procedure, an open surgery, a robotic surgery, an appendectomy, a carotid endarterectomy, a carpal tunnel release, a cataract surgery, a cesarean section, a cholecystectomy, a colectomy (such as a partial colectomy, a total colectomy, etc.), a coronary angioplasty, a coronary artery bypass, a debridement (for example of a wound, a burn, an infection, etc.), a free skin graft, a hemorrhoidectomy, a hip replacement, a hysterectomy, a hysteroscopy, an inguinal hernia repair, a knee arthroscopy, a knee replacement, a mastectomy (such as a partial mastectomy, a total mastectomy, a modified radical mastectomy, etc.), a prostate resection, a prostate removal, a shoulder arthroscopy, a spine surgery (such as a spinal fusion, a laminectomy, a foraminotomy, a diskectomy, a disk replacement, an interlaminar implant, etc.), a tonsillectomy, a cochlear implant procedure, brain tumor (for example meningioma, etc.) resection, interventional procedures such as percutaneous transluminal coronary angioplasty, transcatheter aortic valve replacement, minimally invasive surgery for intracerebral hemorrhage evacuation, or any other medical procedure involving some form of incision. While the present disclosure is described in reference to surgical procedures, it is to be understood that it may also apply to other forms of medical procedures or procedures generally.

An operating room may be any suitable facility (e.g., a room within a hospital) where surgical operations are carried out in an aseptic environment. The operating room may be configured to be well-lit and to have overhead surgical lights. The operating room may feature controlled temperature and humidity and may be windowless. In an example embodiment, the operating room may include air handlers that may filter the air and maintain a slightly elevated pressure within the operating room to prevent contamination. The operating room may include an electricity backup system in case of a black-out and may include a supply of oxygen and anesthetic gases. The room may include a storage space for common surgical supplies, containers for disposables, an anesthesia cart, an operating table, cameras, monitors, and/or other items for surgery. A dedicated scrubbing area that is used by surgeons, anesthetists, operating department practitioners (ODPs), and nurses prior to surgery may be part of the operating room. Additionally, a map included in the operating room may enable the terminal cleaner to realign the operating table and equipment to the desired layout during cleaning. In various embodiments, one or more operating rooms may be a part of an operating suite that may form a distinct section within a healthcare facility. The operating suite may include one or more washrooms, preparation and recovery rooms, storage and cleaning facilities, offices, dedicated corridors, and possibly other supportive units. In various embodiments, the operating suite may be climate- and air-controlled, and separated from other departments.

In various embodiments, visual data captured by image sensors may track an ongoing surgical procedure. In some cases, visual data may be used to track a region of interest (ROI) such as a region of a body of a patient in which an operation is conducted (e.g., a region 127, as shown in FIG. 1). In an example embodiment, cameras 115-125 may capture visual data by tracking the ROI via camera motion, camera rotation, or by zooming towards the ROI. For instance, camera 115 may be movable and point at the ROI, at which video/image data needs to be captured during, before, or after a surgical procedure. For example, as shown in FIG. 1, camera 115 may be rotated as indicated by arrows 135A showing a pitch direction, and arrows 135B showing a yaw direction for camera 115. In various embodiments, pitch and yaw angles of cameras (e.g., camera 115) may be controlled to track the ROI.

In an example embodiment, camera 115 may be configured to track a surgical instrument (also referred to as a surgical tool, a medical instrument, etc.) within location 127, an anatomical structure, a hand of surgeon 131, an incision, a movement of anatomical structure, and/or any other object. In various embodiments, camera 115 may be equipped with a laser 137 (e.g., an infrared laser) for precision tracking. In some cases, camera 115 may be tracked automatically via a computer based control application that uses an image recognition algorithm for positioning the camera to capture video/image data of the ROI. For example, the control application may identify an anatomical structure, identify a surgical tool, hand of a surgeon, bleeding, motion, and the like at a particular location within the anatomical structure, and track that location with camera 115 by rotating camera 115 by appropriate yaw and pitch angles. In some embodiments, the control application may control positions (i.e., yaw and pitch angles) of various cameras 115-125 to capture video/image date from more than one ROI during a surgical procedure. Additionally or alternatively, a human operator may control the position of various cameras 115-125, and/or the human operator may supervise the control application in controlling the position of the cameras.

As used herein, the term "anatomical structure" may include any particular part of a living organism, including, for example, one or more organs, tissues, ducts, arteries, cells, or any other anatomical parts. In some cases, prosthetics, artificial organs, and the like may be considered as anatomical structures.

Cameras 115-125 may further include zoom lenses for magnifying one or more ROIs. In an example embodiment, camera 115 may include a zoom lens 138 for magnifying a ROI (e.g., a surgical tool in the proximity of an anatomical structure). Camera 121 may include a zoom lens 139 for capturing video/image data from a larger area around the ROI. For example, camera 121 may capture video/image data for the entire location 127. In some embodiments, video/image data obtained from camera 121 may be analyzed to identify a ROI during the surgical procedure, and the control application may be configured to cause camera 115 to zoom towards the ROI identified by camera 121.

In various embodiments, the control application may be configured to coordinate the position and zoom of various cameras during a surgical procedure. For example, the control application may direct camera 115 to visually track an anatomical structure, and may direct camera 121 and 125 to track a surgical instrument. Cameras 121 and 125 may track the same ROI (e.g., a surgical instrument) from different view angles. For example, video/image data obtained from different view angles may be used to determine the position of the surgical instrument relative to a surface of the anatomical structure.

In various embodiments, control of position and zoom of cameras 115-125 may be rule-based and follow an algorithm developed for a given surgical procedure. For example, the control application may be configured to direct camera 115 to track a surgical instrument, to direct camera 121 to location 127, to direct camera 123 to track the motion of the surgeon's hands, and to direct camera 125 to an anatomical structure. The algorithm may include any suitable logical statements determining position and zoom (magnification) for cameras 115-125 depending on various events during the surgical procedure. For example, the algorithm may direct at least one camera to a region of an anatomical structure that develops bleeding during the procedure.

In various cases, when a camera (e.g., camera 115) tracks a moving or deforming object (e.g., when camera 115 tracks a moving surgical instrument, or a moving/pulsating anatomical structure) the control application may determine a maximum allowable zoom for camera 115, such that the moving or deforming object does not escape a field of view of the camera. In an example embodiment, the control application may initially select the first zoom for camera 115, evaluate whether the moving or deforming object escapes the field of view of the camera, and adjust the zoom of the camera as necessary to prevent the moving or deforming object from escaping the field of view of the camera. In various embodiments, the camera zoom may be readjusted based on a direction and a speed of the moving or deforming object. In some cases, the control application may be configured to predict future position and orientation of cameras 115-125 based on the movement of the hand of the surgeon, the movement of a surgical instrument, the movement of a body of the surgeon, historical data reflecting likely next steps, or any other data from which future movement may be derived.

The visual data captured by image sensors may be communicated via a network to a computer system for further analysis and storage. For example, FIG. 14 shows an example system 1401 that may include a computer system 1410, a network 1418, and image sensors 1421 (e.g., cameras positioned within the operating room), and 1423 (e.g., image sensors being part of a surgical instrument) connected via network 1418 to computer system 1401. System 1401 may include a database 1411 for storing various types of data related to previously conducted surgeries (i.e., historical surgical data that may include historical image, video or audio data, text data, doctors' notes, data obtained by analyzing historical surgical data, and other data relating to historical surgeries). In various embodiments, historical surgical data may be any surgical data related to previously conducted surgical procedures. Additionally, system 1401 may include one or more audio sensors 1425, light emitting devices 1427, and a schedule 1430.

Computer system 1410 may include one or more processors 1412 for analyzing the visual data collected by the image sensors, a data storage 1413 for storing the visual data and/or other types of information, an input module 1414 for entering any suitable input for computer system 1410, and software instructions 1416 for controlling various aspects of operations of computer system 1410.

One or more processors 1412 of system 1410 may include multiple core processors to handle concurrently multiple operations and/or streams. For example, processors 1412 may be parallel processing units to concurrently handle visual data from different image sensors 1421 and 1423. In some embodiments, processors 1412 may include one or more processing devices, such as, but not limited to, microprocessors from the Pentium™ or Xeon™ family manufactured by Intel™, the Turion™ family manufactured by AMD™, or any of various processors from other manufacturers. Processors 1412 may include a plurality of coprocessors, each configured to run specific operations such as floating-point arithmetic, graphics, signal processing, string processing, or I/O interfacing. In some embodiments, processors may include a field-programmable gate array (FPGA), central processing units (CPUs), graphical processing units (GPUs), and the like.

Database 1411 may include one or more computing devices configured with appropriate software to perform operations for providing content to system 1410. Database 1411 may include, for example, Oracle™ database, Sybase™ database, and/or other relational databases or non-relational databases, such as Hadoop™ sequence files, HBase™, or Cassandra™. In an illustrative embodiment, database 1411 may include computing components (e.g., database management system, database server, etc.) configured to receive and process requests for data stored in memory devices of the database and to provide data from the database. As discussed before, database 1411 may be configured to collect and/or maintain the data associated with surgical procedures. Database 1411 may collect the data from a variety of sources, including, for instance, online resources.

Network 1418 may include any type of connections between various computing components. For example, network 1418 may facilitate the exchange of information via network connections that may include Internet connections, Local Area Network connections, near field communication (NFC), and/or other suitable connection(s) that enables the sending and receiving of information between the components of system 1401. In some embodiments, one or more components of system 1401 may communicate directly through one or more dedicated communication links.

Various example embodiments of the system 1401 may include computer-implemented methods, tangible non-transitory computer-readable mediums, and systems. The computer-implemented methods may be executed, for example, by at least one processor that receives instructions from a non-transitory computer-readable storage medium such as medium 1413, as shown in FIG. 14. Similarly, systems and devices consistent with the present disclosure may include at least one processor and memory, and the memory may be a non-transitory computer-readable storage medium. As used herein, a non-transitory computer-readable storage medium refers to any type of physical memory on which information or data readable by at least one processor can be stored. Examples may include random access memory (RAM), read-only memory (ROM), volatile memory, non-volatile memory, hard drives, CD ROMs, DVDs, flash drives, disks, and any other known physical storage medium whether some or all portions thereof are physically located in or near the operating room, in another room of the same facility, at a remote captive site, or in a cloud-based server farm. Singular terms, such as "memory" and "computer-readable storage medium," may additionally refer to multiple structures, such a plurality of memories or computer-readable storage mediums. As referred to herein, a "memory" may include any type of computer-readable storage medium unless otherwise specified. A computer-readable storage medium may store instructions for execution by at least one processor, including instructions for causing the processor to perform steps or stages consistent with an embodiment herein. Additionally, one or more computer-readable storage mediums may be utilized in implementing a computer-implemented method. The term "computer-readable storage medium" should be understood to include tangible items and exclude carrier waves and transient signals.

Input module 1414 may be any suitable input interface for providing input to one or more processors 1412. In an example embodiment, input interface may be a keyboard for inputting alphanumerical characters, a mouse, a joystick, a touch screen, an on-screen keyboard, a smartphone, an audio capturing device (e.g., a microphone), a gesture capturing device (e.g., camera), and other device for inputting data. While a user inputs the information, the information may be displayed on a monitor to ensure the correctness of the input. In various embodiments, the input may be analyzed verified or changed before being submitted to system 1410.

Software instructions 1416 may be configured to control various aspects of operation of system 1410, which may include receiving and analyzing the visual data from the image sensors, controlling various aspects of the image sensors (e.g., moving image sensors, rotating image sensors, operating zoom lens of image sensors for zooming towards an example ROI, and/or other movements), controlling various aspects of other devices in the operating room (e.g., controlling operation of audio sensors, chemical sensors, light emitting devices, and/or other devices).

As previously described, image sensors 1421 may be any suitable sensors capable of capturing image or video data. For example, such sensors may be cameras 115-125.

Audio sensors 1425 may be any suitable sensors for capturing audio data. Audio sensors 1425 may be configured to capture audio by converting sounds to digital information. Some examples of audio sensors 1425 may include microphones, unidirectional microphones, bidirectional microphones, cardioid microphones, omnidirectional microphones, onboard microphones, wired microphones, wireless microphones, any combination of the above, and any other sound-capturing device.

Light emitting devices 1427 may be configured to emit light, for example, in order to enable better image capturing by image sensors 1421. In some embodiments, the emission of light may be coordinated with the capturing operation of image sensors 1421. Additionally or alternatively, the emission of light may be continuous. In some cases, the emission of light may be performed at selected times. The emitted light may be visible light, infrared light, ultraviolet light, deep ultraviolet light, x-rays, gamma rays, and/or in any other portion of the light spectrum.

As described below, schedule 1430 may include an interface for displaying a scheduled time associated with completion of the ongoing surgical procedure, as well as scheduled times for starting and finishing future surgical procedures. Schedule 1430 may be implemented using any suitable approach (e.g., as a standalone software application, as a website, as a spreadsheet, or any other suitable computer-based application or a paper-based document). An example schedule 1430 may include a list of procedures and list of starting and finishing times associated with a particular procedure. Additionally or alternatively, schedule 1430 may include a data structure configured to represent information related to a schedule of at least one operating room and/or related to a schedule of at least one surgical procedure, such as a scheduled time associated with completion of the ongoing surgical procedure, as well as scheduled times for starting and finishing future surgical procedures.

Figure 15:
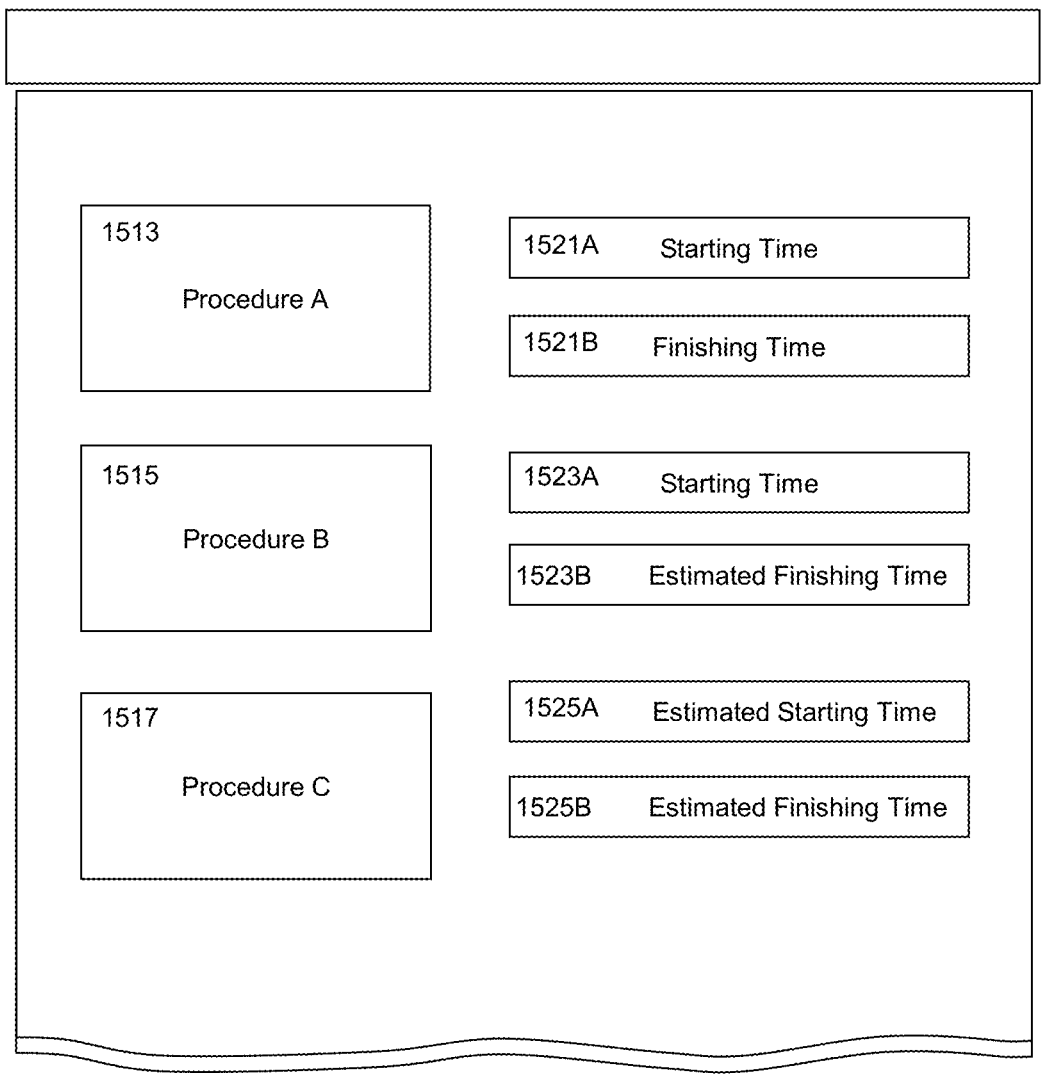
FIG. 15 is an exemplary schedule consistent with disclosed embodiments.

FIG. 15 shows an example schedule 1430 that may include a listing of procedures such as procedures A C (e.g., surgical procedures, or any other suitable medical procedures that may be performed in an operating room for which schedule 1430 is used). For each procedure A C, a corresponding starting and finishing times may be determined. For example, for a past procedure A, a starting time 1521A and a finishing time 1521B may be the actual starting and finishing times. (Since procedure A is completed, the schedule 1430 may be automatically updated to reflect actual times). FIG. 15 shows that for a current procedure B, a starting time 1523A may be actual and a finishing time 1523B may be estimated (and recorded as an estimated time). Additionally, for procedure C, that is scheduled to be performed in the future, a starting time 1525A and a finishing time 1525B may be estimated and recorded. It should be noted that schedule 1430 is not limited to displaying and/or holding listings of procedures and starting/finishing times for the procedures, but may include various other data associated with an example surgical procedure. For example, schedule 1430 may be configured to allow a user of schedule 1430 to interact with various elements of schedule 1430 (for cases when schedule 1430 is represented by a computer based interface such as a webpage, a software application, and/or another interface). For example, a user may be allowed to click over or otherwise select areas 1513, 1515 or 1517 to obtain details for procedures A, B or C respectively. Such details may include patient information (e.g., patients name, age, medical history, etc.), surgical procedure information (e.g., a type of surgery, type of tools used for the surgery, type of anesthesia used for the surgery, and/or other characteristics of a surgical procedure), and healthcare provider information (e.g., a name of a surgeon, a name of an anesthesiologist, an experience of the surgeon, a success rate of the surgeon, a surgeon rating based on surgical outcomes for the surgeon, and/or other data relating to a surgeon). Some or all of the forgoing information may already appear in areas 1513, 1515 and 1517, without the need for further drill down.

In various embodiments, information for a surgical procedure may be entered by a healthcare provider (e.g., a nurse, a surgical assistant, a surgeon, and/or other healthcare professional) via an example form 1601, as shown in FIG. 16. For example, form 1601 may have an "URGENCY" field, in which the healthcare provider may specify the urgency of the scheduled surgical procedure, a "SURGERY TYPE" field, in which the healthcare provider may specify a type of the surgical procedure (or a name of the surgical procedure), a "Complications" field, in which the healthcare provider may specify medical historical events for a patient that may lead to complications during the surgical procedure, "Patient Profile" fields such as "Name", "Address", "Birthday", "Contact", and "Emergency Contact", in which the healthcare provider may specify the corresponding information about the patient. Further, form 1601 may include a "Medical History" field that may be used to describe medical history of a patient (e.g., "Medical History" field may be a pulldown list, a space in which the healthcare provider may type text describing the medical history for the patient, or any other suitable graphical user interface element that can be used for the description of the medical history for the patient. Additionally, form 1601 may include "Surgical Team" related fields that may specify names and responsibilities of medical personnel who are scheduled to provide the surgical procedure for the patient. Information about multiple healthcare providers may be added by means of "Add Next Member" button, as shown in FIG. 16. Form 1601 is only one illustrative example of a form with a few exemplary fields that can be used to input information about surgical procedures into schedule 1430, and any other suitable form may be used that allows for entering relevant information for schedule 1430. The number of fields of information on the form and the type of information identified for capture may be a matter of administrator preference. Additionally or alternatively, information for a surgical procedure may be received from other sources, such as a Hospital Information System (HIS), an Electronic Medical Record (EMR), a planned operating room schedule, a digital calendar, an external system, and so forth.

Aspects of embodiments for enabling adjustments of an operating room schedule may include accessing a data structure containing information based on historical surgical data and analyzing the visual data of the ongoing surgical procedure and the historical surgical data to determine an estimated time of completion of the ongoing surgical procedure. In various embodiments, any steps of the method may be executed by one or more processors of system 1410 executing software instructions 1416.

The data structure may be stored in database 1411 and may be accessed via network 1418, or may be stored locally in a memory of system 1410. The data structure containing historical surgical data may include any suitable data (e.g., image data, video data, text data, numerical data, spreadsheets, formulas, software codes, computer models, and/or other data objects), as well as any suitable relationships among various data values (or combinations of data values). The data may be stored linearly, horizontally, hierarchically, relationally, non-relationally, uni dimensionally, multidimensionally, operationally, in an ordered manner, in an unordered manner, in an object-oriented manner, in a centralized manner, in a decentralized manner, in a distributed manner, in a custom manner, or in any manner enabling data access. By way of non-limiting examples, data structures may include an array, an associative array, a linked list, a binary tree, a balanced tree, a heap, a stack, a queue, a set, a hash table, a record, a tagged union, ER model, and a graph. For example, a data structure may include an XML code, an XML database, an RDBMS database, an SQL database or NoSQL alternatives for data storage/search such as, for example, MongoDB, Redis, Couchbase, Datastax Enterprise Graph, Elastic Search, Splunk, Solr, Cassandra, Amazon DynamoDB, Scylla, HBase, and Neo4J. A data structure may be a component of the disclosed system or a remote computing component (e.g., a cloud-based data structure). Data in the data structure may be stored in contiguous or non contiguous memory. Moreover, a data structure, as used herein, does not require information to be co-located. It may be distributed across multiple servers, for example, that may be owned or operated by the same or different entities. Thus, the term "data structure" as used herein in the singular is inclusive of plural data structures.

In an example embodiment, the data structure may include a type of procedure (e.g., bypass surgery, bronchoscopy, or any other surgical procedure as described above), one or more characteristics of a patient (e.g., age, gender, medical considerations that may affect the procedure, past medical history, and/or other patient information), name(s) and/or characteristics of operating surgeon and/or anesthesiologist, and a time that it took to complete the procedure. In some cases, time for completion of the procedure may include a time for preparing the operating room, a time for preparing a patient for the surgical procedure, a time needed for medical personnel (i.e., nurses, surgeon, anesthesiologist, etc.) a time needed for the patient to be anesthetized or to fall asleep, a time needed for cleaning the operating room or any other surgery-related time needed to place the operating room in a condition for the next surgical procedure.

Figures 17A, 17B:
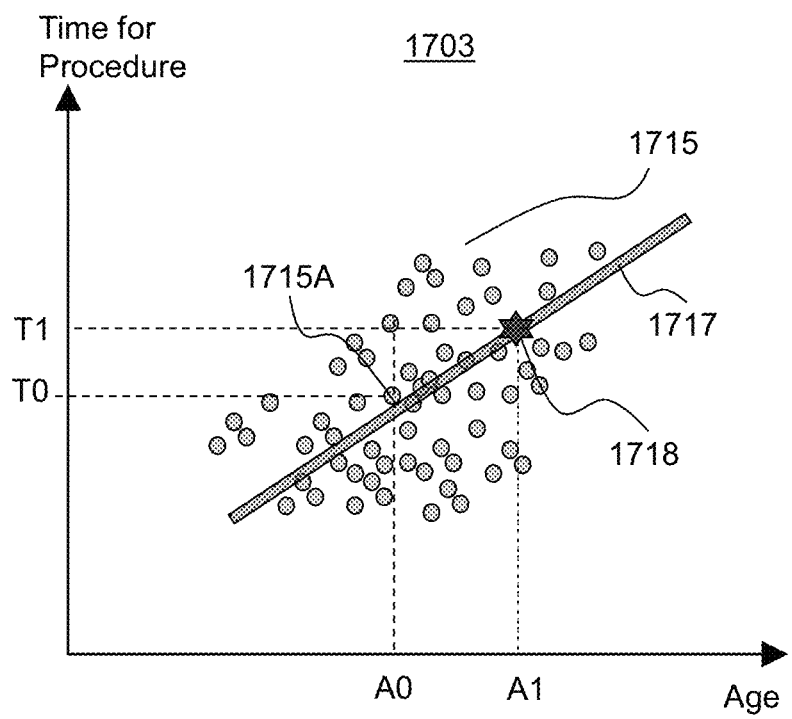
FIG. 17A shows an exemplary data structure consistent with disclosed embodiments.
FIG. 17B shows an exemplary plot of data of historic completion times consistent with disclosed embodiments.

In an example embodiment, the data structure may be a relational database having one or more database tables. For instance, FIG. 17A illustrates an example of data structure 1701 that may include data tables 1711 and 1713. In an example embodiment, data structure 1701 may be part of relational databases, may be stored in memory, and so forth. Tables 1711 and 1713 may include multiple records (e.g., records 1 and 2, as shown in FIG. 17A) and may have various fields, such as fields "Record Number", "Procedure", "Age", "Gender", "Medical Considerations", "Time", and "Other Data". For instance, field "Record Number" may include a label for a record that may be an integer, field "Procedure" may include a name of a surgical procedure, field "Age" may include an age of a patient, field "Gender" may include a gender of the patient, field "Medical Considerations" may include information about medical history for the patient that may be relevant to the surgical procedure having the name as indicated in field "Procedure", field "Time" may include time that it took for the surgical procedure, and field "Other Data" may include links to any other suitable data related to the surgical procedure. For example, as shown in FIG. 17A, 1711 may include links to data 1712A that may correspond to image data, data 1712B that may correspond to video data, data 1712C that may correspond to text data (e.g., notes recorded during or after the surgical procedure, patient records, postoperative report, etc.), and data 1712D that may correspond to an audio data. In various embodiments, image, video, or audio data may be captured during the surgical procedure. In some cases, video data may also include audio data. Image, video, text or audio data 1712A-1712D are only some of the data that may be collected during the surgical procedure. Other data may include vital sign data of the patient, such as heart rate data, blood pressure data, blood test data, oxygen level, or any other patient-related data recorded during the surgical procedure. Some additional examples of data may include room temperature, type of surgical instruments used, or any other data related to the surgical procedure and recorded before, during or after the surgical procedure.

As shown in FIG. 17A, tables 1711 and 1713 may include a record for a surgical procedure. For example, record 1 of table 1711 indicates that a bypass surgical procedure was performed on a male of 65 years old, having a renal disease and that the bypass surgery was completed in 4 hours. A record 2 of table 1711 indicates that a bypass surgical procedure was performed on a female of 78 years old, having no background medical condition that may complicate the surgical procedure, and that the bypass surgery was completed in 3 hours. Table 1713 indicates that the bypass surgery for the male of 65 years old was conducted by Dr. Mac, and that the bypass surgery for the female of 78 years old was conducted by Dr. Doe. The patient characteristics such as age, gender, and medical considerations listed in table 1711 are only some of the example patient characteristics, and any other suitable characteristics may be used to differentiate one surgical procedure from another. For example, patient characteristics may further include patient allergies, patient tolerance to anesthetics, various particulars of a patient (e.g., how many arteries need to be treated during the bypass surgery), a weight of the patient, a size of the patient, particulars of anatomy of the patient, or any other patient related characteristics which may have an impact on a duration (and success) of the surgical procedure.

Data structure 1701 may have any other number of suitable tables that may characterize any suitable aspects of the surgical procedure. For example, 1701 may include a table indicating an associated anesthesiologist's identity, the time of day of the surgical procedure, whether the surgical procedure was a first, a second, a third, etc. procedure conducted by a surgeon (e.g., in the surgeon lifetime, within a particular day, etc.), an associated anesthesiologist nurse assistant, whether there were any complications during the surgical procedure, and any other information relevant to the procedure.

Accessing a data structure may include reading and/or writing information to the data structure. For example, reading and/or writing from/to the data structure may include reading and/or writing any suitable historical surgical data such as historic visual data, historic audio data, historic text data (e.g., notes during an example historic surgical procedure), and/or other historical data formats. In an example embodiment, accessing the data structure may include reading and/or writing data from/to database 111 or any other suitable electronic storage repository. In some cases, writing data may include printing data (e.g., printing reports containing historical data on paper).

Disclosed embodiments may further include analyzing the visual data of the ongoing surgical procedure using the data structure to determine an estimated completion time of the ongoing surgical procedure. The estimated completion time may be any suitable indicator of estimated completion of a surgical procedure, including, for example, a time of day at which a surgical procedure is expected to complete, a time remaining until completion, an estimated overall duration of the surgical procedure, a probability distribution time values for completion of a surgical procedure, and so forth. Furthermore, completion time may include additional statistical information indicating a likelihood of completion, based on historical surgical data (e.g., standard deviation associated with historical completion times, average historical completion times, mean for historical completion times, and/or other statistical metrics of completion times). In some examples, a machine learning model may be trained using training examples to estimate completion time of surgeries from images and/or videos, and the trained machine learning model may be used to analyze the visual data and determine the estimated completion time of the ongoing surgical procedure. An example of such training example may include an image and/or a video of a surgical procedure, together with a label indicating the estimate completion time of the surgical procedure. For example, labels of the training examples may be based on at least one of the data structure containing information based on historical surgical data, the historical data, user input, and so forth. For example, the training example may include images and/or videos from at least one of the data structure containing information based on historical surgical data, the historical data, and so forth.

In one example, prior to starting the surgical procedure, the historical surgical data may be analyzed to determine an initial estimated completion time of the ongoing surgical procedure (also herein referred to as a time of completion), or the initial estimated completion time of the ongoing surgical procedure may be received in other ways, for example from a user, from a scheduling system, from an external system, and so forth.

In some embodiments, an average historical completion time may be used to determine an estimated completion time. For example, the average historical completion time may be calculated for historical surgical procedures that are of the same type as an ongoing surgical procedure, and the average historical completion time may be used as the estimated completion time. In another example, similar historical surgical procedures may be selected (for example, using a k-Nearest Neighbors algorithm, using a similarity measure between surgical procedures, etc.), and the average historical completion time may be calculated for the selected similar historical surgical procedures.

The analysis of the historical data may involve any suitable statistical data analysis, such as determining an expected completion time value based on a probability distribution function, using Bayesian interference, to determine how the probability distribution function is affected by various patient/surgeon characteristics (e.g., an age of the patient), linear regression, and/or other methods of quantifying statistical relationships. For instance, FIG. 17B shows an example graph 1703 of points 1715 representing a distribution of completion time of a particular surgical procedure (e.g., a bypass surgery) for patients of different ages. For example, a point 1715A shows that in a particular case, for a patient of age A0, it took time T0 to complete the surgical procedure. Data for points 1715 may be used to construct a linear regression model 1717, and regression model 1717 may be used to determine expected completion time T1 for a patient of age A1 according to point 1718 on the linear regression model. While graph 1703 shows the dependence of the completion time on one characteristic parameter of a patient (e.g., age of the patient), completion time may depend on multiple characteristic parameters (e.g., the weight of a patient, characteristics of the healthcare professional conducting a surgical procedure, characteristics of an anesthesiologist, and other data describing a patient or procedure), as previously discussed, and points 1715 may be plotted in a multi-dimensional Cartesian coordinate system, and regression model 1717 may include multivariate regression model. In other examples, regression model 1717 may include a non-linear regression model.

In an example embodiment, determining the estimated completion time may be based on one or more stored characteristics associated with a healthcare professional conducting the ongoing surgical procedure. Such characteristics may include age, a name, years of experience, a location, of the healthcare professional, past performances, and/or other information describing a healthcare professional, for example, as described above. The characteristics may be stored using any suitable data structure using any suitable electronic (or in some cases, paper) storage. In an example embodiment, the characteristics may be stored in a database (e.g., database 1411, as shown in FIG. 14). For instance, based on an analysis of a historical data for a given healthcare professional for a given type of surgery, an expected completion time may be estimated (e.g., the expected completion time may be an average completion time determined from the historical data for a given healthcare professional for a given type of surgery). Furthermore, using historic data for a given healthcare professional for a given type of surgery other statistics may be determined (e.g., standard deviation from the expected completion time, correlation of the expected completion time with other characteristics of a surgical procedure, such as an age of a patient or a time of the day the surgery is performed, and/or other statistic generated from historic completion times).

Figure 18:
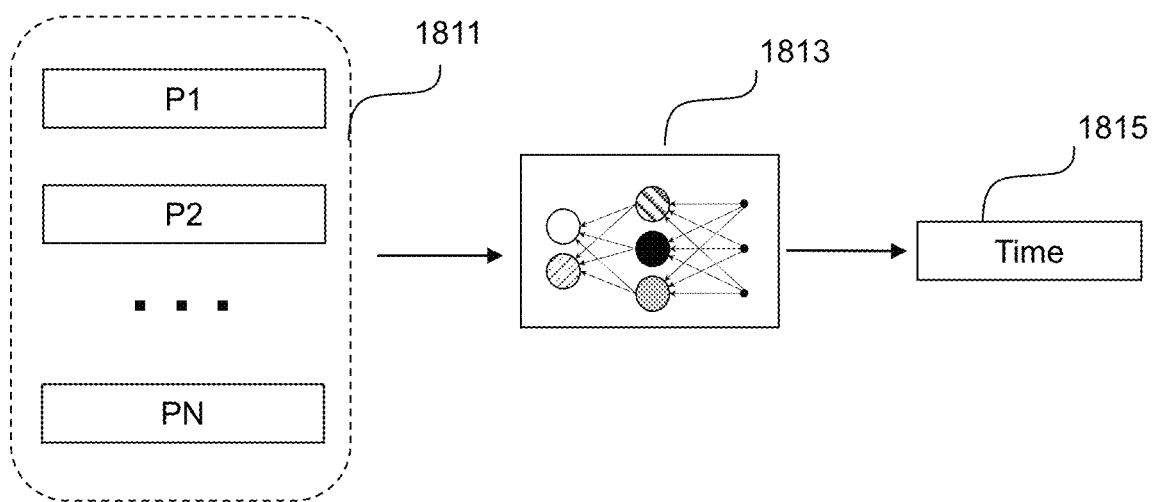
FIG. 18 shows an example of a machine-learning model consistent with disclosed embodiments.

FIG. 18 shows an exemplary embodiment of obtaining a completion time 1815 using a machine learning model 1813. Model 1813 may take as input parameters 1811 various characteristics of a patient, various characteristics of medical personnel, as well as a type of surgical procedure administered to the patient. For example, parameter P1, as shown in FIG. 18, may indicate a type of surgical procedure, parameter P2 may indicate an age of a patient, parameter PN may indicate the weight of the patient, and the like. Various other parameters may be used, such as a type of surgical instrument being used, a size of anatomical structure being operated on, and the like.

In various embodiments, completion time 1815 may be calculated using model 1813 that may include machine learning models, such as neural networks, decision trees, models based on ensemble methods (such as random forests), or any other machine learning model, for example as described above. In some cases, model 1813 may be configured to return a single number related to a completion time, and in some embodiments, model 1813 may be configured to return a probability distribution for a completion time.

In various embodiments, model 1813 may be trained using a data set containing suitable parameters 1811 corresponding to historical surgical data that may include historical completion times for various patients undergoing a given surgical procedure.

Embodiments of the disclosure may further include analyzing the visual data of the ongoing surgical procedure and the historical surgical data to determine an estimated time of completion of the ongoing surgical procedure. Such analyzing may occur through machine learning and/or other techniques described herein for determining an estimated completion time. In one example embodiment, to determine the completion time for the surgery, the method may utilize a machine learning model that takes as an input information (such as a type of the surgical procedure, one or more of visual data of the ongoing surgical procedure such as images of the surgery or video data of the surgery, patient and/or medical personnel characteristics), and as an output returns an estimate of completion time. In some examples, the historical surgical data and the visual data of the ongoing surgical procedure may be analyzed to identified records in the historical surgical data that are similar to the ongoing surgical procedure, for example using a visual similarity function, using an inexact graph matching algorithm on graphs representing the visual data, using a k-Nearest Neighbors algorithm, and so forth. Further, in some examples, the identified records may be used to determine the estimated time of completion of the ongoing surgical procedure. For example, a function (such as mean, median, mode, statistical function, linear function, non-linear function, etc.) of the time of completion from the identified records may be calculated, the estimated time of completion of the ongoing surgical procedure may be based on the calculated function. In an example embodiment, the visual data of the ongoing surgical procedure may be collected at times separated by predetermined time intervals (e.g., the visual data may be collected every second, every few seconds, every few tens of seconds, every minute, or at any other appropriate interval.

Additionally or alternatively, the visual data may be collected at times requested by medical personnel (e.g., the visual data may be collected at times requested by a surgeon and/or anesthesiologist and/or a nurse, or any other designated individual). For example, the surgeon may produce a visual/audio signal (e.g., a hand gesture, a body gesture, a visual signal produced by a light source generated by a medical instrument, a spoken word, or any other trigger) that may be captured by one or more image sensors/audio sensors and recognized as a trigger for collecting the visual data. Additionally or alternatively, the visual data may be collected based on a detected characteristic event during a surgical procedure, as further described below.

In various embodiments, adjusting an operating room schedule may include using historical visual data to train a machine learning model to estimate completion times, and wherein calculating the estimated time of completion includes implementing the trained machine learning model. An example of input data for a machine learning model may include multiple visual data records and parameters. A record of the visual data may be a set of images and/or multiple frames of a video captured by image sensors for a particular time interval during the surgical procedure. For example, visual data record may be video data for the first few minutes of the surgical procedure, the visual data record may be video data for the next few minutes of the surgical procedure, and the visual data record may be video data for the following few minutes of the surgical procedure. In some examples, the machine learning model may be trained and/or used as described above.

Aspects of disclosed embodiments may include accessing a schedule for the surgical operating room, including a scheduled time associated with completion of the ongoing surgical procedure. In an example embodiment, accessing may include reading and/or writing information to a schedule. One example of such schedule may include schedule 1430, or a data structure containing information similar to the information described in relation to schedule 1430. For example, reading and/or writing from/to schedule 1430 may include reading and/or writing any suitable data related to a past, present or future surgical procedure that correspondingly was previously performed, or ongoing or scheduled to be performed in the surgical operating room. Such data may include a name of a procedure, a surgeon performing the procedure, a name of a patient, any characteristic parameters related to the patient or/and medical personnel, a starting time (or an estimated starting time) for the procedure and a finishing time (or an estimated finishing time) for the procedure. In various embodiments, system 1410 may be used to read and/or write to schedule 1430.

Various embodiments may further include calculating, based on the estimated completion time of the ongoing surgical procedure, whether an expected time of completion is likely to result in a variance from the scheduled time associated with the completion, and outputting a notification upon calculation of the variance, to thereby enable subsequent users of the surgical operating room to adjust their schedules accordingly. For example, the estimated (also referred to as expected) time of completion of the ongoing surgical procedure may be obtained using any of the approaches discussed above (e.g., using machine learning models described above and/or linear regression models for historical surgical data). The expected time of completion may be compared to an estimated finishing time for an example medical procedure (e.g., estimated finishing time 1523B, as shown in FIG. 15) and if expected time of completion does not substantially match time 1523B (e.g., expected time of completion is later than or prior to time 1523B), the method may be configured to calculate a difference between the expected time of completion and time 1523B. If the difference is smaller than a predetermined threshold value (e.g., the threshold value may be a minute, a few minutes, five minutes, ten minutes, fifteen minutes, and/or other time values), the method may determine that the expected time of completion is substantially the same as time 1523B. Alternatively, if the difference is sufficiently large (i.e., larger than a predetermined threshold value), the method may calculate (i.e., determine) based on the estimated time of completion of the ongoing surgical procedure that expected time of completion is likely to result in a variance from the scheduled time associated with the completion. In various embodiments, the estimated completion time may be a duration of time for completing a surgical procedure, and the expected time for completion may be an expected time at which the surgical procedure is completed.

In various embodiments, if the variance is detected, a notification may be outputted upon determining the variance (e.g., the variance may be determined by calculating the difference between the expected time of completion and time 1523B). In an example embodiment, the notification may include an updated operating room schedule. For example, updates to schedule 1430 may include text updates, graphics updates, or any other suitable updates (e.g., video data, animations, or audio data). Additionally or alternatively, the notification may be implemented as a warning signal (e.g., light signal, audio signal, and/or other types of transmission signals). In some cases, the notification may be an SMS message, an email, and/or other type of communication delivered to any suitable devices (e.g., smartphones, laptops, pagers, desktops, TVs, and others previously discussed) in possession of various users (e.g., various medical personnel, administrators, patients, relatives or friends of patients, and other interested individuals). For example, the notification may be an electronic message transmitted to a device (as described earlier) associated with a subsequent scheduled user (e.g., a surgeon, an anesthesiologist, and/or other healthcare professional) of the surgical operating room. Such notification may enable various users (e.g., users of the operating room) to adjust their schedules in accordance with an update to the schedule. In various embodiments, the updated operating room schedule may enable a queued healthcare professional to prepare for a subsequent surgical procedure. For example, if the expected time for completion of a surgical procedure is past the estimated finishing time (e.g., time 1523B), a queued healthcare professional (e.g., a surgeon, an anesthesiologist, a nurse, etc.) may delay preparing for the surgical procedure. Alternatively, if the expected time for completion of a surgical procedure is prior to time 1523B), a queued healthcare professional (e.g., a surgeon, an anesthesiologist, a nurse, etc.) may start preparation for the surgical procedure at an earlier time than previously scheduled.

Aspects of disclosed embodiments may further include determining an extent of variance from a scheduled time associated with completion, in response to a first determined extent, outputting a notification, and in response to a second determined extent, forgoing outputting the notification. For example, if the first determined extent is above a predetermined threshold value (e.g., above a few minutes, a few tens of minutes, and/or other measure of time), some embodiments may determine that such a first determined extent may influence scheduling time of other surgical procedures. In such cases, a notification of the variance may be transmitted to any suitable receiving party (e.g., to healthcare providers administering a following surgical procedure). Alternatively, if it is determined that the second determined extent is sufficiently small (e.g., smaller than a predetermined threshold value), embodiments may be configured not to transmit a notification.

Aspects of disclosed embodiments may further include determining whether an expected completion time is likely to result in a delay of at least a selected threshold amount of time from a scheduled time associated with completion. In some embodiments, such determination may be made using a suitable machine learning model, such as model 1813 as described above. The selected threshold amount may be any suitable predetermined amount (e.g., a few minutes, a few tens of minutes, a half an hour, an hour, and/or other measure of time). For example, the selected threshold amount may be based on operations of the surgical operating room. Additionally or alternatively, the selected threshold amount may be based on a future event in a schedule for a surgical operating room. For example, if there is a second surgical procedure scheduled thirty minutes after completion of a first surgical procedure, the selected threshold amount for the first surgical procedure may not exceed the thirty minutes. Additionally or alternatively, the selected threshold amount of time may be selected based on subsequent users of the surgical operating room. For example, if a surgical procedure for subsequent users may require substantial advanced preparation, the selected threshold amount may be sufficiently small (e.g., a few minutes). Alternatively, if the surgical procedure for subsequent users may not require substantial advanced preparation, and may be easily delayed or rescheduled, the selected threshold amount may be sufficiently large (e.g., thirty minutes, an hour, and/or other measure of time.) In some cases, urgency or importance of a surgical procedure for subsequent users may determine a selected threshold amount. For example, for urgent subsequent surgical procedures, an early notification may be needed, thus, requiring a short selected threshold amount.

In response to a determination that the expected time of completion is likely to result in a delay of at least the selected threshold amount of time, disclosed embodiments may include outputting a notification. As described before, the notification may be any type of electronic or paper data that may be output (such as by system 1410, as shown in FIG. 14) for analyzing completion times. In an example embodiment, system 1410 may be configured to output a notification as an electronic message to a device of a healthcare provider, consistent with disclosed embodiments. In response to a determination that the expected time of completion is not likely to result in a delay of at least the selected threshold amount of time, the method may be configured to forgo outputting the notification.

In some cases, disclosed embodiments may further include determining whether a surgical procedure is likely to conclude ahead of time (i.e., an expected completion time for a surgical procedure is shorter than a planned time for the surgical procedure). In response to a determination that the expected completion time is likely to be shorter than the planned time for the surgical procedure by at least a selected threshold amount of time, embodiments may be configured to output a notification and/or forgo outputting the notification.

Figure 19:
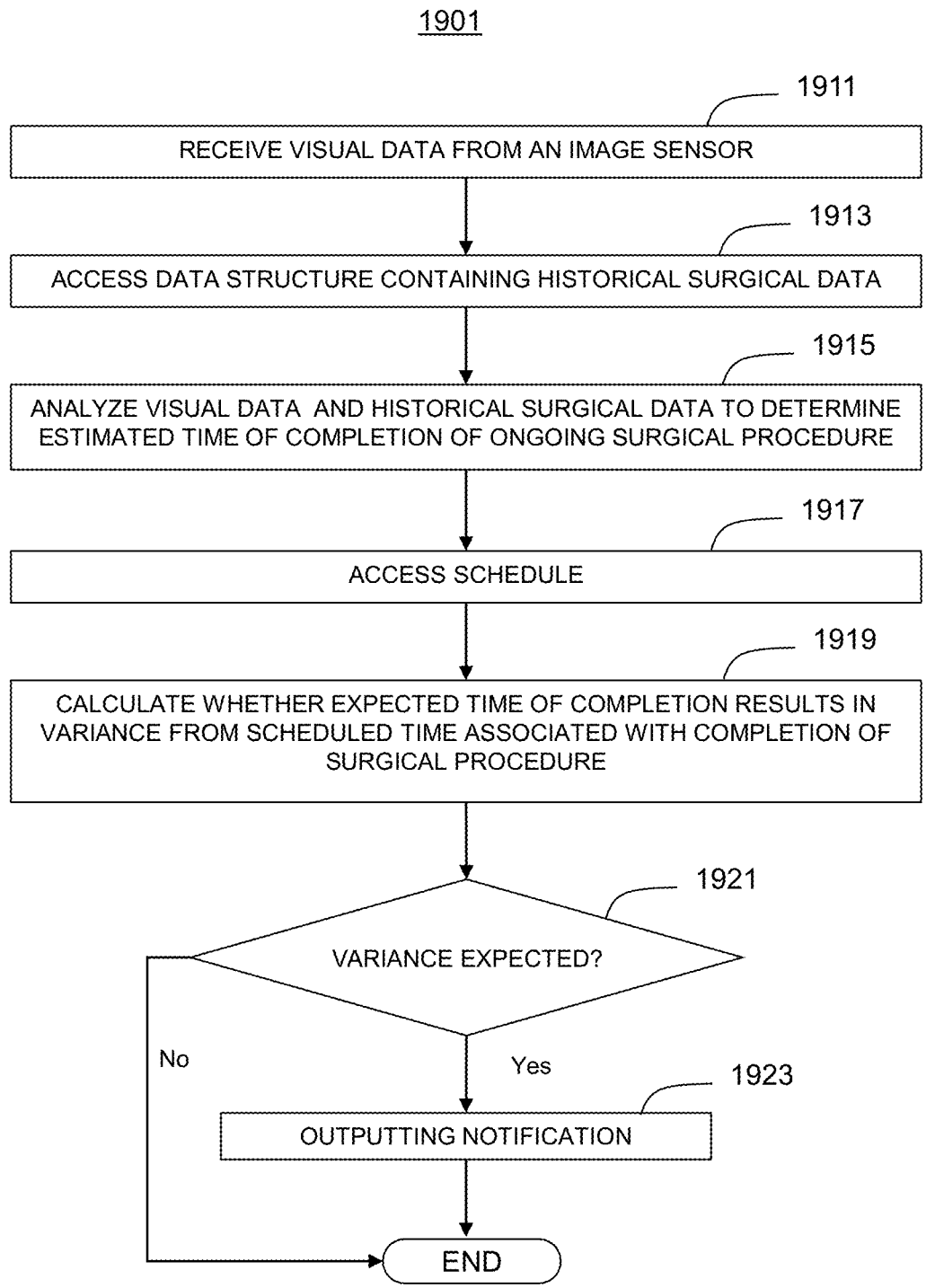
FIG. 19 shows an exemplary process for adjusting an operating room schedule consistent with disclosed embodiments.

FIG. 19 shows an example process 1901 for adjusting an operating room schedule consistent with disclosed embodiments. At step 1911, the process may include receiving visual data from an image sensor. The visual data may include image/video data tracking an ongoing surgical procedure. In an example embodiment, the visual data may be collected by various image sensors. In some cases, two or more image sensors (e.g., cameras) may capture the visual data of the same region of the surgical procedure (e.g., a ROI) from different viewpoints. Additionally or alternatively, two or more image sensors may capture the visual data of the ROI using different magnifications. For example, a first image sensor may capture an overview of the ROI, and a second image sensor may capture an immediate area in the vicinity of a surgical tool located within the ROI.

At step 1913, process 1901 may include accessing a data structure containing historical surgical data as described above. At step 1915, process 1901 may include analyzing the visual data of the ongoing surgical procedure and historical surgical data to determine an estimated time of completion of the ongoing surgical procedure. As previously described, the analysis may use a statistical approach for analyzing first historical surgical data (e.g., calculating the average estimated time of completion for surgical procedures that are of the same type as the ongoing surgical procedure and have similar characteristics as the ongoing surgical procedure). Additionally or alternatively, the analysis may involve training and using a machine learning method for determining an estimated time of completion for an ongoing surgical procedure. In some cases, several different analysis approaches may be used, and estimated time of completion may be determined as an average time for times of completion obtained using different analysis approaches.

At step 1917, process 1901 may include accessing a schedule for the surgical operating room using any suitable means. For example, accessing may include accessing via a wired or wireless network via input devices (e.g., keyboard, mouse, etc.) or via any other means for allowing reading and/or writing data from/to the schedule.

At step 1919, process 1901 may include calculating whether the expected time of completion may result in a variance from the scheduled time associated with completion of surgical procedure, as described above. If the variance is expected (step 1921, Yes), process 1901 may include outputting a notification at step 1923, as described above. Following step 1923, process 1901 may be completed. If the variance is not expected (step 1921, No), process 1901 may be completed.

Aspects of the disclosed embodiments for enabling adjustments of an operating room schedule may include analyzing the visual data, where a process of analyzing may include detecting a characteristic event in the received visual data, assessing the information based on historical surgical data to determine an expected time to complete the surgical procedure following an occurrence of the characteristic event in historical surgical data and determining the estimated time of completion based on the determined expected time to complete. For example, the characteristic event may be detected in the received visual data, as described above. In some examples, the historical surgical data may include a data structure connecting characteristic events with expected time to complete a surgical procedure. For example, the historical surgical data may include a data structure that specifies a first time to complete a surgical procedure from a first event, and a second time to complete a surgical procedure from a second event, the second time may differ from the first time. Further, the data structure may be accessed using the detected characteristic event to determine the time to complete the surgical procedure from the occurrence of the characteristic event.

In various embodiments, a detected characteristic event in the received visual data may refer to a particular procedure or action performed by a medical professional (e.g., by a surgeon, by an anesthesiologist, nurse, and/or other medical professional). For example, characteristic events of a laparoscopic cholecystectomy surgery may include trocar placement, calot's triangle dissection, clipping and cutting of cystic duct and artery, gallbladder dissection, gallbladder packaging, cleaning and coagulation of liver bed, gallbladder retraction, and so forth. In another example, surgical characteristic events of a cataract surgery may include povidone-iodine injection, corneal incision, capsulorhexis, phaco-emulsification, cortical aspiration, intraocularlens implantation, intraocular-lens adjustment, wound sealing, and so forth. In yet another example, surgical characteristic events of a pituitary surgery may include preparation, nasal incision, nose retractor installation, access to the tumor, tumor removal, column of nose replacement, suturing, nose compress installation, and so forth. Some other examples of surgical characteristic events may include incisions, laparoscope positioning, suturing, and so forth. In this context, characteristic event may include any event commonly occurring within a particular stage of a surgical procedure, any event commonly suggesting a particular complication within a surgical procedure, or any event commonly occurring in response to a particular complication within a surgical procedure. Some non-limiting examples of such characteristic events may include usage of particular medical tools, performance of particular actions, infusion of a particular substance, call to a particular specialist, order of a particular device, instrument, equipment medication, blood, blood products, or supply, particular physiological response, and so forth.

A characteristic event (also referred to as an intraoperative surgical event) may be any event or action that occurs during a surgical procedure or phase. In some embodiments, an intraoperative surgical event may include an action that is performed as part of a surgical procedure, such as an action performed by a surgeon, a surgical technician, a nurse, a physician's assistant, an anesthesiologist, a doctor, or any other healthcare professional. The intraoperative surgical event may be a planned event, such as an incision, administration of a drug, usage of a surgical instrument, an excision, a resection, a ligation, a graft, suturing, stitching, or any other planned event associated with a surgical procedure or phase. In some embodiments, the intraoperative surgical event may include an adverse event or a complication. Some examples of intraoperative adverse events may include bleeding, mesenteric emphysema, injury, conversion to unplanned open surgery (for example, abdominal wall incision), incision significantly larger than planned, and so forth. Some examples of intraoperative complications may include hypertension, hypotension, bradycardia, hypoxemia, adhesions, hernias, atypical anatomy, dural tears, periorator injury, arterial occlusions, and so forth. The intraoperative event may include other errors, including technical errors, communication errors, management errors, judgment errors, decision-making errors, errors related to medical equipment utilization, miscommunication, or any other mistakes.

In various embodiments, events may be short or may last for a duration of time. For example, a short event (e.g., incision) may be determined to occur at a particular time during the surgical procedure, and an extended event (e.g., bleeding) may be determined to occur over a time span. In some cases, extended events may include a well defined beginning event and a well defined ending event (e.g., beginning of suturing and ending of the suturing), with suturing being an extended event. In some cases, extended events are also referred to as phases during a surgical procedure.

A process of assessing information based on historical surgical data to determine an expected time to complete a surgical procedure following an occurrence of a characteristic event in historical surgical data may involve using a suitable statistical approach for analyzing completion times of historical surgical procedures that include the occurrence of the characteristic event. For example, the completion times may be analyzed to determine an average completion time for such procedures, and the average completion time may be used as the expected time to complete the surgical procedure. In Some embodiments may include determining an estimated time of completion (i.e., a time at which an example surgical procedure containing a characteristic event will be completed) based on the determined expected time to complete (i.e., the duration of time needed to complete the surgical procedure).

Embodiments for adjusting an operating room schedule may further include using historical visual data to train a machine learning model to detect characteristic events. In various embodiments, the machine learning model for recognizing a feature (or multiple features) may be trained via any suitable approach, such as, for example, a supervised learning approach. For instance, historic visual data containing features corresponding to a characteristic event may be presented as input data for the machine learning model, and the machine learning model may output the name of a characteristic event corresponding to the features within the historic visual data.

In various embodiments, detecting the characteristic event includes implementing the trained machine learning model. The trained machine learning model may be an image recognition model for recognizing a feature (or multiple features) within the visual data that may be used as a trigger (or triggers) for the characteristic event. The machine learning model may recognize features within one or more images or within a video. For example, features may be recognized within a video in order to detect a motion and/or other changes between frames of the video. In some embodiments, image analysis may include object detection algorithms, such as Viola-Jones object detection, convolutional neural networks (CNN), or any other forms of object detection algorithms. Other example algorithms may include video tracking algorithms, motion detection algorithms, feature detection algorithms, color-based detection algorithms, texture based detection algorithms, shape-based detection algorithms, boosting based detection algorithms, face detection algorithms, or any other suitable algorithm for analyzing video frames.

In some cases, characteristic events may be classified as positive (i.e., events that lead to positive outcomes) and adverse (i.e., events that lead to negative outcomes). The positive outcomes and the negative outcomes may have different effect on the estimated completion time.

In some cases, the image recognition model may be configured not only recognize features within the visual data but also configured to form conclusions about various aspects of the ongoing (or historical) surgical procedure based on analysis of the visual data (or historical visual data). For example, by analyzing visual data of an example surgical procedure, the image recognition model may be configured to determine a skill level of a surgeon, or determine a measure of success of the surgical procedure. For example, if there are no adverse events determined in the visual data, the image recognition model may assign a high success level for the surgical procedure and update (e.g., increase) the skill level of the surgeon. Alternatively, if adverse events are determined in the visual data, the image recognition model may assign a low success level for the surgical procedure and update (e.g., decrease) the skill level of the surgeon. The algorithm for assigning success level for the surgical procedure and the process of updating the skill level of the surgeon may be determined based on multiple factors such as the type of adverse events detected during an example surgical procedure, the likelihood of an adverse event during the surgical procedure, given specific characteristics of a patient (e.g., patient age), the average number of adverse events for historical surgical procedures of the same type conducted for patients having similar patient characteristics, the standard deviation from the average number of adverse events for historical surgical procedures of the same type conducted for patients having similar patient characteristics, and/or other metrics of adverse events.

In some cases, a process of analyzing visual data may include determining a skill level of a surgeon in the visual data, as discussed above. In some cases, calculating the estimated time of completion may be based on the determined skill level. For example, for each determined skill level for a surgical procedure, an estimated time of completion may be determined. In an example embodiment, such an estimated time of completion may be based on historical times of completion corresponding to historical surgical procedures performed by surgeons with the determined skill level. For example, average historical times of completion calculated for above-referenced historical times of completion may be used to determine the estimated time of completion. Such an estimated time of completion may be stored in a database and may be retrieved from the database based on a determined skill level.

Detecting a characteristic event using a machine learning method may be one possible approach. Additionally or alternatively, the characteristic event may be detected in the visual data received from image sensors using various other approaches. In one embodiment, the characteristic event may be identified by a medical professional (e.g., a surgeon) during the surgical procedure. For example, surgeon may identify the characteristic event using a visual or an audio signal from the surgeon (e.g., a hand gesture, a body gesture, a visual signal produced by a light source generated by a medical instrument, a spoken word, or any other signal) that may be captured by one or more image sensors/audio sensors and recognized as a trigger for the characteristic event.

In various embodiments, enabling adjustments of an operating room schedule may include analyzing historical times to complete the surgical procedure following an occurrence of the characteristic event in historical visual data. For example, embodiments may include computing average historical time to complete the surgical procedure (also referred herein as an average historical completion time) following the occurrence of the characteristic event in the historical visual data, and using the average historical completion time as an estimate for the completion time of the ongoing surgical procedure. In some cases, however, the estimated completion time may be calculated using other approaches discussed above (e.g., using machine learning methods), and the average historical completion time may be updated based on the determined actual time to complete the ongoing surgical procedure (as determined after the completion of the ongoing procedure). In various embodiments, the average historical completion time may be first updated using an estimated completion time, and then the update may be finalized after completion of the surgical procedure.

Additionally or alternatively, analyzing historical completion times following an occurrence of the characteristic event in order to estimate the completion time may include using a machine learning model. The machine learning model may be trained using a training examples to estimate completion time after occurrences of events, and the trained machine learning model may be used to estimate the completion time based on the occurrence of the characteristic event. An example of such training example may include an indication of a characteristic event together with a label indicating the desired estimation of the completion time. In one example, a training example may be based on historical surgical data, for example representing an actual time to completion in an historical surgical procedure after the occurrence of the characteristic event in the historical surgical procedure. In another example, a training example may be based on user input, may be received from an external system, and so forth. The machine learning model may also be trained to base the estimation of the completion time on other input parameters, such as various characteristics of a patient, various characteristics of a medical personnel, as well as a type of surgical procedure administered to the patient (e.g., parameters 1811, as shown in FIG. 18) as well as one or more characteristic events during the surgical procedure. Further, such input parameters may be provided to the trained machine learning model to estimate the completion time.

As described before, embodiments of the present disclosure may include a system, process, or computer readable media for analyzing the visual data of the ongoing surgical procedure and the historical surgical data to determine an estimated time of completion of the ongoing surgical procedure. In an example embodiment, analyzing may include determining the estimated time of completion based on the analysis of the historical times. The estimate for the completion time may be determined using any suitable approaches such as using a machine learning method (as described above), or by computing an average historical time to complete the surgical procedure, and using such average historical time as the estimated completion time.

Aspects of embodiments for enabling adjustments of an operating room schedule may further include detecting a medical tool in the visual data and calculating the estimated completion time based on the detected medical tool. The medical tool (also referred to as a surgical tool) may be one of the characteristic parameters of the surgery, such as parameters P1-PN, as shown in FIG. 18 that may affect a calculation of the estimated time of completion of the surgical procedure. As discussed above, in an example embodiment, a machine learning method may be used to calculate the estimated completion time based on various parameters P1-PN, such as, for example, a type of medical tool used during the surgical procedure. Furthermore, detection of the medical tool in the visual data tracking the ongoing surgical procedure may be achieved using any suitable approach (e.g., using a suitable image recognition algorithm as described above). In one example, in response to a detection of a first medical tool, a first completion time may be estimated, and in response to a detection of a second medical tool, a second completion time may be estimated, the second completion time may differ from the first completion time. In one example, in response to a detection of a first medical tool, a first completion time may be estimated, and in response to a detection of no medical tool, a second completion time may be estimated, the second completion time may differ from the first completion time.

In some cases, embodiments for analyzing visual data may also include detecting an anatomical structure in the visual data and calculating the estimated time of completion based on the detected anatomical structure. The anatomical structure may be detected and identified in the visual data using an image recognition algorithm. Additionally or alternatively, the anatomical structure may be identified by a healthcare professional during an ongoing surgical procedure (e.g., the healthcare professional can use gestures, sounds, words, and/or other signals) to identify an anatomical structure. The visual data of the ongoing surgical procedure depicting the anatomical structure may be used to calculate the estimated completion time. For example, such visual data may be used as an input to a machine learning method to obtain estimated completion time. In one example, in response to a detection of a first anatomical structure, a first completion time may be estimated, and in response to a detection of a second anatomical structure, a second completion time may be estimated, the second completion time may differ from the first completion time. In one example, in response to a detection of a first anatomical structure, a first completion time may be estimated, and in response to a detection of no anatomical structure, a second completion time may be estimated, the second completion time may differ from the first completion time.

Aspects of embodiments for analyzing visual data may include detecting an interaction between an anatomical structure and a medical tool in the visual data and calculating the estimated time of completion based on the detected interaction. For example, the interaction between an anatomical structure and a medical tool may be detected as described above. The interaction may include any action by the medical tool that may influence the anatomical structure or vice versa. For example, the interaction may include a contact between the medical tool and the anatomical structure, an action by the medical tool on the anatomical structure (such as cutting, clamping, grasping, applying pressure, scraping, etc.), a physiological response by the anatomical structure, the medical tool emitting light towards the anatomical structure (e.g., medical tool may be a laser that emits light towards the anatomical structure), a sound emitted towards anatomical structure, an electromagnetic field created in a proximity of the anatomical structure, a current induced into an anatomical structure, or any other suitable forms of interaction. In one example, in response to a detection of a first interaction between an anatomical structure and a medical tool, a first completion time may be estimated, and in response to a detection of a second interaction between an anatomical structure and a medical tool, a second completion time may be estimated, the second completion time may differ from the first completion time. In one example, in response to a detection of a first interaction between an anatomical structure and a medical tool, a first completion time may be estimated, and in response to a detection of no interaction between an anatomical structure and a medical tool, a second completion time may be estimated, the second completion time may differ from the first completion time.

The visual data of the ongoing surgical procedure depicting the anatomical structure and the medical tool may be used to calculate the estimated completion time. For example, such visual data may be used as an input to a machine learning method to obtain estimated completion time, for example, as described above.

As previously discussed, the present disclosure relates to methods and systems for enabling adjustments of an operating room schedule, as well as non-transitory computer-readable medium that may include instructions that, when executed by at least one processor, cause the at least one processor to execute operations enabling adjustment of an operating room schedule and may include various steps of the method for enabling adjustments of an operating room schedule as described above.

Disclosed systems and methods may involve analyzing surgical footage to identify features of surgery, patient conditions, and other features to determine insurance reimbursement. Insurance reimbursement may need to be determined for various steps of a surgical procedure. Steps of a surgical procedure may need to be identified, and insurance reimbursement codes may need to be associated with the identified steps. Therefore, there is a need for identifying steps of a surgical procedure using information obtained from surgical footage and associating insurance reimbursement with these steps.

Aspects of this disclosure may relate to methods, systems, devices, and computer readable media for analyzing surgical images to determine insurance reimbursement. For ease of discussion, a method is described below, with the understanding that aspects of the method apply equally to systems, devices, and computer readable media. For example, some aspects of such a method may occur electronically over a network that is either wired, wireless, or both. Other aspects of such a method may occur using non-electronic means. In the broadest sense, the method is not limited to particular physical and/or electronic instrumentalities, but rather may be accomplished using many differing instrumentalities.

Consistent with disclosed embodiments, a method for analyzing surgical images to determine insurance reimbursement may include accessing video frames captured during a surgical procedure on a patient. Embodiments for analyzing surgical images may include using any suitable approach (e.g., using a machine-learning approach) for determining phases of surgical procedure, events during a surgical procedure, anatomical structures being operated on, surgical instruments used during a surgical procedure, interactions of surgical instruments and anatomical structures, motion of surgical instruments, motion of anatomical structures, deformation of anatomical structures, color changes of anatomical structures, leakage (e.g., bleeding) of anatomical structures, incisions within anatomical structures, or any other changes to anatomical structures (e.g., a rupture of an anatomical structure) during an example surgical procedure.

In various embodiments, insurance reimbursement may include information regarding how much money may be paid by an insurance company and/or an insurance program (such as a government health insurance program) for a given surgical procedure or segments (portions) thereof. For example, insurance reimbursement may cover costs associated with all, or some of the segments of a surgical procedure. A segment of the surgical procedure may correspond to a segment of surgical footage of the surgical procedure. In some cases, insurance reimbursement may cover an entire cost associated with a segment of a surgical procedure, and in other cases, the insurance reimbursement may partially cover a cost associated with a segment of a surgical procedure. Depending on a type of surgical procedure (e.g., if the surgical procedure is elective for a patient), the insurance reimbursement may not cover costs associated with a segment (or an entirety) of a surgical procedure. In other examples, different reimbursement means (e.g., different reimbursement codes) may exist for different patients and/or different surgical procedures (or for different actions associated with the surgical procedures) based on a condition of the patient and/or on properties of the surgical procedures.

In some embodiments, accessing video frames captured during a surgical procedure may include accessing a database (e.g., database 1411, as shown in FIG. 14) by a suitable computer-based software application. For example, a database may be configured to store video frames captured during various surgical procedures and may be configured to store any other information related to a surgical procedure (e.g., notes from surgeons conducting a surgical procedure, vital signals collected during a surgical procedure). As described herein, the surgical procedure may include any medical procedure associated with or involving manual or operative activities performed on a patient's body.

Consistent with disclosed embodiments, analyzing video frames captured during a surgical procedure to identify in the video frames at least one medical instrument, at least one anatomical structure, and at least one interaction between the at least one medical instrument and the at least one anatomical structure, for example as described above. In various embodiments, analyzing video frames captured during a surgical procedure may include using image recognition, as discussed herein. When analyzing surgical footage, at least some frames may capture an anatomical structure (herein, also referred to as a biological structure). Such portions of surgical footage may include one or more medical instruments (as described herein) interacting with one or more anatomical structures.

A medical instrument and an anatomical structure may be recognized in surgical footage using image recognition, as described in this disclosure and consisted with various disclosed embodiments. An interaction between a medical instrument and an anatomical structure may include any action by the medical instrument that may influence the anatomical structure or vice versa. For example, the interaction may include a contact between the medical instrument and the anatomical structure, an action by the medical instrument on the anatomical structure (such as cutting, clamping, grasping, applying pressure, scraping, etc.), a physiological response by the anatomical structure, the medical instrument emitting light towards the anatomical structure (e.g., surgical tool may be a light-emitting laser) a sound emitted towards anatomical structure, an electromagnetic field in proximity to the anatomical structure, a current induced into the anatomical structure, or any other form of interaction.

In some cases, detecting an interaction may include identifying proximity of the medical instrument to an anatomical structure. For example, by analyzing the surgical video footage, a distance between the medical instrument and a point (or a set of points) of an anatomical structure may be determined through image recognition techniques, as described herein.

Aspects of disclosed embodiments may further include accessing a database of reimbursement codes correlated to medical instruments, anatomical structures, and interactions between medical instruments and anatomical structures. By way of example, a correlation of a reimbursement code with one or more medical instruments, one or more anatomical structures and one or more interactions between medical instruments and anatomical structures may be represented in a data structure such as one or more tables, linked lists, XML data, and/or other forms of formatted and/or stored data. In some embodiments, a correlation may be established by a code-generating machine-learning model. In various cases, the reimbursement codes together with information on how the codes are correlated with medical instruments, anatomical structures and interactions between medical instruments and anatomical structures may be stored in a data structure.

Figure 20:
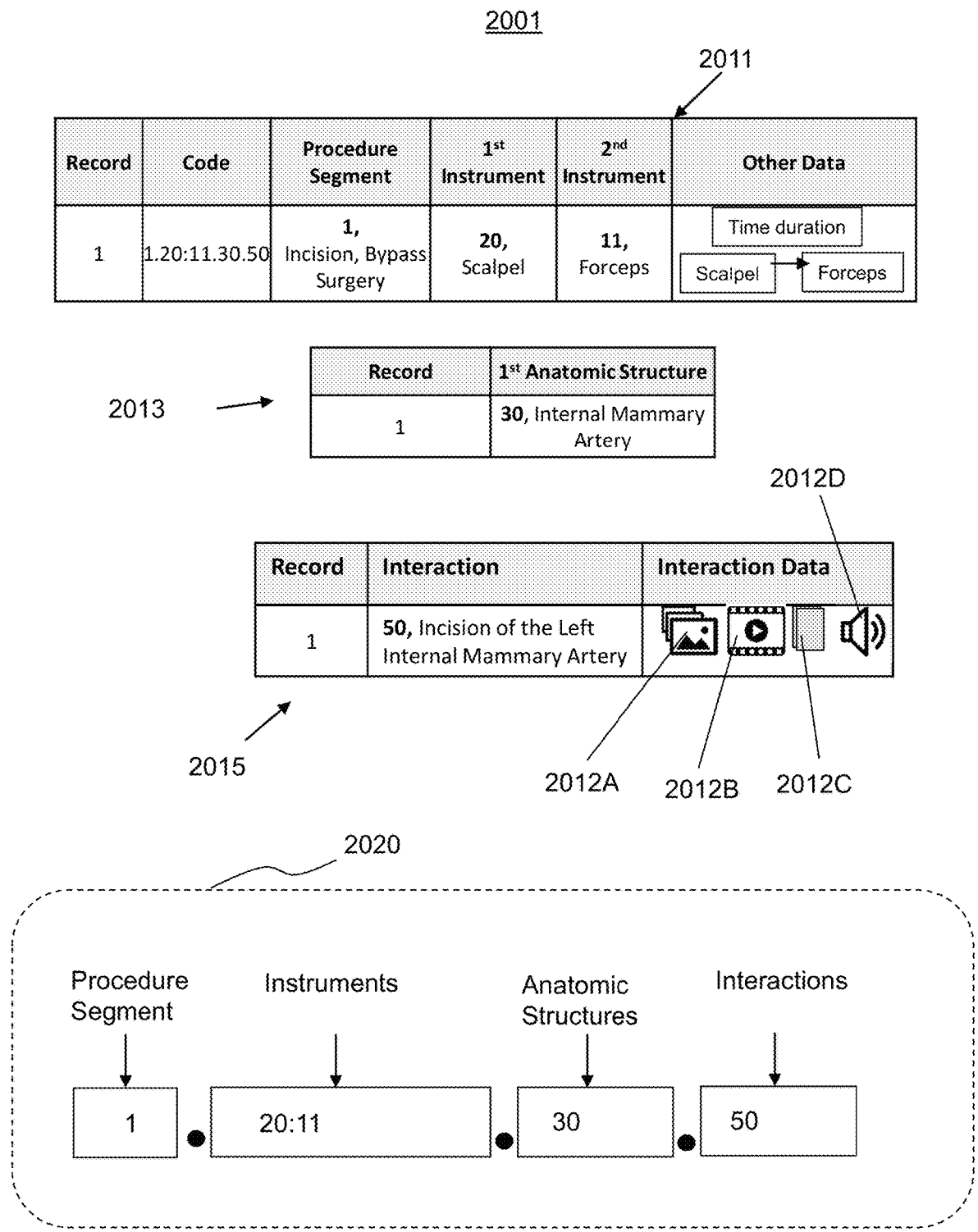
FIG. 20 is an exemplary data structure for storing correlations between reimbursement codes and information obtained from surgical footage, consistent with disclosed embodiments.

FIG. 20 shows an example of data structure 2001 for providing information on how reimbursement codes are correlated with medical instruments, anatomical structures, and interactions between medical instruments. For example, data structure 2001 may include several tables such as tables 2011, 2013 and 2015. In various embodiments, an example table may include records (e.g., rows) and fields (e.g., columns). For example, table 2011 may have a field entitled "Record" containing record labels (e.g., "1", as shown in FIG. 20). For each record, a field entitled "Code" may contain a reimbursement code (e.g., a code "1.20:11.30.50"), a field entitled "Procedure Segment" may contain a number and possibly a name of a segment of a surgical procedure (e.g., "1, Incision, Bypass Surgery"), a field entitled "1st Instrument" may contain a number and possibly a name of a first medical instrument used during the segment of the surgical procedure (e.g., "20, Scalpel"), a field entitled "2nd Instrument" may contain a number and possibly a name of a second medical instrument used during the segment of the surgical procedure (if such an instrument was present) (e.g., "11, Forceps"), a field entitled "Other Data" may contain any related data that may be used further to characterize the surgical procedure or segment thereof (e.g., such data may include a duration of the segment of the surgical procedure, a sequence of events during the segment of the surgical procedure, a sequence of instruments used during the surgical procedure (e.g., "Scalpel→Forceps" may indicate that scalpel was used before forceps), and/or other characteristics of the segment. An example table 2013 may contain other related fields such as a field entitled "1st Anatomical Structure" that may contain a number and possibly a name of an" anatomical structure (e.g., "30, Internal Mammary Artery"), associated with record "1", as labeled in a field entitled "Record" in table 2013. Further, an example table 2015 may include field entitled "Record" for identifying the record, and a field "Interaction" that may contain a description of an interaction between a medical instrument and an anatomical structure that may be represented by a number and possibly a name (e.g., "50, Incision of the Left Internal Mammary Artery"). Further, table 2015 may include a field entitled "Interaction Data" that may include links to image data 2012A, video data 2012B, text data 2012C, and/or audio data 2012D, as shown in table 2015.

In various embodiments, reimbursement codes may have an internal data structure, as shown by structure 2020. For example, a first number for reimbursement code may be a number associated with a segment of a surgical procedure (e.g., number "1"), a second set of numbers may be associated with surgical instruments used during the segment of the surgical procedure (e.g., numbers "20:11" may be associated with the first instrument labeled "20" and the second instrument labeled "11"), a third set of numbers may associated with anatomical structures being operated (e.g., "30"), and a fourth set of numbers may be associated with interactions of instruments and anatomical structures (e.g., "50"). In a different example, reimbursement code may be set by the insurance program or by a regulator. In some examples, a single reimbursement code may be associated with the entire surgical procedure.

Using a data structure to determine reimbursement codes based on medical instruments, anatomical structures, and interactions of medical instruments and anatomical structures may be one possible approach. Additionally, a code-generating machine-learning method may be used to determine a reimbursement code for a surgical procedure or a segment thereof. For example, a code-generating machine-learning method may take as an input a segment of surgical footage and output a reimbursement code for a segment of a surgical procedure represented by the segment of the surgical footage. In various embodiments, a code-generating machine-learning method may be a collection of various machine-learning methods configured for various tasks. For example, the code-generating machine-learning method may include a first image recognition algorithm for recognizing a medical instrument in a segment of surgical footage and a second image recognition algorithm for recognizing anatomical structures in a segment of the surgical footage. In various embodiments, image recognition algorithms may be any suitable algorithms (e.g., neural networks), as described herein and consistent with various disclosed embodiments.

Disclosed embodiments may further include comparing an identified at least one interaction between at least one medical instrument and at least one anatomical structure with information in the database of reimbursement codes to determine at least one reimbursement code associated with the surgical procedure. For example, embodiments may include comparing an identified interaction with various details about interactions stored in a database. Thus, by way of example, a machine-learning model (e.g., an image recognition algorithm) may be configured to identify an interaction within surgical footage and to classify the interaction (e.g., an interaction may be classified by assigning a name to the interaction or determining a type of the interaction). For example, a name or a type of an interaction may be "incision of the left internal mammary artery." In some embodiments, a machine-learning model may be configured to analyze surgical footage and select the most appropriate interaction from a list of possible interactions. Once the interaction is identified, the name (or other identification for the interaction) may be compared with an identification of interactions stored in a database, and the database may be used to find a reimbursement code corresponding to the identified interaction, or to a surgical procedure that includes the identified interaction.

Identifying interactions using a machine-learning algorithm is one possible approach. Additionally or alternatively, interactions may be identified by a surgeon administering a surgical procedure, a nurse practitioner present during the surgical procedure, and/or other healthcare professionals. For example, an interaction may be identified by selecting a segment of surgical footage corresponding to the interaction and assigning a name that may tag a segment. In various embodiments, a computer-based software application may be used to do various manipulations with segments of surgical footage (such as assigning name tags to different segments, selecting different segments, and/or other data operations). The computer-based software application may be configured to store related data (e.g., name tags for different segments of surgical footage, and starting and finishing time for segments of surgical footage) in a database.

Various embodiments may further include outputting at least one reimbursement code for use in obtaining insurance reimbursement for the surgical procedure. For example, a code-generating machine-learning model may be used to output at least one reimbursement code, as described above. Alternatively, the reimbursement code may be output via a query to a database containing reimbursement codes corresponding to interactions of medical instruments with anatomical structures.

In some cases, outputting the reimbursement code may include transmitting the reimbursement code to an insurance provider using any suitable transmission approaches consistent with disclosed embodiments and discussed herein.

In some cases, at least one reimbursement code outputted includes a plurality of outputted reimbursement codes. For example, multiple reimbursement codes may correspond to one or more segments of a surgical procedure. In one embodiment, the first reimbursement code might correspond to an incision-related segment, and a second reimbursement code may, for example, correspond to suturing-related segment. In some cases, multiple reimbursement codes may correspond to multiple medical instruments used to perform one or more operative actions during a segment of a surgical procedure. When more than one surgeon (or any other healthcare professional) is present during a surgical procedure, multiple reimbursement codes may be determined for a procedure performed by each surgeon. And when more than one reimbursable procedure is performed in a single segment, more than one reimbursement code may be output for that single segment.

In an example embodiment, at least two of the plurality of outputted reimbursement codes may be based on differing interactions with a common anatomical structure. For example, the first interaction may include a first medical instrument interacting with an anatomical structure, and a second interaction may include a second medical instrument interacting with the anatomical structure. In some cases, the same instrument may be used for different types of interactions with an anatomical structure (e.g., forceps may be used to interact with an anatomical structure in different ways).

In some embodiments, at least two outputted reimbursement codes are determined based in part on detection of two different medical instruments. For example, a first and a second medical instrument may be detected in surgical footage using any suitable method (e.g., using a suitable machine-learning approach or using information from a healthcare provider). Both the first and the second medical instrument may be used at the same time, and in some cases, a second medical instrument may be used after using the first medical instrument. The use of a first medical instrument may partially overlap (in time) with the use of a second medical instrument. In such instances, two or more reimbursement codes may be outputted, regardless of whether the medical instruments that triggered the codes were being used at the same time or at differing times.

In various embodiments determining at least one reimbursement code may be based on an analysis of a post-operative surgical report. For example, to determine the reimbursement code for a particular segment of a surgical procedure, a post-operative surgical report may be consulted to obtain information about the segment of the surgical procedure. Any information related to a segment of a surgical procedure, and/or the information obtained from the post-operative report, may be used to determine the reimbursement codes (e.g., events that occurred during a segment of a surgical procedure, surgical instruments used, anatomical structures operated upon, interactions of surgical instruments and anatomical structures, imaging performed, various measurements performed, number of surgeons involved, and/or other surgical actions).

In various embodiments, video frames of surgical footage may be captured from an image sensor positioned above the patient, as described herein and consistent with various described embodiments. For example, image sensors 115, 121, 123, and/or 125, as described above in connection with FIG. 1 may be used to capture video frames of surgical footage. In addition, or alternatively, video frames may be captured from an image sensor associated with a medical device, as described herein and consistent with various described embodiments. FIG. 3 shows one example of a medical device having associated image sensors, as described herein.

Embodiments for analyzing surgical images to determine insurance reimbursement may include updating a database by associating at least one reimbursement code with the surgical procedure. The database may be updated using any suitable means (e.g., using a machine-learning model, by sending appropriate data to the database, through SQL commands, by writing information to memory, and so forth). For example, surgical footage of a surgical procedure may be analyzed, as described above, to determine various segments of the surgical procedure for which reimbursement codes may be associated. Once the reimbursement codes are determined, the codes may be associated with the surgical procedure and be configured for storage in the data structure. The data structure may assume any form or structure so long as it is capable or retaining data. By way of one example, the data structure may be a relational database and include tables with table fields storing information about the surgical procedure (e.g., an example table field may include a name of the surgical procedure) and storing reimbursement codes associated with the surgical procedure.

Various embodiments may include generating correlations between processed reimbursement codes and at least one of a plurality of medical instruments in historical video footage, a plurality of anatomical structures in the historical video footage, or a plurality of interactions between medical instruments and anatomical structures in the historical video footage; and updating the database based on the generated correlations. In an exemplary embodiment, correlations may be generated using any suitable means such as using machine-learning methods and/or using an input of healthcare professionals, healthcare administrators and/or other users. Correlations may be represented by tables (e.g., tables 2011-2015, as shown in FIG. 20), as described above. In some cases, the correlations may be generated for processed reimbursement codes (e.g., reimbursement codes relating to portions of historical surgical procedures, for which a health insurer of a patient has previously reimbursed a healthcare provider). For example, historical surgical data (e.g., historical surgical footage) may be analyzed (e.g., using a machine-learning method) to determine one or more medical instruments in historical video footage, one or more anatomical structures in the historical video footage, or one or more interactions between medical instruments and anatomical structures in the historical video footage. Provided that segments of historical surgical procedure have associated processed reimbursement codes (e.g., the processed reimbursement codes were assigned to the segments of the historical surgical procedure using any suitable approach available in the past, such as inputs from a healthcare provider), the processed reimbursement codes may be correlated with information obtained from the historical surgical data (e.g., information about medical instruments, anatomical structures, and interactions between medical instruments and anatomical structures identified in the historical surgical data).

In various embodiments, a machine-learning method for generating correlations may be trained, as discussed in this disclosure. Historical surgical data may be used as part of the training process. For example, historical surgical footage for a given segment of a surgical procedure may be provided as a machine-learning input, which thereafter determines a reimbursement code. A reimbursement code may be compared with a processed reimbursement code for the given segment of the surgical procedure to determine if the machine-learning model outputs a correct prediction. Various parameters of the machine-learning model may be modified using, for example, a backpropagation training process.

In various embodiments, as discussed herein, historical video frames may be used to train any suitable machine learning model for various tasks based on information contained within the video frames (i.e., any suitable image-based information). As previously discussed, machine-learning models may detect at least one of medical tools, anatomical structures, or interactions between medical tools and anatomical structures. Once the model recognizes correlations, those correlations can then be extrapolated to current video under analysis.

In some cases, generating correlations may include implementing a statistical model. For example, historical processed reimbursement codes may be analyzed for similar segments of historical surgical procedures to determine a correlation. A correlation may be between a reimbursement code and various aspects of a segment of a surgical procedure. Surgical segments can be characterized by medical instruments, anatomical structures, and interactions between medical instruments and anatomical structures. If different processed reimbursement codes were used for such similar segments, then correlations may be generated by evaluating the most likely reimbursement code that should be used. For example, if for a segment of a historical procedure of a given type, a processed reimbursement code C1 was used 100 times, a processed reimbursement code C2 was used 20 times, and a processed reimbursement code C3 was used 10 time, then reimbursement code C1 may be selected as the most likely reimbursement code that should be used.

In some cases, when processed reimbursement codes are different for the same (or similar) segments of historical surgical procedures, characteristics of these segments may be analyzed to determine if some differences in the characteristics of these segments may be responsible for a difference in processed reimbursement codes. In various embodiments, differences in characteristics of segments of historical surgical procedures may correlate the difference in processed reimbursement codes (as measured using any suitable statistical approach).

In various embodiments, after generating the correlations, as described above, a database may be updated based on the generated correlations. For example, for a given medical instrument interacting with a given anatomical structure, an expected reimbursement code (or, in some cases, a set of possible reimbursement codes) may be associated and stored in the database. A set of possible reimbursement codes may be used to further narrow a particular one of the reimbursement codes based on characteristics associated with a segment of a surgical procedure identified in surgical footage.

Additionally or alternatively, disclosed embodiments may include receiving a processed reimbursement code associated with a surgical procedure and updating the database based on the processed reimbursement code. The processed reimbursement code may be provided by a healthcare provider, a healthcare administrator, and/or other users. Or, as discussed herein, the processed reimbursement code may be provided via a machine-learning method for analyzing historical surgical procedures and identifying processed reimbursement codes that were used for historical surgical procedures. In various embodiments, a processed reimbursement code may differ from at least one of the outputted reimbursement codes. This may occur after manual identification of a correct code by a healthcare professional, or after further machine learning analysis determines a more accurate reimbursement code candidate.

As previously described, some embodiments may include using a machine learning model to detect, in the historical video footage, the at least one plurality of medical instruments, plurality of anatomical structures, or plurality of interactions between medical instruments and anatomical structures. As described herein, the machine-learning method may be any suitable image recognition method trained to recognize one or more medical instruments, anatomical structures, and interactions between the instruments and the structures. In an example embodiment, a machine-learning method may employ multiple image recognition algorithms, with each algorithm trained to recognize a particular medical instrument or a particular anatomical structure.

Aspects of disclosed embodiments may further include analyzing video frames captured during a surgical procedure to determine a condition of an anatomical structure of a patient and determining at least one reimbursement code associated with the surgical procedure based on the determined condition of the anatomical structure. Procedures performed on anatomical structures in poor condition, for example, may justify higher reimbursement than procedures performed on anatomical structures in better condition. In an example embodiment, a machine-learning method may be used based on information obtained from various sensors for determining the condition of an anatomical structure of a patient. A condition of an anatomical structure may be determined based on observed visual characteristics of the anatomical structure such as a size, color, shape, translucency, reflectivity of a surface, fluorescence, and/or other image features. A condition may be based on one or more of the anatomical structure, temporal characteristics (motion, shape change, etc.) for the anatomical structure, sound characteristics (e.g., transmission of sound through the anatomical structure, sound generated by the anatomical structure, and/or other aspects of sound), imaging of the anatomical structure (e.g., imaging using x-rays, using magnetic resonance, and/or other means), or electromagnetic measurements of the structure (e.g., electrical conductivity of the anatomical structure, and/or other properties of the structure). Image recognition can be used to determine anatomical structure condition. Additionally or alternatively, other specialized sensors (e.g., magnetic field sensors, electrical resistance sensors, sound sensors or other detectors) may be used in condition determination.

Figure 21:
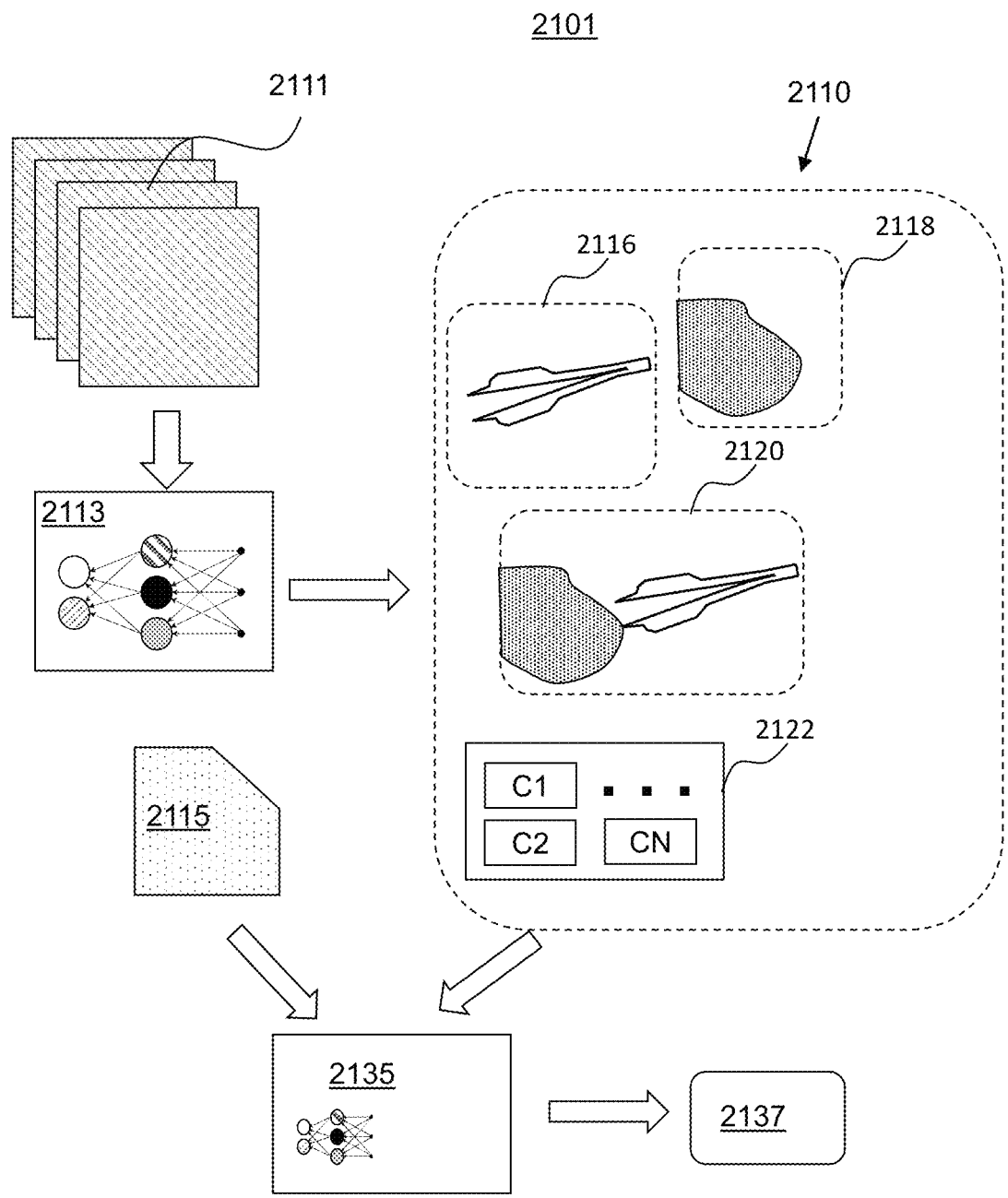
FIG. 21 is block diagram of an exemplary machine learning method consistent with disclosed embodiments.

In various embodiments, upon determining a condition of an anatomical structure, a reimbursement code may be identified using, for example, a suitable machine-learning mode. For instance, the machine-learning model may take a condition of an anatomical structure as one possible parameter for determining one or more reimbursement codes. FIG. 21 shows an example system 2101 for determining one or more reimbursement codes (e.g., codes 2137, as schematically shown in FIG. 21). In an example embodiment, surgical footage 2111 may be processed by a machine-learning method 213, and method 213 may identify medical instruments 2116, anatomical structures 2118, interactions of medical instrument and anatomical structures 2120, and various parameters 2122 (herein also referred to as properties or characteristics) such as parameters C1-CN describing instruments 2116, anatomical structures 2118, interactions 2120, and any other information that might impact a reimbursement code. An example parameter C1 may be a size of the incision, parameter C2 may be a condition of an anatomical structure (e.g., a size, a color, a shape, and/or other image property of the anatomical structure), and parameter CN may be a location at which an example medical instrument interacted with an example anatomical structure. Information about medical instruments 2116, anatomical structures 2118, interactions 2120, and parameters 2122 may be used as an input 2110 for a computer-based software application, such as a machine-learning model 2135. Model 2135 may process input 2110 and output one or more reimbursement codes associated with a segment of a surgical procedure having information as described by input 2110.

In some of the embodiments, analyzing surgical images to determine insurance reimbursement may include analyzing video frames captured during a surgical procedure to determine a change in a condition of an anatomical structure of a patient during the surgical procedure, and determining the at least one reimbursement code associated with the surgical procedure based on the determined change in the condition of the anatomical structure. A process of analyzing video frames to determine a change in the condition of an anatomical structure of the patient may be performed using any suitable machine-learning method. For example, the change in a condition of an anatomical structure may include a change in shape, color, size, location, and/or other image property of the anatomical structure. Such change may be determined by image recognition algorithm as described herein and consistent with various described embodiments. An image recognition algorithm may identify an anatomical structure in a first set of frames of surgical procedure, identify an anatomical structure in a second set of frames of surgical procedure and evaluate if the anatomical structure changed from the first to the second set of frames. If the change is observed, the image recognition algorithm may qualify the change by assigning a change related identifier. By way of a few examples, the change-related identifier may be a string "removed tumor," "removed appendix," "carotid arteries with a removed blockage," and/or other data describing a change. Change-related identifiers may be selected from a list of preconfigured identifiers, and may include one of the parameters of a surgical procedure, such as parameters C1-CN, as shown in FIG. 21, used as part of an input for a machine-learning model (e.g., model 2135) to output reimbursement codes (e.g., codes 2137). In this way, a reimbursement code may be associated with the surgical procedure based on the determined change in the condition of the anatomical structure.

Disclosed embodiments may also include analyzing the video frames captured during a surgical procedure to determine usage of a particular medical device, and determining at least one reimbursement code associated with the surgical procedure based on the determined usage of the particular medical device. The use of certain medical instruments may impact reimbursement codes. For example, the detection of certain disposable medical devices may trigger reimbursement for those devices. Or the use of a costly imaging machine (MRI, CT, etc.), may trigger reimbursement for usage of that device. Moreover, the usage of certain devices, regardless of their cost, can be correlated to the complexity, and therefore the cost of a procedure.

Some embodiments may further include analyzing video frames captured during a surgical procedure to determine a type of usage of a particular medical device, and in response to a first determined type of usage, determining at least a first reimbursement code associated with the surgical procedure; and in response to a second determined type of usage, determining at least a second reimbursement code associated with the surgical procedure, the at least a first reimbursement code differing from the at least a second reimbursement code. A type of usage may be any technique or manipulation of the medical device, such as incision making, imaging, suturing, surface treatment, radiation treatment, chemical treatment, cutting, and/or other treatment modalities. In various embodiments, the type of usage may be analyzed by analyzing video frames captured during a surgical procedure (i.e., surgical footage).

Consistent with various embodiments described herein, detection of type of usage may occur through image recognition, as previously discussed. In some cases, the location of a device relative to an anatomical structure may be used to determine the interaction of the medical device with the anatomical structure. In various embodiments, for each type of treatment using a medical device, a corresponding reimbursement code may be used. In some cases, the same medical device may be used for different types of treatments that may have different associated reimbursement codes. For example, forceps can be used first to clamp an anatomical structure, and then used to extract an anatomical structure. In some examples, a type of usage of a particular medical device may be determined by analyzing video frames captured during a surgical procedure. For example, a machine learning model may be trained using training example to determine types of usages of medical devices from images and/or videos of surgical procedures, and the trained machine learning model may be used to analyze the video frames captured during a surgical procedure and determine the type of usage of the particular medical device. An example of such training example may include an image and/or a video of at least a portion of a surgical procedure, together with a label indicating the type of usage of a particular medical device in the surgical procedure.

In some examples, a machine learning model may be trained using training examples to determine reimbursement codes for surgical procedures based on information related to the surgical procedures. An example of such training example may include information related to a particular surgical procedure, together with a label indicating the desired reimbursement code for the particular surgical procedure. Some non-limiting examples of such information related to the surgical procedures may include images and/or videos of the surgical procedure, information based on an analysis of the images and/or videos of the surgical procedure (some non-limiting examples of such analysis and information are described herein), an anatomical structure related to the surgical procedure, a condition of an anatomical structure related to the surgical procedure, a medical instrument used in the surgical procedure, an interaction between a medical instrument and an anatomical structure in the surgical procedure, phases of the surgical procedure, events that occurred in the surgical procedure, information based on an analysis of a post-operative report of the surgical procedure, and so forth. Further, in some examples, the trained machine learning model may be used to analyze the video frames captured during the surgical procedure to determine the at least one reimbursement code associated with the surgical procedure. In other examples, the trained machine learning model may be used to determine the at least one reimbursement code associated with the surgical procedure based on any information related to the surgical procedure, such as at least one interaction between at least one medical instrument and at least one anatomical structure in the surgical procedure (for example, the at least one interaction between the at least one medical instrument and the at least one anatomical structure identified by analyzing the video frames captured during the surgical procedure), an analysis of a postoperative surgical report of the surgical procedure, a condition of an anatomical structure of the patient (for example, a condition of an anatomical structure of the patient determined by analyzing the video frames captured during the surgical procedure), a change in a condition of an anatomical structure of the patient during the surgical procedure (for example, a change in a condition of an anatomical structure of the patient during the surgical procedure determined by analyzing the video frames captured during the surgical procedure), a usage of a particular medical device (for example, a usage of a particular medical device determined by analyzing the video frames captured during the surgical procedure), a type of usage of a particular medical device (for example, a type of usage of the particular medical device determined by analyzing the video frames captured during the surgical procedure), an amount of a medical supply of a particular type used in the surgical procedure (for example, an amount of a medical supply of the particular type used in the surgical procedure and determined by analyzing the video frames captured during the surgical procedure), and so forth.

Additionally, embodiments may include analyzing video frames captured during a surgical procedure to determine an amount of a medical supply of a particular type used in the surgical procedure and determining the at least one reimbursement code associated with the surgical procedure based on the determined amount. In an example embodiment, the amount of a medical supply of a particular type may be determined using an image recognition algorithm for observing video frames of a surgical procedure that may indicate an amount of a medical supply that was used during the surgical procedure. The medical supply may be any material used during the procedure, such as medications, needles, catheters, or any other disposable or consumable material. The amount of supply may be determined from video frames of a surgical procedure. For example, the amount of medication used by a patient may be determined by observing an intravenous (IV) apparatus for supplying medications and fluids to a patient. Bags of intravenous blood or fluids may be counted as they are replaced. In various embodiments, a suitable machine-learning model may be used to identify an amount of a medical supply of a particular type used during, prior, and/or after the surgical procedure, and determining at least one reimbursement code associated with the surgical procedure based on the determined amount. The machine-learning model may be trained using historical surgical footage of a historical surgical procedure and historical data for amounts of a medical supply used during the historical surgical procedure. In some examples, an amount of a medical supply of a particular type used in a surgical procedure may be determined by analyzing video frames captured during the surgical procedure. For example, a machine learning model may be trained using training example to determine amounts of medical supplies of particular types used in surgical procedures from images and/or videos of surgical procedures, and the trained machine learning model may be used to analyze the video frames captured during a surgical procedure and determine the amount of the medical supply of the particular type used in the surgical procedure. An example of such training example may include an image and/or a video of at least a portion of a particular surgical procedure, together with a label indicating the amount of the medical supply of the particular type used in the particular surgical procedure.

Figure 22:
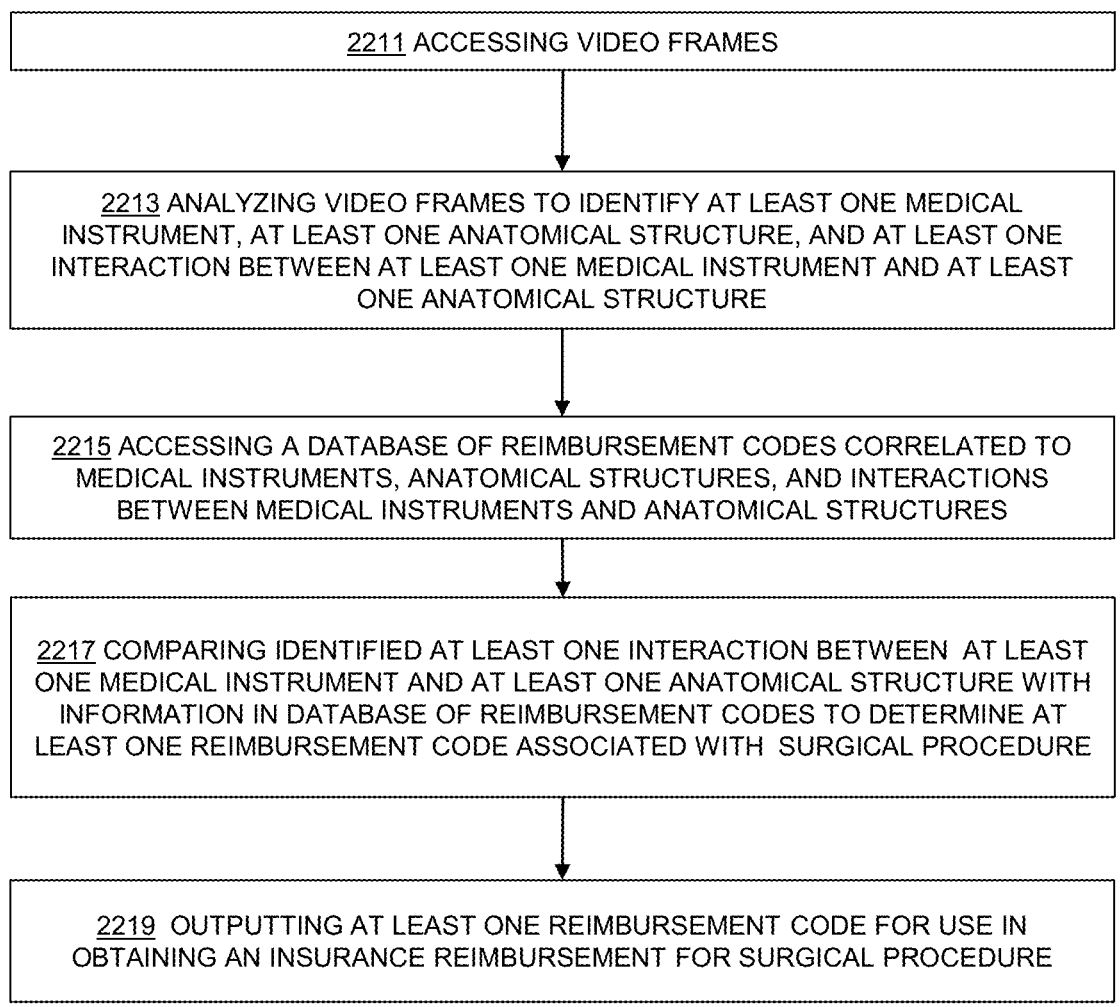
FIG. 22 is a flow chart of an exemplary process for analyzing surgical images to determine insurance reimbursement, consistent with disclosed embodiments.

Aspects of a method of analyzing surgical images to determine insurance reimbursement code are illustrated by an example process 2201, as shown in FIG. 22. At step 2211 of process 2201, a method may include accessing video frames captured during a surgical procedure on a patient. Video frames may be captured using any suitable image sensors and may be accessed using a machine-learning method and/or a healthcare provider, as discussed above. At step 2213, the method may include analyzing the video frames captured during the surgical procedure to identify in the video frames at least one medical instrument, at least one anatomical structure, and at least one interaction between the at least one medical instrument and the at least one anatomical structure, as described above. For example, the frames may be analyzed using a suitable machine-learning method, such as an image recognition algorithm, as previously discussed. At step 2215, the method may include accessing a database of reimbursement codes correlated to medical instruments, anatomical structures, and interactions between medical instruments and anatomical structures. At step 2217, the method may include comparing the identified at least one interaction between the at least one medical instrument and the at least one anatomical structure with information in the database of reimbursement codes to determine at least one reimbursement code associated with the surgical procedure, as previously described, and at step 2219, the method may include outputting the at least one reimbursement code for use in obtaining an insurance reimbursement for the surgical procedure.

As previously discussed, the present disclosure relates to methods and systems for analyzing surgical images to determine insurance reimbursement, as well as a non-transitory computer-readable media that may include instructions that, when executed by at least one processor, cause the at least one processor to execute operations enabling analyzing surgical images to determine insurance reimbursement, as described above.

Disclosed systems and methods may involve analyzing surgical footage to identify features of surgery, patient conditions, and surgical intraoperative events to obtain information for populating the postoperative report. A post-operative report may be populated by analyzing surgical data obtained from a surgical procedure to identify features of surgery, patient conditions, and surgical intraoperative event and extracting information from the analyzed data for populating the postoperative report. Therefore, there is a need for analyzing surgical data, and extracting information from the surgical data that may be used for populating a postoperative report.

Aspects of this disclosure may relate to populating a post-operative report of a surgical procedure, including methods, systems, devices, and computer readable media. For ease of discussion, a method is described below, with the understanding that aspects of the method apply equally to systems, devices, and computer readable media. For example, some aspects of such a method may occur electronically over a network that is either wired, wireless, or both. Other aspects of such a method may occur using non-electronic means. In the broadest sense, the method is not limited to particular physical and/or electronic instrumentalities, but rather may be accomplished using many differing instrumentalities.

Consistent with disclosed embodiments, a method for populating a post-operative report of a surgical procedure may include receiving an input of an identifier of a patient. Further, the method may include receiving an input of an identifier of a health care provider. A post-operating report may be any suitable computer-based or paper-based report documenting a surgical procedure. In various embodiments, a post-operative report may include multiple frames of surgical footage, audio data, image data, text data (e.g., doctor notes) and the like. In an example embodiment, a post-operative report may be populated, partially populated, or not populated. For example, the post-operative report may contain fields (e.g., regions of the report) for holding various details obtained during the surgical procedure. In an example embodiment, at least some fields may have an associated characteristic (also referred to as a field name) that may determine what type of information can be entered in the field. For instance, a field with an associated name "Name of a Patient" may allow a name of a patient to be entered in that field. A field named "Pulse Plot" may be a field for displaying a pulse of a patient during the surgical procedure plotted as a function of time. In various embodiments, when the report is not populated, all the fields in the report may be empty; when the report is partially populated, some of the fields may contain information obtained from a surgical procedure; and when the report is fully populated (or mostly populated) the vast majority of the fields may contain information relating to an associated surgical procedure. In some examples, at least part of a post-operative report may have a free form format, allowing users and/or automatic processes to enter data in various organizations and/or formats, such as free text, which in some examples may include other elements embedded freely in the free text or accompanying it, such as links to external elements, images, videos, audio recordings, digital files, and so forth. It is appreciated that any detail described herein as included in a post-operative report in a particular field may be equally included in a post-operative report as part of such free textual information, embedded in the free text, or accompanying it.

Figure 23:
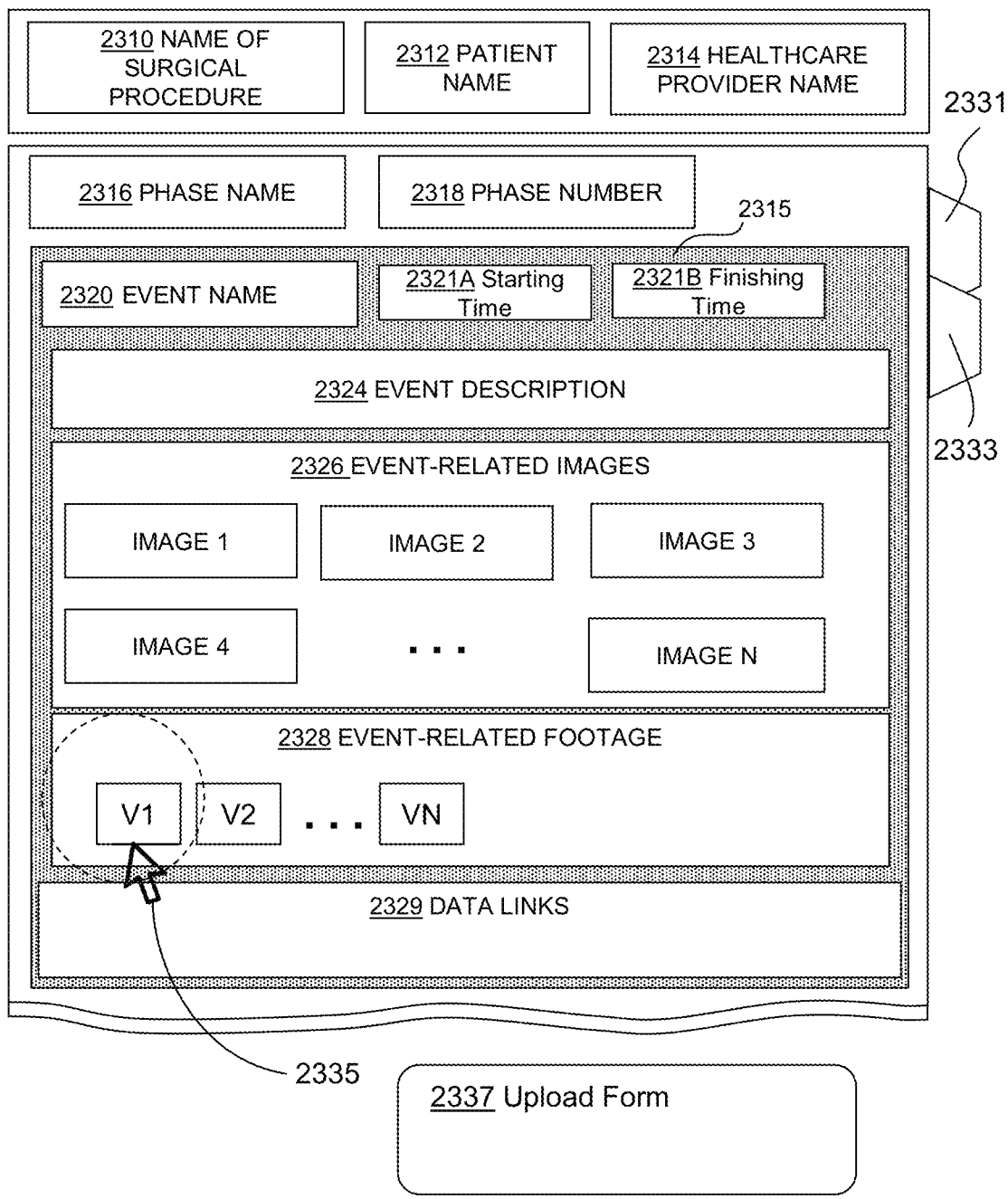
FIG. 23 is an example post-operative report containing fields, consistent with disclosed embodiments.

An example post-operative report 2301 is shown in FIG. 23. Report 2301 may contain multiple fields, sections, and subsections. Different fields may contain different types of information. For example, field 2310 may contain a name of the surgical procedure, field 2312 may contain a name of a patient and field 2314 may contain a name of a healthcare provider. Field 2316 may include a name of a phase of a surgical procedure, and field 2318 may include a sequential number of a phase (e.g., a first phase of a surgical procedure). Multiple instances of fields 2314 and/or 2316 may be included in postoperative report 2301, to described a plurality of phases of the surgical procedure. Report 2301 may include a section 2315 that may describe a particular event during a surgical procedure. Multiple sections for describing multiple events may be present in report 2301. One or more of the events may be connected to a particular surgical phase, while other events may not be connected to any surgical phase. In an example embodiment, section 2315 may include a field 2320 containing a name of the event, field 2321A containing a starting time for the event, field 2321B containing a finishing time for the event, and field 2324 containing description of the event (e.g., field 2324 may contain notes from a healthcare provider describing the event). Section 2315 may include subsection 2326 for containing fields for images such as fields IMAGE 1 through IMAGE N, as well as subsection 2328 for containing event-related surgical footage. For example, subsection 2328 may include fields V1-VN. Additionally, section 2315 may include subsection 2329 that may contain links to various other data related to a surgical procedure. In various embodiments, a post-operative report may be partitioned into different portions indicated by tabs 2331 and 2333, as shown in FIG. 23. For example, when a user selects tab 2331, information related to a first portion of a surgical report may be displayed, and when a user selects tab 2333, information related to a second portion of a surgical report may be displayed. In various embodiments, a surgical report may include any suitable number of portions.

FIG. 23 also shows that information may be uploaded into report 2301, via an upload input form 2337. For example, a user may click on a field (e.g., field V1, as shown in FIG. 23), and form 2337 may be presented to the user for uploading data for the field V1. In various embodiments, fields, sections, subsections, and tabs, as shown in FIG. 23 are only illustrative, and any other suitable fields, sections, subsections, and tabs may be used. Furthermore, a number and types of fields, sections, subsections, and tabs may depend on information entered in post-operative report 2301.

Figure 24A:
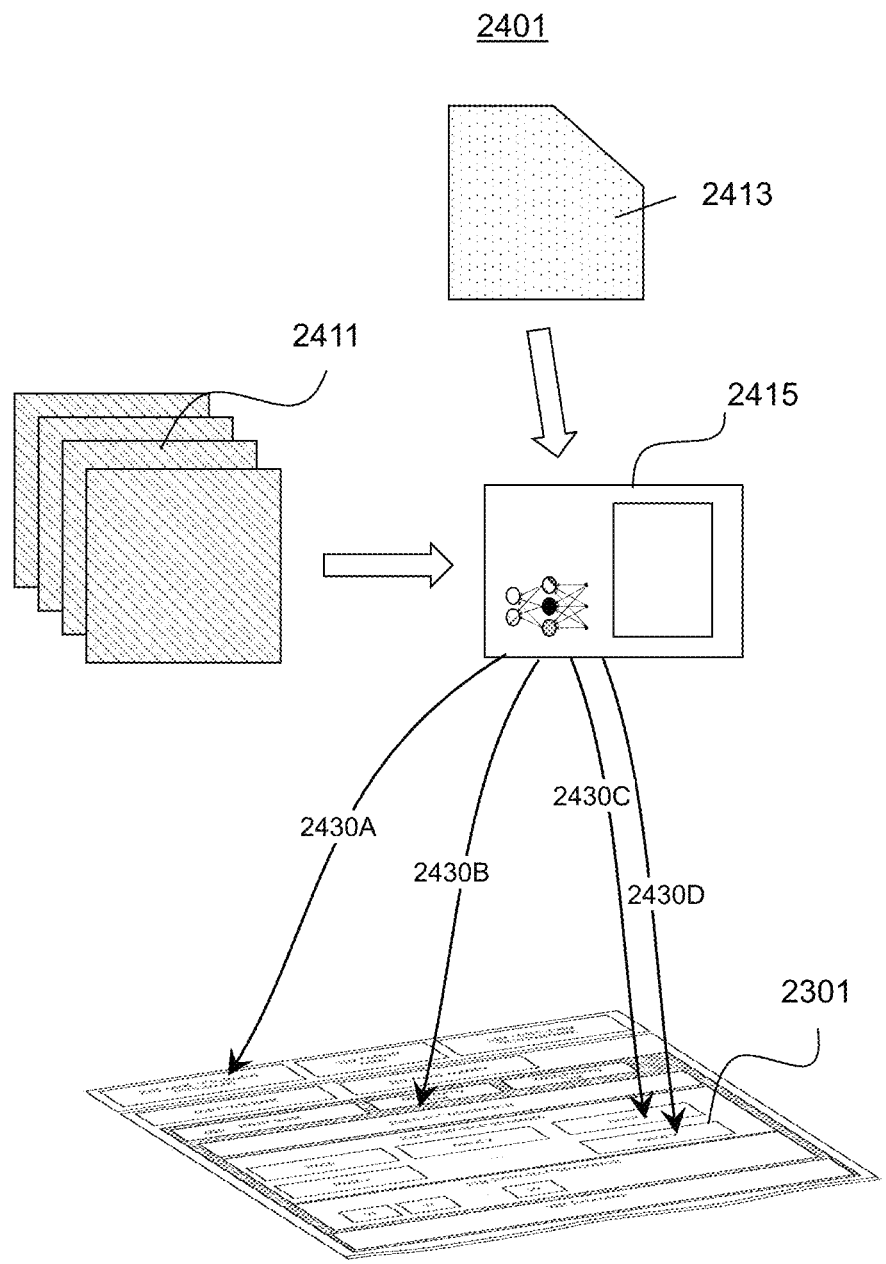
FIG. 24A is an example of a process, including structure, for populating a post-operative report, consistent with disclosed embodiments.
Figure 24B:
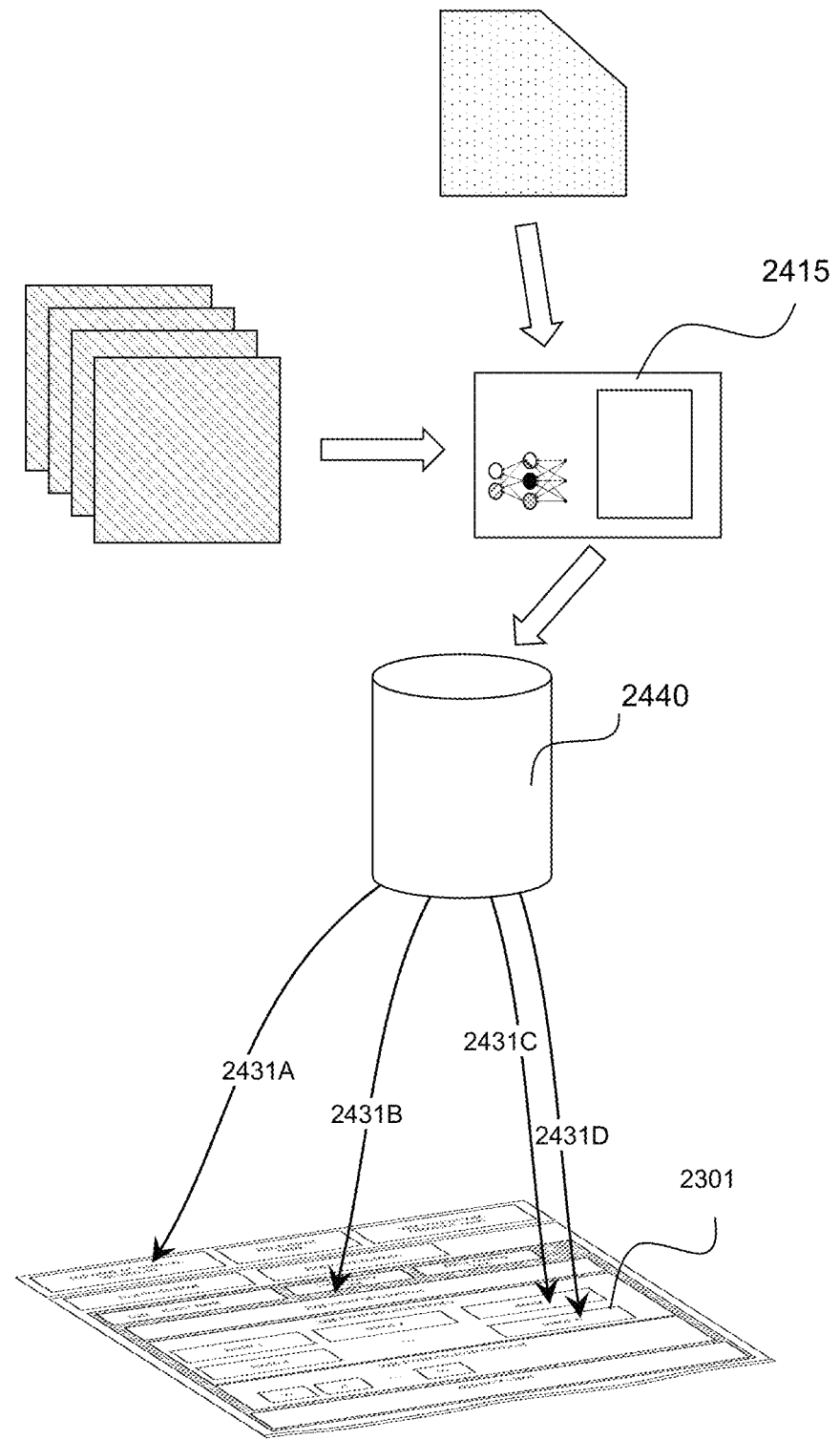
FIG. 24B is another example of a process, including structure, for populating a post-operative report, consistent with disclosed embodiments.

In various embodiments, information for populating at least part of a post-operative report may be obtained from surgical footage of a surgical procedure. Such information may be referred to as image-based information. Additionally, information about a surgical procedure may be obtained from notes of a healthcare provider or a user, previously filed forms for a patient (e.g., a medical history for the patient), medical devices used during a surgical procedure, and the like. Such information may be referred to as auxiliary information. In an example embodiment, auxiliary information may include vital signs, such as pulse, blood pressure, temperature, respiratory rate, oxygen levels, and the like reported by various medical devices used during a surgical procedure. Image-based information and auxiliary information may be processed by a suitable computer-based software application and the processed information may be used to populate a post-operative report. For example, FIG. 24A shows an example of a process 2401 for processing information and populating a post-operative report 2301. In an example embodiment, image-based information 2411 and auxiliary information 2413 may be used as an input to a computer-based software application 2415, and application 2415 may be configured to process information 2411 and 2413, extract data for various fields present in a post-operative report (e.g., report 2301, as shown in FIG. 24A), and populate the various fields (as schematically indicated by arrows 2430A-2430D). FIG. 24B shows an example system 2402 for processing information and populating a post-operative report 2301. 2402 may differ from system 2401 in that various data processed by application 2415 may be stored in a database 2440 prior to populating post-operative report 2301. By storing data in database 2440, the data may be easily accessed for use in generating various other reports. Database 2440 may be configured to execute a software application for mapping data from database 2440 to fields of report 2301 as schematically shown by arrows 2431A-2431D.

As described above, embodiments for populating a post-operative report may include receiving an input of an identifier of a patient and a healthcare provider. The identifier of a patient may be any suitable data or physical indicator (e.g., a patient's name, date of birth, social security number or other government identifier, patient number or other unique code, patient image, DNA sequence, a vocal ID, or any other indicator that uniquely identifies the patient. In some cases, a group of identifiers may be used as a combined identifier. In an example embodiment, an identifier may be an alphanumerical string that uniquely identifies the patient.

In various embodiments, of the patient identifier may be received as an input. This may occur using any suitable process of transmission (e.g., a process of transmission of data over a wired or wireless network, a process of transmission of data using a suitable input device such as a keyboard, mouse, joystick, and the like). In some cases, "receiving an input" may include receipt through mail or courier (e.g., a paper document delivered in person).

Similar to the patient identifier, the identifier of a health care provider may be any suitable indication of identity, such as a name, a code, an affiliation, an address, an employee number, a Physician License Number, or any other mechanism of identifying the healthcare provider. In an example embodiment, an identifier may be an alphanumerical string that uniquely identifies the healthcare provider.

Disclosed embodiments may further include receiving an input of surgical footage of a surgical procedure performed on the patient by the health care provider. Surgical footage may be received as input by a computer-based software application for analyzing the input (e.g., application 2415, as shown in FIG. 24A) and/or, in some cases, receiving an input may include receiving the input by a healthcare professional or a user. This may occur, for example, when a healthcare professional or the user uploads the video footage from a storage location and/or directly from sensors capturing the video footage.

The surgical footage of a surgical procedure may include any form of recorded visual data, including recorded images and/or video data, which may also include sound data. Visual data may include a sequence of one or more images captured by image sensors, such as cameras 115, 121, 123, and/or 125, as described above in connection with FIG. 1. Some of the cameras (e.g., cameras 115, 121, and 125) may capture video/image data of operating table 141, and camera 121 may capture video/image data of a surgeon 131 performing the surgery. In some cases, cameras may capture video/image data associated with surgical team personnel, such as an anesthesiologist, nurses, surgical tech and the like located in operating room 101.

In various embodiments, image sensors may be configured to capture the surgical footage by converting visible light, x-ray light (e.g., via fluoroscopy), infrared light, or ultraviolet light to images, a sequence of images, videos, and the like. The image/video data may be stored as computer files using any suitable format such as JPEG, PNG, TIFF, Audio Video Interleave (AVI), Flash Video Format (FLV), QuickTime File Format (MOV), MPEG (MPG, MP4, M4P, etc.), Windows Media Video (WMV), Material Exchange Format (MXF), and the like.

A surgical procedure may include any medical procedure associated with or involving manual or operative procedures on a patient's body. Surgical procedures may include cutting, abrading, suturing, or other techniques that involve physically changing body tissues and/or organs. Surgical procedures may also include diagnosing patients or administering drugs to patients. Some examples of such surgical procedures may include a laparoscopic surgery, a thoracoscopic procedure, a bronchoscopic procedure, a microscopic procedure, an open surgery, a robotic surgery, an appendectomy, a carotid endarterectomy, a carpal tunnel release, a cataract surgery, a cesarean section, a cholecystectomy, a colectomy (such as a partial colectomy, a total colectomy, etc.), a coronary angioplasty, a coronary artery bypass, a debridement (for example of a wound, a burn, an infection, etc.), a free skin graft, a hemorrhoidectomy, a hip replacement, a hysterectomy, a hysteroscopy, an inguinal hernia repair, a knee arthroscopy, a knee replacement, a mastectomy (such as a partial mastectomy, a total mastectomy, a modified radical mastectomy, etc.), a prostate resection, a prostate removal, a shoulder arthroscopy, a spine surgery (such as a spinal fusion, a laminectomy, a foraminotomy, a diskectomy, a disk replacement, an interlaminar implant, etc.), a tonsillectomy, a cochlear implant procedure, brain tumor (for example meningioma, etc.) resection, interventional procedures such as percutaneous transluminal coronary angioplasty, transcatheter aortic valve replacement, minimally Invasive surgery for intracerebral hemorrhage evacuation, or any other medical procedure involving some form of incision. While the present disclosure is described in reference to surgical procedures, it is to be understood that it may also apply to other forms of medical procedures or procedures generally.

In various embodiments, the surgical procedure may be performed on the patient by a healthcare provider, with the patient being identified by the identifier, as described above. The healthcare provider may be a person, a group of people, an organization, or any entity authorized to provide health services to a patient. For example, the healthcare provider may be a surgeon, an anesthesiologist, a nurse practitioner, a general pediatrician, or any other person or a group of people that may be authorized and/or able to perform a surgical procedure. In various embodiments, the healthcare provider may be a surgical team for performing the surgical procedure and may include a head surgeon, an assistant surgeon, an anesthesiologist, a nurse, a technician, and the like. The healthcare provider may administer a surgical procedure, assist with the surgical procedure for a patient and the like. A hospital, clinic, or other organization or facility may also be characterized as a healthcare provider, consistent with disclosed embodiments. Likewise, a patient may be a person (or any living creature) on whom a surgical procedure is performed.

Aspects of disclosed embodiments may include analyzing a plurality of frames of the surgical footage to derive image-based information for populating a post-operative report of the surgical procedure. In various embodiments, image-based information may include information about events that occurred during the surgical procedure, information about phases of the surgical procedure, information about surgical tools used during the surgical procedure, information about anatomical structures on which the surgical procedure was performed, data from various devices (e.g., vital signs, such as pulse, blood pressure, temperature, respiratory rate, oxygen levels, and the like), or any other suitable information that may be obtained from the images and may be applicable to be documented in the post-operative report. Some other non-limiting examples of information based on an analysis of surgical footage and/or algorithms for analyzing the surgical footage and determining the information are described in this disclosure.

In various embodiments, the image-based information may be derived from the surgical footage using any suitable trained machine-learning model (or other image recognition algorithms) for identifying events, phases of surgical procedures, surgical tools, anatomical structures within the surgical footage, and the like, for example as described above. In some cases, the machine learning method may identify various properties of events, phases, surgical tools, anatomical structures, and the like. For example, a property of an event such as an incision may include the length of the incision, and a property of an anatomical structure may include a size of the structure or shape of the structure. In various embodiments, any suitable properties may be identified using a machine-learning method, for example as described above, and once identified may be used to populate a surgical report.

In various embodiments, the derived image-based information may be used for populating a post-operative report of the surgical procedure. A process of populating the post-operative report may include populating fields of the report with information specific to the fields. In an example embodiment, populating a post-operative report may be done by a computer-based application (e.g., application 2415, as shown in 24A). For example, the computer-based application may be configured to retrieve a field from the post-operative report, determine a name associated with the field, determine what type of information (e.g., image-based information, or any other suitable information) needs to be entered in the field based on a determined name, and retrieve such information from either surgical footage or from auxiliary information (e.g., auxiliary information 2413, as shown in FIG. 24A). In an example embodiment, retrieving information may include deriving image-based information from the surgical footage. For example, if the field name "Surgical Tools Used," retrieving information may include using an image recognition algorithm for identifying (in the surgical footage) surgical tools used during the surgical procedure, and populating the surgical report with the names of the identified tools. Thus, derived image-based information may be used to populate the post-operative report of the surgical procedure. Other examples of image-based information that may be used to populate the report may include the starting and ending times of a procedure or portion thereof, complications encountered, conditions of organs, and other information that may be derived through analysis of video data. These might also include, characteristics of a patient, characteristics of one or more healthcare providers, information about an operating room (e.g., the type of devices present in the operating room, type of image sensors available in the operating room, etc.), or any other relevant data.

Figure 25:
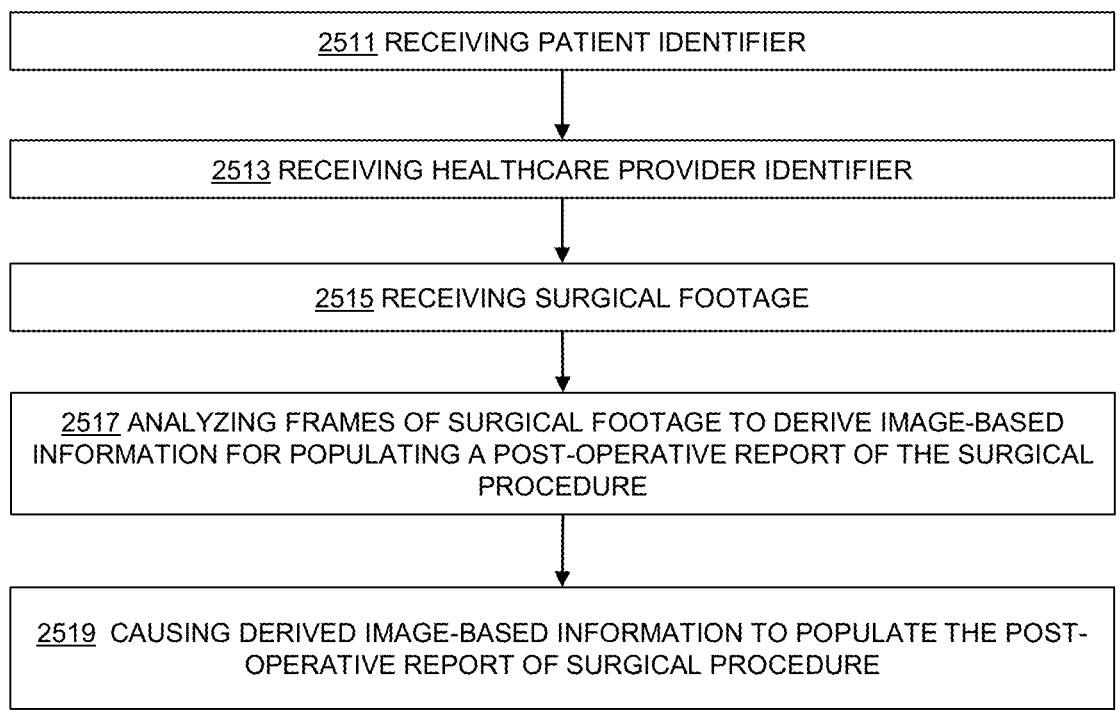
FIG. 25 is a flow diagram of an exemplary process for populating a post-operative report, consistent with disclosed embodiments.

Aspects of a method of populating a post-operative report of a surgical procedure are illustrated by an example process 2501, as shown in FIG. 25. At step 2511 of process 2501, the method may include receiving an input of an identifier of a patient, and at step 2513, the method may include receiving an input of an identifier of a health care provider, as described above. At step 2515, the method may include receiving an input of surgical footage of a surgical procedure performed on a patient by a health care provider. Receiving the input of surgical footage may include receiving the input by a suitable computer-based software application or a healthcare professional, as discussed above. At step 2517, the method may include analyzing a plurality of frames of the surgical footage to derive image-based information for populating a post-operative report of the surgical procedure, as described herein, and at step 2519, the method may include causing the derived image-based information to populate the post-operative report of the surgical procedure, as previously described.

Aspects of a method of populating a post-operative report of a surgical procedure may include analyzing the surgical footage to identify one or more phases of the surgical procedure. The phases may be distinguished from each other automatically based on a training model trained to distinguish one portion of a surgical procedure from another, for example as described herein.

For the purposes of the present disclosure, a phase may refer to a particular period or stage of a process or series of events. Accordingly, a surgical phase may refer to a sub-portion of a surgical procedure. For example, surgical phases of a laparoscopic cholecystectomy surgery may include trocar placement, preparation, calot's triangle dissection, clipping and cutting of cystic duct and artery, gallbladder dissection, gallbladder packaging, cleaning and coagulation of liver bed, gallbladder retraction, and so forth. In another example, surgical phases of a cataract surgery may include preparation, povidone-iodine injection, corneal incision, capsulorhexis, phaco-emulsification, cortical aspiration, intraocularlens implantation, intraocular-lens adjustment, wound sealing, and so forth. In yet another example, surgical phases of a pituitary surgery may include preparation, nasal incision, nose retractor installation, access to the tumor, tumor removal, column of nose replacement, suturing, nose compress installation, and so forth. Some other examples of surgical phases may include preparation, incision, laparoscope positioning, suturing, and so forth.

In some examples, the user may identify a phase by marking a section of the surgical footage with a word/sentence/string that identifies a name or a type of a phase. The user may also identify an event, procedure, or device used, which input may be associated with particular video footage (e.g., for example through a lookup table or other data structure). The user input may be received through a user interface of a user device, such as a desktop computer, a laptop, a tablet, a mobile phone, a wearable device, an internet of things (IoT) device, or any other means for receiving input from a user. The interface may provide, for example, one or more drop-down menus with one or more pick lists of phase names; a data entry field that permits the user to enter the phase name and/or that suggests phase names once a few letters are entered; a pick list from which phase names may be chosen; a group of selectable icons each associated with a differing phase, or any other mechanism that allows users to identify or select a phase.

In some embodiments, analyzing the surgical procedure to identify one or more phases of the surgical procedure may involve using computer analysis (e.g., a machine-learning model) to analyze frames of the video footage, for example as described above. Computer analysis may include any form of electronic analysis using a computing device. In some embodiments, computer analysis may include using one or more image recognition algorithms to identify features of one or more frames of the video footage. Computer analysis may be performed on individual frames or may be performed across multiple frames, for example, to detect motion or other changes between frames.

In some embodiments, analyzing the surgical procedure to identify at least one phase of the surgical procedure may involve associating a name with at least one phase. For example, if the identified phase includes gallbladder dissection, a name "gallbladder dissection" may be associated with that phase. In various embodiments, derived image-based information (derived from surgical footage of a surgical procedure by identifying a phase), may include an associated phase name, as described above.

Further, aspects of a method of populating a post-operative report of a surgical procedure may include identifying a property of at least one phase of identified phases. A property of a phase may be any characteristics of a phase such as a duration of the phase, a place of the phase in a sequence of phases during the surgical procedure, a phase complexity, an identification of a technique used, information related to medical instruments used in the phase, information related to actions performed in the phase, changes in a condition of an anatomical structure during the phase, or any other information that may characterize the phase. A phase property may be expressed in the form of an alphanumerical string. For instance, "a first phase" may identify the phase as a first phase in a sequence of phases during a surgical procedure, "one hour" may describe that the phase has a duration of one hour, "bronchoscopy" may identify a phase as a bronchoscopy, and the like. Additionally or alternatively, a property of a phase may be non-textural data (e.g., image, audio, numerical, and/or video data) collected during a surgical procedure. For example, a representative image of an anatomical structure (or surgical instrument, or an interaction of a surgical instrument with an example anatomical structure) performed during a phase of a surgical procedure may be used as a property of a phase. In one example, a machine learning model may be trained using training examples to identify properties of surgical phases from images and/or videos. An example of such training example may include an image and/or a video of at least a portion of a surgical phase of a surgical procedure, together with a label indicating one or more properties of the surgical phase. Some non-limiting examples of such properties may include a name of the surgical phase, a textual description of the surgical phase, or any other property of a surgical phase described above. Further, in some examples, the trained machine learning model may be used to analyze the surgical footage to identify the property of the at least one phase of identified phases. In various embodiments, the derived image-based information (used for populating the surgical record) may be based on the identified at least one phase and the identified property of the at least one phase. For example, the combination of both the phase and the property together may enable the phase to be recorded in a way that is more meaningful. For example, during a phase of suturing of a valve, if an intraoperative leak is detected (a property of the phase), the phase/property combination may be recorded in the surgical record. In some cases, the derived image-based information may include a segment of a video captured during the phase of the surgical procedure.

Aspects of a method of populating a post-operative report of a surgical procedure may include determining at least a beginning of the at least one phase; and wherein the derived image-based information is based on the determined beginning. The beginning of at least one phase may be determined by performing a computer image analysis on surgical footage, for example as described above. For example, using a trained machine learning model (such as a recurrent convolutional neural network), the beginning of a particular phase may be distinguished from the end of a prior phase, and the location may be identified and stored in the surgical record. In another example, a phase may start when a particular medical instrument first appears in the video footage, and an object detection algorithm may be used to identify the first appearance of the particular medical instrument in the surgical footage.

In some cases, a time marker may be associated with the at least one phase, and the derived image-based information may include the time marker associated with the at least one phase. The time marker may be recorded in a number of ways, including, a time elapsed from the beginning of the surgical procedure, the time as measured by the time of day, or a time as it relates to some other intraoperative recorded time. In various embodiments, a time marker may be associated with the beginning of each identified phase (e.g., a time marker may be associated with the beginning location of the surgical phase within the surgical footage). The time marker may be any suitable alphanumerical identifier, or any other data identifier (e.g., an audio signal or an image) and may include information about a time (and/or possibly a time range), associated with the beginning of the identified phase.

An example surgical event, such as an incision, may be detected using action detection algorithms, for example as discussed above. Such an identified surgical event may identify a beginning of a surgical phase. In an example embodiment, an event that begins a surgical phase may be detected based on machine learning techniques. For example, a machine learning model may be trained using historical surgical footage including known events that begin the surgical phase.

Further, disclosed embodiments may include determining at least an ending of the at least one phase, and derived image-based information may be based on the determined ending. The end of the surgical phase may be determined by detecting an end location of the surgical phase within the surgical footage. In various embodiments, a time marker may be associated with the end of each identified phase (e.g., the time marker may be associated with the end location of the surgical phase within the surgical footage). As discussed above, the ending marker may be recorded in the same manner as the starting marker, and may be characterized by any suitable alphanumerical identifier, or any other data identifier. For example, the surgical footage may be analyzed to identify the beginning of a successive surgical phase, and the ending of one phase may be identical to the beginning of the successive surgical phase. In another example, a phase may end when a particular medical instrument last appears in the video footage, and an object detection algorithm may be used to identify the last appearance of the particular medical instrument in the surgical footage.

Embodiments for automatically populating a post-operative report of a surgical procedure may also include transmitting data to a health care provider, the transmitted data, including a patient identifier and derived image-based information. During or after a surgical procedure, video captured during the surgical procedure may be transmitted to a healthcare provider for populating the patient's associated surgical record. In order to ensure that the video populates the appropriate record, the patient identifier may accompany the video in the transmission. In some embodiments, this may enable the surgical record to be automatically updated with the video, without human intervention. In other embodiments, either on the transmission and/or the receiving end, a human may select the video for transmission, or accept the video for incorporation into the patient's medical record. In some cases, transmitting data may involve mailing (or delivering in person) a physical copy (e.g., a paper copy, a CD-ROM, a hard drive, a DVD, a USB drive, and the like) of documents describing the data. Additionally or alternatively, transmitting data may include transmitting data to at least one of a health insurance provider or a medical malpractice carrier.

Aspects of the disclosure may include analyzing the surgical footage to identify at least one recommendation for post-operative treatment; and providing the identified at least one recommendation. As described earlier, surgical footage may be analyzed in various ways (e.g., using a machine-learning method, by a healthcare provider, and the like). In various embodiments, a machine-learning method may be configured not only to recognize events within the video frames but also configured to form conclusions about various aspects of the surgical procedure based on an analysis of surgical footage. For example, post-operative wound care may vary depending on the nature of the surgical wound. Video analysis might determine that nature, and might also provide a recommendation for post-operative treatment of the wound site. Such information may be transmitted to and stored in the surgical record. In some cases, the machine-learning method may identify intraoperative events (e.g., adverse events) and may provide indications for these events for which specific post-operative treatments are needed. This may be analyzed through machine learning and the recommendation for post-operative treatment may be automatically provided. In one example, in response to a first surgical event identified in the surgical footage, a first recommendation for post-operative treatment may be identified, and in response to a second event identified in the surgical footage, a second recommendation for post-operative treatment may be identified, the second recommendation may differ from the first recommendation. In one example, in response to a first condition of an anatomical structure identified in the surgical footage, a first recommendation for post-operative treatment may be identified, and in response to a second condition of the anatomical structure identified in the surgical footage, a second recommendation for post-operative treatment may be identified, the second recommendation may differ from the first recommendation. In some examples, a machine learning model may be trained using training examples to generate recommendations for post-operative treatment from surgical images and/or surgical videos, and the trained machine learning model may be used to analyze the surgical footage and identifying the at least one recommendation for post-operative treatment. An example of such training example may include an image or a video of at least a portion of a surgical procedure, together with a label indicating the desired recommendations for post-operative treatment corresponding to the surgical procedure.

Such recommendations may include suggesting physical therapy, medications further physical examination, a follow on surgical procedure, and the like. In some cases, recommendations may not directly relate to medical activities but may include diet recommendations, sleep recommendations, recommendations for physical activity, or recommendations for stress management. In various embodiments, the identified recommendation may be provided to a healthcare professional responsible for a post-operative treatment for the patient. Additionally or alternatively, the recommendation may be provided to a third party which may be a patient, a family member, a friend, and the like.

In one embodiment, an analysis of surgical footage may include identifying that during a given time of a surgical procedure, a surgeon may have worked too closely to intestines of a patient, for example, using an energy device. When such an event is identified (for example using an object detection algorithm, using a trained machine learning model, etc.), a notification (e.g., a push notification) may be send to alert a surgeon (or any other healthcare professional supervising a post-operative treatment of a patient) to further analyze the surgical footage and to have special procedures planned to avoid a catastrophic post-operative event (e.g., bleeding, cardiac arrest, and the like).

In various embodiments, populating a post-operative report of a surgical procedure may include enabling a health care provider to alter at least part of derived image-based information in the post-operative report. For example, the healthcare provider (also referred to as a healthcare professional) may access a post-operative report via a software application configured to display information in the post-operative report. In various embodiments, a healthcare professional may be enabled to alter some or all fields within the post-operative report. In some embodiments, particular fields may be locked as unalterable without administrative rights. Examples of alterable fields may be those containing text-based data (e.g., alterable by inputting new data via keyboard, mouse, microphone, and the like), image data (e.g., by uploading one or more images related to a surgical procedure, overlaying information over the one or more images, etc.), video data (e.g., by uploading one or more videos related to a surgical procedure overlaying information over one or more frames of the one or more videos, etc.), audio data (e.g., the audio data captured during a surgical procedure), and the like.

In various embodiments, updates to a post-operative report may be tracked using a version tracking system. In an example embodiment, the version tracking system may maintain all data that was previously used to populate a post-operative report. The version tracking system for may be configured to track differences between different versions of a post-operative report, and may be configured to track information about a party (e.g., a name of a healthcare professional, a time of the update, and the like) that made changes to the report.

In some embodiments, populating a post-operative report of a surgical procedure may be configured to cause at least part of derived image-based information to be identified in a post-operative report as automatically generated data. In various embodiments, as derived image-based information is used to populate a post-operative report, populating the report may include identifying how the derived image-based information was generated. For example, if an elevated heart rate was determined using computer vision analysis of detected pulses in vascular, the source of that determination might be noted as being based on a video determination. Similarly, video analysis might automatically estimate a volume of blood loss as the result of a rupture, and the surgical report might note, along with the estimated loss, that the volume of loss is an estimation based on video analysis. Indeed, any indication derived from video analysis might be so noted in the post-surgical report using any textual, graphical, or icon based information to reflect the source of the data. For example, a movie icon may appear next to data derived from video. Alternatively, if a healthcare professional identifies an event within surgical footage and provides a segment of surgical footage corresponding to the identified event as a derived image-based information, such information may be considered as generated by the healthcare professional and may not be classified as automatically generated data.

Disclosed embodiments may include analyzing surgical footage to identify a surgical event within the surgical footage, for example as described above. The analysis, as previously discussed, may occur using a machine learning model. The identification may be derived from historical data where surgical events were already identified, along with a name for the event. Thus, when a similar even is detected through machine learning, the previously identified name for that event can similarly be applied to a current event identification.

Further, consistent with disclosed embodiments, not only may an event be identified, but also a property of a surgical event may also be identified. The property of a surgical event may be a type of an event or any other information characterizing the event. For example, if the event is an incision, the machine-learning model may be configured to return a name "incision" as a type of the event, and a length and a depth of the incision as a property of the event. In some cases, a predetermined list of possible types for various events may be provided to a machine-learning model, and the machine-learning model may be configured to select a type from the list of event types to accurately characterize an event. The number of properties can vary based on the type of event identified. Some rather straightforward events may have a relatively short list of associated properties, while other events may have many more associated alternative properties.

As discussed, machine-learning models are one way for identifying events, with the models trained using examples to identify (or determine) events. The training may involve any suitable approach, such as for example, a supervised learning approach. For instance, historical surgical footage containing features corresponding to an event may be presented as input data for the machine-learning model, and the machine-learning model may output the name of the event corresponding to the features within the footage. Various parameters of the machine-learning model may be adjusted to train the machine-learning model to correctly identify events corresponding to the features within the historical visual data. For example, if the machine-learning model is a neural network, parameters of such a neural network (e.g., weights of the network, number of neurons, activation functions, biases of the network, number of layers within the network, and the like) may be adjusted using any suitable approach (e.g., weights of the neural network may be adjusted using a backpropagation process).

In one embodiment, the event may be identified by a medical professional (e.g., a surgeon), and the event may be tagged at the time of its occurrence. If a machine learning model identifies surgical activity as potentially of interest but lacks an associated name for the activity, the associated footage may be saved and a user might later be prompted to provide an associated name.

In some cases, a surgeon may mark an event during a surgical procedure for subsequent identification. For example, the surgeon may mark the event using a visual or an audio signal (e.g., a hand gesture, a body gesture, a visual signal produced by a light source generated by a medical instrument, a spoken word, and the like) that may be captured by one or more image sensors/audio sensors and recognized as a trigger for an event.

In various embodiments, derived image-based information may be based on an identified surgical event and an identified property of the event. After an event and one or more properties of the event are identified as discussed earlier, the combination of can be analyzed to determine image-based information that may not have been derivable from either the event or the property alone. For example, if a particular property of a particular event is associated with a known risk of post-operative complication, that risk may be determined and included in the image-based information. Alternatively, by way of example, the derived image-based information may include one or more of a name of the event, a segment of a surgical footage corresponding to the event, a name and/or image of a surgical instrument used during the event, a name and/or image of an anatomical structure operated during the event, an image of interaction of the surgical instrument and the anatomical structure, a duration time for the event, and/or any other information derived from the video.

As mentioned, the surgical footage may be analyzed to determine an event name of the identified surgical event. As described above, the event name may be determined using a suitable machine-learning model. Alternatively, a name of the event may be identified by a healthcare professional. In various embodiments, the derived image-based information may include the determined event name.

Aspects of disclosed embodiments may also include associating a time marker with an identified surgical event. A process of associating a time marker with an identified surgical event may be similar to the process of associating a time marker with a phase of a surgical procedure. For example, a time marker may be associated with a beginning of an event of a surgical procedure (e.g., the beginning or some other intermediate location or range of locations of a surgical event within surgical footage). A time marker may be any suitable alphanumerical identifier, or any other graphical or data identifier. For example, the time marker may be an icon or other graphic that appears on an active or static timeline of some or all of a surgical procedure. If active, the time marker may be clickable (or otherwise selectable) to cause footage of the associated event to be presented. The marker may be caused to appear in footage, either through a textual or graphic overlay on the footage or through an identifying audio indicator embedded for playback presentation. Such indicators may include one or more pieces of information such as temporal data (time or time range of the occurrence), location data (wherein the event occurred), or characterizing data (describing properties of the occurrence.) In some situations, a time marker may be associated with an end of an event (e.g., the time marker may be associated with an end location of the event within the surgical footage). Derived image-based information may include multiple time markers, for multiple events and/or for multiple locations within events.

In some embodiments, providing the derived image-based information may occur in a form that enables updating an electronic medical record. For example, derived image-based information may include text data, image data, video data, audio data, and the like, that may be in a form that can be uploaded to a software application that may store and display an electronic medical record (e.g., a standalone application for storing and displaying a medical record, a web-interface for displaying a medical record using information stored in a database, and the like). In various embodiments, the software application for storing and displaying a medical record may include an interface for updating the electronic medical record using derived image-based information. The interface may include graphical user elements for uploading image, video and audio data, for uploading text data, for typing text data into the electronic medical record, for updating the electronic medical record using a computer mouse, and the like.

In various embodiments, the derived image-based information may be based in part on a user input. For example, a user, such as a healthcare professional, may provide inputs while the surgical footage is being captured, for example as described above, and the derived image-based information may be partly based on such inputs. For example, such input may indicate a particular point in time within the surgical footage.

In various embodiments, the derived image-based information may include a first part associated with a first portion of a surgical procedure and a second part associated with a second portion of a surgical procedure. Separating image-based information into parts may facilitate classifying the image-based information. For example, if the first portion of the surgical procedure involves making multiple incisions and a second portion of the surgical procedure involves suturing, such portions may be used to classify those portions of the surgical procedure. In some cases, during a first portion of a surgical procedure, a first set of sensors may be used to collect image-based information, and during a second portion of the surgical procedure, a different set of sensors may be used to collect image-based information. For example, during the first portion, image sensors located on a surgical instrument may be used to capture surgical footage, and during the second portion of the surgical procedure, overhead image sensors (i.e., image sensors located above an operating table) may be used to capture the surgical footage.

In various embodiments, the post-operative report may include a first portion corresponding to the first portion of the surgical procedure and a second portion corresponding to the second portion of the surgical procedure. The start of the first portion of the post-operative report may be indicated by a first position (e.g., the first position may be a pointer in a data file, a location of a cursor in a text file, a data record in a database, and the like). The start of the second portion of the post-operative report may be indicated by a second position, which may be any suitable indication of location in the file that is a starting point of the second portion of the post-operative report (e.g., the first position may be a pointer in a data file, a location of a cursor in a text file, a data record in a database, and the like). In various embodiments, a post-operative report may be separated into portions based on corresponding portions of a surgical procedure. In an example embodiment, a machine-learning method (or a healthcare provider) may identify portions of the surgical procedure and configure the post-operative report to have such identified portions. The post-operative report may not be limited to two portions but may include more or less than two portions.

Aspects of disclosed embodiments may include receiving a preliminary post-operative report. The post-operative report may be received by any entity, whether an organization, individual, or a computer (e.g., an insurance company or healthcare organization, a healthcare professional, or a computer-based program for populating post-operative reports, such as application 2415, as shown in FIG. 24A). In various embodiments, analyzing a preliminary post-operative report may involve selecting a first position and a second position within the preliminary post-operative report, the first position is associated with a first portion of the surgical procedure and the second position is associated with a second portion of the surgical procedure. Such selection may enable someone (or a machine) analyzing the report to skip directly to an area of interest in the report. Thus, analyzing a preliminary post-operative report may include identifying indicators for one or more of a first position and a second position. The indicators may be any suitable alphanumeric or graphical indicators. For example, an indicator for the first position may be a text string "this is a start of the first portion of the post-operative report" or a graphical start icon. In one example, Natural Language Processing (NLP) algorithms may be used to analyze textual information included in the preliminary post-operative report, to identify in the textual information portions that discuss different aspects of the surgical procedure (such as different surgical phases, different surgical events, usage of different medical instruments, and so forth), and associate the identified portions of the textual information with different portions of the surgical procedure (for example, with the corresponding surgical phase, with the corresponding surgical events, with the usage of the corresponding medical instruments, and so forth). Further, in some examples, the first position and the second position (as well as additional positions) within the preliminary post-operative report may be based on and/or linked with the identified portions of the textual information.

Further, embodiments may include causing a first part of derived image-based information to be inserted at a selected first position and a second part of the derived image-based information to be inserted at a selected second position. For example, a first portion of a post-operative report may include a first set of fields that may be populated by derived image-based information captured during a first portion of the surgical procedure, and a second portion of the post-operative report may include a second set of fields that may be populated by derived image-based information captured during a second portion of the surgical procedure. In another example, a first part of derived image-based information may correspond to a first portion of the surgical procedure and a second part of derived image-based information may correspond to a second portion of the surgical procedure, the first position within the preliminary post-operative report may be identified as corresponding to the first portion of the surgical procedure (as described above), the second position within the preliminary post-operative report may be identified as corresponding to the second portion of the surgical procedure (as described above), and in response, the first part of derived image-based information may be inserted at the first position and the second part of the derived image-based information may be inserted at the second position. Some non-limiting examples of the first and second portions of the surgical procedure may include different surgical phases, different surgical events, usage of different medical instruments, different actions, and so forth.

Aspects of the present disclosure may also include analyzing surgical footage to select at least part of at least one frame of the surgical footage; and causing the selected at least part of at least one frame of the surgical footage to be included in a post-operative report of a surgical procedure. For example, if a post-operative report includes a field configured to hold one or more images of a surgical instrument used during a surgical procedure, an example machine-learning model may be configured to identify one or more frames of the surgical footage and select parts of the identified frames that contain a surgical instrument. Further, the selected part (or parts) of at least one frame may be inserted (e.g. populate) into the post-operative report. The machine-learning model may also be configured to extract other relevant frames of surgical footage. For example, frames of the surgical footage depicting an anatomical structure that is the focus of an operation, or frames depicting an interaction between a surgical instrument and an anatomical structure may be extracted. Such relevant frames may also populate the post-operative report.

Disclosed embodiments may also include receiving a preliminary post-operative report and analyzing the preliminary post-operative report and surgical footage to select the at least part of at least one frame of the surgical footage. For example, a machine-learning model may be configured to analyze a post-operative report and identify a discussion of an adverse event (e.g., bleeding). The adverse event may be identified, for example, through an indication stored in the post-operative report, using an NLP algorithm, and so forth. The indication may, for example, be an indication of a name of the adverse event. It may include a time when the adverse event occurred during a surgical procedure. The adverse event may be determined using a machine-learning model configured to retrieve surgical footage for the surgical procedure and identify a portion of a frame that shows a visual data representing the adverse event (e.g., a portion of a frame that shows bleeding). Further, in some examples, the identify portion of the frame may be inserted to the post-operative report in connection with the discussion of the adverse event, or be associated with the discussion of the adverse event in another way.

Additional aspects of disclosed embodiments may include analyzing the preliminary post-operative report and surgical footage to identify at least one inconsistency between the preliminary post-operative report and the surgical footage. In various embodiments, inconsistency may be determined by comparing information stored in the report with information derived through a machine learning model that determines an error. For illustrative purposes, one of a virtual infinite number of potential inconsistencies could occur when a medical professional indicates in the report that the surgical site was closed with sutures, while the video reveals that the site was closed with staples. The video revelation might occur, for example, with a computer-based software application (e.g., application 2415, as shown in FIG. 24A) where a post-operative report is compared with video footage of the associated procedure. If a difference is noted, a computer-based software application may determine the source of the error, may note the error, may send a notification of the error, and/or may automatically correct the error. For example, the application may analyze various versions of a preliminary post-operative report (using, for example, a version tracking system, as described above) to identify at which step of generating the preliminary post-operative report the difference first appeared.

As previously mentioned, embodiments of the disclosure may include providing an indication of the identified at least one inconsistency. The indication may be provided by transmitting a notification to a healthcare professional using any suitable means, as discussed above.

Various embodiments may include receiving an input of a patient identifier and an input of an identifier of a health care provider, as previously described. Further, the method may include receiving an input of surgical footage of a surgical procedure performed on the patient by the health care provider, as previously described. The method may also include analyzing a plurality of frames of the surgical footage to identify phases of the surgical procedure based on detected interactions between medical instruments and biological structures and, based on the interactions, associate a name with each identified phase. For example, at least some of the frames of the surgical footage may indicate a portion of the surgical footage in which a surgical operation is being performed on a biological structure (herein, also referred to as an anatomical structure). As discussed above, the interaction may include any action by the medical instrument that may influence the biological structure or vice versa. For example, the interaction may include a contact between the medical instrument and the biological structure, an action by the medical instrument on the biological structure (such as cutting, clamping, grasping, applying pressure, scraping, etc.), a physiological response by the biological structure, the medical instrument emitting light towards the biological structure (e.g., surgical tool may be a laser that emits light towards the biological structure) a sound emitted towards anatomical structure, an electromagnetic field created in a proximity of the biological structure, a current induced into the biological structure, or any other suitable forms of interaction.

In some cases, detecting an interaction may include identifying proximity of the medical instrument to a biological structure. For example, by analyzing the surgical video footage, an image recognition model may be configured to determine a distance between the medical instrument and a point (or a set of points) on a biological structure.

Aspects of the present disclosure may involve associating a name with each identified phase based on detected interactions between medical instruments and biological structures. The name may be associated with each identified phase using any suitable means. For example, as described above, the name may be supplied by a user or may be automatically determined using a suitable machine learning method, as described above. In particular, a process of identifying a phase of a surgical procedure involves associating a name with each identified phase. In various embodiments, the name associated with the phase may include a name for a biological structure and a name of a surgical instrument interacting with the structure.

In various embodiments, the name associated with the identified phase may be updated, modified, quantified, or otherwise altered during the ongoing surgical phase or after the completion of the surgical phase. For example, a machine learning model may initially determine a name for the surgical phase as "incision" and may later update the name of the surgical phase, based on detected interactions between medical instruments and biological structures, to an illustrative name "a Lanz incision extending medially towards rectus abdominis, made via laparoscopic surgery using laparoscopic scissors." Additionally or alternatively, a separate record (herein also referred to as a note) may be added to the name identifying the surgical phase, with the note containing various details and/or characteristics of the surgical phase. Such details may include an instrument used during the surgical phase, a light used during the surgical phase, a pressure value for the pressure applied on an example biological structure, an area over which the pressure was applied, one or more images of the biological structure and/or medical instrument during the surgical phase, identifications for events (e.g., adverse events such as bleeding), or any other related information characterizing the surgical phase.

Aspects of the present disclosure may also involve transmitting data to a health care provider, the transmitted data including the patient identifier, the names of the identified phases of the surgical procedure, and time markers associated with the identified phases.

An embodiment may include determining at least a beginning of each identified phase, and associating a time marker with the beginning of each identified phase, as discussed above. Additionally or alternatively, the time marker may identify an end of the identified phase, as discussed above. The transmitted data may include text, graphics, video data, animations, audio data, and the like. In some cases, the transmitted data may be an SMS message, an email, and the like delivered to any suitable devices (e.g., smartphones, laptops, desktops, TVs, etc.) in possession of various health care providers (e.g., various medical personnel, administrators, and other interested individuals or systems). In some cases, the transmitted data may also be provided to patients, relatives or friends of patients.

Further, aspects of the present disclosure may include populating a post-operative report with transmitted data in a manner that enables the health care provider to alter phase names in a post-operative report. Such alterations may occur through an interface that enables post-operative report alterations. For example, the interface may allow a healthcare provider to update the phase names by typing new phase names using a keyboard. In various embodiments, the interface may be also configured for altering names of various events identified in surgical footage and recorded in a post-operative report.

Disclosed systems and methods may involve analyzing surgical footage to identify events during the surgical procedure, comparing the events with a sequence of recommended events, and determining if any events from the sequence of the recommended events were not performed during the surgical procedure. Omitted surgical events may need to be identified during or after a surgical procedure. The events may be compared with a sequence of recommended events, and when some events were not performed during the surgical procedure, as determined by comparing with the sequence of recommended events, a notification may be provided to indicate which event has been omitted. Therefore, there is a need for analyzing surgical footage and identifying omitted events during a surgical procedure.

Aspects of this disclosure may relate to enabling determination and notification of an omitted event in a surgical procedure, including related methods, systems, devices, and computer readable media.

For ease of discussion, a method is described below, with the understanding that aspects of the method apply equally to systems, devices, and computer readable media. For example, some aspects of such a method may occur electronically over a network that is either wired, wireless, or both. Other aspects of such a method may occur using non-electronic means. In the broadest sense, the method is not limited to particular physical and/or electronic instrument, but rather may be accomplished using many differing instruments.

Disclosed embodiments may include enabling determination and notification of an omitted event may involve accessing frames of video captured during a specific surgical procedure. As used herein, frames of the video may include sequential or non-sequential images captured by an image capture device. Such images may be captured by, for example, cameras 115, 121, 123, and/or 125, as described above in connection with FIG. 1. In some cases, frames of the video may have corresponding audio signals forming a soundtrack for the video, with the audio signals being captured by audio capturing devices (e.g., microphone $D_{111}$, as shown in FIG. 1). The video frames may be stored as individual files or may be stored in a combined format, such as a video file, which may include corresponding audio data. In some embodiments, a video may be stored as raw data and/or images output from an image capture device. In other embodiments, the video frames may be processed. For example, video files may include Audio Video Interleave (AVI), Flash Video Format (FLV), QuickTime File Format (MOV), MPEG (MPG, MP4, M4P, etc.), Windows Media Video (WMV), Material Exchange Format (MXF), a non-compressed video file, a lossless compressed video file, a lossy compressed video file, or any other suitable video file formats.

A specific surgical procedure, as used herein, may include any medical action, operation, diagnosis, or other medical related procedure or action. Such procedures may include cutting, ablating, suturing, or other techniques that involve physically changing body tissues and organs. Some examples of such surgical procedures may include a laparoscopic surgery, a thoracoscopic procedure, a bronchoscopic procedure, a microscopic procedure, an open surgery, a robotic surgery, an appendectomy, a carotid endarterectomy, a carpal tunnel release, a cataract surgery, a cesarean section, a cholecystectomy, a colectomy (such as a partial colectomy, a total colectomy, etc.), a coronary artery bypass, a debridement (for example of a wound, a burn, an infection, etc.), a free skin graft, a hemorrhoidectomy, a hip replacement, a hysteroscopy, an inguinal hernia repair, a sleeve gastrectomy, a ventral hernia repair, a knee arthroscopy, a knee replacement, a mastectomy (such as a partial mastectomy, a total mastectomy, a modified radical mastectomy, etc.), a prostate resection, a prostate removal, a shoulder arthroscopy, a spine surgery (such as a spinal fusion, a laminectomy, a foraminotomy, a diskectomy, a disk replacement, an interlaminar implant, etc.), a tonsillectomy, a cochlear implant procedure, brain tumor (for example meningioma, etc.) resection, interventional procedures such as percutaneous transluminal coronary angioplasty, transcatheter aortic valve replacement, minimally invasive surgery for intracerebral hemorrhage evacuation, thoracoscopic procedure, bronchoscopy, hernia repair, hysterectomy (e.g., a simple hysterectomy, or a radical hysterectomy), radical prostatectomy, partial nephrectomy, thyroidectomy, hemicolectomy, or any other medical procedure involving some form of incision, diagnosis, treatment or tissue alteration, or involving for example, treatment, diagnosis, drug administration, excision, repair, implantation, reconstruction, or improvement.

A deviation between a specific surgical procedure and a recommended sequence of events may be specific to a surgical procedure, as each type of surgical procedure may involve one or more of its own recommended sequences of events. When one such recommended sequence is not followed, a deviation may be said to have occurred, and a notification may be provided (for example as described below). In some gallbladder surgeries (such as a laparoscopic or a robotic cholecystectomy), for example, a deviation may include neglecting to clear a hepatocytic triangle of fat and fibrous tissue, to separate a gallbladder from a liver, to expose a cystic plate, or a failure to identify a cystic duct and a cystic artery entering a gallbladder. By way of another example, in some appendix surgeries (such as a laparoscopic or a robotic appendectomy), a deviation may include neglecting to dissect an appendix from surrounding adhesions or may include a failure to identify a base on an appendix circumferentially. In some hernia surgeries (such as a laparoscopic ventral hernia repair), a deviation may include neglecting to reduce hernia content, neglecting to visualize the fascia surrounding the hernia before anchoring a mesh, neglecting to isolate a fascia surrounding the hernia or neglecting to identify and/or isolate an inguinal canal element, and so forth. An example of such inguinal canal element may be a testicular artery, a pampiniform plexus of veins, nerves, a vas, and so forth. In some uterine surgery, such as a laparoscopic simple hysterectomy, a deviation may include neglecting to identify and/or ligate uterine arteries, neglecting to identify ureters, and so forth. In some other uterine surgeries, such as a robotic radical hysterectomy, a deviation may include neglecting to identify iliac blood vessels, neglecting to identify an obturator nerve, and so forth. In some prostate surgeries, such as a robotic radical prostatectomy, a deviation may include neglecting to identify a bladder neck in an anterior bladder wall, neglecting to identify a bladder neck in a posterior bladder wall, neglecting to identify ureteral orifices, and/or neglecting to identify other anatomical structures. In procedures involving the kidney, such as a laparoscopic or a robotic partial nephrectomy, the deviation may include neglecting to identify a renal hilum, where neglecting to identify the renal hilum may include neglecting to identify at least one of an artery, a vein, and collecting system including a ureter. In thyroid surgery, such as an open or a robotic thyroidectomy, a deviation may include neglecting to identify a recurrent laryngeal nerve. In colon procedures (such as a colectomy or a hemicolectomy, whether open, laparoscopic or robotic), a deviation may include neglecting to dissect a colon from a retroperitoneum, neglecting to dissect a colon from a liver, neglecting to dissect a colon from splenic flexures, or neglecting to perform an anastomosis, neglecting to visualize a colon free from adhesions and/or with no tension, neglecting to perform anastomosis, neglecting to visualize a tension free and/or well perfused and/or technically well sealed anastomosis, and so forth. The forgoing are just a few examples. More broadly, any divergence from an expected or recognized course of action may be considered a deviation.

A surgical procedure may take place in an operating room or any other suitable location. An operating room may be a facility (e.g., a room within a hospital) where surgical operations are carried out in an aseptic environment. The operating room may be configured to be well-lit and to have overhead surgical lights. The operating room may feature controlled temperature and humidity and may be windowless. In an exemplary embodiment, the operating room may include air handlers that filter the air and maintain a slightly elevated pressure within the operating room to prevent contamination. The operating room may include an electricity backup system in case of a black-out and may include a supply of oxygen and anesthetic gases. The room may include a storage space for common surgical supplies, containers for disposables, an anesthesia cart, an operating table, cameras, monitors, and other items for surgery. A dedicated scrubbing area that is used by surgeons, anesthetists, operating department practitioners (ODPs), and nurses prior to surgery may be part of the operating room. Additionally, a map included in the operating room may enable the terminal cleaner to realign the operating table and equipment to the desired layout during cleaning. In various embodiments, one or more operating rooms may be a part of an operating suite that may form a distinct section within a healthcare facility. The operating suite may include one or more washrooms, preparation and recovery rooms, storage and cleaning facilities, offices, dedicated corridors, and possibly other supportive units. In various embodiments, the operating suite may be climate- and/or air-controlled and separated from other departments.

Accessing the video frames of video captured during a specific surgical procedure may include receiving the frames from an image sensor (or multiple image sensors) located in an operating room. An image sensor may be any detector capable of capturing image or video data. A video frame may include at least a portion of one of many still images that compose a moving picture, such as a clip of any duration. Capturing of video may occur when one or more still images or portions thereof are received from an image sensor. Alternatively or additionally, capture may occur when one or more still images or portions thereof are retrieved from memory in a storage location. For example, video frames may be accessed from a local memory, such as a local hard drive, or may be accessed from a remote source, for example, through a network connection. In an example embodiment, the video frames may be retrieved from database 1411, as shown in FIG. 14. For example, processor 1412 of system 1410 may be configured to execute instructions (e.g., instructions implemented as software 1416) to retrieve the video frames from database 1411. The video frames may be retrieved for a specific surgical procedure.

Aspects of embodiments for enabling determination and notification of an omitted event may further include accessing stored data identifying a recommended sequence of events for the surgical procedure. As used herein, an event for the surgical procedure (also referred to as a surgical event) may refer to an action that is performed as part of a surgical procedure (e.g., an intraoperative surgical event), such as an action performed by a surgeon, a surgical technician, a nurse, a physician's assistant, an anesthesiologist, a doctor, or any other healthcare professional. An intraoperative surgical event may be a planned event, such as an incision, administration of a drug, usage of a surgical instrument, an excision, a resection, a ligation, a graft, suturing, stitching, or any other planned event associated with a surgical procedure or phase.

An example of a surgical event in a laparoscopic cholecystectomy surgery may include trocar placement, calot's triangle dissection, clipping and cutting of cystic duct and artery, gallbladder dissection, gallbladder packaging, cleaning and coagulation of liver bed, gallbladder retraction, and so forth. In another example, surgical events of a cataract surgery may include povidone-iodine injection, corneal incision, capsulorhexis, phaco-emulsification, cortical aspiration, intraocularlens implantation, intraocular-lens adjustment, wound sealing, and so forth. In yet another example, surgical characteristic events of a pituitary surgery may include preparation, nasal incision, nose retractor installation, access to the tumor, tumor removal, column of nose replacement, suturing, nose compress installation, and so forth. The foregoing are just a few examples to illustrate the distinction between a surgical procedure and an event within the surgical procedure and are not intended to be limiting of the embodiments described herein. Some other examples of common surgical events may include incisions, laparoscope positioning, suturing, and so forth.

In some embodiments, the surgical event may include an unplanned event, an adverse event or a complication. Some examples of adverse surgical events may include bleeding, mesenteric emphysema, injury, conversion to unplanned open surgery (for example, abdominal wall incision), incision significantly larger than planned, and so forth. Some examples of intraoperative complications may include hypertension, hypotension, bradycardia, hypoxemia, adhesions, hernias, atypical anatomy, dural tears, periorator injury, arterial occlusions, and so forth. In some cases, surgical events may include other errors, including technical errors, communication errors, management errors, judgment errors, situation awareness errors, decision-making errors, errors related to medical equipment utilization, and so forth. In various embodiments, events may be short or may last for a duration of time. For example, a short event (e.g., incision) may be determined to occur at a particular time during the surgical procedure, and an extended event (e.g., bleeding) may be determined to occur over a time span. In some cases, extended events may include a well-defined beginning event and a well-defined ending event (e.g., beginning of suturing and ending of the suturing), with suturing being an extended event. In some cases, extended events are also referred to as phases during a surgical procedure.

In various embodiments, a recommended event may be an event that is required during a surgical procedure. Similarly, a recommended event may be an event that is suggested to occur during a surgical procedure. For example, a recommended event during bronchoscopy may include insertion of a bronchoscope through a patient's nose or mouth, down the patient's throat into the patient's lungs. A recommended sequence of events may include a recommended sequence of recommended events. In some cases, a surgical event may identify a group of sub-events (i.e., more than one sub-event or steps). For example, an event of administering general anesthesia to a patient may include several steps such as a first step of providing medication to a patient via an IV line to induce unconsciousness, and a second step of administering a suitable gas (e.g., isoflurane or desflurane) to maintain the general anesthesia.

In an example embodiment, a recommended event may include administering a patient a pain-relief medicine, placing a patient in a preferred position, obtaining a biopsy sample from the patient, or any other suggested event that is not required.

The recommended sequence of events may include any suitable established sequence of events used during a surgical procedure. The recommended sequence of events may be established by healthcare professionals (e.g., surgeons, anesthesiologists, or other healthcare professionals) by analyzing historical surgical procedures and determining guidelines for surgical procedures. Examples of the recommended sequence of events may include, for example, inspecting an appendix base in a circumferential view. In some cases, the recommended sequence of events may be based on a critical view of safety (CVS), as known in the art. For example, during a laparoscopic cholecystectomy critical view of safety may be used to identify a cystic duct and a cystic artery to minimize injuries to a bile duct. In other embodiments, a determination of mandatory and recommended sequences of events may be determined automatically through the application of artificial intelligence to historical surgical video footage.

By way of illustration, in some embodiments, a CVS may be used to avoid biliary injury. The CVS may be used to identify the two tubular structures that are divided in a cholecystectomy, i.e., the cystic duct and the cystic artery. The CVS may be used as a process in an open cholecystectomy in which both cystic structures are putatively identified, after which the gallbladder is taken off the cystic plate so that it is hanging free and attached by the two cystic structures. In laparoscopic surgery, a complete separation of the body of the gallbladder from the cystic plate makes clipping of the cystic structures difficult. Thus, for the laparoscopy, the requirement may be that a lower part of the gallbladder (about one-third) may be separated from the cystic plate. The other two requirements may be that the hepatocytic triangle is cleared of fat and fibrous tissue and that there are two and only two structures attached to the gallbladder. Not until all three elements of CVS are attained, may the cystic structures be clipped and divided. Intraoperatively CVS should be confirmed in a "time-out" in which the three elements of CVS are demonstrated. It should be noted that CVS is not a method of dissection but a method of target identification akin to concepts used in safe hunting procedures.

The recommended sequence of events may include conditional clauses. As an illustrative example, recommended sequence of events for bypass surgery may include (1) administering general anesthesia for a patient, (2) preparing the arteries that will be used as bypass grafts, (3) making an incision at the center of a patient's chest, through a sternum (breast bone), to access heart and coronary arteries of the patient, (4) connecting a heart-lung bypass machine, (5) sewing one section of the artery around an opening below the blockage in the diseased coronary artery while a patient's heart is beating, (6) checking if the patient's heart continues to pump blood, (7) if the patient's heart stops beating activate the heart-lung bypass machine, (8) attaching the other end to an opening made in the aorta, and the like. As described above, the event of activating the heart-lung bypass machine may be part of the recommended sequence of events and may be triggered by any suitable surgical events (or lack of thereof), such as a surgical event of cessation of heart beats. In some cases, the recommended sequence of events may include a decision tree for determining the next event in the sequence of events. In some examples, the recommended sequence of events may include events that are required to occur within a particular time interval that may be specified in the recommended sequence of events. For example, an event may be required to occur within a particular time interval of the surgical procedure, within a particular time interval after the beginning of the surgical procedure, within a particular time interval before the completion of a surgical procedure, within a particular time interval of the surgical procedure after an occurrence of a second event (e.g., after the completion of the second event, after the beginning of the second event, etc.), within a particular time interval of the surgical procedure before an occurrence of a second event, and so forth.

Accessing the stored data identifying a recommended sequence of events may include retrieving the stored data from a suitable storage location (e.g., a data storage device such as a memory, a hard drive, a database, a server, and the like). In an example embodiment, the stored data may be retrieved from database 1411, as shown in FIG. 14. For example, processor 1412 of system 1410 may be configured to execute instructions (e.g., instructions implemented as software 1416) to retrieve stored data from database 1411. The stored data may be retrieved for a specific surgical procedure. In some examples, identifying a recommended sequence of events may include selecting the recommended sequence of events of a plurality of alternative sequences. For example, the recommended sequence of events may be selected based on the type of the surgical procedure, based on a medical instrument being used or projected to be used in the surgical procedure, based on a condition of an anatomical structure related to the surgical procedure, based on characteristics of a patient associated with the surgical procedure (some examples of such characteristics are described above), based on characteristics of a surgeon or a medical care professional associated with the surgical procedure (some examples of such characteristics are described above), based on characteristics of an operating room associated with the surgical procedure, and so forth. In some examples, the recommended sequence of events may be selected (or modified) during a surgical procedure according to one or more events that already occurred in the surgical procedure. For example, an occurrence of a particular event in a surgical procedure may indicate a type of the surgical procedure (for example, a location and/or a length of an incision may indicate whether the surgical procedure is an open surgical procedure or a laparoscopic surgical procedure, a usage of a particular medical instrument may indicate an election of a particular technique which may require particular sequence of events, etc.) or a technique that a surgeon elected for the particular surgical procedure, and a corresponding recommended sequence of events may be selected. In another example, an occurrence of a particular event in a surgical procedure may indicate a complication that necessitates a different recommended sequence of events, and a corresponding sequence of events may be selected. In yet another example, in response to a first event occurring in a particular ongoing surgical procedure, a first recommended sequence of events may be selected for a remaining portion of the particular ongoing surgical procedure, and in response to a second event occurring in a particular ongoing surgical procedure, a second recommended sequence of events may be selected for the remaining portion of the particular ongoing surgical procedure, the second recommended sequence of events may differ from the first recommended sequence of events. In some examples, image data captured from a particular ongoing surgical procedure may be analyzed to select a recommended sequence of events for a remaining portion of the particular ongoing surgical procedure. For example, the image data may be analyzed to detect events and/or conditions in the particular ongoing surgical procedure (for example, as described above), and the recommended sequence of events may be selected based on the detected events and/or conditions. In another example, a machine learning model may be trained using training examples to select recommended sequence of events based on images and/or videos, and the trained machine learning model may be used to analyze the image data and select the recommended sequence of events for a remaining portion of the particular ongoing surgical procedure. An example of such training example may include an image and/or a video depicting a first part of a surgical procedure, together with a label indicating a desired selection of a recommended sequence of events for a remaining part of the surgical procedure.

Figure 26:
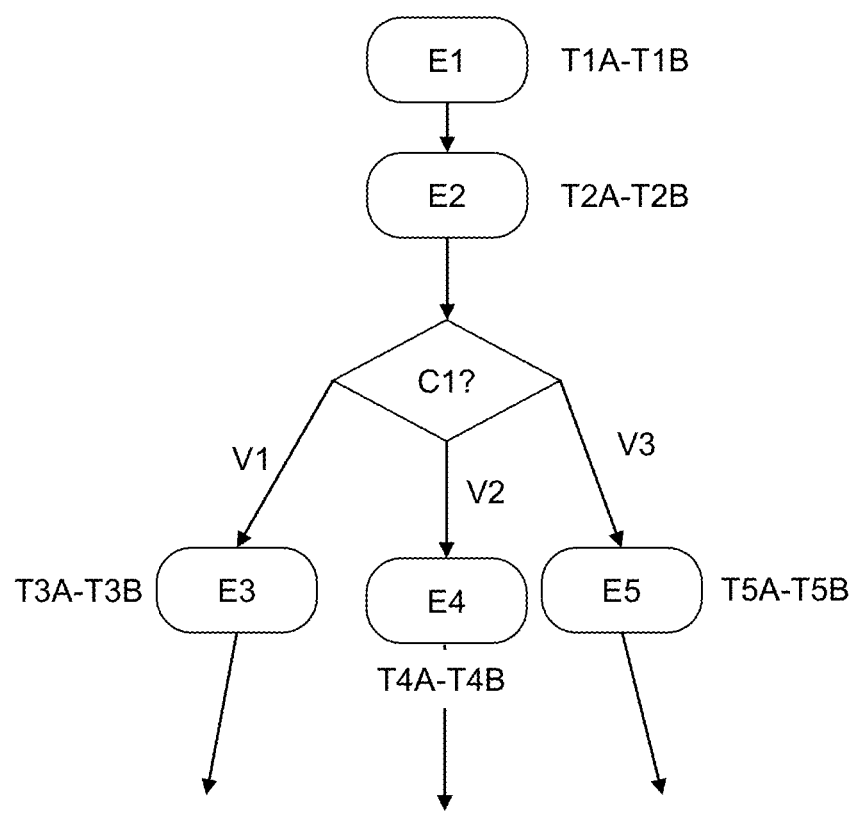
FIG. 26 is a schematic illustration of an exemplary sequence of events, consistent with disclosed embodiments.

An example recommended sequence of events 2601 is schematically illustrated in FIG. 26. For example, an event E1 (e.g., connecting a heart-lung bypass machine) may be a first event in the recommended sequence. Event E1 may be required to occur during a time interval T1A-T1B of the surgical procedure. An event E2 (e.g., suturing), may be a second event and may be required to occur during a time interval T2A-T2B of the surgical procedure (or in other examples, during a time interval T2A-T2B after the completion of event E1, during a time interval T2A-T2B after the beginning of event E1, and so forth). After completion of event E2, a conditional statement C1 (e.g., determining a pulse of a patient's heart) may be evaluated. If conditional statement C1 evaluates to value V1 (e.g., if the patient has no pulse), an event E3 (e.g., activate the heart-lung bypass machine) may be required during a time interval T3A-T3B. If statement C1 evaluates to value V2 (e.g., pulse of ten beats per minute) an event E4 (e.g., administer a first medicine to the patient) may be required during a time interval T4A-T4B, and if statement C1 evaluates to value V3 (e.g., pulse of hundred beats per minute) an event E5 (e.g., administer a second medicine to the patient) may be required during a time interval T5A-T5B.

Aspects of the method for enabling determination and notification of the omitted event may further include comparing the accessed video frames with the recommended sequence of events to identify an indication of a deviation between the specific surgical procedure and the recommended sequence of events for the surgical procedure. In some examples, a machine learning model may be trained using training examples to identify indications of deviations between the surgical procedures and recommended sequence of events for the surgical procedures from images and/or videos, and the trained machine learning model may be used to analyze the video frames and identify the indication of the deviation between the specific surgical procedure and the recommended sequence of events for the surgical procedure. An example of such training example may include a sequence of events and images and/or videos depicting a surgical procedure, together with a label indicating whether the surgical procedure deviated from the sequence of events.

In some examples, comparing the accessed video frames with the recommended sequence of events may include analyzing the video frames and identifying events within the video frames, for example as described above. For example, identifying events within the video frames may be accomplished using a trained machine-learning model, for example as described above. In one example, identifying an event may include at least one of identifying a type of the event, identifying a name of the event, identifying properties of the event (some examples of such properties are described above), identifying an occurrence time (or a time interval) of the event, and so forth. Further, in some examples, the identified events may be compared with the recommended sequence of events to identify the indication of the deviation between the specific surgical procedure and the recommended sequence of events for the surgical procedure. In some examples, the analysis of the video frames and the identification of the events within the video frames may occurred while the specific surgical procedure is ongoing, and the deviation between the specific surgical procedure and the recommended sequence of events for the surgical procedure may be identified while the specific surgical procedure is ongoing. In other examples, the analysis of the video frames and the identification of the events within the video frames may occurred after a completion of the specific surgical procedure, and/or the deviation between the specific surgical procedure and the recommended sequence of events for the surgical procedure may be identified after the specific surgical procedure is completed.

Detecting a characteristic event using a machine-learning method may be one possible approach. Additionally or alternatively, the characteristic event may be detected in the video frames received from image sensors using various other approaches. In one embodiment, the characteristic event may be identified by a medical professional (e.g., a surgeon) during the surgical procedure. For example, the characteristic event may be identified using a visual or an audio signal from the surgeon (e.g., a hand gesture, a body gesture, a visual signal produced by a light source generated by a medical instrument, a spoken word, and the like) that may be captured by one or more image sensors/audio sensors and recognized as a trigger for the characteristic event.

Further, comparing the accessed video frames with the recommended sequence of events may include comparing a sequence of the identified events within the video frames with the recommended sequence of events for the surgical procedure. For example, FIG. 27 shows a sequence 2701 of recommended (or mandatory) events and a sequence 2702 of the identified events within the video frames. When comparing sequence 2701 with sequence 2702, a deviation of sequence 2702 from sequence 2701 may be determined. Sequence 2702 may deviate from sequence 2701 in a variety of ways. In some cases, sequence 2702 may have different events than sequence 2701. For example, sequence 2701, as shown in FIG. 27 may have events E1-E4, and sequence 2702 may have events S1-S5. Sequences 2701 and 2702 may be compared for each of intervals I1-I4, as shown in FIG. 27. For example, event E1 of sequence 2701 may be compared with event S1 for interval I1 of the sequences. In an example embodiment, event E1 may deviate from event S1. Alternatively, event E1 may be substantially the same as event S1. In some cases, event E1 may be substantially different from event S1.

In various embodiments, to quantify a difference between event E1 and event S1, a suitable measure function F(E1,S1) may be defined that may have a range of values. In an example embodiment, measure function F may return a single number that determines a difference between events E1 and S1. For instance, if $F(E1,S1)<F_0(E1)$, events E1 and S1 are determined to be substantially the same, whereas if $F(E1,S1)>F_1(E1)$, events E1 and S1 are determined to be substantially different. Herein, values $F_0$ and $F_1$ may be any suitable predetermined threshold values, which may be selected for each type of event (i.e., threshold values $F_0(E1)$ and $F_1(E1)$ for event E1 may be different from threshold values $F_0(E2)$ and $F_1(E_2)$ for event E2). In various cases, events E1 and S1 may be characterized by a set of parameters (also referred to as event characteristics). For example, event E1 may be characterized by parameters $P1_{E1}$-$PN_{E1}$, as shown in FIG. 27. Parameters $P1_{E1}$-$PN_{E1}$ may include words, numbers, or data that may be represented by an array of numbers (e.g., images). For instance, parameter $P1_{E1}$ may indicate a type of event E1 characterized by a text string (e.g., "incision"), parameter $P2_{E1}$ may be a number characterizing a length of the incision (e.g., one centimeter), parameter $P3_{E1}$ may be the depth of the incision (e.g., three millimeters), parameter $P4_E$, may be a location of the incision that may be characterized by two numbers (e.g., {10,20}). The location of incision may be specified by identifying the incision in one or more of the video frames captured during the surgical procedure, and parameter $PN_{E1}$ may indicate a type of surgical tool used for the incision (e.g., "CO2 laser"). Event E1 may have as many parameters as needed to fully characterize the event. Further event E1 may be characterized by a starting time $TS_{E1}$ and a finishing time $TF_{E1}$ which may be defined to any suitable precision (e.g., to a precision of a millisecond). $TS_{E1}$ and $TF_{E1}$ may be represented using any suitable time format (e.g., the format may be hour:minute:second:millisecond). Similarly, event S1 may be characterized by parameters $P1_{S1}$-$PN_{S1}$, starting time $TS_{S1}$, and a finishing time $TF_{S1}$, as shown in FIG. 27. As an illustrative example, parameters $\{P1_{E1}, P2_{E1}, P3_{E1}, P4_{E1}, PN_{E1}, TS_{E1}, TF_{E1}\}$ may be represented by any suitable data structure (e.g., $\{P1_{E1}, P2_{E1}, P3_{E1}, P4_{E1}, PN_{E1}, TS_{E1}, TF_{E1}\}$={"incision", 1 [cm], 3 [mm], {10,20}, "CO2 laser", 13:20:54:80, 13:20:59:76}).

In various embodiments, measure function F(E1,S1) may be defined in any suitable way. As an example embodiment, measure function may be defined as $F(E1,S1)=\Sigma_I (P_{I_{E1}}-P_{I_{S1}})^2+\Sigma_k M(P_{k_{E1}}, P_{k_{S1}})$, where $P_{I_{E1}}$ and $P_{I_{S1}}$ are related numerical parameters, when event E1 and event S1 are of the same type (e.g., both events are of type "incision"), where parameters $P_{k_{E1}}$, and $P_{k_{S1}}$ are text strings (or data, such as images, that may be represented by arrays of numbers), and where function M returns zero if text strings $P_{k_{E1}}$, and $P_{k_{S1}}$ contain the same meaning, or returns one if text strings $P_{k_{E1}}$, and $P_{k_{S1}}$ contains a different meaning. For cases when $P_{k_{E1}}$, and $P_{k_{S1}}$ correspond to images, function M may return zero if images are substantially the same or return one if images are different. In various embodiments, the images may be compared using any suitable image recognition algorithm further described below. Alternatively, function M may be configured to execute any suitable algorithm for comparing $P_{k_{E1}}$, and $P_{k_{S1}}$ depending on a type of data represented by parameters $P_{k_{E1}}$, and $P_{k_{S1}}$, where the data may include text strings, an array of numbers, images, videos, audio signals, and the like.

For cases when events E1 and S1 are not of the same type (e.g., event E1 may correspond to "incision" and event S1 may correspond to "administering a medication"), and when sequence 2702 does not contain an event of the same type as event E1, the measure function F(E1,S1) may be evaluated to a large predetermined number (or string) indicating that events E1 and S1 are substantially different.

As described above the deviation between sequence of events 2701 and 2702 may be determined by evaluating a suitable measure function $F(E_i,S_i)$ for each interval of a surgical procedure I1-I4. A complete deviation may be calculated as a sum of measure functions $\Sigma_i(E_i,S_i)$, where i={I1 ... I4}. In various embodiments, however, calculating all the deviations for all of the events S1-S4 from the corresponding events E1-E4 may not be important and/or necessary. In various cases only large deviations (i.e., deviations where $F(E_i, S_i) > F_1(E_i)$) may be important. For such deviations, events $E_i$, $S_i$ may be identified and stored for further analysis. Additionally, a value of measure function $F(E_i, S_i)$ may be stored for further analysis as well. In various embodiments, data related to events $E_i$, $S_i$, and measure function $F(E_i, S_i)$ may be stored using any suitable means (e.g., hard drive, database 111, and the like).

Using a measure function may be one possible approach of identifying an indication of a deviation between the specific surgical procedure and the recommended sequence of events for the surgical procedure. For example, any algorithm for comparing lists and/or graphs may be used to compare the actual sequence of events with the recommended sequence of events and to identify an indication of a deviation between the specific surgical procedure and the recommended sequence of events for the surgical procedure. Alternatively or additionally, identifying an indication of a deviation occurs using a machine learning model trained using training examples to identify indications of deviations between a sequence of events and surgical footage, for example as described above. In an example embodiment, an illustrative training example may include surgical footage such as frames of a video captured during a surgical procedure of a particular type (e.g., cholecystectomy), as well as the recommended sequence of events for that type of surgical procedure. The training example may be used as an input for the machine-learning training algorithm, and the resulting machine learning model may be a suitable measure of deviation between the specific surgical procedure and the recommended sequence of events for the surgical procedure. The measure of deviation may be any suitable measure. In an example embodiment, the measure may list or classify events during the surgical procedure, which are substantially different from the recommended events. For example, if a recommended event requires suturing, but surgical glue was used instead during the surgical procedure, such an event may be listed or classified as substantially different from the recommended event. Additionally or alternatively, the measure may list recommended events that were not performed during the surgical procedure (e.g., if suturing was required but not performed, such event may be listed as not being performed). Furthermore, the measure may list events during the surgical procedure that were performed but are not recommended events. For example, an event of administering a pain-relieving medicine to a patient during the surgical procedure may be performed and may not be recommended. Additionally, the machine-learning model may output deviations between characteristics of events performed during the surgery and the corresponding recommended events, as described above. For example, if during an incision event during the surgical procedure, the incision length is shorter than an incision described by the recommended event, such deviation may be identified by the machine-learning method and recorded (e.g., stored) for further analysis.

In various embodiments, identifying an indication of a deviation includes comparing the frames to reference frames depicting the recommended sequence of events. The reference frames may be historical frames captured during historical surgical procedures. In an example embodiment, the video frames and the reference frames depicting the recommended sequence of events may be synchronized by an event (herein also referred to as a starting event) that may be the same (or substantially similar) as a corresponding starting event of the recommended (or mandatory) sequence of events. In some cases, a frame depicting the beginning of the starting event may be synchronized with a reference frame depicting the starting event of the recommended sequence of events. In some cases, events of the surgical procedure may be first correlated to corresponding reference events of the recommended sequence, using any suitable approaches described above (e.g., using an image recognition algorithm for recognizing events). After correlating an example surgical event with a corresponding reference event of the recommended sequence, a frame depicting the start of the surgical event may be synchronized with a reference frame depicting the start of the corresponding recommended event.

Additionally or alternatively, identifying an indication of a deviation may be based on an elapsed time associated with an intraoperative surgical procedure. For example, if the elapsed time associated with the surgical procedure is significantly longer (or shorter) than an average elapsed time associated with the surgical procedure, having a recommended sequence of events, the method may be configured to determine that the deviation from the recommended sequence of events has occurred.

Aspects of the method may also include identifying a set of frames of the surgical procedure associated with the deviation and providing the notification that the deviation has occurred. The notification may include displaying the identified set of frames associated with the deviation. For example, the set of frames associated with the deviation may depict a particular event during the surgical procedure that is different (e.g., have different characteristics) than a reference corresponding recommended event. Alternatively, the set of frames associated with the deviation may include frames for an event that is not present in the recommended sequence of events. In various embodiments, the notification may include displaying the frames as still images or displaying the frames as video data. The frames may be displayed on any suitable screen of an electronic device or (in some cases) may be printed. In some embodiments, some of the frames may be selected from the set of frames and displayed using any suitable means (e.g., using display screens of electronic devices).

Aspects of the method for enabling determination and notification of the omitted event may further include training the machine learning model using the training examples to identify deviations between a sequence of events and surgical footage, for example as described above. For example, training examples may be used as an input for the machine-learning model, and the measure of the deviation returned by the model may be analyzed (e.g., the measure of the deviation may be analyzed by a model training specialist, such as a healthcare professional). If the measure of the deviation returned by the model does not coincide with a desired measure of the deviation, various parameters of the machine-learning model may be adjusted to train the machine-learning model to correctly predict the measure of the deviation. For example, if the machine-learning model is a neural network, parameters of such a neural network (e.g., weights of the network, number of neurons, activation functions, biases of the network, number of layers within the network, and the like) may be adjusted using any suitable approach (e.g., weights of the neural network may be adjusted using a backpropagation process). In various embodiments, such adjustments may be made automatically (e.g., using the backpropagation process), or in some cases, adjustments may be made by the training specialist.

In various embodiments, how well the measure of the deviation coincides with the desired measure of the deviation may be asserted using any suitable, appropriate mathematical measure function G. For example, if a measure of a deviation for an event is a number, (e.g., d), and the desired measure of the deviation is another number (e.g., $d_0$) then an example mathematical measure function for a given event $E_i$ may be $G_i(d,d_0)$ may be $G_i(d,d_0)=d-d_0$, and the measure function may be, for example, a number $G=\Sigma_i G_i(d_i,d_{i_0})^2$. Alternatively, in another example embodiment, G may be a vector $G=\{G_i(d_i,d_{i_0})\}$.

To further illustrate a process of determining the deviation of sequence 2702 from sequence 2701, FIG. 27 shows intervals I1-I4 at which events E1-E4 of sequence 2701 may be compared with events S1-S5 of sequence 2702. For example, during interval I1, event S1 may be substantially the same as event E1, and during interval I2 event S2 may deviate from event E2 but may be sufficiently similar to event E2. For example, event S2 may correspond to "incision" having an incision length of three centimeters, and event E2 may correspond to "incision" having an incision length of two centimeters. In an example embodiment, during interval I3 of the surgical procedure, event E3 may be substantially different from event S3 (e.g., event E3 may be identified as an "incision" and event S3 may be identified as "suturing"). During interval I4, event E4 may be substantially different from event S4 but may be substantially the same (as indicated by arrow 2711, as shown in FIG. 27) as event S5 identified during interval I5. When calculating the deviation of sequence 2702 from 2701, event S4 of sequence 2702 may be identified as an "inserted" event that does not have a corresponding counterpart in sequence 2701. Such characterization of event S4 may be recorded (e.g., stored on a hard drive, database 111, or some other location) for further analysis.

Aspects of disclosed embodiments may further include identifying an indication of a deviation between a specific surgical procedure and a recommended sequence of events for the surgical procedure. In some cases, identifying an indication of a deviation may include identifying an indication of a deviation during an ongoing surgical procedure, such as, for example, in real time during the surgical procedure. In various embodiments, the deviation may be identified with a small delay as measured from the ongoing time of the surgical procedure due to processing related to identifying an indication of a deviation. The delay may be a millisecond, a second, a few seconds, a few tens of seconds, a minute, a few minutes, and the like. Once the deviation is identified, disclosure embodiments may include providing a notification during the ongoing surgical procedure. (e.g., provide the notification as soon as the deviation is identified). For example, providing a notification may occur in real time during the surgical procedure.

Aspects of disclosed embodiments may include receiving an indication that a particular action is about to occur in a specific surgical procedure. The indication that the particular action is about to occur may be based on an analysis of the frames of a surgical procedure. In an exemplary embodiment, the indication may be received from a computer-based software application such as a machine-learning model for analyzing surgical footage of an ongoing surgical procedure. For example, the machine-learning model may be an image recognition algorithm consistent with disclosed embodiments described herein.

In some embodiments, an image recognition algorithm may recognize a surgical tool in proximity to an anatomical structure and determine, based on the recognized surgical tool, that a particular action is about to occur in a surgical procedure. In some embodiments, the presence of a surgical tool, an anatomical structure, and/or an interaction between a surgical tool and an anatomical structure may serve as an indicator that a particular action is about to occur. As disclosed herein, an image recognition algorithm may analyze frames of a surgical procedure to identify any of the forgoing. For example, the image recognition algorithm may determine a type of interaction between an instrument and an anatomical structure, a name of interaction, a name of an anatomical structure involved in the interaction, or any other identifiable aspects of the interaction.

Additionally or alternatively, locations of healthcare professionals in an operating room, movements of any one of the healthcare professionals, hand motions of any one of the healthcare professionals, location and/or position of a patient, placement of medical devices, and other spatial features of healthcare professionals, patients, or instruments may further indicate that a particular action is about to occur. In some cases, an indication that the particular action is about to occur may be based on an input from a surgeon performing the specific surgical procedure. For example, audio sounds from any one of the healthcare professionals, gestures, or any other signals identifiable within surgical footage, audio data, image data, or device-based data (e.g., data related to vital signs of a patient) may be used as an indication that a particular action is about to occur.

Disclosed embodiments may include identifying, using the recommended sequence of events, a preliminary action to a particular action. For example, for a particular action such as suturing, a preliminary action may be clasping portions of an anatomical structure with forceps, administering a medication to a patient, repositioning image sensors within an operating room, measuring vital signals, connecting a medical device to a patient (e.g., connecting an ECMO machine to a patient) or any other operation that needs to be performed prior to performing a particular action.

Disclosed embodiments may further include determining, based on an analysis of the accessed frames, that the identified preliminary action did not yet occur and in response, identifying the indication of the deviation. In one example, determining that the identified preliminary action did not yet occur may be accomplished using image recognition, as previously discussed. For example, image recognition may identify that preliminary action did not yet occur by determining that a surgical instrument has not appeared in surgical footage or that there was no interaction between a surgical instrument and an anatomical structure (as identified by analyzing surgical footage), or determining that there are no changes to the anatomical structure (e.g., determining that a shape, color, size, or position of an anatomical structure is unchanged). Additionally or alternatively, image recognition may determine an absence of the preliminary action in other ways (e.g., by determining that healthcare professional has not yet approached a patient, by determining that an ECMO machine is not connected yet to a patient) or by using any other indication that may be identified in surgical footage. In an example embodiment, an indication of deviation between the specific surgical procedure and the recommended sequence of events may be the absence of the preliminary action. Alternatively, if the preliminary action is identified, one or more characteristics of the preliminary action may be an indication of the deviation. For example, when preliminary action is an incision, the length of the incision may be a characteristic of the preliminary action. If, for example, incision length is expected to be in a range of 10-20 cm, and the length is identified to be 3 cm, such characteristic of the preliminary action may indicate a deviation.

Aspects of disclosed embodiments may include providing a notification of a deviation between the specific surgical procedure and the recommended sequence of events before the particular action is performed. The notification may be any suitable electronic notification as described herein and consistent with disclosed embodiments. Alternatively, the notification may be any suitable sound signal, visual signal, or any other signal (e.g., tactile signal, such as vibration) that may be transmitted to a healthcare professional (e.g., a surgeon administering a surgical procedure).

Aspects of disclosed embodiments may include providing the notification postoperatively (i.e., after completion of the surgical procedure). For example, the deviation may be identified during or after the surgical procedure, and the notification may be provided after the deviation is evaluated using any one of (or any combination of) approaches described above. Additionally or alternatively, the deviation between the specific surgical procedure and the recommended sequence of events for the surgical procedure may be analyzed and/or evaluated by a healthcare professional.

Aspects of disclosed embodiments may include determining a name of an intraoperative surgical event associated with the deviation. For example, when a deviation between the specific surgical procedure and the recommended sequence of events is identified, a name and/or a type of event responsible for the deviation may be identified. For example, a deviation between an event of sequence 2702 and recommended sequence 2701 is identified (e.g., when event E3 is substantially different from event S3), a name and/or type of event S3 (e.g., the name may be "suturing") may be determined. Additionally, the name and/or type of event E3 may be determined. In an example embodiment, the name of event S3 may be identified using a machine-learning image recognition model, as described above.

In various embodiments, a name of the intraoperative surgical event associated with the deviation may be the name of a preliminary action prior to a particular action identified in a surgical event. Alternatively, a name of an intraoperative surgical event associated with the deviation may be the name of a particular action. In some cases, a name of an intraoperative surgical event may be a text string containing multiple names of events or actions that contribute to the deviation. In some cases, punctuation (or any other suitable means, such as characters, paragraph marks, or new lines) may be used to separate different names within the text string. For example, the name of an intraoperative surgical event associated with the deviation may be "clasping an artery with forceps; applying a laser beam; suturing the artery."

In some embodiments, determining a name includes accessing a data structure that correlates names with video footage characteristics. A data structure may be any suitable data structure, such as structure 1701, as shown in FIG. 17A. For example, determining a name may include accessing surgical footage (herein, also referred to as video footage) and determining video footage characteristics, such as events, actions, or event characteristics, as described in the present disclosure and consistent with various embodiments of the disclosure.

In various embodiments, upon determining the name of the intraoperative surgical event associated with a determined deviation, a notification of the deviation, including the name of the intraoperative surgical event associated with the deviation may be provided. In an example embodiment, the notification may be provided to various users (e.g., medical personnel, administrators, and the like). In some cases, the notification may be provided to patients, relatives or friends of patients, and the like. The notification may include text data, graphics data, or any other suitable data (e.g., video data, animations, or audio data). Additionally or alternatively, the notification may be implemented as a warning signal (e.g., light signal, audio signal, and the like). In some cases, notification may be an SMS message, an email, and the like delivered to any suitable devices (e.g., smartphones, laptops, desktops, monitors, pagers, TVs, and the like) in possession of various users authorized to receive the notification (e.g., various medical personnel, administrators, patients, relatives or friends of patients, and the like).

Aspects of disclosed embodiments may include receiving an input indicating that a healthcare professional is about to perform an action. Such input may enable providing the notification of the deviation (for example, of a skipped step required according to the recommended sequence of events) before the action is taken by the surgeon. In some cases, such input from a surgeon or from another healthcare professional may include a press of a button, an audible input, a gesture, or any other suitable input, as discussed above, indicating that the surgeon is about to perform the particular action.

An action (about to be performed by a healthcare professional) may be any procedure-related action. For example, the action may include suturing, incision, dissection, suctioning, placement of a camera adjacent to or inside a body of a patient, or anything else that may occur during a procedure. In some cases, the action may include administering a medicine to a patient or measuring patient vital signals such as a pulse, a blood pressure, oxygen levels, and the like.

In various cases, receiving an input may include receiving an input from the healthcare professional. For instance, a surgeon may provide an input via a visual or an audio signal (e.g., using a hand gesture, a body gesture, a visual signal produced by a light source generated by a medical instrument, a spoken word, and the like) that may be captured by one or more image sensors/audio sensors and recognized as an input indicating that a healthcare professional is about to perform an action. In some cases, the healthcare professional may press a button, or use any other device (e.g., a smartphone, a laptop, and the like) to provide the input.

In some cases, the input may indicate what type of action is going to be performed. For example, a surgeon may pronounce a name of the action that is about to be performed, and an audio signal from the surgeon may be captured using a microphone. In an example embodiment, a speech recognition model may be used to recognize one or more words pronounced by the surgeon.

In some cases, receiving an input indicating that a healthcare professional is about to perform an action may include receiving the input from a user who is not a healthcare professional. For example, the input may be received from a person observing the surgical procedure.

Additionally or alternatively, the input may be received from a machine-learning algorithm that is trained to recognize various surgical events leading to possible future actions during surgical procedures. For example, the machine-learning algorithm may be configured to recognize that an incision is about to be performed based on a specific surgical event, such as a surgeon holding and/or moving a scalpel in the proximity of an anatomical structure.

In various embodiments, an indication that the particular action is about to occur may be an entrance of a particular medical instrument to a selected region of interest (ROI). For example, such indication may be determined using an object detection algorithm to detect the presence of the particular medical instrument in the selected ROI. In various embodiments, a presence of a surgical tool in the proximity of a given ROI during a time (or time interval) of the surgical procedure may be used (for example, by a machine-learning model) to recognize that a particular action is about to be taken. For different times during the surgical procedure, the presence of the surgical tool in the proximity of the ROI may indicate different actions that are about to be taken. In some cases, the method may include providing a notification when a given surgical tool is present in the proximity of the ROI and forgoing providing the notification when the surgical tool is not in the ROI. As described above, the notification may be any suitable notification provided to a healthcare professional, a healthcare administrator, or anyone else authorized to receive such information.

In various embodiments, identify that a particular medical instrument entered a selected region of interest (ROI) may be accomplished using any suitable approach, such as using image recognition for analyzing frames of a surgical procedure, as described herein and consistent with disclosed embodiments. In some cases, an ROI may be selected based on a location of an anatomical structure. Or, if a second medical instrument is used during a surgical procedure, an ROI may be selected based on a location of a second medical instrument. Additionally or alternatively, an ROI may be selected based on a field of view of an image sensor. For example, a field of view of a particular image sensor (e.g., a sensor that displays a magnified portion of an anatomical structure) may be used to select an ROI.

In various embodiments, based on the input indicating that a health care professional is about to perform an action, the method may include accessing the stored data structure identifying the recommended sequence of events. The stored data structure may be any suitable data structure such as an array, an associative array, a linked list, a binary tree, a balanced tree, a heap, a stack, a queue, a set, a hash table, a record, a tagged union, an XML code, an XML database, an RDBMS database, an SQL database, and the like. The data structure may include a recommended sequence of events. For example, the data structure may list the names of the events in a table with one event following the other. Alternatively, events may be organized and linked via a linked list. In various embodiments, the data structure may be any suitable data structure that is configured to identify recommended events and to order the events to form a sequence.

Aspects of disclosed embodiments may further include detecting the presence of a surgical tool in a predetermined anatomical region. As used herein, the surgical tool may be any instrument or device that may be used during a surgical procedure, which may include, but is not limited to, cutting instruments (such as scalpels, scissors, saws, etc.), grasping and/or holding instruments (such as Billroth's clamps, hemostatic "mosquito" forceps, atraumatic hemostatic forceps, Deschamp's needle, Hopfner's hemostatic forceps, etc.), retractors (such as Farabef's C-shaped laminar hook, blunt-toothed hook, sharp-toothed hook, grooved probe, tamp forceps, etc.), tissue unifying instruments and/or materials (such as needle holders, surgical needles, staplers, clips, adhesive tapes, mesh, etc.), protective equipment (such as facial and/or respiratory protective equipment, headwear, footwear, gloves, etc.), laparoscopes, endoscopes, patient monitoring devices, and so forth. A surgical tool (also referred to as a medical tool or medical instrument) may include any apparatus or a piece of equipment used as part of a medical procedure.

An anatomical region may be any region that includes anatomical structures of a living organism. For example, the anatomical region may include cavities (e.g., a surgical cavity), organs, tissues, ducts, arteries, cells, or any other anatomical parts. In some cases, prosthetics, artificial organs, and the like may be considered as anatomical structures and appear within anatomical regions. In one example, a machine learning model may be trained using training examples to identify anatomical regions in images and/or videos, and the trained machine learning model may be used to analyze various captured frames of the surgical procedure and detect an anatomical region. An example of such training example may include an image and/or a video, together with a label indicating an anatomical region within the image and/or within the video.

The presence of the surgical tool in a predetermined anatomical region may be detected using any suitable means. In an example embodiment, a trained machine learning model may be used to analyze various captured frames of the surgical procedure to detect the presence of the surgical tool in a predetermined anatomical region. The trained machine-learning model may be an image recognition model for recognizing an image feature, such as a surgical tool in a predetermined anatomical region. In various embodiments, based on the presence of the surgical tool in a predetermined anatomical region, the method may include accessing the stored data structure identifying the recommended sequence of events, as discussed above.

Aspects of preferred embodiments may further include identifying an indication of a deviation between the specific surgical procedure and the recommended sequence of events for the surgical procedure by determining that a surgical tool is in a particular anatomical region. For example, if it is determined (e.g., using a machine-learning method, or using an indication from a healthcare professional) that the surgical tool is present in a particular anatomical region, some embodiments may determine that a deviation has occurred. In some cases, if the surgical tool is present in a particular anatomical region during a time (or a time interval) of the surgical procedure when it should not be present, some embodiments may determine that the deviation has occurred. Alternatively, in some cases, identifying an indication of a deviation may include determining that a surgical tool is not in a particular anatomical region. For example, if during a time (or a time interval) of the surgical procedure, the surgical tool is not present in a particular anatomical region, some embodiments may be configured to determine that the deviation has occurred.

Additionally or alternatively, identifying an indication of a deviation may include identifying an interaction between a surgical tool and an anatomical structure. A process of identifying the interaction between a surgical tool and an anatomical structure may involve analyzing frames of the surgical procedure to identify the interaction, for example as described above. For example, at least some of the frames of the surgical procedure may indicate a portion of the surgical procedure in which a surgical operation is being performed on the anatomical structure. As discussed above, the interaction may include any action by the surgical tool that may influence the anatomical structure or vice versa. For example, the interaction may include a contact between the surgical tool and the anatomical structure, an action by the surgical tool on the anatomical structure (such as cutting, clamping, grasping, applying pressure, scraping, etc.), a physiological response by the anatomical structure, the surgical tool emitting light towards the anatomical structure (e.g., surgical tool may be a laser that emits light towards the anatomical structure), a sound emitted towards anatomical structure, an electromagnetic field created in a proximity of the anatomical structure, a current induced into an anatomical structure, or any other recognizable forms of interaction.

In some cases, identifying interaction may include identifying the proximity of the surgical tool to an anatomical structure. For example, by analyzing the surgical video footage of a surgical procedure, the image recognition model may be configured to determine a distance between the surgical tool and a point (or a set of points) on a surface of an anatomical structure or within an anatomical structure.

In various embodiments, if the interaction between a surgical tool and an anatomical structure during a surgical procedure is identified and no such interaction is expected for a reference surgical procedure (i.e., the surgical procedure that follows a recommended sequence of events), then an embodiment may be configured to determine that the deviation has occurred. Alternatively, if the interaction between a surgical tool and an anatomical structure is not identified (e.g., if the interaction is not present during a surgical procedure), and the interaction is expected for a reference surgical procedure, then an embodiment may be configured to determine that the deviation has occurred. Some embodiments may be configured to determine that there is no substantial deviation of a surgical procedure and a reference surgical procedure if an interaction between a surgical tool and an anatomical structure is present (or absent) in both the surgical procedure and the reference surgical procedure.

Figure 28:
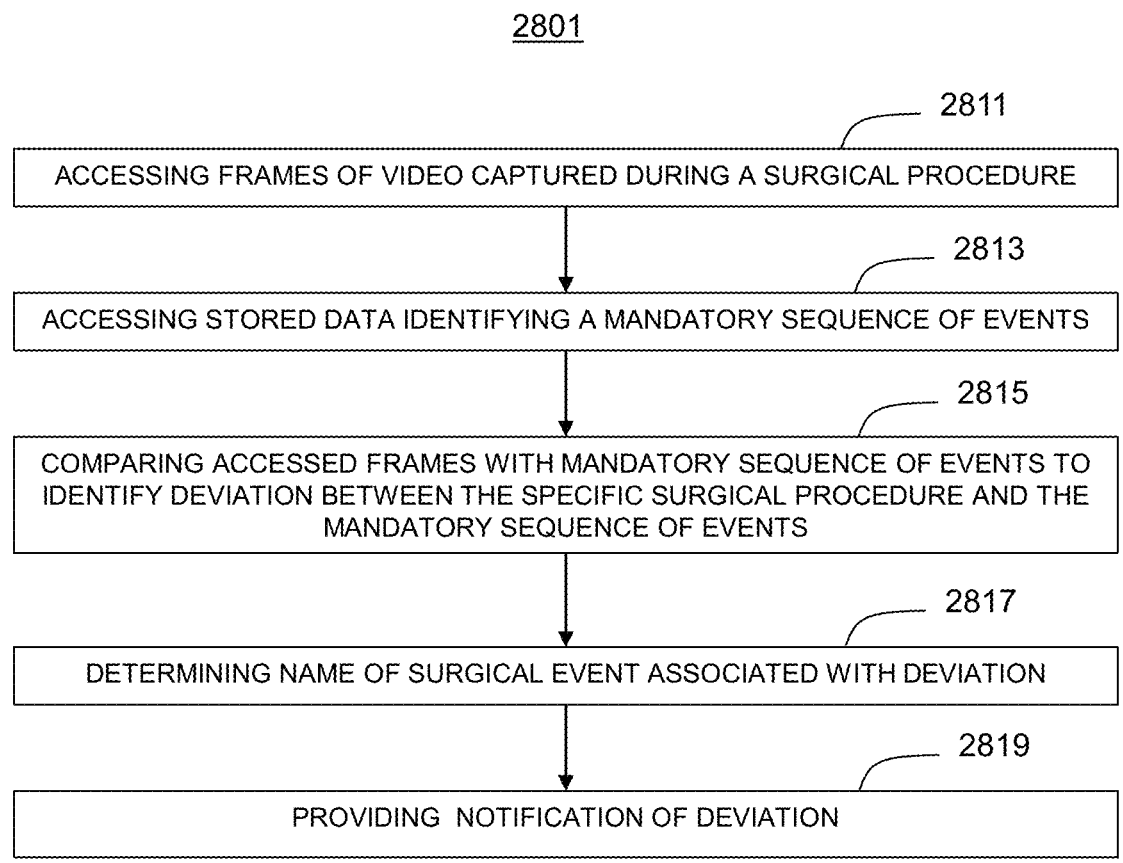
FIG. 28 shows an exemplary process of enabling determination and notification of an omitted event, consistent with disclosed embodiments.

Aspects of embodiments for enabling determination and notification of an omitted event in a surgical procedure are illustrated in FIG. 28 by a process 2801. At step 2811, process 2801 may include accessing frames of video captured during a specific surgical procedure using any suitable means. For example, accessing may include accessing via a wired or wireless network via input devices (e.g., keyboard, mouse, etc.) or via any other means for allowing reading/writing data.

At step 2813, process 2801 may include accessing stored data identifying a recommended sequence of events for the surgical procedure, as described above. At step 2815, process 2801 may include comparing the accessed frames with the recommended sequence of events to identify an indication of a deviation between the specific surgical procedure and the recommended sequence of events for the surgical procedure. The deviation between the specific surgical procedure and the recommended sequence of events for the surgical procedure may be determined using any suitable approaches described above (e.g., by calculating the difference between different events using a suitable measure function, by using a machine-learning model, and so forth). At step 2817, process 2801 may include determining a name of an intraoperative surgical event associated with the deviation using any suitable approach described above (e.g., using a machine-learning model to identify the intraoperative surgical event). Process 2801 may conclude with step 2819 for providing a notification of the deviation, including the name of the intraoperative surgical event associated with the deviation. As described above, the notification may be any suitable notification (e.g., SMS text, video, images, etc.) and may be delivered to healthcare professionals, administrators, or any other authorized individual.

As previously discussed, the present disclosure relates to methods and systems for enabling determination and notification of an omitted event in a surgical procedure, as well as non-transitory computer-readable media that may include instructions that, when executed by at least one processor, cause the at least one processor to execute operations enabling determination and notification of an omitted event in a surgical procedure. The operations may include various steps of methods for enabling determination and notification of an omitted event in a surgical procedure, as described above.

Disclosed systems and methods may involve analyzing current and/or historical surgical footage to identify features of surgery, patient conditions, and other features to predict and improve surgical outcomes. Conventional approaches for providing decision support for surgical procedures may be unable to be performed in real time or may be unable to determine decision making junctions in surgical videos and develop recommendations to perform specific actions that improve surgical outcomes. In such situations, surgeons may miss critical decision making points and/or fail to perform particular actions that can improve outcomes, and surgeries may result in suboptimal outcomes for patients. In contrast, some embodiments of the present disclosure provide unconventional approaches that efficiently, effectively, and in real time provide decision support for surgical procedures.

In accordance with the present disclosure, a method for providing decision support for surgical procedures is disclosed. A surgical procedure may include a procedure performed by one or more surgeons. A surgeon may include any person performing a surgical procedure, including a doctor or other medical professional, any person assisting a surgical procedure, and/or a surgical robot. A patient may include any person undergoing a surgical procedure. Non-limiting examples of surgical procedures may include inserting an implant into a patient, cutting, stitching, removing tissue, grafting, cauterizing, removing an organ, inserting an organ, removing a limb or other body part, adding a prosthetic, removing a tumor, performing a biopsy, performing a debridement, a bypass, and/or any other action to treat or diagnose a patient. An implant or implant unit may include a stent, a monitoring unit, and/or any other material used within the body to replace a missing biological structure, support a damaged biological structure, or enhance an existing biological structure. Surgical tools, such as laparoscopes, cameras, cutters, needles, drills, and/or any other device or implant may be used during a surgical procedure. In addition, during a surgical procedure, medicine (such as an anesthetic drug, an intravenous fluid, a treatment drug, and/or any other compound or preparation) may be used.

Decision support may include providing recommendations that may guide surgeons in making decisions. Decision support may include analyzing video footage of prior similar surgical procedures, identifying a course of action most likely to result in a positive outcome, and providing a corresponding recommendation to an operating surgeon. More generally, decision support for surgical procedures may include providing information to a medical professional during a surgical procedure, such as a recommendation (in information illuminating a decision) to take or avoid an action. In some embodiments, decision support may include providing a computerized interface for alerting a medical professional to a situation. An interface may include, for example, a display, a speaker, a light, a haptic feedback component, and/or any other input and/or feedback mechanism. In some embodiments, providing decision support for surgical procedures may include providing real-time recommendations to a surgeon (i.e., a method for providing decision support for surgical procedures may be performed in real time during a surgical procedure). Real-time recommendations may include providing recommendations via an interface in an operating room (e.g., an operating room depicted in FIG. 1). Real-time recommendations may be updated during a surgical procedure.

In some embodiments, a method may include receiving video footage of a surgical procedure performed by a surgeon on a patient in an operating room. Video footage may include video captured by one or more cameras and/or sensors. Video footage may include continuous video, video clips, video frames, an intracavitary video, and/or any other video footage. Video footage may depict any aspect of a surgical procedure and may depict a patient (internally or externally), a medical professional, a robot, a medical tool, an action, and/or any other aspect of a surgical procedure. In some embodiments, video footage may include images from at least one of an endoscope or an intracorporeal camera (e.g., images of an intracavitary video). An endoscope may include a rigid or flexible tube, a light, an optical fiber, a lens, an eyepiece, a camera, a communication component (e.g., a wired or wireless connection), and/or any other component to assist in collecting and transmitting images from within a patient's body. An intracorporeal camera may include any image sensor used to collect images from within a patient's body before, during, or after a surgical procedure.

Receiving video footage may occur via a sensor (e.g., an image sensor above a patient, within a patient, or located elsewhere within an operating room), a surgical robot, a camera, a mobile device, an external device using a communication device, a shared memory, and/or any other connected hardware and/or software component capable of capturing and/or transmitting images. Video footage may be received via a network and/or directly from a device via a wired and/or wireless connection. Receiving video footage may include reading, retrieving, and/or otherwise accessing video footage from data storage, such as a database, a disk, a memory, a remote system, an online data storage, and/or any location or medium where information may be retained.

Consistent with disclosed embodiments, an operating room may include any room configured for performing surgery, including a room in a hospital, in a clinic, in a temporary clinic (e.g., a room or tent configured for surgery during a disaster relief or war event), and/or any in any other location where surgical procedures may be performed. An exemplary operating room is depicted in FIG. 1.

Consistent with disclosed embodiments, a method for providing decision support for surgical procedures may include accessing at least one data structure including image-related data characterizing surgical procedures. Accessing a data structure may include receiving data of a data structure via a network and/or directly from a device via a wired and/or wireless connection. Accessing a data structure may include retrieving data of a data structure from data storage, consistent with some disclosed embodiments.

Consistent with the present embodiments, a data structure may include primitive types, such Boolean, character, floating point, integer, reference, and enumerated type; composite types such as container, list, tuple, multimap, associative array, set, multiset, stack, queue, graph, tree, heap; any form of hash-based structure or graph. Further examples may include relational databases, tabular data, and/or other form of information organized for retrieval. Data within the data structure may be organized following a data schema including a data type, a key-value pair, a label, metadata, a field, a tag, an index, and/or other indexing feature.

Video and/or image-related data characterizing surgical procedures may be included within the data structure. Such image-related data may include video-characterizing information and/or some or all of the video footage itself, images, and/or a preprocessed version of the video and/or image data. In another example, such video and/or image-related data may include information based on an analysis of the video and/or image. In yet another example, such video and/or image-related data may include information and/or one or more rules for analyzing image data. One example of a data structure is illustrated in FIG. 17A.

Consistent with disclosed embodiments, image-related data characterizing surgical procedures may include data relating to an event characteristic, an event location, an outcome, a deviation between a surgical procure and a mandatory sequence of events, a skill level, an event location, an intraoperative surgical event, an intraoperative surgical event characteristics, a characteristic event, a leakage situation, an event within a surgical phase, a tag, a mandatory sequence of events, an omitted event, a recommended sequence of event, an anatomical structure, a condition, contact between an anatomical structure and a medical instrument, an interaction, and/or any other information describing or defining aspects of surgical procedures.

In some embodiments, a method for providing decision support for surgical procedures may include analyzing received video footage using image-related data to determine an existence of a surgical decision making junction. A surgical decision making junction may include a time (e.g., a time-point or time period) in a surgical video. For example, it may relate to an event or situation that poses an opportunity to pursue alternative courses of action. For example, a decision making junction may reflect a time in which a surgeon may take one or more actions to change a surgical outcome, to follow a surgical procedure, to change to a different surgical procedure, to deviate from a surgical procedure, and/or to vary any other approach.

Analyzing received video footage may include performing methods of image analysis on one or more frames of received video footage, consistent with disclosed embodiments. Analyzing received video footage may include, for example, methods of object recognition, image classification, homography, pose estimation, motion detection, and/or other video analysis methods, for example as described above. Analyzing received video footage may include using a trained machine learning model, and/or training and/or implementing a machine learning model, consistent with disclosed embodiments. For example, received video footage may be analyzed using a machine learning model trained using training examples to detect and/or identify a surgical decision juncture from images and/or videos. For example, received video footage may be analyzed using an artificial neural network configured to detect and/or identify a surgical decision juncture from images and/or videos. In some embodiments, received video footage may be compared with image-related data to determine an existence of a surgical decision juncture. This may occur, for example, through video analysis, and may occur in real time. (E.g., as video is captured of the surgeon operating, analysis may be performed on the video in real time, and surgical junctions may be identified.) In one example, the image-related data may comprise one or more rules for analyzing image data (such as trained machine learning models, artificial neural networks, etc.), and the one or more rules may be used to analyze the received video footage to determine the existence of the surgical decision making junction. In one example, a Markov model may be utilized based on an analysis of frames from the received video footage to determine the existence of the surgical decision making junction. In other examples, an artificial neural network (such as a Recurrent Neural Network or a Long Short-Term Memory neural network) may be used to analyze the received video footage and determine the existence of the surgical decision making junction.

By way of example, a decision making junction may arise upon detection of an inappropriate access or exposure, a retraction of an anatomical structure, a misinterpretation of an anatomical structure or a fluid leak, and/or any other surgical event posing an opportunity to pursue alternative courses of action. Inappropriate access or exposure may include opening and/or cutting a wrong tissue, organ, and/or other anatomical feature. Retraction may involve movement, traction, and/or counter-traction of tissues to expose tissue, or organ, and/or other anatomical structure for viewing by a surgeon. A misinterpretation of an anatomical structure or fluid leak may include a misclassification (e.g., classification of a wrong structure or fluid type) and/or an incorrect estimation of a source and/or severity of a fluid leak. More generally, misinterpretation may include any incorrect conclusion reached by a system or person during a surgical procedure.

In some embodiments, a decision making junction may be determined by an analysis of a plurality of differing historical procedures where differing courses of action occurred following a common surgical situation. For example, a plurality of differing historical procedures may be included in historical video footage and/or in received video footage. Historical procedures may depict one or more surgical procedures, one or more patients, one or more conditions, one or more outcomes, and/or one or more surgeons. In some embodiments, differing courses of action may include differing actions during surgical procedures, as described herein. Differing courses of action may include actions which are not the same (e.g., an action to suture a laceration and an action to staple a laceration may be considered differing actions). Differing courses of action may include different methods of performing a same action (e.g., applying one contact force and applying another contact force may be different methods of performing a same action). Differing courses of action may include using different medical tools. A common surgical situation may refer to a situation that includes a type of surgical procedure (such as a cholecystectomy), a surgical event (e.g., an incision, a fluid leakage event, etc.), and/or any other aspect of a surgery that may be common to a plurality of historical surgical procedures.

In some embodiments, determining a presence of a decision making junction may be based on a detected physiological response of an anatomical structure and/or a motion associated with a surgical tool. A physiological response may include a movement of an anatomical structure, a leakage, and/or any other physiological activity. A physiological response may include a change in a heart rate, a breathing rate, a blood pressure, a temperature, a blood flow, and/or a change in any other biological parameter or health status. Other non-limiting examples of possible physiological responses are described above. A motion associated with a surgical tool any include any movement (e.g., translation and/or rotation) of a surgical tool. A surgical tool may include any surgical tool, as disclosed herein. Detecting a physiological response and/or a motion associated with a surgical tool may include performing a method of image analysis, as also described herein.

In some embodiments, a method for providing decision support for surgical procedures may include accessing, in at least one data structure, a correlation between an outcome and a specific action taken at a decision making junction. Accessing a correlation may include determining an existence of a correlation, reading a correlation from memory, and/or determining in any other manner that a correlation exists between a particular action and an outcome. In some embodiments, a correlation may be accessed in a data structure based on an index, the index including at least one of a tag, a label, a name, or other identifier of a specific action, a decision making junction, and/or an outcome. In some embodiments, accessing a correlation may include determining (e.g., generating, looking up, or identifying) a correlation using an algorithm such as a model, a formula, and/or any other logical approach. Consistent with disclosed embodiments, a correlation may indicate a probability (e.g., likelihood) of a desired outcome (e.g., positive outcome) and/or undesired outcome (e.g., negative outcome) associated with a specific action. A correlation may include a correlation coefficient, a goodness of fit measure, a regression coefficient, an odds ratio, a probability, and/or any other statistical or logical interrelationship. In one example, one correlation may be used for all decision making junction of a particular type, while in another example, a plurality of correlations may be used for different subsets of the group of all decision making junction of the particular type. For example, such subset may correspond to a particular group of patients, to a particular group of surgeons (and/or other healthcare professionals), to a particular group of surgeries, to a particular group of operating rooms, to particular previous events in the surgical procedure, to any union or intersection of such groups, and so forth.

A specific action may include any action performed by a surgeon (e.g., a human or robotic surgeon) during a surgical procedure, or by a person or robot assisting a surgical procedure. Examples of specific actions may include remedial actions, diagnostic actions, actions following a surgical procedure, actions deviating from a surgical procedure, and/or any other activity that might occur during a surgical procedure. Such actions may include engaging a medical instrument with a biological structure, administering a medication, cutting, suturing, altering surgical contact, conducting a medical test, cleaning an anatomical structure, removing excess fluid, and/or any other action that may occur during a surgical procedure.

A specific action may include a single step or a plurality of steps (e.g., a plurality of actions performed during a surgery). A step may include any action or subset of an action as described herein. Non-limiting examples of specific actions may include one or more of steps to make an incision, to insert an implant, to attach an implant, and to seal an incision.

In some embodiments, a specific action may include introducing an additional surgeon to an operating room. For example, the additional surgeon may have more experience, a higher skill level, a particular expertise (e.g., a technical expertise, a particular problem-solving expertise, and/or other expertise), than a surgeon already present in the operating room. Bringing a surgeon to an operating room may include transmitting a notification requesting or instructing a surgeon to come to an operating room. In some embodiments, an additional surgeon may be a surgical robot, and bringing an additional surgeon to an operating room may include activating the robot and/or providing instructions to the robot to perform and/or assist a surgical procedure. Providing instructions to a robot may include instructions to perform one or more actions.

In some embodiments, a method for providing decision support for surgical procedures may include outputting a recommendation to a user to undertake and/or to avoid a specific action. Such a recommendation may include any guidance, regardless of the form of the guidance (e.g., audio, video, text-based, control commands to a surgical robot, or other data transmission that provides advice and/or direction). In some instances, the guidance may be in the form of an instruction, in others it may be in the form of a recommendation. The trigger for such guidance may be a determined existence of a decision-making junction and an accessed correlation. Outputting a recommendation may include transmitting a recommendation to a device, displaying a recommendation on an interface, and/or any other mechanism for supplying information to a decision maker. Outputting a recommendation to a user may include outputting a recommendation to a person in an operating room, to a surgeon (e.g., a human surgeon and/or a surgical robot), to a person assisting a surgical procedure (e.g., a nurse), and/or any to other user. For example, outputting a recommendation may include transmitting a recommendation to a computer, a mobile device, an external device, smart glasses, a projector, a surgical robot, and/or any other device capable of conveying information to the user. In some embodiments, a surgeon may be a surgical robot and a recommendation may be provided in the form of an instruction to the surgical robot (e.g., an instruction to undertake a specific action and/or avoid a specific action).

Outputting a recommendation may occur via a network and/or via a direct connection. In some embodiments, outputting a recommendation may include providing output at an interface in an operating room. For example, outputting a recommendation may include causing a recommendation to be presented via an interface (e.g., a visual and/or audio interface in an operating room). In some embodiments, outputting a recommendation may include playing a sound, altering a light (e.g., turning a light on or off, pulsing a light), providing a haptic feedback signal, and/or any other method of alerting a person or providing information to a person or surgical robot.

By way of example, a recommendation may include a recommendation to conduct a medical test. In some embodiments, a medical test may include a blood analysis, a medical imaging of a patient, a urine analysis, data collection by a sensor, and/or any other analysis. Medical imaging may include an intraoperative medical imaging (i.e., an imaging that occurs during a surgical procedure), such as X-ray imaging, computerized tomography (CT), medical resonance imaging (MRI), other procedures involving a contrasting agent, ultrasound, or other techniques for creating body part images for diagnostic and/or treatment purposes.

In some embodiments, a method for providing decision support for surgical procedures may include outputting a recommendation (e.g., a first recommendation, second recommendation, and/or an additional recommendation) to a user to undertake or to avoid a specific action based a determined existence of a decision making junction, an accessed correlation, and a received result of a medical test. A method for providing decision support for surgical procedures may therefore include receiving a result of a medical test. A result of a medical test may include medical data, sensor data, instrument data, and/or any other information reflective of a biological condition. A result of a medical test may include an indicator of a health status and/or a condition of a patient. A result may include, for example, a presence or absence of a biomarker, a presence or absence of a tumor, a location of an anatomical feature, an indicator of metabolic activity (e.g., glucose uptake), an enzyme level, a heart status (e.g., heart rate), a temperature, a breathing indicator, and/or any other health or condition indicator. A result may be received via network and/or from a connected device. Receiving a result may include receiving and/or accessing a data storage, consistent with disclosed embodiments. For example, in response to a first value of the received result of the medical test, a recommendation to undertake (or to avoid) a first action may be outputted, and in response to a second value of the received result of the medical test, outputting the recommendation to undertake (or to avoid) the first action may be withheld.

In some embodiments, a recommendation may include a name and/or other identifier (e.g., an employee ID) of an additional surgeon. In some embodiments, outputting a recommendation may include providing an indication to an additional surgeon. An indication may include a notification, an alert, a request to come to an operating room, a result of a medical test, information indication that assistance may be needed during a surgical procedure, and/or any other indication. In one example, the additional surgeon may be selected (for example, from a plurality of alternative additional surgeons) based on one or more of a characteristic of the patient undergoing the surgical procedure, the surgeon currently performing the surgical procedure, the operating room, a tool used in the surgical procedure, a condition of an anatomical structure related to the surgical procedure, an interaction between a medical instrument and an anatomical structure in the surgical procedure, a physiological response related to the surgical procedure, characteristics of the additional surgeon, and so forth.

Consistent with the present embodiments, a recommendation may include a description of a current surgical situation, guidance, an indication of preemptive or corrective measures, an indication of alternative approaches, danger zone mapping, and/or any other information that might inform the surgeon relative to a surgical procedure. A description of a current surgical situation may include a health status and/or a condition of a patient (e.g., a condition reflected in sensor data such as heart rate monitor data, brain activity data, temperature data, leakage data, and/or any other health data). A description of a current surgical situation may also or alternatively include an evaluation of a current or possible future outcome. A preemptive measure and/or a corrective measure may include an action to follow and/or change a surgical procedure. A preemptive measure and/or a corrective measure may include any action by a surgeon and/or person assisting a surgery, and/or an action that may result in avoiding a negative outcome. A corrective measure may include an action that may improve an outcome. In some embodiments, danger zone mapping may include identifying one or more specific actions and likely outcomes (e.g., a set of specific actions associated with negative outcomes such as death, disability, or other undesirable eventuality). Danger zone mapping may include, for example, identification of anatomical regions that if not accessed properly, may adversely impact patient safety and surgery outcomes. For example, in inguinal hernia, danger zones may include the 'triangle of doom' that lies between the Vas deferens in men or round ligament of the uterus in women (medially) and the testicular vessels in men (laterally), and holds important structures such as iliac vessels, femoral nerve, genital branch of the genitofemoral nerve, and/or the 'triangle of pain' that lies between the testicular vessels (medially), the psoas muscle (laterally) and the ileopubic tract (superiorly) and holds important structures such as the femoral branch of the genitofemoral nerve and the lateral femoral cutaneous nerve, are critical. Injuries to structures within the "triangle of doom" may, in some cases, be fatal. Injuries to structures within the "triangle of pain" may, in some cases, result in chronic pain. In some examples, a machine learning model may be trained using training examples to identify danger zones in surgical images and/or surgical videos, and the trained machine learning model may be used to analyze the video footage and identify and/or map the danger zones. An example of such training example may include an image and/or a video, together with a label indicating the danger zones depicted in the image and/or in the video. In one example, a description of a danger zone mapping may include textual description of relevant identified danger zones. In another example, a description of a danger zone mapping may include visual marking of relevant identified danger zones, for example as an overlay over at least one frame of the video footage, in an augmented reality system, and so forth.

By way of example, a recommendation may include a recommended placement of a surgical drain, such as to drain inflammatory fluid, blood, bile, and/or other fluid from a patient.

A recommendation may include a confidence level that a desired surgical outcome will occur if a specific action is taken, and/or a confidence level that a desired outcome will not occur if a specific action is not taken. A confidence level may be based on an analysis of historical surgical procedures, consistent with disclosed embodiments, and may include a probability (i.e., likelihood) that an outcome will occur. A desired outcome may be a positive outcome, such as an improved health status, a successful placement of a medical implant, and/or any other beneficial eventuality. In some embodiments, a desired outcome may include an avoidance of a possible undesired situation following a decision making junction (e.g., an avoidance of a side effect, a post-operative complication, a fluid leakage event, a negative change in a health status of a patient, and/or any other undesired situation).

In some embodiments, outputting a recommendation may be based on a time elapsed since a particular point in a surgical procedure. For example, a recommendation may be based on a time elapsed since a surgical event, consistent with disclosed embodiments. A recommendation may be based on a surgical event that occurred at least a specified number of minutes before a decision making junction. In some embodiments, a surgical event may include a past action performed by a surgeon prior to a decision making junction. A recommendation may also include an alternative course of action. A course of action may include a set, a sequence, and/or a pattern of actions. An alternative course of action may differ from actions associated with an ongoing surgical procedure being followed by a surgeon.

In some embodiments, a recommendation may include an indication of an undesired surgical outcome likely to occur if a specific action is not undertaken. Such an indication may include a confidence level, a description of an undesired surgical outcome (e.g., a name of an outcome), and/or any other indication.

In some embodiments, a recommendation may be based on a skill level of a surgeon. For example, a surgeon with a high skill level may receive a different recommendation than a surgeon with a lower skill level. In some embodiments, a recommendation may include a specific action selected from a plurality of alternative actions, and a selection of a specific action may be based on a skill level of a surgeon and complexity levels associated with a plurality of alternative actions. A skill level may be based on a historical performance score, a number of surgeries performed, overall time spent as a surgeon (e.g., a number of years; number of hours spent in surgery), an indication of a level of training, a classification of a surgeon's skill, and/or any other assessment of a surgeon's skill whether derived from manual input, data analysis, or video image analysis.

In some embodiments, a recommendation may be based on a surgical event that occurred in a surgical procedure prior to a decision making junction (i.e., a prior surgical event). A prior surgical event may include any surgical event as described herein, and which preceded the decision making junction. A prior surgical event may be correlated with a positive or negative outcome after a decision making junction, and a recommendation may include a recommendation to perform a specific action that increases the likelihood of achieving a later positive outcome or of avoiding a later negative outcome. Thus, such a method may include determining that a prior surgical event is correlated with a later outcome. Such a correlation may be time-based, in that the correlation may be determined based on an elapsed time between a surgical event and the decision making junction.

In some embodiments, outputting a recommendation may include presenting a first instruction to perform a first step, receiving an indication of that a first step was performed successfully, and, in response to the received indication that a first step was performed successfully, presenting a second instruction to perform a second step. In some embodiments, outputting a recommendation may include presenting a first instruction to perform a first step and receiving an indication that the first step was not performed successfully. In some embodiments, outputting a recommendation may include forgoing presenting a second instruction in response to a received indication that a first step was not performed successfully. In some embodiments, in response to a received indication that a first step was not performed successfully, outputting a recommendation may include presenting an alternative instruction to perform an alternative step, the alternative step differing from a second step.

An indication that a first step was performed successfully or unsuccessfully may be based on an analysis of video footage, consistent with disclosed embodiments. Receiving an indication may include receiving video footage after presenting an instruction to perform a first step and generating an indication based on an analysis of video footage.

In some embodiments, a method for providing decision support for surgical procedures may include receiving a vital sign of a patient, and a recommendation may be based on an accessed correlation and a vital sign. A vital sign may be received from a medical instrument, a device, an external device, a data storage, a sensor, and/or any other computing component, and may include any indicator a condition of a patient health status (e.g., a heart rate, a breathing rate, a brain activity, and/or other vital sign). In some embodiments, vital signs may be received via a network from a connected device, and may be detected either via a traditional sensor or through analysis of video footage.

In some embodiments, a recommendation may be based on a condition of a tissue of a patient and/or a condition of an organ of a patient. Generally, a condition of a tissue or an organ may refer to any information that indicates to a state or characteristic of a tissue or organ. For example, a condition may be based on an assessment such as whether tissue or organ is normal, abnormal, damaged, leaking, hydrated, oxygenated, dehydrated, retracted, enlarged, shrunken, present, absent, and/or any other appearance or status. Consistent with disclosed embodiments, a condition of a tissue and/or organ of a patient may be determined based on an analysis of video footage. For example, such an analysis may determine a color of a tissue, a texture of an anatomical structure, a heart rate, a lung capacity, a presence of a lump or other irregularity and/or any other characteristic of an anatomical structure. In some embodiments, a recommendation may be based on a condition reflected in sensor data such as heart rate monitor data, brain activity data, temperature data, leakage data, and/or any other health data.

As another example, a recommendation of a specific action may include a suggestion or direction to form a stoma, or a particular type of a stoma (e.g., loop stoma, end stoma, loop colostomy, end colostomy, loop ileostomy, end ileostomy, urostomy, and/or any other type of stoma). The recommendation may suggest a stoma creation technique, an indication of a portion of a colon and/or ileum for creation of a stoma, and/or a location on a skin of a patient for creation of a stoma. Or, a recommendation may suggest that a stoma not be created when, for example, a creation of a stoma is correlated to an undesirable outcome.

A recommendation to create or avoid creating a stoma (or to take any other course of action) may be based on a physiological impact on a patient, and a threshold of a measure of a possible improvement to an outcome. A threshold may be selected based on a patient characteristic (e.g., an age, a prior health status, a family history, a vital sign, and/or other characteristic). For example, a lower threshold may be selected for a patient who previously had a stoma associated with a desired outcome. A threshold may also be based on whether a patient was informed of a possibility of a stoma prior to a surgery.

One example of a decision making junction may include deciding whether or not to mobilize the ileum and/or the cecum, for example in the preparation phase of an appendectomy, and the recommendation may include a suggestion to mobilize the ileum and/or the cecum or a suggestion not to mobilize the ileum and/or the cecum. Some non-limiting examples of factors that may influence the decision may include procedure complexity level, age of the patient, the gender of the patient, previous inflammation and prior surgery. The recommendation may be based on at least one of these factors. The decision made at this junction may impact the ability to resect the diseased appendix. Another example of a decision making junction may include deciding if the appendix can be safely divided or not, for example in the dissection and skeletonization phase of an appendectomy, and the recommendation may include a suggestion to dissect or not to dissect the appendix. Some non-limiting examples of factors that may influence the decision may include procedure complexity level, achieving a free appendix, and whether or not ileum/cecum was mobilized properly. The recommendation may be based on at least one of these factors. The decision made at this junction may dictate whether or not there will be the recurrence of appendicitis ('stump appendicitis'). Another example of a decision making junction may include deciding what instrument to use for the division of the appendix, for example in the division phase of appendectomy, and the recommendation may include a suggestion of an instrument for the division. Some non-limiting examples of factors that may influence the decision may include procedure complexity level, whether or not a circular view of the appendix was achieved, and patient body mass index. The recommendation may be based on at least one of these factors. The decision made at this junction may influence the length and cost of treatment. Another example of a decision making junction may include deciding whether or not to treat an appendiceal stump, for example in the division phase of an appendectomy. Some options that may include avoiding action for treating the appendiceal stump, to cauterize, or to oversew. A recommendation may include a suggestion of whether to treat the appendiceal stump, and/or a suggestion of a particular action to be taken for treating the appendiceal stump. Some non-limiting examples of factors that may influence the decision may include procedure complexity level and which instrument was used to divide the appendix. The recommendation may be based on at least one of these factors. The decision made at this junction may influence postoperative infection and fistulae rates. Another example of a decision making junction may include deciding how to remove the resected sample (e.g., in an endobag or through the trocar), for example in the packaging phase of appendectomy, and the recommendation may include a suggestion on how to remove a resected sample. For example, the decision may be based on the procedure complexity level. The decision made at this junction may influence surgical site infection rate. Another example of a decision making junction may include deciding whether or not to perform irrigation, for example in the final inspection phase of appendectomy, and the recommendation may include a suggestion to perform irrigation or a suggestion not to perform irrigation. Some non-limiting examples of factors that may influence the decision may include procedure complexity level, patient pre-existing comorbidities, and patient gender. The recommendation may be based on at least one of these factors. The decision made at this junction may influence infection rate. Another example of a decision making junction may include deciding whether or not to place a drain, for example in the final inspection phase of appendectomy, and the recommendation may include a suggestion to place a drain or a suggestion not to place a drain. Some non-limiting examples of factors that may influence the decision may include procedure complexity level, patient age, and patient pre-existing comorbidities. The recommendation may be based on at least one of these factors. The decision made at this junction may influence infection rate, complication rate and postoperative length of stay.

One example of a decision making junction in an access phase of a laparoscopic cholecystectomy may include a selection of an insertion method (such as Veres needle, Hasson technique, OptiView) and/or a selection of port placement arrangement (such as 'Regular' and 'Alternative'), and the recommendation may include a suggestion of an insertion method and/or a suggestion of a port placement arrangement. One example of a decision making junction in an adhesiolysis phase of a laparoscopic cholecystectomy may include a selection of whether to decompress the gallbladder, and the recommendation may include a suggestion of whether to decompress the gallbladder. For example, when the gallbladder is distended and/or tense, or when other signs of acute cholecystitis are present, the recommendation may include a suggestion to decompress the gallbladder. One example of a decision making junction in a laparoscopic cholecystectomy may include a selection of a gallbladder dissection approach (such as Traditional, Dome-down Dissection, Sub-total, and so forth), and the recommendation may include a suggestion of a gallbladder dissection approach. For example, in case of a severe cholecystitis, a recommendation of a Dome-down Dissection may be provided. In another example, in case of an inability to obtain exposure, a recommendation to bail out may be provided, for example due to an increase risk for large collaterals in the liver bed. One example of a decision making junction in a laparoscopic cholecystectomy may include a selection of whether or not to place a drain, and the recommendation may include a suggestion to place a drain or a suggestion not to place a drain.

In some examples, the recommendation to the user to undertake and/or to avoid the specific action to be outputted may be determined using a trained machine learning model. For example, a machine learning model may be trained using training examples to determine recommendations based on information related to surgical decision making junctions, and the trained machine learning model may be used to determine the recommendation to be outputted to the user to undertake and/or to avoid the specific action for a particular occurrence of a surgical decision making junction based on information related to the particular occurrence of the surgical decision making junction. Some non-limiting examples of such information related to an occurrence of a surgical decision making junction are described above. For example, the information may include a type of the surgical decision making junction, properties of the surgical decision making junction, time of the surgical decision making junction (e.g., within the surgical procedure), characteristics of a patient undergoing the surgical procedure, characteristics of a surgeon (or another healthcare professional) performing at least part of the surgical procedure, characteristics of an operating room related to the surgical procedure, an anatomical structure related to the surgical decision making junction, a condition of the anatomical structure related to the surgical decision making junction, a medical instrument used in the surgical procedure, an interaction between a medical instrument and an anatomical structure in the surgical procedure, a physiological response related to the surgical decision making junction, one or more surgical events that occurred in the surgical procedure prior to the surgical decision making junction, duration of the one or more surgical events that occurred in the surgical procedure prior to the surgical decision making junction, duration of surgical phases in the surgical procedure, one or more correlations between outcomes and possible actions that may be taken at the surgical decision making junction, past responses of the user to previously provided recommendations, and so forth. An example of such training example may include information related to a surgical decision making junction, together with a label indicating a desired recommendation. For example, the label may include a desired textual and/or graphical content for the desired recommendation. In another example, the label may be based on a correlation between an outcome and a specific action taken at such surgical decision making junction.

FIG. 29 is a flowchart illustrating an example process 2900 for decision support for surgical procedures, consistent with disclosed embodiments. Process 2900 may be performed using at least one processor, such as one or more microprocessors. In some embodiments, process 2900 is not necessarily limited to steps illustrated, and any of the various embodiments described herein may also be included in process 2900. As one of skill in the art will appreciate, steps of process 2900 may be performed by a system including, for example, components of system 1401. In some embodiments, a non-transitory computer readable medium including instructions that, when executed by at least one processor, cause the at least one processor to execute operations for providing decision support for surgical procedures according to process 2900. In some embodiments, process 2900 may be performed in real time during a surgical procedure. Based on the steps described in process 2900, the surgeon or other users may be able to more effectively and more efficiently perform surgical procedures with positive outcomes and/or avoid negative outcomes.

At step 2902, the process may include receiving video footage of a surgical procedure performed by a surgeon on a patient in an operating room, consistent with disclosed embodiments and as previously described by way of examples. FIG. 1 provides an example of an operating room, surgeon, patient, and cameras configured for capturing video footage of a surgical procedure. Video footage may include images from at least one of an endoscope or an intracorporeal camera (e.g., images of an intracavitary video).

At step 2904, the process may include accessing at least one data structure including image-related data characterizing surgical procedures, consistent with disclosed embodiments and as previously described by way of examples. In some embodiments, accessing a data structure may include receiving data of a data structure via a network and/or from a device via a connection. Accessing a data structure may include retrieving data from a data storage, consistent with disclosed embodiments.

At step 2906, the process may include analyzing the received video footage using the image-related data to determine an existence of a surgical decision making junction, consistent with disclosed embodiments and as previously describe by way of examples. Analyzing received video footage may include performing methods of image analysis on one or more frames of received video footage, consistent with disclosed embodiments. Analyzing received video footage may include implementing a model trained to determine an existence of a surgical decision making junction. A decision making junction may include an inappropriate access or exposure, a retraction of an anatomical structure, a misinterpretation of an anatomical structure or a fluid leak, and/or any other surgical event, as previously described. In some embodiments, a decision making junction may be determined by an analysis of a plurality of differing historical procedures where differing courses of action occurred following a common surgical situation. In some embodiments, determining a presence of a decision making junction may be based on a detected physiological response of an anatomical structure and/or a motion associated with a surgical tool.

At step 2908, the process may include accessing, in the at least one data structure, a correlation between an outcome and a specific action taken at the decision making junction, as previously described by way of examples. As discussed, a specific action may be correlated with a positive or negative outcome, consistent with disclosed embodiments. Accessing a correlation may include generating a correlation, reading a correlation from memory and/or any other method of accessing a correlation in a data structure. A specific action may include a single step or a plurality of steps (e.g., a plurality of actions performed by a surgeon). A specific action may include summoning an additional surgeon to the operating room.

At step 2910, the process may include outputting a recommendation to a user to undertake the specific action, consistent with disclosed embodiments, as previously described by way of examples. Outputting a recommendation may be based on a determined existence of a decision making junction and an accessed correlation, consistent with the present embodiments. In some embodiments, outputting a recommendation may include providing output via an interface in an operating room. In some embodiments, a surgeon is a surgical robot and a recommendation may be provided in the form of an instruction to the surgical robot (e.g., an instruction to undertake a specific action and/or avoid a specific action). By way of example, a recommendation may include a recommendation to conduct a medical test. A recommendation (e.g., a first recommendation, second recommendation, and/or an additional recommendation) may include a recommendation to the user to undertake or to avoid a specific action based a determined existence of a decision making junction, an accessed correlation, and a received result of a medical test. A recommendation may include a name and/or other identifier (e.g., an employee ID) of an additional surgeon. A recommendation may include a description of a current surgical situation, an indication of preemptive or corrective measures, and/or danger zone mapping. In one example, as previously mentioned, a recommendation may include a recommended placement of a surgical drain to remove inflammatory fluid, blood, bile, and/or other fluid from a patient. A confidence level that a desired surgical outcome will or will not occur if a specific action is taken or not taken may be part of a recommendation. A recommendation may be based on a skill level of a surgeon, a correlation and a vital sign, and/or a surgical event that occurred in a surgical procedure prior to a decision making junction (i.e., a prior surgical event). In some embodiments, a recommendation may be based on a condition of a tissue of a patient and/or a condition of an organ of a patient. As another example, a recommendation of the specific action may include a creation of a stoma, as previously discussed by way of example.

Disclosed systems and methods may involve analyzing current and/or historical surgical footage to identify features of surgery, patient conditions, and other features to estimate surgical contact force. Exerting too much contact force during a procedure may have adverse health consequences to a patient. Conversely, insufficient contact force may result in suboptimal results for some procedures. Assessing an appropriate level of force to apply in any given surgical situation may be difficult, resulting in suboptimal outcomes for patients. Therefore, there is a need for unconventional approaches that efficiently, effectively, and in real-time or post-operatively determine surgical contact force.

In accordance with the present disclosure, a method for estimating contact force on an anatomical structure during a surgical procedure is disclosed. Contact force may include any force exerted by a surgeon or by a surgical tool on one or more anatomical structures (e.g., a tissue, limb, organ, or other anatomical structure of a patient) during a surgical procedure. The term "contact force" as used herein, refers to any force that may be applied to an anatomical structure, whether that force is characterized in a unit of weight (e.g., kilograms or pounds applied), a unit of force (e.g., Newtons), a pressure applied to an area (e.g., pounds applied per square inch), a tension (e.g., pulling force), or pressure (e.g., pushing force).

Contact force may be applied directly or indirectly in many ways. For example, a contact force may be applied through direct contact of a surgeon with an anatomical structure (e.g., applied by a surgeon's hands), or may be applied through a surgical instrument, tool or other structure in the surgeon's hands. In cases where the surgeon is a surgical robot, the robot may exert a contact force via a robotic structure (robotic arm, fingers, graspers) either directly or through a tool, instrument or other structure manipulated by the robot.

Contact force may include a normal (i.e., orthogonal) force, a shear force, and/or a combination of normal and shear forces. More generally, contact force may include any force or pressure applied to any part of a patient's body during a surgery.

Consistent with the present embodiments, estimating contact force may include analyzing images and/or surgical video to generate an estimate of a magnitude of an actual contact force according to a scale. Force estimation through image analysis may involve an examination of a tissue/modality interface to observe an effect on the tissue. For example, if the modality is a medical instrument such as forceps pressing against an organ such as a gallbladder, machine vision techniques applied to the location of force application may reveal movement and/or changes of the organ that is reflective of the force applied. Based on historical video footage from prior procedures where force application was previously observed, an estimate of the magnitude of force applied can be made for the current video. The force magnitude estimate may include a unit of measurement (e.g., pounds, pounds per square inch, Newtons, kilograms, or other physical units) or may be based on a relative scale. A relative scale may include a categorical scale, a numeric scale, and/or any other measure. A categorical scale may reflect a level of force (e.g., a scale including multiple levels such as a high force, a medium force, a low force, or any other number of levels). A contact force may be estimated according to a numerical scale such as a scale of 1-10. Moreover, the force may be estimated at discrete points in time or may be estimated continuously. In some embodiments, an estimate of a contact force may include an estimate of a contact location, a contact angle, and/or an estimate of any other feature of contact force.

In some embodiments, a method for estimating contact force on an anatomical structure may include receiving, from at least one image sensor in an operating room, image data of a surgical procedure. An image sensor may include a camera and/or any other image capture device. An image sensor may be configured to collect image data and/or video data and may be positioned anywhere in any operating room, such as, for example, above a patient or within a patient (e.g., in an intracorporeal cavity). Image data may include surgical video, video clips, video footage, image frames, continuous video and/or any other information derived from video. For example, image data may include pixel data, color data, saturation data, and/or any other data representing an image, regardless of storage format. Image data may include time data (e.g., a time an image was captured by a sensor), location data, information relating to a surgical procedure (e.g., a patient identifier, a name of a surgical procedure) and/or any other metadata. In some embodiments, image data of a surgical procedure may be collected by an image sensor in an operating room and stored in a data structure (e.g., a data structure of FIG. 17A) in, near, or even remote from the operating room. While the force estimation may occur in real time, it may also be estimated in non-real time, such as when the data is retrieved from a data structure.

In some embodiments, a method for estimating contact force on an anatomical structure may include analyzing received image data to determine an identity of an anatomical structure reflected in image data. Analyzing received image data may include any method of image analysis, consistent with the present embodiments. Some non-limiting examples of algorithms for identifying anatomical structures in images and/or videos are described above. Analyzing received image data may include, for example, methods of object recognition, image classification, homography, pose estimation, motion detection, and/or other image analysis methods. Analyzing received image data may include artificial intelligence methods including implementing a machine learning model trained using training examples, consistent with disclosed embodiments. For example, received image data may be analyzed using a machine learning model trained using training examples to detect and/or identify an anatomical structure, for example as described above. For example, received image data may be analyzed using an artificial neural network configured to detect and/or identify an anatomical structure from images and/or videos. Training examples may include image data labeled or otherwise classified as depicting an anatomical structure (e.g., images classified as depicting a pancreas).

In some embodiments, a method for estimating contact force on an anatomical structure may include analyzing received image data to determine a condition of anatomical structure. Generally, a condition of an anatomical structure may refer to any information that indicates a state or characteristic of an anatomical structure. For example, a condition may reflect whether an anatomical structure is normal, abnormal, damaged, leaking, hydrated, dehydrated, oxygenated, retracted, enlarged, shrunken, present, absent, and/or any other assessment. A condition may include a measure of a vitality of an anatomical structure, a level of oxygenation, a level of hydration, a level of distress, and/or a measure of any other state of an anatomical structure. In one example, a condition of an anatomical structure may be represented as a vector of numerical values corresponding to a point in a mathematical space. In some examples, a machine learning model may be trained using training examples to identify conditions of anatomical structures from images and/or videos, and the trained machine learning model may be used to analyze the received image data and determine the condition of the anatomical structure. An example of such training example may include an image and/or a video of an anatomical structure, together with a label indicating the condition of the anatomical structure.

In some embodiments, an analysis may determine a condition based on a characteristic of an anatomical structure that indicates a condition. As a non-limiting example, an analysis may determine a color of a tissue, a texture of an anatomical structure, a heart rate, a lung capacity, and/or any other characteristic of an anatomical structure. In some embodiments, a recommendation may be based on a characteristic reflected in sensor data such as heart rate monitor data, brain activity data, temperature data, blood pressure data, blood flow data, leakage data, and/or any other health data. Such characteristics of an anatomical structure may indicate a condition of the anatomical structure and may be correlated with known conditions. For example, reduced brain activity might be indicative of a vessel blockage or increased cranial pressure might be indicative of a brain hemorrhage. Such correlations may be stored a data structure such as a data structure of FIG. 17A).

In some embodiments, a method for estimating contact force on an anatomical structure may include selecting a contact force threshold associated with an anatomical structure. A contact force threshold may include a minimum or maximum contact force. In some embodiments, selecting a contact force threshold may be based on information indicating a likely outcome associated with applying forces above or below a threshold. Selecting a contact force threshold may be based on data indicating a recommended contact force (e.g., a maximum safe force or a minimum effective force). For example, selecting a contact force threshold may be based on a table of anatomical structures including corresponding contact force thresholds. A table may include indications of conditions of anatomical structures. In some embodiments, a selected contact force threshold may be based on a determined condition of an anatomical structure. For example, a selected contact force threshold may increase or decrease based on information indicating an anatomical structure is leaking, has a particular color, has a particular level of retraction, and/or any other condition. In another example, in response to a first determined condition of the anatomical structure, a first contact force threshold may be selected, and in response to a second determined condition of the anatomical structure, a second contact force threshold may be selected, the second contact force threshold may differ from the first contact force threshold. In yet another example, the determined condition of the anatomical structure may be represented as a vector (as described above), and the contact force threshold may be calculated using a function of the vector representation of the determined condition. In some examples, a selected contact force threshold may be a function of a type of the contact force (such as tension, compression, and so forth). For example, in response to a first type of contact force, the selected contact force threshold may have a first value, and in response to a second type of contact force, the selected contact force threshold may have a second value, the second value may differ from the first value.

In some embodiments, a contact force threshold may be associated with a tension level (i.e., a level of force that pulls on an anatomical structure) or a level of retraction. Retraction may involve movement, traction, and/or counter-traction of tissues to expose tissue, organ, and/or other anatomical structure for viewing by a surgeon. In some embodiments, a contact force threshold may be associated with a pressure level (e.g., an amount of contact force that pushes on an anatomical structure) and/or a compression level. A compression level may include a degree or amount of compression of an anatomical structure (e.g., a reduction in size of an anatomical structure due to contact force).

Consistent with the present embodiments, selecting a contact force may be based on data relating to a manner of contact between an anatomical structure and a medical instrument. For example, in some embodiments, selecting a contact force threshold may be based on a location of contact between an anatomical structure and a medical instrument, as some regions of anatomical structures may have greater force sensitivity than others. A location may be determined by analyzing received image data, consistent with disclosed embodiments. Thus, a selected contact force threshold may be higher at one location of contact between an anatomical structure and a medical instrument than at another. Selecting a contact force threshold may also be based on an angle of contact between an anatomical structure and a medical instrument. An angle of contact may be determined by analyzing image data to identify the incidence angle between an anatomical structure and a medical instrument. For example, pose estimation algorithms may be used to analyze the image data and determining a pose of the anatomical structure and/or a pose of the medical instrument, and an angle between the anatomical structure and the medical instrument may be determined based on the determined poses. In another example, a machine learning algorithm may be trained using training examples to determine angles between anatomical structures and medical instruments, and the trained machine learning model may be used to analyze the image data and determine the angle between the anatomical structure and the medical instrument. An example of such training example may include an image depicting an anatomical structure and a medical instrument, together with a label indicating the angle between the anatomical structure and the medical instrument. In some examples, a selected contact force threshold may be a function of a contact angle related to the contact force. For example, in response to a first contact angle, the selected contact force threshold may have a first value, and in response to a second contact angle, the selected contact force threshold may have a second value, the second value may differ from the first value.

In some embodiments, selecting a contact force threshold may include implementing and/or using a model (e.g., a statistical model and/or a machine learning model). For example, selecting a contact force threshold may include providing a condition of an anatomical structure to a regression model as an input and selecting a contact force threshold based on an output of a regression model. In some embodiments, a regression model may be fit to historical data comprising contact forces applied to anatomical structures with corresponding conditions and surgical outcomes.

In some embodiments, selecting a contact force threshold may include using a machine learning model trained using training examples to select a contact force threshold. For example, a machine learning model may be trained using training examples to select contact force thresholds based on input data. Such input data may include image data of a surgical procedure, image data depicting an anatomical structure, a type of a surgical procedure, a phase of a surgical procedure, a type of action, a type of an anatomical structure, a condition of an anatomical structure, a skill level of a surgeon, a condition of a patient, and so forth. An example of such training example may include a sample input data together with a label indicating the desired contact force threshold. In one example, the desired contact force threshold may be selected based on known medical guidelines. In another example, the desired contact force threshold may be selected manually. In yet another example, the desired contact force threshold may be selected based on an analysis of correlations of applied contact force and outcome in historical cases or in a define subset of a group of historical cases, for example to select a contact force threshold that is highly correlated with positive outcome (for example, ensure positive outcome according to historical data, ensure positive outcome in a selected ratio of cases according to historical data, and so forth). Further, in some examples, the trained machine learning model may be used to analyze such input data corresponding to a particular case (such as a particular surgical procedure, a particular phase of a surgical procedure, a particular action in a surgical procedure, a particular surgeon, a particular patient, a particular anatomical structure, etc.) and select the contact force threshold. For example, the trained machine learning model may be used to analyze the image data of the surgical procedure and/or the determined identity of the anatomical structure and/or the determined condition of the anatomical structure and/or characteristics of a current state of the surgical procedure to select the contact force threshold.

In some embodiments, a machine learning model may be trained using training examples to determine contact properties (such as contact location, a contact angle, a contact force) from images and/or videos, and the trained machine learning model may be used to analyze the video footage and determine the properties of an actual contact occurring in the surgical procedure, such as the actual contact location, the actual contact angle, the actual contact force, and so forth. An example of a training example may include image data depicting a particular contact together with a label indicating properties of the particular contact, such as a contact location, a contact angle, a contact force, and so forth. For example, a training example may include measurements of contact force collected using a sensor (e.g., a sensor embedded in a medical instrument). In another example, a training example may include estimates of contact force included in a medical record (e.g., an estimate of contact force stored in a record, an estimate based on sensor data or a surgeon's opinion).

In some embodiments, selecting a contact force threshold may be based on one or more actions performed by a surgeon. For example, a method may include analyzing image data to identify actions performed by a surgeon (e.g., a human or a surgical robot), for example using action recognition algorithms. In one example, the selected contact force threshold may be based on historical data correlating one or more actions performed by a surgeon, contact forces, and outcomes. For example, a contact force threshold that is highly correlated with positive outcome may be selected (for example, that ensures positive outcome according to historical data, that ensures positive outcome in a selected ratio of cases according to historical data, and so forth). In one example, a data structure may specify the contact force thresholds for different actions. In one example, the contact force threshold may be based on a level of skill of a surgeon, consistent with disclosed embodiments.

In some embodiments, a method for estimating contact force on an anatomical structure may include receiving an indication of actual contact force on an anatomical structure. An indication of an actual contact force may be associated with a contact between a surgeon (e.g., a human or robotic surgeon) and an anatomical structure, directly or indirectly. For example, an actual contact force may be associated with a contact between a medical instrument and an anatomical structure (e.g., between an anatomical structure and a reactor, a scalpel, a surgical clamp, a drill, a bone cutter, a saw, scissors, forceps, and/or any other medical instrument). In some embodiments, an actual force may be associated with a tension level, a level of retraction, a pressure level, and/or a compression level. An indication may include an estimate of contact force, including a level of contact, consistent with disclosed embodiments. More generally, an indication of an actual force may include any indication of any contact force, as described herein, that is applied during a surgical event. In one example, the indication of the actual contact force may include at least one of an indication of a contact angle, an indication of a magnitude or level of the contact force, and indication of a type of the contact force, and so forth.

In some embodiments, an indication of actual contact force may be estimated based on an image analysis of image data. An image analysis of image data to estimate an indication of contact force may include any method of image analysis as disclosed herein. In some embodiments, an indication of contact force may be based on image analysis methods that associate a contact force with a change in an anatomical structure (e.g., a deformation of an anatomical structure), a position of a surgeon or surgical instrument, a motion of a surgeon and/or a surgical instrument, and/or any other feature of a surgical event. In some embodiments, an indication of actual contact force may be estimated using a regression model fit to historical data associating a contact force with a feature of surgical event. Also, an indication of actual contact force may be estimated using a machine learning model, for example as described above.

In some embodiments, an indication of actual contact force may be based on sensor data that directly or indirectly measures force. For example, an actual force may be based on a force sensor that measures force at a location of contact between a medical instrument or surgical robot and an anatomical structure (e.g., a force sensor embedded in a medical instrument or robot). In an exemplary embodiment, an indication of actual contact force may be received from a surgical tool or other medical instrument. Similarly, an indication of actual contact force may be received from a surgical robot.

In some embodiments, a method for estimating contact force on an anatomical structure may include comparing an indication of actual contact force with a selected contact force threshold, which may include determining whether an actual contact force exceeds or fails to exceed a selected contact force threshold. Comparing an indication of actual contact force with a selected contact force threshold may include calculating a difference, a ratio, a logarithm, and/or any other function of an actual contact force and a selected contact force threshold.

In some embodiments, a method for estimating contact force on an anatomical structure may include outputting a notification based on a determination that an indication of actual contact force exceeds a selected contact force threshold. Outputting a notification may include transmitting a recommendation to a device, displaying a notification at an interface, playing a sound, providing haptic feedback, and/or any other method of notifying an individual of excessive force applied. A notification may be output to a device in an operating room, to a device associated with a surgeon (e.g., a human surgeon and/or a surgical robot), and/or to any other system. For example, outputting a notification may include transmitting a notification to a computer, a mobile device, an external device, a surgical robot, and/or any other computing device. In another example, outputting a notification may include logging the notification in a file.

In some embodiments, a notification may include information specifying that a contact force has exceeded or failed to exceed a selected contact force threshold. In some embodiments, a notification may include information relating to a selected contact force and/or an estimate of an actual contact force, including an indication of a contact angle, a magnitude of a contact force, a contact location, and/or other information relating to a contact force.

In some examples, notifications of different intensity (i.e., severity or magnitude) may be provided according to an indication of actual force. For example, outputting a notification may be based on a difference between an indication of actual force and a selected force threshold or a comparison of an indication of actual force with a plurality of thresholds. A notification may be based on a level of intensity of an actual force or an intensity of a difference between an actual force and a selected force threshold. In some embodiments, a notification may include information specifying a level of intensity.

Consistent with the present embodiments, a notification may be output in real time during a surgical procedure, such as to provide warning to a surgeon conducting a surgical procedure. In some embodiments, a notification may include an instruction to a surgical robot to vary a force application. As an illustrative example, a notification may include an instruction to alter a magnitude, angle, and/or location of a contact force.

In some embodiments, a method for estimating contact force on an anatomical structure may include determining from received image data that a surgical procedure is in a fight mode, where extraordinary measures may be required. In such circumstances, typical contact force thresholds may be suspended. Determining from received image data that a surgical procedure may be in a fight mode may include using a method of image analysis, as disclosed herein. For example, certain physiological responses and/or surgical activities depicted in the video may indicate that the surgical procedure is in fight mode. A fight mode determination may include using a statistical model (e.g., a regression model) and/or a machine learning model, such as a model trained to recognize fight mode using historical examples of surgical video classified as depicting portions of surgeries that are and are not in a fight mode. In some embodiments, a notification may be suspended during a fight mode. For example, outputting a notification may be delayed indefinitely or at least until a determination is made that a surgical procedure may be not in a fight mode. In some embodiments, outputting a notification may be delayed for a predetermined time period (e.g., a number of minutes or any other time period). In other examples, the type of the outputted notifications may be determined based on whether the patient undergoing the surgical procedure is in a fight mode. In some examples, the contact force thresholds may be selected based on whether the patient undergoing the surgical procedure is in a fight mode.

In some embodiments, a method for estimating contact force on an anatomical structure may include determining from received image data that a surgeon may be operating in a mode ignoring contact force notifications. A contact force notification may include a notification including information relating to a contact force (e.g., an actual contact force and/or a selected contact force threshold). In some embodiments, a determination that a surgeon may be operating in a mode ignoring contact force notifications may include analyzing one or more indications of actual contact force following one or more contact force notifications. For example, embodiments may include determining whether one more actual contact force indications exceed or fails to exceed a selected contact force threshold following output of one or more contact force notifications. Determining from received image data that a surgeon may be operating in a mode ignoring contact force notifications may include using a method of image analysis, and may include using a statistical model (e.g., a regression model) and/or a machine learning model. Such machine learning models may be trained to determine that a surgeon may be operating in a mode ignoring contact force notifications using historical examples of surgical video classified as surgeons that are and are not ignoring contact force notifications.

Embodiments may include suspending (delaying) at least temporarily, further contact force notifications based on a determination that a surgeon may be operating in a mode ignoring contact force notifications. In some embodiments, contact force notifications may resume following a predetermined time period (e.g., a number of minutes or any other time period).

FIG. 30 is a flowchart illustrating an exemplary process 3000 for estimating contact force on an anatomical structure, consistent with the disclosed embodiments. Process 3000 may be performed by at least one processor, such as one or more microprocessors. In some embodiments, process 3000 is not necessarily limited to the steps illustrated, and any of the various embodiments described herein may also be included in process 3000. As one of skill in the art will appreciate, steps of process 3000 may be performed by a system including, for example, components of system 1401. In some embodiments, a non-transitory computer readable medium including instructions that, when executed by at least one processor, cause the at least one processor to execute operations for estimating contact force on an anatomical structure according to process 3000. In some embodiments, process 3000 may be performed in real time during a surgical procedure.

At step 3002, the process may include receiving, from at least one image sensor in an operating room, image data of a surgical procedure, as previously described through various examples. An image sensor may be placed anywhere in any operating room, and image data may include any video data, data representing an image, and/or metadata.

At step 3004, the process may include analyzing the received image data to determine an identity of an anatomical structure and to determine a condition of the anatomical structure as reflected in the image data, consistent with disclosed embodiments, as describe previously through examples. Analyzing received image data may include any method of image analysis, as previously described, and a condition of an anatomical structure may refer to any information that indicates a state or characteristic of an anatomical structure. As discussed previously, analyzing the received image data may include using a machine learning model trained using training examples to determine a condition of an anatomical structure in image data.

At step 3006, the process may include selecting a contact force threshold associated with the anatomical structure, the selected contact force threshold being based on the determined condition of the anatomical structure. As previously discussed in greater detail, selecting a contact force threshold may be based on data indicating a recommended contact force (e.g., a maximum safe force or a minimum effective force). Selecting a contact force threshold may be based on a location and/or angle of contact force and may include implementing a model (e.g., a statistical model such as a regression model and/or a machine learning model). Further, a table of anatomical structures including corresponding contact force thresholds may be used as part of selecting a contact force threshold. A contact force threshold may be associated with a tension level or a compression level. In some examples, selecting a contact force threshold may include using a machine learning model trained using training examples to select a contact force threshold. Further, selecting a contact force threshold may be based on one or more actions performed by a surgeon. Other non-limiting examples of the selection of a contact force threshold are described above.

At step 3008, the process may include receiving an indication of actual contact force on the anatomical structure (for example, as discussed previously), such as with a force associated with a contact between a medical instrument and an anatomical structure. An actual force may be associated with a tension level, a level of retraction, a pressure level, and/or a compression level. An indication of actual contact force may be estimated based on an image analysis of image data. An indication of actual contact force may be based on sensor data that directly or indirectly measures force. In some embodiments, an indication of actual contact force may be estimated based on an image analysis of image data and/or may be an indication of an actual contact force received from a surgical tool, surgical robot, or other medical instrument.

At step 3010, the process may include comparing the indication of actual contact force with the selected contact force threshold, as discussed previously. Comparing an indication of actual contact force with a selected contact force threshold may include calculating a difference, a ratio, a logarithm, and/or any other function of an actual contact force and a selected contact force threshold.

At step 3012, the process may include outputting a notification based on a determination that the indication of actual contact force exceeds the selected contact force threshold, as previously described. Outputting a notification may be performed in real time during an ongoing surgical procedure. For example, outputting a notification may include providing a real time warning to a surgeon conducting a surgical procedure or an instruction to a surgical robot.

Disclosed systems and methods may involve analyzing current and/or historical surgical footage to identify features of surgery, patient conditions, and other features to update a predicted surgical outcome. Over the course of a surgical procedure, conditions may change, or events may transpire that change a predicted outcome of the surgical procedure. Conventional approaches to performing surgery may lack decision support systems to updated predicted outcomes during real time based on surgical events as they occur. As a result, surgeons may be unaware of likely surgical outcomes and thereby may be unable to perform actions that may improve outcomes or that may avoid worsening outcomes. Therefore, aspects of the current disclosure relate to unconventional approaches that efficiently, effectively, and in real time update predicted surgical outcomes.

In accordance with the present disclosure, a systems, methods and computer readable media may be provided for updating a predicted outcome during a surgical procedure is disclosed. For example, image data may be analyzed to detect changes in a predicted outcome, and a remedial action may be communicated to a surgeon. A predicted outcome may include an outcome that may occur with an associated confidence or probability (e.g., a likelihood). For example, a predicted outcome may include a complication, a health status, a recovery period, death, disability, internal bleeding, hospital readmission after the surgery, and/or any other surgical eventuality. In some embodiments, a predicted outcome includes a score, such as a lower urinary tract symptom (LUTS) outcome score. More generally, a predicted outcome may include any health indicator associated with a surgical procedure.

In some embodiments, a predicted outcome may include a likelihood of hospital readmission, such as a likelihood of a hospital readmission of the patient undergoing the surgical procedure within a specified time interval after the patient is been discharged from the hospital following the surgical procedure. Hospital readmission may be based on a health condition related to a surgical procedure, or may be based on other factors. For example, a hospital readmission may arise due to a post-operative complication (e.g., swelling, bleeding, an allergic reaction, a ruptured suture, and/or any other complication). In some embodiments, a likelihood of hospital readmission may be determined based on an analysis of image data (e.g., using image analysis methods as described herein). Further, in some embodiments, a likelihood of hospital readmission may be determined based on information of a patient undergoing a surgical procedure. For example, a likelihood of hospital readmission may be based on a patient characteristic (e.g., an age, a prior health status, a family history, a vital sign, and/or other patient-related data). Hospital readmission may be defined for different time intervals (e.g., readmission within 24 hours, within a week, within a month, or within another time period).

In some embodiments, a predicted outcome may be based on at least one model, such as statistical model and/or a machine learning model. For example, a predicted outcome may be based on statistical correlations between information associated with a surgical procedure (e.g., patient characteristic and/or a surgical event) and historical outcomes. A predicted outcome may be generated by a machine learning model trained to associate outcomes with information associated with a surgical procedure (e.g., patient characteristic and/or a surgical event) using training examples (for example, using training examples based on historical data).

Disclosed embodiments may include receiving, from at least one image sensor arranged to capture images of a surgical procedure, image data associated with a first event during a surgical procedure, consistent with disclosed embodiments. Image data associated with a first event may include still images, image frames, clips and/or video-related data associated with a surgical procedure. A first event may include any surgical event, consistent with disclosed embodiments. In an illustrative embodiment, a first event may include an action performed by a surgeon (e.g., a human or robotic surgeon). In another example, a first event may include a physiological response to an action. In yet another example, a first event may include a change in a condition of an anatomical structure. Some other non-limiting examples of such surgical events are described above. Image data associated with a first event may be received in memory and/or a data structure, as described by way of example herein.

An image sensor may include any image sensor as also described herein (e.g., a camera or other detector). In some embodiments, an image sensor may be positioned in an operating room. For example, an image sensor may be positioned above a patient undergoing a surgical procedure or within a patient undergoing a surgical procedure (e.g., an intracavitary camera).

Disclosed embodiments may include determining, based on received image data associated with a first event, a predicted outcome associated with a surgical procedure, consistent with disclosed embodiments. A predicted outcome may include any health outcome associated with a surgical procedure, as described above. For example it may include an eventuality that is correlated in some way to the first event. The prediction may be binary (e.g., likely to result in a rupture vs. not likely to result in a rupture), or it may provide a relative confidence or probability (e.g., percent chance of rupture; chance of rupture on a scale of 1-5; and so forth). A determined predicted outcome may include a score reflecting a property of an outcome such as a post-operative health status (e.g., a LUTS outcome score). A predicted outcome may be associated with a confidence or probability.

A first event, as mentioned in the preceding paragraph, may include any intraoperative occurrence. For example, a first event may include an action performed by a surgeon, a change in a patient characteristic, a change in a condition of an anatomical structure, and/or any other circumstance. In some embodiments, at least one time point associated with a first event may be received, such that in addition to an indicator of the event itself, an indicator of the time the event occurred is also received. The time point may coincide with a counter on a video timeline, or might include any other marker or indicator of reflecting an absolute or relative time when an event occurred.

Some embodiments may involve identifying an event, such as a first event. Such identification may be based, for example, on detection of a medical instrument, an anatomical structure, and/or an interaction between a medical instrument and an anatomical structure. The detection can occur using video analysis techniques described throughout this disclosure. For example, the event may be identified by analyzing the image data using a machine learning model as described above.

In some embodiments, determining a predicted outcome may include identifying an interaction between a surgical tool and an anatomical structure and determining a predicted outcome based on the identified interaction. For example, the interaction between the surgical tool and the anatomical structure may be identified by analyzing the image data, for example as described above. Further, in one example, in response to a first identified interaction, a first outcome may be predicted, and in response to a second identified interaction, a second outcome may be predicted, the second outcome may differ from the first outcome. In another example, a machine learning model may be trained using training examples to predict outcome of surgical procedures based on interactions between surgical tools and anatomical structures, and the trained machine learning model may be used to predict the outcome based on the identified interaction. An example of such training example may include an indication of an interaction between a surgical tool and an anatomical structured, together with a label indicating the desired predicted outcome. The desired predicted outcome may be based on an analysis of historical data, based on user input (such as expert opinion), and so forth.

In some embodiments, determining a predicted outcome may be based on a skill level of a surgeon depicted in image data, such as data previously stored in a data structure. The surgeon's level of skill may be determined based on an analysis of image data, for example as described above. For example, a face recognition algorithm may be applied to image data to identify a known surgeon, and a corresponding level of skill may be retrieved from a data structure, such as a database. In some embodiments, a level of skill of a surgeon may be determined based on a sequence of events identified in image data (e.g., based on a length of time to perform one or more actions, based on a patient response detected in image data during surgery, and/or based on other information indicating a level of skill of a surgeon). In one example, in response to a first determined skill level, a first outcome may be predicted, and in response to a second determined skill level, a second outcome may be predicted, the second outcome may differ from the first outcome. In another example, a machine learning model may be trained using training examples to predict outcome of surgical procedures based on skill levels of surgeons, and the trained machine learning model may be used to predict the outcome based on the determined skill level. An example of such training example may include an indication of a skill level of a surgeon, together with a label indicating the desired predicted outcome. The desired predicted outcome may be based on an analysis of historical data, based on user input (such as expert opinion), and so forth.

Determining a predicted outcome may also be based, in some instances, on a condition of an anatomical structure depicted in image data. For example, a predicted outcome may be determined based on historical outcomes correlated with organ condition. Complications with organs in poor condition might, for example, be greater than with organs in good condition. A condition of an anatomical structure may be determined, in some embodiments, based on an analysis of image data as described throughout this disclosure. The anatomical structure's condition may be transient or chronic and/or include a medical condition, such as a condition being treated by a surgical procedure or a separate medical condition. A condition of an anatomical structure may be indicated by color, texture, size, level of hydration, and/or any other observable characteristic. In one example, in response to a first determined condition of the anatomical structure, a first outcome may be predicted, and in response to a second determined condition of the anatomical structure, a second outcome may be predicted, the second outcome may differ from the first outcome. In another example, a machine learning model may be trained using training examples to predict outcome of surgical procedures based on conditions of anatomical structures, and the trained machine learning model may be used to predict the outcome based on the determined condition of the anatomical structure. An example of such training example may include an indication of a condition of an anatomical structure, together with a label indicating the desired predicted outcome. The desired predicted outcome may be based on an analysis of historical data, based on user input (such as expert opinion), and so forth.

Additionally or alternatively, a predicted outcome may be determined based on an estimated contact force on an anatomical structure. For example, an excessive force applied to the anatomical structure may render a favorable outcome less likely. For example, the contact force may be estimated by analyzing the image data, for example as described above. In another example, the contact force may be received from a sensor, for example as described above. In one example, in response to a first estimated contact force, a first outcome may be predicted, and in response to a second estimated contact force, a second outcome may be predicted, the second outcome may differ from the first outcome. In another example, a machine learning model may be trained using training examples to predict outcome of surgical procedures based on contact forces on anatomical structures, and the trained machine learning model may be used to predict the outcome based on the estimated contact force. An example of such training example may include an indication of a contact force, together with a label indicating the desired predicted outcome. The desired predicted outcome may be based on an analysis of historical data, based on user input (such as expert opinion), and so forth.

Determining a predicted outcome may be performed in various ways. It may include using a machine learning model trained to determine predicted outcomes based on historical surgical videos and information indicating surgical outcome corresponding to historical surgical videos. For example, received image data of a first event may be analyzed using an artificial neural network configured to predict outcome of surgical procedures from images and/or videos. As another example, determining a predicted outcome may include identifying a first event based on received image data and applying a model (e.g., a statistical model or a machine learning model) to information relating to a first event to predict an outcome. Such a model may receive inputs, including information relating to a first event (e.g., an identifier of a first event, a duration of a first event, and/or other property of a first event such as a surgical contact force) and/or information relating to a surgical procedure (e.g., a patient characteristic, a level of skill of a surgeon, or other information). Based on inputs such as the examples provide above, the system may return a predicted outcome as an output.

Disclosed embodiments may include receiving, from at least one image sensor arranged to capture images of a surgical procedure, image data associated with a second event during a surgical procedure, consistent with disclosed embodiments. A second event may occur after the first event and may be different from the first event. At least one time point associated with a second event may be received. The image sensor for capturing data associated with the second event may be the same as or may be different from the image sensor used to capture data associated with the first event.

Disclosed embodiments may include determining, based on received image data associated with a second event, a change in a predicted outcome, causing a predicted outcome to drop below a threshold. For example, using any of the methods described above to determine a predicted outcome, a new predicted outcome may be determined and compared to a previously determined predicted outcome (such as the predicted outcome determined based on the received image data associated with the first event) to thereby determine a change in a predicted outcome. In another example, the new predicted outcome may be determined based on a previously determined predicted outcome (such as the predicted outcome determined based on the received image data associated with the first event) and an analysis of the received image data associated with the second event. For example, a machine learning model may be trained using training examples to determine new predicted outcomes based on previous predicted outcomes and images and/or videos, and the trained machine learning model may be used to analyze the previously determined predicted outcome and the received image data associated with the second event to determine the new predicted outcome. An example of such training example may include a previously determined predicted outcome and an image data depicting an event, together with a label indicating the new predicted outcome. In another example, a Markov model may be used to update the previously determined predicted outcome and obtain the new predicted outcome, where the transitions in the Markov model may be based on values determined by analyzing the received image data associated with the second event. As discussed, a predicted outcome may include a probability, confidence, and/or score reflecting a property of an outcome such as a post-operative health status (e.g., a LUTS outcome score). Determining a change in a predicted outcome may involve a change in such a confidence, probability or score. In some examples, a change in a predicted outcome may be determined without calculating a new predicted outcome. For example, a machine learning model may be trained using training examples to determine a change in predicted outcomes based on previous predicted outcomes and images and/or videos, and the trained machine learning model may be used to analyze the previously determined predicted outcome and the received image data associated with the second event to determine an occurrence of a change in a predicted outcome. An example of such training example may include a previously determined predicted outcome and an image data depicting an event, together with a label indicating whether the predicted outcome have changed in response to the second event.

In some embodiments, a change in a confidence, probability, and/or score may cause a predicted outcome to drop below a threshold (e.g., a threshold confidence, a threshold probability, a threshold score). Such threshold may be automatically generated using artificial intelligence methods, may be determined based on user input, and so forth. A threshold may correspond to a negative outcome (such as a hospital readmission, a complication, death, or any undesirable eventuality), or to a positive outcome.

In some illustrative embodiments, determining a change in a predicted outcome may be based on elapsed time between two markers. For example, a duration between an incision and suturing that exceeds a threshold may serve as an indicator of an increased likelihood of infection. For example, in response to a first elapsed time, a change in the predicted outcome may be determined, and in response to a second elapsed time, no change in the predicted outcome may be determined.

In some examples, two or more variables may be correlated to either positive or negative outcomes, for example using statistical methods, using machine learning methods, and so forth. The variables may be endless. Such variables may relate to the condition of the patient, the surgeon, the complexity of the procedure, complications, the tools used, the time elapsed between two or more events, or any other variables or combination of variables that may have some direct or indirect impact on predicted outcome. One such variable may be fluid leakage (e.g., a magnitude, duration, or determined source). For example, determining a change in a predicted outcome may be based on a magnitude of bleeding. A feature of a fluid leakage event (e.g., a magnitude of bleeding, a source of bleeding) may be determined based on an analysis of image data.

Disclosed embodiments may include determining a skill level of a surgeon depicted in image data, and determining a change in a predicted outcome may be based on the skill level. For example, a determining a change in a predicted outcome may be based on an updated estimate of a level of skill of a surgeon (e.g., an image analysis may determine that a surgeon has made one or more mistakes, causing an estimate of level of skill to decrease). As another example, a previously determined predicted outcome may be based on a level of skill of a first surgeon and a change in a predicted outcome may be based on a level of skill of a second surgeon who steps in to assist. A level of skill may be determined in various ways, as described herein (e.g., via an image analysis as described above and/or by retrieving a level of skill from a data structure).

By way of additional examples, determining a change in a predicted outcome may be based on one or more changes in color, texture, size, condition, or other appearance or characteristic of at least part of an anatomical structure. Examples of conditions of anatomical structures that may be used for outcome prediction may vitality, a level of oxygenation, a level of hydration, a level of distress, and/or any other indicator of the state of the anatomical structure.

A condition of an anatomical structure may be determined in a variety of ways, such as through a machine learning model trained with examples of known conditions. In some embodiments, an object recognition model and/or an image classification model may be trained using historical examples and implemented to determine a condition of an anatomical structure. Training may be supervised and/or unsupervised. Some other non-limiting examples of methods for determining conditions of anatomical structures are described above.

Embodiments may include a variety of ways of determining a predicted outcome based on a condition of an anatomical structure and/or any other input data. For example, a regression model may be fit to historical data that include conditions of anatomical structures and outcomes. More generally, using historical data, a regression model may be fit to predict an outcome based on one or more of a variety of input data, including a condition of an anatomical structure, a patient characteristic, a skill level of a surgeon, an estimated contact force, a source of fluid leakage, an extent of fluid leakage characteristic, and/or any other input data relating to a surgical procedure. An outcome may be predicted based on other known statistical analysis including, for example, based on correlations between input data relating to a surgical procedure and outcome data.

Disclosed embodiments may include accessing a data structure of image-related data based on prior surgical procedures, consistent with disclosed embodiments. Accessing may include reading and/or writing data from a data structure. In some embodiments, this may be accomplished using a data structure such as is presented in FIG. 17 or a data structure such as is presented in FIG. 6. Image related data may include any data derived directly or indirectly from images. This data may include, for example, patient characteristics, surgeon characteristics (e.g., a skill level), and/or surgical procedure characteristics (e.g., an identifier of a surgical procedure, an expected duration of a surgical procedure). Image related data may include correlations or other data describing statistical relationships between historical intraoperative surgical events and historical outcomes. In some embodiments, a data structure may include data relating to recommended actions, alternative courses of action, and/or other actions that may change a probability, likelihood, or confidence of a surgical outcome. For example, a data structure may include information correlating a break from a surgical procedure with an improved outcome. Depending on implementation, a data structure may include information correlating a skill level of a surgeon, a request for assistance from another surgeon, and outcomes. Similarly, a data structure may store relationships between surgical events, actions (e.g., remedial actions), and outcomes. While a host of correlation models may be used for prediction as discussed throughout this disclosure, exemplary predictive models may include a statistical model fit to historical image-related data (e.g., information relating to remedial actions) and outcomes; and a machine learning models trained to predict outcomes based on image-related data using training data based on historical examples.

Disclosed embodiments may include identifying, based on accessed image-related data, a recommended remedial action. For example, a recommended remedial action may include a recommendation for a surgeon to use a different tool or procedure; administer a drug, request assistance from another surgeon, make a revision to a surgical procedure, take a break from a surgical procedure (for example, to increase alertness), and/or to undertake any other action that might impact outcome. When a recommended remedial action includes a suggestion to request assistance, the suggestion may recommend that a surgeon be summoned with a higher or different level of experience than the operating surgeon. A remedial action that suggests a revision to a surgical procedure may include a suggestion to perform additional actions not previously part of a surgical procedure, or to avoid certain expected actions.

Identifying a remedial action may be based on an indication, derived at least in part from image-related data, that a remedial action may be likely to raise a predicted outcome above a threshold. For example, a data structure may contain correlations between historical remedial actions and predicted outcomes, and a remedial action may be identified based on the correlations. In some embodiments, identifying a remedial action may include using a machine learning model trained to identify remedial actions using historical examples of remedial actions and surgical outcomes. Training may be supervised or unsupervised. For example, the machine learning model may be trained using training example to identify the remedial actions, and the training examples may be based on an analysis of the historical examples of remedial actions and surgical outcomes.

Disclosed embodiments may include outputting a recommended remedial action. Outputting a recommended remedial action may include transmitting a recommendation to a device, causing a notification to be displayed on an interface, playing a sound, providing haptic feedback, and/or any other method of conveying a desired message, whether to an operating room, a device associated with a surgeon (e.g., a human surgeon and/or a surgical robot), and/or to any other system. For example, outputting a recommended remedial action may include transmitting a notification to a computer, a mobile device, an external device, a surgical robot, and/or any other computing device.

Further, in some embodiments a method may include updating a scheduling record associated with a surgical room related to a surgical procedure in response to predicted outcome dropping below a threshold. For example, a change in an expected duration of a surgery may trigger an automated change in a scheduling record, such that a surgery on a next patient is pushed back in time to account for a delay in a current operation. More general, a change in any predicted outcome may be associated with an increase or decrease in an expected duration. In some embodiments, a data structure (e.g., data structure of FIG. 17) may correlate predicted outcomes with respective expected durations of surgery. A model (e.g., a regression model or a trained machine learning model) may be used to generate an expected duration based on predicted outcomes, consistent with the present embodiments. Thus, if a predicted outcome change impacts a duration of surgery, a surgical schedule may be automatically updated to inform succeeding medical staff of change in operating room schedule. The update may be automatically displayed on an electronic operating room scheduling board. Alternatively or additionally, the update may be broadcast via email or other messaging app to accounts associated with the impacted medical professionals. Scheduling may be correlated to predicted outcome as discussed, but might also correlate to other factors. For example, even if the predicted outcome does not change, machine vision analysis performed on the video footage of the surgical procedure may reveal that the surgery is behind schedule (or ahead of schedule), and an update to the schedule may be automatically pushed, as previously discussed.

FIG. 31 is a flowchart illustrating an example process 3100 for updating a predicted outcome during surgery, consistent with the disclosed embodiments. Process 3100 may be performed by at least one processor, such as one or more microprocessors. In some embodiments, process 3100 is not necessarily limited to the steps illustrated, and any of the various embodiments described herein may also be included in process 3100. As one of skill in the art will appreciate, steps of process 3100 may be performed by a system including, for example, components of system 1401. In some embodiments, a non-transitory computer readable medium including instructions that, when executed by at least one processor, cause the at least one processor to execute operations for updating a predicted outcome according to process 3100. In some embodiments, process 3100 may be performed in real time during a surgical procedure.

At step 3102, the process may include receiving, from at least one image sensor arranged to capture images of a surgical procedure, image data associated with a first event during the surgical procedure, consistent with disclosed embodiments. An image sensor may be positioned anywhere in an operating room (e.g., above a patient, within a patient), as previously discussed.

At step 3104, the process may include determining, based on the received image data associated with the first event, a predicted outcome associated with the surgical procedure, as previously discussed and illustrated with examples. As discussed, for example, determining a predicted outcome may include identifying an interaction between a surgical tool and an anatomical structure and determining a predicted outcome based on the identified interaction. Determining a predicted outcome may be based on a skill level of a surgeon depicted in the image data. In some embodiments, determining a predicted outcome may be based on a condition of an anatomical structure depicted in the image data, and may include using a machine learning model trained to determine predicted outcomes based on historical surgical videos and information indicating surgical outcome corresponding to the historical surgical videos. One example of a predicted outcome may include a likelihood of hospital readmission. Other examples were previously provided.

At step 3106, the process may include receiving, from at least one image sensor arranged to capture images of a surgical procedure, image data associated with a second event during the surgical procedure, as previously discussed and illuminated with examples.

At step 3108, the process may include determining, based on the received image data associated with the second event, a change in the predicted outcome, causing the predicted outcome to drop below a threshold, as also discussed previously. For example, determining a change in a predicted outcome may be based on a time elapsed between a particular point in the surgical procedure and the second event. In other examples, determining a change in a predicted outcome may be based on a magnitude of bleeding, a change of a color of at least part of an anatomical structure, a change of appearance of at least part of the anatomical structure. Determining a condition of an anatomical structure may include using a machine learning model trained using training examples to determine the condition of the anatomical structure.

At step 3110, the process may include accessing a data structure of image-related data based on prior surgical procedures, as discussed previously and as was illustrated with examples. As mentioned, a data structure such as the one illustrated in FIG. 17 may be accessed. This is but one example, and many other types and forms of data structures may be employed consistent with the disclosed embodiments.

At step 3112, the process may include identifying, based on the accessed image-related data, a recommended remedial action, as described previously. For example, a recommended remedial action may include a recommendation to alter a surgical process, use a different surgical tool, call-in another surgeon, revise the surgical procedure, take a break and/or any other action that might impact the outcome of the surgical procedure. Identifying a remedial action may include using a machine learning model trained to identify remedial actions using historical examples of remedial actions and surgical outcomes.

At step 3114, the process may include outputting the recommended remedial action, as previously described.

Disclosed systems and methods may involve analyzing current and/or historical surgical footage to identify features of surgery, patient conditions, and other features to detect fluid leakage. During a surgery, fluids may leak. For example, blood, bile, or other fluids may leak from an anatomical structure. Often, a source or an extent of fluid leakage may be unknown. If left unchecked, fluid leakage can cause negative health outcomes. Therefore, aspects of the present disclosure relate to unconventional approaches that automatically and effectively determine a source and/or extent of fluid leakage during surgery.

In accordance with the present disclosure, systems, methods and computer readable media may be provided for analysis of fluid leakage during surgery. Analysis may be performed in real time during an ongoing surgical procedure. Embodiments may include providing information related to the fluid leakage to a surgeon in real time. For example, analysis of fluid leakage may enable a surgeon to identify a magnitude and/or source of a fluid leakage, thereby allowing a surgeon to perform a remedial action that mitigates fluid leakage. Fluid leakage may include leakage of a fluid from inside an organ or tissue to a space external to a tissue or organ (e.g., from inside to outside a blood vessel, from inside to outside a gall bladder, etc.). Leaked fluids may include blood, bile, chyme, urine, and/or any other type of body fluid.

Analysis of fluid leakage during surgery may include receiving in real time, intracavitary video of a surgical procedure, consistent with disclosed embodiments. An intracavitary video may be captured by an image sensor located within a patient, consistent with disclosed embodiments. For example, an image sensor located external to a patient may collect intracavitary video (e.g., when a cavity is opened during a surgery). Receiving an intracavitary video in real time may include receiving a video via a network or directly from an image sensor.

Consistent with the present embodiments, an intracavitary video may depict various aspects of a surgical procedure. For example, an intracavitary video may depict a surgical robot and/or a human surgeon performing some or all of a surgical procedure. An intracavitary video may depict a medical instrument, an anatomical structure, a fluid leakage situation, a surgical event, and/or any other aspect of a surgical procedure, consistent with disclosed embodiments.

Analysis of fluid leakage during surgery may involve analyzing frames of an intracavitary video to determine an abnormal fluid leakage situation in the intracavitary video, consistent with disclosed embodiments. Analyzing frames may include using any method of image analysis to determine an abnormal fluid leakage. For example, analyzing images may include analyzing difference images (e.g., images generated by subtracting pixel data of a preceding image from pixel data of a subsequent image), using methods of homography, applying image registration techniques, and/or other image processing methods. An analysis may employ object recognition models, machine learning models, regression models, and/or any other models. Such models may be trained to determine an abnormal fluid leakage situation using training data comprising historical examples. For example, a machine learning model may be trained using training examples to detect abnormal fluid leakage situations and/or to determine properties of abnormal fluid leakage situations from images and/or videos, and the trained machine learning model may be used to analyze the intracavitary video to determine the abnormal fluid leakage situation and/or properties of the abnormal fluid leakage situation. Some non-limiting examples of such properties may include a type of fluid, a magnitude of fluid leakage, a location source of fluid leakage, an anatomical structure related to the fluid leakage, and so forth. An example of such training example may include an intracavitary image and/or an intracavitary video, together with a label indicating whether an abnormal fluid leakage situation is depicted in the intracavitary image and/or in the intracavitary video, and/or together with a label indicating properties of an abnormal fluid leakage situation depicted in the intracavitary image and/or in the intracavitary video.

Determining an abnormal fluid leakage situation (i.e., an abnormal fluid leakage event) may include determining various aspects of a fluid leakage, include a presence of a fluid in or on an anatomical structure, a magnitude of fluid leakage that is over a threshold (e.g., over a predetermined quantile, over a number of standard deviations), a type of fluid (e.g., blood, bile, urine, chyme, and/or other type), a location source of fluid leakage, and/or any other feature of a fluid leakage situation. Some fluid leakages may be normal (e.g., below a threshold magnitude, in a location associated with normal fluid leakage, of a normal fluid type for a particular surgical event, etc.), while others are abnormal (e.g., above a threshold magnitude, in an undesired location, not connected to a surgical event that is associated a normal fluid leakage, and/or of an abnormal fluid type).

Disclosed techniques for determining a leakage source may include identifying a ruptured anatomical organ, vessel, and/or other anatomical structure. A ruptured anatomical structure may be identified based on an analysis of fluid leakage properties (e.g., magnitude, flow rate, flow direction, color, or other fluid leakage properties). A ruptured anatomical structure may include any organ, a vessel (e.g., an artery), a passageway (e.g., a trachea), a tissue (e.g., a lining), and/or any other anatomical structure. The term rupture, as used herein, may refer to any break, tear, puncture, or other damage to an anatomical structure.

In some embodiments, an identified ruptured anatomical structure may be visible in image frames of an intracavitary video captured by an image sensor in an operating room (e.g., a room as depicted in FIG. 1). Alternatively or additionally, a ruptured anatomical structure may not be visible in frames of an intracavitary video (e.g., it may be obscured by other anatomical structures) and it may be identified based on information reflected in frames (e.g., information relating to a fluid leakage situation). Identifying a ruptured structure may involve comparing prior frames of an intracavitary video to subsequent frames, by using a regression model, by using a machine learning model, by performing methods of object recognition, and/or by any other method of image analysis. For example, a machine learning model may be trained using training examples to identify ruptured anatomical organs, vessels, and/or other anatomical structures from intracavitary images and/or intracavitary videos, and the trained machine learning model may be used to analyze the intracavitary video to identify the ruptured anatomical organ, vessel, and/or other anatomical structure. An example of such training example may include an intracavitary image and/or an intracavitary video, together with a label indicating whether a ruptured anatomical organ, vessel, and/or other anatomical structure should be identified for the intracavitary image and/or the intracavitary video.

Embodiments may include analyzing frames of an intracavitary video to identify a blood splash and at least one property of a blood splash. A blood splash may refer to a presence of blood and/or a leakage of blood. Identifying a blood splash may be based on color data of an intracavitary video. In some embodiments, a property of a blood splash may be associated with a source of a blood splash, an intensity (rate) of a blood splash, a color of a blood splash, a viscosity of a blood splash, and/or a volume (magnitude) of a blood splash. More generally, a property of a blood splash may include any characteristic of a blood splash. For example, a machine learning model may be trained using training examples to identify blood splashes and/or to determine properties of blood splashes from images and/or videos, and the trained machine learning model may be used to analyze the intracavitary video to identify the blood splash and/or properties of the blood splash. Some non-limiting examples of such properties of a blood splash may include a source of the blood splash, an intensity of the blood splash, a rate of the blood splash, a color of the blood splash, a viscosity of the blood splash, a volume of the blood splash, a magnitude of the blood splash, and so forth. An example of such training example may include an intracavitary image and/or an intracavitary video, together with a label indicating whether a blood splash is depicted in the intracavitary image and/or in the intracavitary video, and/or together with a label indicating properties of a blood splash depicted in the intracavitary image and/or in the intracavitary video.

Embodiments may include analyzing frames of an intracavitary video to identify a spray of blood and/or to identify at least one property of a spray of blood. In some examples, identifying a spray of blood may be based on color data of an intracavitary video, on motion within the intracavitary video, and so forth. In some embodiments, a property of a spray of blood may be associated with a source of a spray of blood, an intensity (rate) of a spray of blood, a color of the sprayed blood, a motion (such as speed, direction, etc.) of the sprayed blood, and/or a volume (magnitude) of the sprayed blood. More generally, a property of a spray of blood may include any characteristic of the sprayed blood and/or of the spray. For example, a machine learning model may be trained using training examples to identify sprays of blood and/or to determine properties of sprays of blood from images and/or videos, and the trained machine learning model may be used to analyze the intracavitary video to identify the spray of blood and/or properties of the spray of blood. An example of such training example may include an intracavitary image and/or an intracavitary video, together with a label indicating whether a spray of blood is depicted in the intracavitary image and/or in the intracavitary video, and/or together with a label indicating properties of a spray of blood depicted in the intracavitary image and/or in the intracavitary video.

Further, analyzing frames of an intracavitary video may include determining a property of an abnormal fluid leakage situation. For example, a property may be associated with a volume of a fluid leakage, a color of a fluid leakage, a type of fluid associated with a fluid leakage, a fluid leakage rate, a viscosity of a fluid, a reflectivity of a fluid, and/or any other observable feature of a fluid. Further, analyzing frames may include determining a flow rate associated with a fluid leakage situation, determining a volume of fluid loss associated with a fluid leakage situation, and/or determining any other property of a fluid leakage situation. A property of a fluid or fluid leakage situation may be determined based on hue, saturation, pixel values, and/or other image data. More generally, determining a property of a fluid or a fluid leakage situation may include any method of image analysis, as disclosed herein. For example, determining a property of a fluid or a fluid leakage situation may include usage of a trained machine learning model, as described above.

Consistent with the present embodiments, fluid leakage analysis may include storing an intracavitary video, and, upon determining an abnormal leakage situation in current video, analyzing prior historical frames of stored intracavitary video to determine a leakage source, for example via a comparison, consistent with disclosed embodiments. An intracavitary video may be stored in memory, in a data structure (e.g., data structure of FIG. 17A), and so forth. For example, an abnormal leakage situation may be determined when an amount of leaked fluids is above a selected quantity (for example, above a selected threshold used to distinguish abnormal leakage situations from normal leakage situations), and at that point a leakage source may not be visible in the current video (for example, the leakage source may be covered by the leaked fluids, may be outside the current field of view of the current video, and so forth). However, the leakage source may be visible in the prior historical frames of stored intracavitary video, and the prior historical frames of stored intracavitary video may be analyzed to identify the leakage source, for example as described above. In another example, an abnormal leakage situation may be determined by analyzing the current video using a first algorithm, and at that point a leakage source may not be visible in the current video. In response to such determination, a second algorithm (which may be more computationally intense or otherwise different from the first algorithm) may be used to analyze the prior historical frames of stored intracavitary video to identify the leakage source, which may be visible in the prior historical frames of stored intracavitary video. In yet another example, a trigger (such as user input, an event detect in the current video, an input from a sensor connected to the patient undergoing the surgical procedure, etc.) may cause an analysis of the current video to determine the abnormal leakage situation. Further, in some examples, in response to such determination, the prior historical frames of stored intracavitary video may be analyzed to identify the leakage source, for example as described above.

Analyzing prior frames to determine a leakage source may include comparing frames at different time points (e.g., at two or more time points). For example, embodiments may include generating difference images (e.g., by subtracting pixel data of frames at two different time points) and analyzing the generated difference images. In another example, comparing frames may involve determining a property of a fluid leakage situation at different time points and determining a change in the property.

Embodiments may include instituting a remedial action when an abnormal fluid leakage situation is determined. A remedial action may include any notification, suggested response, or counteractive measure associated with an abnormal fluid leakage situation. The remedial action may be the same regardless of varying characteristics of a fluid leakage or may vary based on varying characteristics of the fluid leakage. In the latter situation, instituting a remedial action may include selecting a remedial action from various options. Thus, in the latter situation, a selection of a remedial action may depend on a determined property or characteristic of a fluid leakage situation. For example, if a determined extent of bleeding is below a certain threshold and the source of the bleeding is identified, an associated remedial action may be a recommendation or instruction to apply pressure to the source of the bleeding. If a more significant rupture is detected, the remedial action may involve a recommendation or instruction to suture the source of the bleeding. Depending on the type of fluid associated with the leakage, the extent of the leakage, and characteristics of the leakage situation, many different potential remedial actions may be possible. To assist with selecting an appropriate remedial action, a data structure may store relationships between fluid leakage situations, remedial actions, and outcomes. Further, a statistical model may be fit based on historical fluid leakage situations, remedial actions, and outcomes, and a remedial action may be selected based on model output. Alternatively or additionally, a selection may be based on output of a machine learning model trained to select remedial actions based on historical fluid leakage situations, remedial actions, and outcomes. In other examples, a data structure may store relationships between fluid leakage situations and recommended remedial actions, and the remedial action may be selected from the data structure based on properties and/or characteristics of the fluid leakage situation. Such data structure may be based on user inputs. For example, in response to a fluid leakage situation with an identified leakage source, a first remedial action may be selected (such as sealing the leakage source using a surgical robot), while in response to a fluid leakage situation with no identified leakage source, a second remedial action may be selected (such as providing notification to a user).

Consistent with the present embodiments, instituting a remedial action may include providing a notification of a leakage source. A notification may include a message identifying the source of the leakage, such as a ruptured vessel, a ruptured organ, and/or any other ruptured anatomical structure. For example, a notification may include an identified leaking anatomical structure, a fluid leakage property (e.g., a volume, flow rate, fluid type, duration of a fluid leakage), and/or any other information related to a fluid leakage situation. Further, a notification may include a suggested course of action that may be taken to remediate or otherwise respond to the leakage. In another example, a notification may include a visual indicator of a leakage source, for example as an overlay over an image and/or a video captured from the surgical procedure, as an indicator in an augmented reality device, and so forth. Providing a notification may involve transmitting a notification to a device, causing a notification to be displayed at an interface, playing a sound, providing haptic feedback, and/or any other method of outputting information such as disclosed above. A notification may be provided to a device in an operating room (e.g., as depicted in FIG. 1), to a device associated with a surgeon (e.g., a human surgeon and/or a surgical robot), and/or to any other system. For example, outputting a notification may include transmitting a notification to a computer, a mobile device, an external device, a surgical robot, and/or any other computing device.

In some embodiments, a remedial action may include sending instructions to a robot. Such instructions may direct the robot to undertake an action that remediates or assists in remediating the leakage. Alternatively or additionally, the instruction may direct the robot to cease a current course of action and/or to move aside to permit human intervention.

Remedial actions can be based on a variety of inputs. For example, instituting a remedial action may be based on a flow rate, a volume of fluid loss, and/or any property of a fluid or fluid leakage situation, for example as described above. Remedial actions may be based on statistical analysis of properties of fluids or fluid leakage situations. For example, a remedial action may be selected based on known (or determined) correlations between properties of a fluid leakage situation and outcomes. Further, a data structure such as a data structure of FIG. 17A may correlate properties of fluid leakage situations with outcomes. Statistical analysis may include using a regression model to identify a remedial action (e.g., a regression model fit to historical data that includes fluid leakage data, remedial action data, and outcome data).

Consistent with the present embodiments, analyzing frames of intracavitary video to determine an abnormal fluid leakage situation in intracavitary video may include determining whether a fluid leakage situation is abnormal. Some fluid leakage situations may be normal (e.g., below a threshold magnitude, in a location associated with normal fluid leakage, of a normal fluid type for a particular surgical event, etc.). Some fluid leakage situations may be abnormal (e.g., above a threshold magnitude, in a location associated with abnormal fluid leakage, of an abnormal fluid type for a particular surgical event, etc.). Properties of fluid leakage situations classified as normal and/or abnormal may be stored in a data structure such as one depicted in FIG. 17A. Determining whether a fluid leakage situation is abnormal may include using a regression model (e.g., a model fit to historical examples) and/or a trained machine learning model (e.g., a model trained to determine whether a determined fluid leakage situation is abnormal using historical examples). For example, a machine learning model may be trained using training examples to determine whether fluid leakage situations are normal or abnormal based on information related to the fluid leakage situations (such as images and/or videos of the fluid leakage situations, properties of the fluid leakage situations determined by analyzing videos depicting the fluid leakage situations as described above, sources of the fluid leakage situations, amounts of leakage, types of fluid leakage situations, type of fluid, characteristics of the patient, the surgical phase that the leakage situation occurred at, etc.), and the trained machine learning model may be used to analyze information related to the fluid leakage situation and determining whether the fluid leakage situation is abnormal. An example of such training example may include information related to a particular fluid leakage situation, together with a label indicating whether the particular fluid leakage situation is abnormal.

Some embodiments may include analyzing frames of an intracavitary video to determine a property of a detected fluid leakage situation, for example as described above. A determined property may be associated with a volume of fluid leakage, a type of fluid leakage, rate of fluid leakage, a source of fluid leakage, and/or any other observable feature of surgical procedure. The determined property may then be used, for example, to ascertain whether the fluid leakage is normal or abnormal. Analyzing the frames to determine such a property may include any method of image analysis as described herein.

In some embodiments, determining whether a fluid leakage situation is an abnormal fluid leakage situation may be based on a measurement of a blood pressure and/or any other vital sign of a patient undergoing a surgical procedure. The vital signs may be derived from surgical video through image analysis techniques described herein, and/or may be derived from sensors configured to measure vital signs. In addition, to using vital signs as a possible indicator of an abnormality, an abnormality may be based on any characteristic of a surgical procedure, such as a surgical event, a type of surgery, and/or any other aspect of a surgical procedure. For example, in response to a first measurement of the blood pressure of the patient undergoing the surgical procedure, a particular fluid leakage situation may be determined to be normal, and in response to a second measurement of the blood pressure of the patient undergoing the surgical procedure, the particular fluid leakage situation may be determined to be abnormal.

Disclosed embodiments may include instituting a remedial action in response to a determination that a detected fluid leakage situation is an abnormal fluid leakage situation. In addition, some embodiments may include forgoing institution of a remedial action in response to a determination that fluid leakage is normal. Forgoing a remedial action may include delaying a remedial action for a time period or indefinitely. For example, if an analysis of a leakage results in a determination that no remedial action is necessary, remedial action may be forgone. Or, if remedial action already began and further analysis revealed that the remedial action is unnecessary, forgoing a remedial action may include providing an updated notification (e.g., a notification may change a recommended remedial action or otherwise present information that differs from a previous notification).

Figure 32:
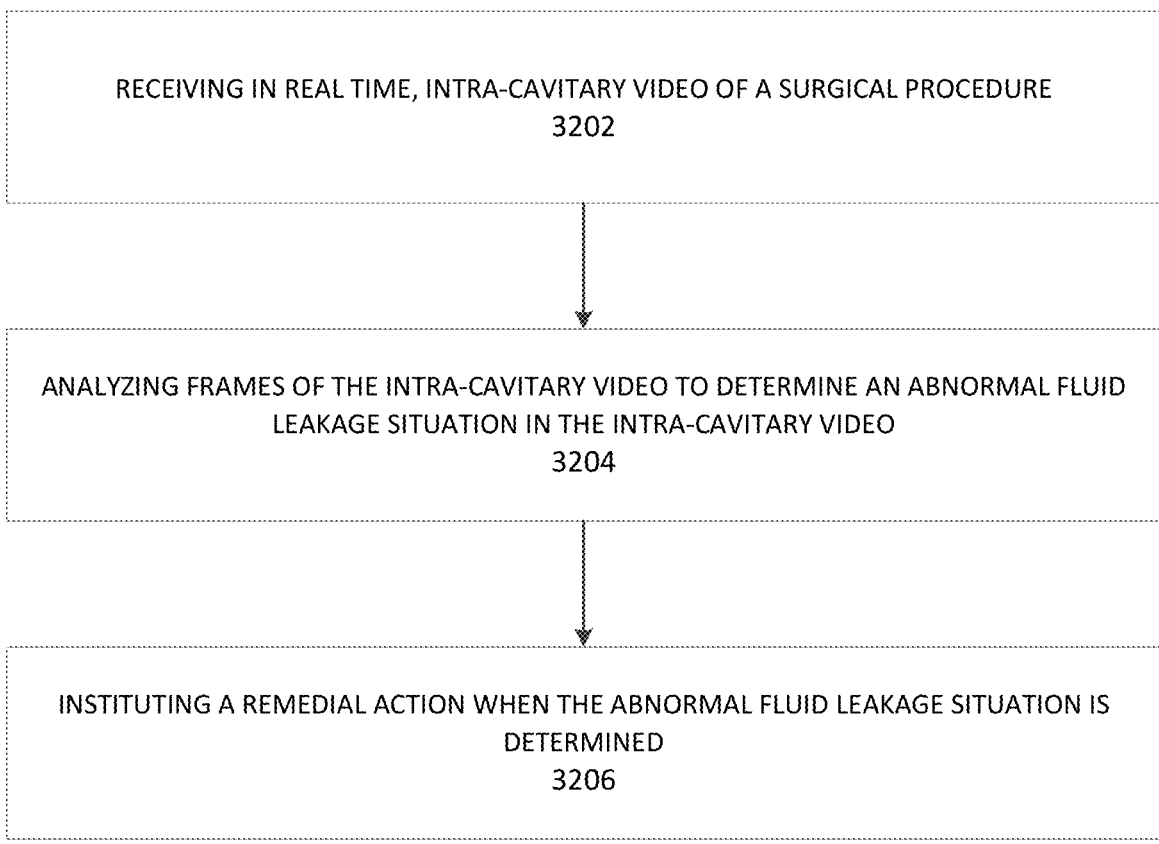
FIG. 32 is a flowchart illustrating an exemplary process for enabling fluid leak detection during surgery, consistent with the disclosed embodiments.

FIG. 32 is a flowchart illustrating an example process 3200 for enabling fluid leak detection during surgery, consistent with the disclosed embodiments. Process 3200 may be performed by at least one processor, such as one or more microprocessors. In some embodiments, process 3200 is not necessarily limited to the steps illustrated, and any of the various embodiments described herein may also be included in process 3200. Steps of process 3200 may be performed by a system including, for example, components of system 1401. In some embodiments, process 3200 may be embodied in a non-transitory computer readable medium including instructions that, when executed by at least one processor, cause the at least one processor to execute operations for analysis of fluid leakage during surgery. In some embodiments, process 3200 may be performed in real time during a surgical procedure.

At step 3202, the process may include receiving, receiving in real time, intracavitary video of a surgical procedure, consistent with disclosed embodiments. Receiving an intracavitary video in real time may include receiving a video via a network or directly from an image sensor. In some embodiments an intracavitary video may depict a surgical robot performing some or all of a surgical procedure, as previously discussed.

At step 3204, the process may include analyzing frames of the intracavitary video to determine an abnormal fluid leakage situation in the intracavitary video as previously discussed and illustrated with examples. As discussed, for example, a fluid may include blood, bile, urine, and/or any other type of body fluid. Determining a leakage source may include identifying a ruptured anatomical organ, identifying a ruptured vessel, and/or identifying any other ruptured anatomical structure. In some embodiments, step 3204 may include analyzing frames of an intracavitary video to identify a blood splash and at least one property of the blood splash. A property of a blood splash may be associated with a source of the blood splash, an intensity (rate) of a blood splash, a color of a blood splash, a viscosity of a blood splash, and/or a volume (magnitude) of a blood splash. Analyzing frames of an intracavitary video may include determining a property of an abnormal fluid leakage situation. For example, a property may be associated with a volume of a fluid leakage, a color of a fluid leakage, a type of fluid associated with a fluid leakage, a fluid leakage rate, a viscosity of a fluid, a reflectivity of a fluid, and/or any other property of a fluid. Further, analyzing frames may include determining a flow rate associated with a fluid leakage situation, determining a volume of fluid loss associated with a fluid leakage situation, and/or determining any other property of a fluid leakage situation. A method may further comprise storing an intracavitary video, and, upon determining the abnormal leakage situation, analyzing prior frames of the stored intracavitary video to determine a leakage source.

At step 3206, the process may include instituting a remedial action when the abnormal fluid leakage situation is determined. A selection of a remedial action may depend on at least one property of an identified blood splash, for example. In some embodiments, a selection of the remedial action may depend on a determined property of a fluid leakage situation.

Disclosed systems and methods may involve analyzing surgical footage to identify events during the surgical procedure, which may affect the post discharge risk for the patient. Post discharge risk for a patient may need to be identified after a surgical procedure, based on intraoperative events during the surgical procedure and based on patient characteristics. Post discharge risk may be determined by identifying events during the surgical procedure and using historical data to determine how the identified events may affect the post discharge risk for a patient. Therefore, there is a need for analyzing surgical footage and identifying events during a surgical procedure that may influence post discharge risk for the patient.

Aspects of this disclosure may relate to predicting post discharge risk after a surgical procedure, including methods, systems, devices, and computer readable media.

For ease of discussion, a method is described below, with the understanding that aspects of the method apply equally to systems, devices, and computer readable media. For example, some aspects of such a method may occur electronically over a network that is either wired, wireless, or both. Other aspects of such a method may occur using non-electronic means. In the broadest sense, the method is not limited to particular physical and/or electronic instrument, but rather may be accomplished using many differing instruments.

Consistent with disclosed embodiments, a method for predicting post discharge risk may involve accessing frames of video captured during a specific surgical procedure on a patient. As used herein, a video may include any form of recorded visual media, including recorded images and/or sound. For example, a video may include a sequence of one or more images captured by an image capture device, such as cameras 115, 121, 123, and/or 125, as described above in connection with FIG. 1. The images may be stored as individual files or may be stored in a combined format, such as a video file, which may include corresponding audio data. In some embodiments, a video may be stored as raw data and/or images output from an image capture device. In other embodiments, the video may be processed. For example, video files may include Audio Video Interleave (AVI), Flash Video Format (FLV), QuickTime File Format (MOV), MPEG (MPG, MP4, M4P, or any other format), Windows Media Video (WMV), Material Exchange Format (MXF), or any other suitable video file formats.

The video footage may refer to a video that has been captured by an image capture device. In some embodiments, the video footage may refer to a video that includes a sequence of images in the order in which they were originally captured. For example, video footage may include a video that has not been edited to form a video compilation. In other embodiments, the video footage may be edited in one or more ways, such as to remove frames associated with inactivity during a surgical procedure or to otherwise compile frames not originally captured sequentially. Accessing the video footage may include retrieving the video footage from a storage location, such as a memory device. The video footage may be accessed from a local memory, such as a local hard drive, or may be accessed from a remote source, for example, through a network connection. Consistent with the present disclosure, indexing may refer to a process for storing data such that it may be retrieved more efficiently and/or effectively. A process of indexing video footage may include associating one or more properties or indicators with the video footage such that the video footage may be identified based on the properties or indicators.

A surgical procedure may include any medical procedure associated with or involving manual or operative procedures on a patient's body. Surgical procedures may include cutting, abrading, suturing, or other techniques that involve physically changing body tissues and/or organs. Surgical procedures may also include diagnosing patients or administering drugs to patients. Some examples of such surgical procedures may include a laparoscopic surgery, a thoracoscopic procedure, a bronchoscopic procedure, a microscopic procedure, an open surgery, a robotic surgery, an appendectomy, a carotid endarterectomy, a carpal tunnel release, a cataract surgery, a cesarean section, a cholecystectomy, a colectomy (such as a partial colectomy, or a total colectomy), a coronary angioplasty, a coronary artery bypass, a debridement (for example of a wound, a burn, or an infection), a free skin graft, a hemorrhoidectomy, a hip replacement, a hysterectomy, a hysteroscopy, an inguinal hernia repair, a knee arthroscopy, a knee replacement, a mastectomy (such as a partial mastectomy, a total mastectomy, or a modified radical mastectomy), a prostate resection, a prostate removal, a shoulder arthroscopy, a spine surgery (such as a spinal fusion, a laminectomy, a foraminotomy, a diskectomy, a disk replacement, or an interlaminar implant), a tonsillectomy, a cochlear implant procedure, brain tumor (for example meningioma) resection, interventional procedures such as percutaneous transluminal coronary angioplasty, transcatheter aortic valve replacement, minimally Invasive surgery for intracerebral hemorrhage evacuation, or any other medical procedure involving some form of incision. While the present disclosure is described in reference to surgical procedures, it is to be understood that it may also apply to other forms of medical procedures or procedures generally.

In some exemplary embodiments, the accessed video footage may include video footage captured via at least one image sensor located in at least one of a position above an operating table, in a surgical cavity of a patient, within an organ of a patient or within a vasculature of a patient. An image sensor may be any sensor capable of recording a video. An image sensor located in a position above an operating table may include an image sensor placed external to a patient configured to capture images from above the patient. For example, the image sensor may include cameras 115 and/or 121, as shown in FIG. 1. In other embodiments, the image sensor may be placed internal to the patient, such as, for example, in a cavity. As used herein, a cavity may include any relatively empty space within an object. Accordingly, a surgical cavity may refer to a space within the body of a patient where a surgical procedure or operation is being performed. It is understood that the surgical cavity may not be completely empty but may include tissue, organs, blood, or other fluids present within the body. An organ may refer to any self-contained region or part of an organism. Some examples of organs in a human patient may include a heart or liver. A vasculature may refer to a system or grouping of blood vessels within an organism. An image sensor located in a surgical cavity, an organ, and/or a vasculature may include a camera included on a surgical tool inserted into the patient.

Accessing frames of video captured during a specific surgical procedure may include accessing at least one of the frames, metadata related by the frames, pixel values of pixels of the frames, information based on an analysis of the frames, and so forth. For example, the frames of video captured during a specific surgical procedure may be accessed by a computerized device reading the information from a memory, for example for processing by at least one processing device. For example, the processing device may analyze the access frames using a machine-learning method configured to analyze various aspects of video data, for example as described above. For example, the machine-learning method may be configured to recognize events within the video frames or recognize surgical instruments, anatomical structures and interactions between surgical instruments and anatomical structures by analyzing the video frames, and so forth. In some cases, accessing frames of video may include accessing the frames by a healthcare professional such as a surgeon, anesthesiologist, or any other healthcare professional. In some cases, the video frames may be accessed by a patient, a family member of a patient, or any other authorized party.

Aspects of this disclosure may include accessing stored historical data identifying intraoperative events, and associated outcomes. As used herein, an intraoperative event for the surgical procedure (also referred to as a surgical event) may refer to an action that is performed as part of a surgical procedure, such as an action performed by a surgeon, a surgical technician, a nurse, a physician's assistant, an anesthesiologist, a doctor, any other healthcare professional, a surgical robot, and so forth. The intraoperative surgical event may be a planned event, such as an incision, administration of a drug, usage of a surgical instrument, an excision, a resection, a ligation, a graft, suturing, stitching, or any other planned event associated with a surgical procedure or phase. Additionally or alternatively, an intraoperative event may also refer to an event occurring to an anatomical structure and/or to a medical instrument related to the surgical procedure, whether the event includes an action performed by a healthcare professional or not. One example of such intraoperative event may include a change in a condition of an anatomical structure. Another example of such intraoperative event may include a change in a state of a medical instrument (for example, from 'partly filled' to 'filled').

An exemplary surgical intraoperative event for a laparoscopic cholecystectomy surgery may include trocar placement, calot's triangle dissection, clipping and cutting of cystic duct and artery, gallbladder dissection, gallbladder packaging, cleaning and coagulation of liver bed, gallbladder retraction, and so forth. In another example, surgical events of a cataract surgery may include povidone-iodine injection, corneal incision, capsulorhexis, phaco-emulsification, cortical aspiration, intraocularlens implantation, intraocular-lens adjustment, wound sealing, and so forth. In yet another example, surgical characteristic events of a pituitary surgery may include preparation, nasal incision, nose retractor installation, access to the tumor, tumor removal, column of nose replacement, suturing, nose compress installation, and so forth. Some other examples of surgical characteristic events may include incisions, laparoscope positioning, suturing, and so forth.

In some embodiments, the surgical intraoperative event may include an adverse event or a complication. Some examples of adverse surgical events may include bleeding, mesenteric emphysema, injury, conversion to unplanned open surgery (for example, abdominal wall incision), incision significantly larger than planned, and so forth. Some examples of intraoperative complications may include hypertension, hypotension, bradycardia, hypoxemia, adhesions, hernias, atypical anatomy, dural tears, periorator injury, arterial occlusions, and so forth. In some cases, surgical events may include other errors, including technical errors, communication errors, management errors, judgment errors, decision-making errors, errors related to medical equipment utilization, miscommunication, and so forth. In various embodiments, events may be short or may last for a duration of time. For example, a short event (e.g., incision) may be determined to occur at a particular time during the surgical procedure, and an extended event (e.g., bleeding) may be determined to occur over a time span. In some cases, extended events may include a well-defined beginning event and a well-defined ending event (e.g., beginning of suturing and ending of the suturing), with suturing being an extended event. In some cases, extended events are also referred to as phases during a surgical procedure.

In some cases, a surgical event may identify a group of sub-events (i.e., more than one sub-event or steps). For example, an event of administering general anesthesia to a patient may include several steps such as a first step of providing a medication to a patient via an IV line to induce unconsciousness, and a second step of administering a suitable gas (e.g., isoflurane or desflurane) to maintain the general anesthesia.

Historical data may include any information related to or based on historical (i.e., previously performed) surgical procedures. For example, the historical data may include historical surgical footage, information based on an analysis of historical surgical footage, historical notes from one or more healthcare providers, historical data from medical devices (e.g., historical vital signals collected during a historical surgical procedure), historical audio data, historical data collected from various sensors (e.g., image sensors, chemical sensors, temperature sensors, electrical sensors), or any other historical data that may be related to one or more historical surgical procedures.

Accessing stored historical data identifying intraoperative events and associated outcomes may include accessing a database containing information about intraoperative events and associated outcomes. For example, a database may include a data structure, such as a table, database, or other organization of data that maintains historical intraoperative events and historical outcomes associated with intraoperative events. For example, an intraoperative event may be "bleeding," and a historically associated outcome may be "anemia." In some cases, one intraoperative event may have associated outcomes with different characteristics. For example, an intraoperative event "bleeding" may have a first associated outcome "loss of hemoglobin" with a first characteristic "dropping from 16 g/dL to 13 g/dL" and a second associated outcome "loss of hemoglobin" with second characteristic "dropping from 15 g/dL to 12 g/dL." In some cases, an intraoperative event such as "bleeding" may have a first outcome "loss of hemoglobin" and a second outcome that may be different from the first outcome (e.g., "cardiac arrest").

Additionally or alternatively, accessing stored historical data identifying intraoperative events and associated outcomes may include accessing the historical data by a computerized device reading at least part of the historical data from a memory, for example for processing by at least one processing device. The historical data may include historical surgical footage, information about historical intraoperative events, etc., and associated historical outcomes. In some cases, processing the accessed historical data may be performed by a machine-learning model configured to analyze various aspects of historical surgical footage (as well as any other historical surgical data). For example, the machine-learning method may be configured to identifying intraoperative events within video frames of historical surgical footage by recognizing surgical instruments, anatomical structures, and interactions between surgical instruments and anatomical structures in the historical surgical footage.

In some cases, accessing stored historical data identifying intraoperative events and associated outcomes may include accessing the historical data by a surgeon, anesthesiologist, nurse, or any other healthcare professional. In some cases, the historical data may be accessed by a patient, a family member of a patient, or any other party authorized to access to the historical data.

In various embodiments, a machine learning model may be used to identify in accessed video frames of a surgical procedure at least one specific intraoperative event, for example as described above. The trained machine-learning model may be an image recognition model for identifying events. For example, the machine-learning model may analyze multiple video frames in order to detect a motion or other changes within the images represented as the frames of the video. In some embodiments, image analysis may include object detection algorithms, such as Viola-Jones object detection, convolutional neural networks (CNN), or any other forms of object detection algorithms. The machine-learning model may be configured to return a name of the event, a type of the event, and a characteristic of the event. For example, if the event is an incision, the machine-learning model may be configured to return the name "incision" for characterizing the event, and the length and the depth of the incision as characteristics of the event. In some cases, a predetermined list of possible names for various events may be provided to the machine-learning model, and the machine-learning model may be configured to select a name from the list of events for accurate characterization of the event.

Some aspects of disclosed embodiments may include using a machine-learning module to identify an occurrence of at least one specific intraoperative event. For example, the machine-learning model may identify that a specific intraoperative event occurs by identifying a beginning of the event. In some cases, the machine-learning model may identify characteristics of the event and/or an end of the specific intraoperative event.

The machine-learning model may be trained to identify intraoperative events using example training data. The example training input data may include a historical footage of surgical procedures that include intraoperative events. In various cases, multiple samples of training data may be generated and used for training the machine-learning model. During a training process, training data (e.g., a first training data) may be used as an input data for the model, and the model may perform computations and output an event identifying string for the intraoperative event (e.g., a name of the event). In various embodiments, the event identifying string may be compared with a known historical name of a corresponding intraoperative event to evaluate an associated error for the model. If the error is below a predetermined threshold value, the model may be trained using other input data. Alternatively, if the error is above the threshold value, model parameters may be modified, and a training step may be repeated using the first training data.

In addition to or as an alternative to detection with a machine-learning model the characteristic event may be detected in the video frames received from image sensors using various other approaches. In one embodiment, the characteristic event may be identified by a medical professional (e.g., a surgeon) during the surgical procedure. For example, surgeon may identify the characteristic event using a visual or an audio signal from the surgeon (e.g., a hand gesture, a body gesture, a visual signal produced by a light source generated by a medical instrument, a spoken word, or any other suitable signal) that may be captured by one or more image sensors/audio sensors and recognized as a trigger for the characteristic event.

Aspects of this disclosure may also include identifying at least one specific intraoperative event based on at least one of a detected surgical tool in the accessed frames, a detected anatomical structure in the accessed frames, an interaction in the accessed frames between a surgical tool and an anatomical structure, or a detected abnormal fluid leakage situation in the accessed frames.

A surgical tool may be any instrument or device that may be used during a surgical procedure, which may include, but is not limited to, cutting instruments (such as scalpels, scissors, or saws), grasping and/or holding instruments (such as Billroth's clamps, hemostatic "mosquito" forceps, atraumatic hemostatic forceps, Deschamp's needle, or Hopfner's hemostatic forceps), retractors (such as Farabef's Cshaped laminar hook, blunt-toothed hook, sharp-toothed hook, grooved probe, or tamp forceps), tissue unifying instruments and/or materials (such as needle holders, surgical needles, staplers, clips, adhesive tapes, or a mesh), protective equipment (such as facial and/or respiratory protective equipment, headwear, footwear, or gloves), laparoscopes, endoscopes, patient monitoring devices, and so forth. A surgical tool (also referred to as a medical tool or medical instrument) may include any apparatus or a piece of equipment used as part of a medical procedure.

The surgical tool may be detected in the surgical video footage using any suitable means, for example as described above.

Similarly, to detecting the surgical tool, an anatomical structure may be detected in the surgical footage using a machine-learning model. An anatomical structure may be any particular part of a living organism, including, for example, organs, tissues, ducts, arteries, or any other anatomical parts. In some cases, prosthetics, implants, or artificial organs may be considered anatomical structures.

Detecting a surgical tool and/or an anatomical structure using a machine learning method may be one possible approach, for example as described above. Additionally or alternatively, the surgical tool (or anatomical structure) may be detected in the surgical video footage received from image sensors using various other approaches. In one embodiment, the surgical tool (or anatomical structure) may be identified by a medical professional (e.g., a surgeon) during the surgical procedure. For example, surgeon may identify the surgical tool (or anatomical structure) by saying the name of the surgical tool and/or anatomical structure, such that the audio sound from the surgeon may be captured by one or more audio sensors and recognized by a speech recognition computer-based model (or by a human operator for recording information during the surgical procedure).

Some aspects of the present disclosure may involve analyzing frames of the surgical footage to identify an interaction between the medical tool and an anatomical structure, for example as described above. For example, at least some of the frames of the surgical footage may indicate a portion of the surgical footage in which a surgical operation is being performed on the anatomical structure. As discussed above, the interaction may include any action by the medical instrument that may influence the anatomical structure or vice versa. For example, the interaction may include a contact between the medical instrument and the anatomical structure, an action by the medical instrument on the anatomical structure (such as cutting, clamping, grasping, applying pressure, or scraping), a physiological response by the anatomical structure, the surgical tool emitting light towards the anatomical structure (e.g., surgical tool may be a laser that emits light towards the anatomical structure) a sound emitted towards anatomical structure, an electromagnetic field created in a proximity of the anatomical structure, a current induced into an anatomical structure, or any other suitable forms of interaction.

In some cases, identifying interaction may include identifying the proximity of the surgical tool to an anatomical structure. For example, by analyzing the surgical video footage of an example surgical procedure, the image recognition model may be configured to determine a distance between the surgical tool and a point (or a set of points) of an anatomical structure.

Aspects of the present disclosure may also involve detecting an abnormal fluid leakage situation in the accessed frames, for example as described above. The abnormal fluid leakage may include bleeding, urine leakage, bile leakage, lymph leakage, or any other leakage. The abnormal fluid leakage may be detected by a corresponding machine-learning model trained to detect abnormal fluid leakage events within the surgical video footage captured during a surgical procedure. It should be noted that a machine-learning model (e.g., a first machine-learning model) for detecting surgical instruments may be configured and/or trained differently from a machine-learning model for detecting anatomical structures (e.g., a second machine-learning model), and may be configured and/or trained differently from a machine-learning model for detecting abnormal leakages (e.g., a third machine-learning model). Further, the second machine-learning model may be configured and/or trained differently than the third machine-learning model. In various embodiments, configuring a machine-learning model may include configuring (e.g., selecting) any suitable parameters of the machine-learning model. For example, if the machine-learning model is a neural network, configuring the neural network may include selecting a number of layers for the neural network, a number of nodes for each layer, weights of the neural network, or any other suitable parameters of the neural network.

Aspects of disclosed embodiments may include analyzing accessed frames and, based on information obtained from historical data, identifying in the accessed frames at least one specific intraoperative event. As previously described, and consistent with various embodiments, a process of analyzing the accessed frames may be performed by a suitable machine-learning model such as an image recognition algorithm, as described above, consistent with disclosed embodiments. In various embodiments, information obtained from historical data may be used to train the image recognition algorithm to recognize specific intraoperative events base on accessed frames of surgical footage, as previously described. In one example, the historical data may include a statistical model and/or a machine learning model based on an analysis of information and/or video footage from historical surgical procedures (for example as described above), and the statistical model and/or the machine learning model may be used to analyze the accessed frames and identify in the accessed frames the at least one specific intraoperative event.

Figure 32A:
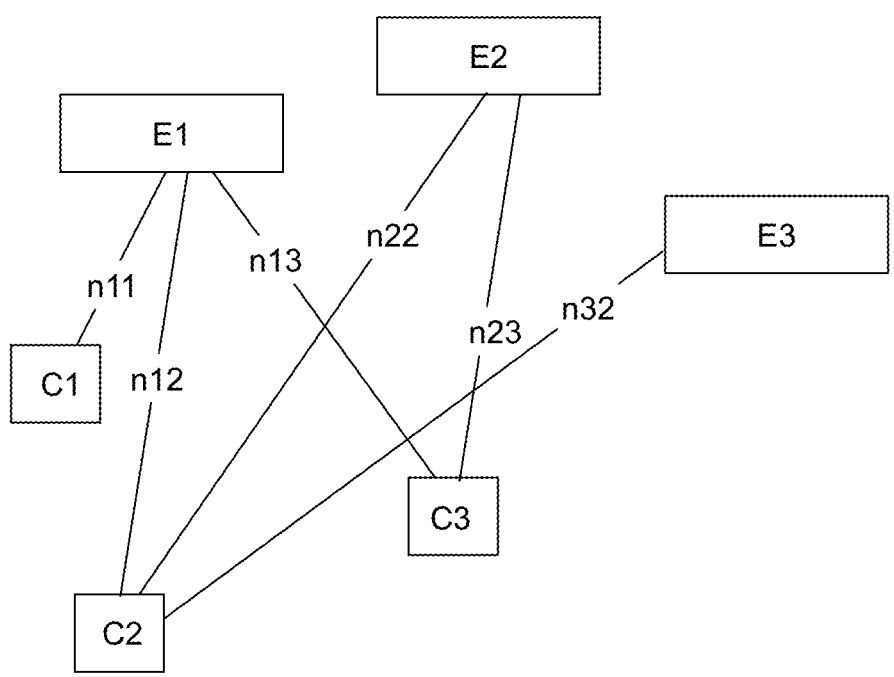
FIG. 32A is an exemplary graph showing a relationship between intraoperative events and outcomes, consistent with disclosed embodiments.

Aspects of this disclosure may include determining, based on information obtained from historical data, and an identified at least one intraoperative event, a predicted outcome associated with a specific surgical procedure. For example, a data structure may include historical data representing relationships between intraoperative events and predicted outcomes. Such data structures may be used to obtain a predicted outcome associated with a specific surgical procedure. For example, FIG. 32A shows an example graph 3200 of intraoperative events E1-E3 connected to possible outcomes C1-C3 using connections n11-n32. In an example embodiment, connection n11 may include information indicating a probability of an outcome C1 (i.e., information indicating how often outcome C1 happens in surgical procedures that includes event E1). For example, connection n11 may indicate that given an occurrence of intraoperative event E1, outcome C1 may happen 30 percent of the time, connection n12 may indicate that outcome C2 may happen 50 percent of the time, and connection n13 may indicate that outcome C3 may happen 20 percent of the time. Similarly, connection n22 may indicate a probability of outcome C2, given an occurrence of intraoperative event E2, and connection n23 may indicate a probability of outcome C3, given an occurrence of intraoperative event E2. A connection n32 may indicate a probability of outcome C2, given an occurrence of intraoperative event E3. Thus, once an intraoperative event is known, using information obtained from historical data (e.g., using information from graph C100), a most probable outcome (e.g., outcome C2) may be determined based on probability assigned to connections n11-n13. In another example, the historical information may include a hypergraph, a hyperedge of the hypergraph may connect a plurality of intraoperative events with an outcome and may indicate a particular probability of the outcome in surgical procedures that included the plurality of events. Thus, once a plurality of intraoperative events is known, using information obtained from historical data (e.g., from the hypergraph), a most probable outcome may be determined based on probability assigned to the hyperedges. In some examples, probabilities assigned to edges of graph C100 or to the hyperedges of the hypergraph may be based on an analysis of historical surgical procedures, for example by calculating the statistical probability of an outcome in a group of historical surgical procedures that include particular group of intraoperative events corresponding to a particular edge or a particular hyperedge. In some other examples, the historical information may include a trained machine learning model for predicting outcome based on intraoperative events, and the trained machine learning model may be used to predict the outcome associated with the specific surgical procedure based on the identified at least one intraoperative event. In one example, the trained machine learning model may be obtained by training a machine learning algorithm using training examples, and the training examples may be based on historical surgical procedure. An example of such training example may include a list of intraoperative surgical events, together with a label indicating an outcome corresponding to the list of intraoperative surgical events. In one example, two training examples may have the same list of intraoperative surgical events, while having different label indicating different outcomes.

In some cases, a predicted outcome may be a particular predicted event following a surgical procedure. For example, the predicted outcome may be a post-discharge mishap, a post-discharge adverse event, a post-discharge complication, or an estimate of a risk of readmission. In some cases, the predicted outcome may be a set of events. For example, such a set of events may include events in which the "well-being" of a patient is evaluated. These events, when the "well-being" of the patient is evaluated, may occur at specific points in time (e.g., at specific hours during the day following the surgical procedure, at specific days following the surgical procedure, at specific weeks, month, years, or other time intervals, following the surgical procedure). The "well-being" may be evaluated using any suitable objective measure such as, e.g., using imaging such as a CAT scan, ultrasound imaging, visual inspection, presence of complications that can be determined during a physical exam, or any other suitable way or test for evaluating a well-being of a patient (e.g., via a blood test). Well-being may also be determined from subjective measures such as by asking the patient to describe his/her overall condition.

Figure 32B:
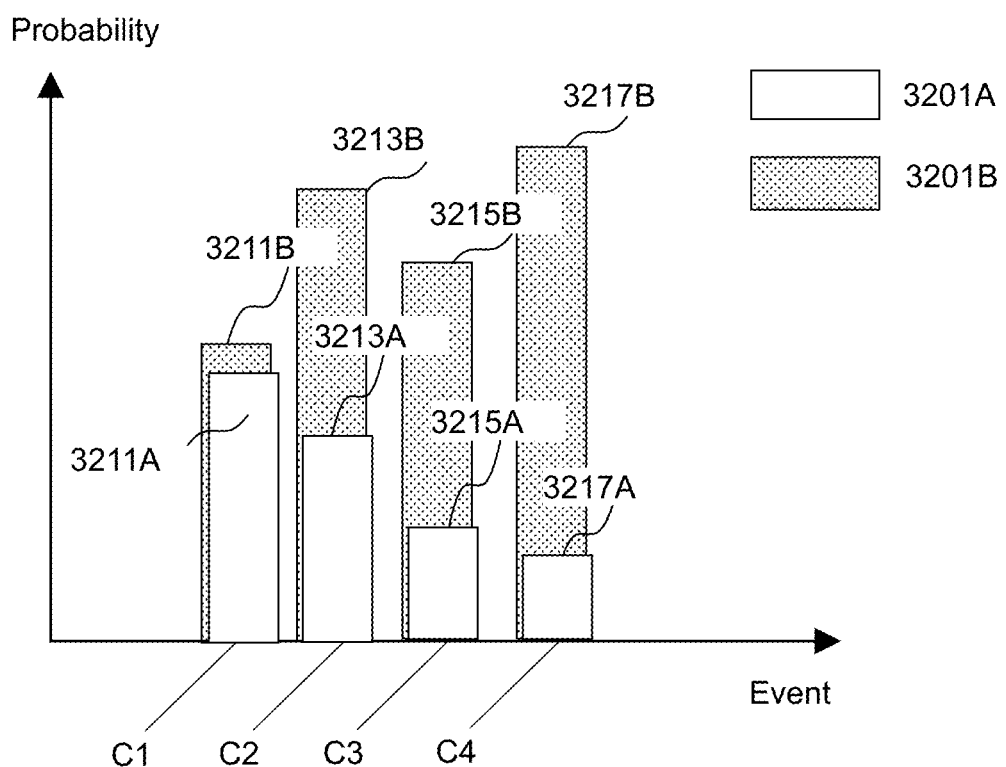
FIG. 32B is an exemplary probability distribution graph for different events with and without the presence of an intraoperative event, consistent with disclosed embodiments.

The determining of the predicted outcome associated with the surgical procedure based on the determined intraoperative event may be accomplished using a statistical analysis. For example, historical surgical data for past (also referred to as historical) surgical procedures containing an intraoperative event, may be analyzed to determine a historical outcome for such past surgical procedures. For example, for a given type of a historical surgical procedure, surgical outcome statistics may be collected, as shown in FIG. 32B. For instance, a probability distribution 3201A represented by bars 3211A-3217A (herein also referred to as probability bars) may determine a probability of corresponding outcomes C1-C4, when an intraoperative event is not present (e.g., when an adverse intraoperative event such as bleeding, cardiac arrest, or any other adverse event is not present). Similarly, probability distribution 3201B represented by probability bars 3211B-3217B may determine a probability of corresponding outcomes C1-C4 when the intraoperative event (e.g., an adverse intraoperative event) is present. In an example embodiment, outcome C1 may correspond to a specific post-discharge mishap (e.g., a foreign object such as gauze is left in a patient's body), outcome C2 may correspond to a specific post-discharge adverse event (e.g., bleeding, pain, nausea, confusion, or any other adverse event), outcome C3 may correspond to a post-discharge complication (e.g., paralysis, pain, bleeding, or any other complication), and outcome C4 may correspond to an elevated risk of readmission. It should be noted that any other suitable outcomes may be used to evaluate the surgical procedure (e.g., an outcome that evaluates an objective measure of a patient's "well-being" several days after the surgical procedure). In an example embodiment, the height of probability bars 3211A-3217A and 3211B-3217B may relate to a probability of occurrence of corresponding outcomes C1-C4.

In an example embodiment, an intraoperative event may affect the probabilities of occurrence of outcomes C1-C4, as shown by bars 3211B-3217B that have different heights than corresponding bars 3211A-3217A. In an illustrative example, if the intraoperative event corresponds to a cardiac arrest during a surgical procedure, bar 3213B corresponding to a probability of outcome C2 (e.g., confusion) may be higher than bar 3211B corresponding to a probability of outcome C2 when the intraoperative event was not detected during the surgical procedure.

Figure 33:
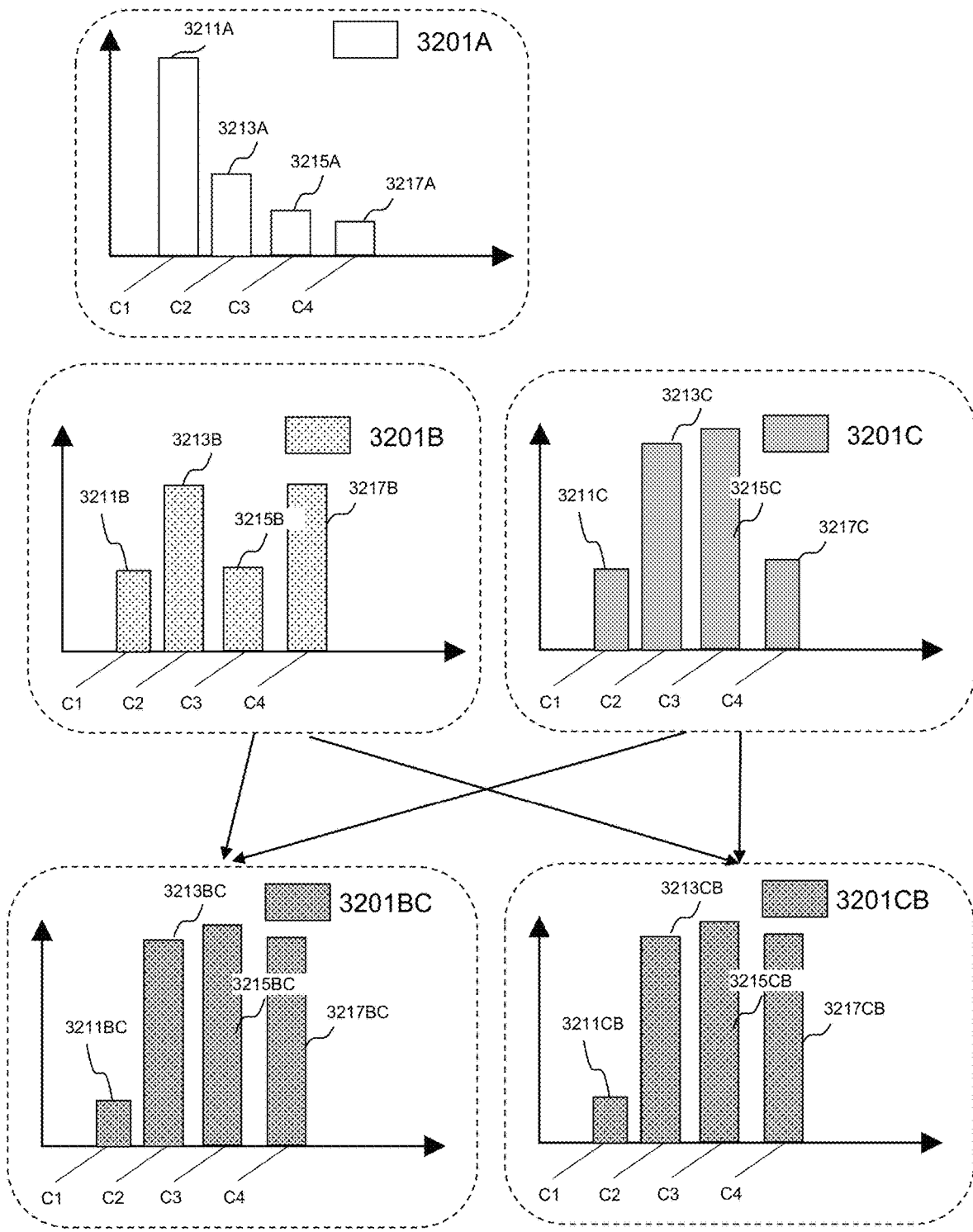
FIG. 33 shows exemplary probability distribution graphs for different events, consistent with disclosed embodiments.

In some cases, a statistical analysis may be used to determine the predicted outcome associated with the surgical procedure based on a determination of several intraoperative events that may occur during the surgical procedure. For example, FIG. 33 shows a probability distribution 3201A with probability bars 3211A-3217A corresponding to probability for outcomes C1-C4 when there are no adverse intraoperative events present (as described above). FIG. 33 also show a probability distribution 3201B with probability bars 3211B-3217B corresponding to probability for outcomes C1-C4 when there is a first adverse event labeled "B" present during a surgical procedure. Likewise, FIG. 33 also shows a probability distribution 3201C with probability bars 3211C-3217C corresponding to probability for outcomes C1-C4 when there is a second adverse event labeled "C" present during a surgical procedure. Further, using statistical data for surgical procedures that include event "B" and event "C", with event "B" starting prior to a start of event "C", the probability distribution 3201BC may be determined as shown by bars 3211BC-3217BC corresponding to probability for outcomes C1-C4.

Figure 34:
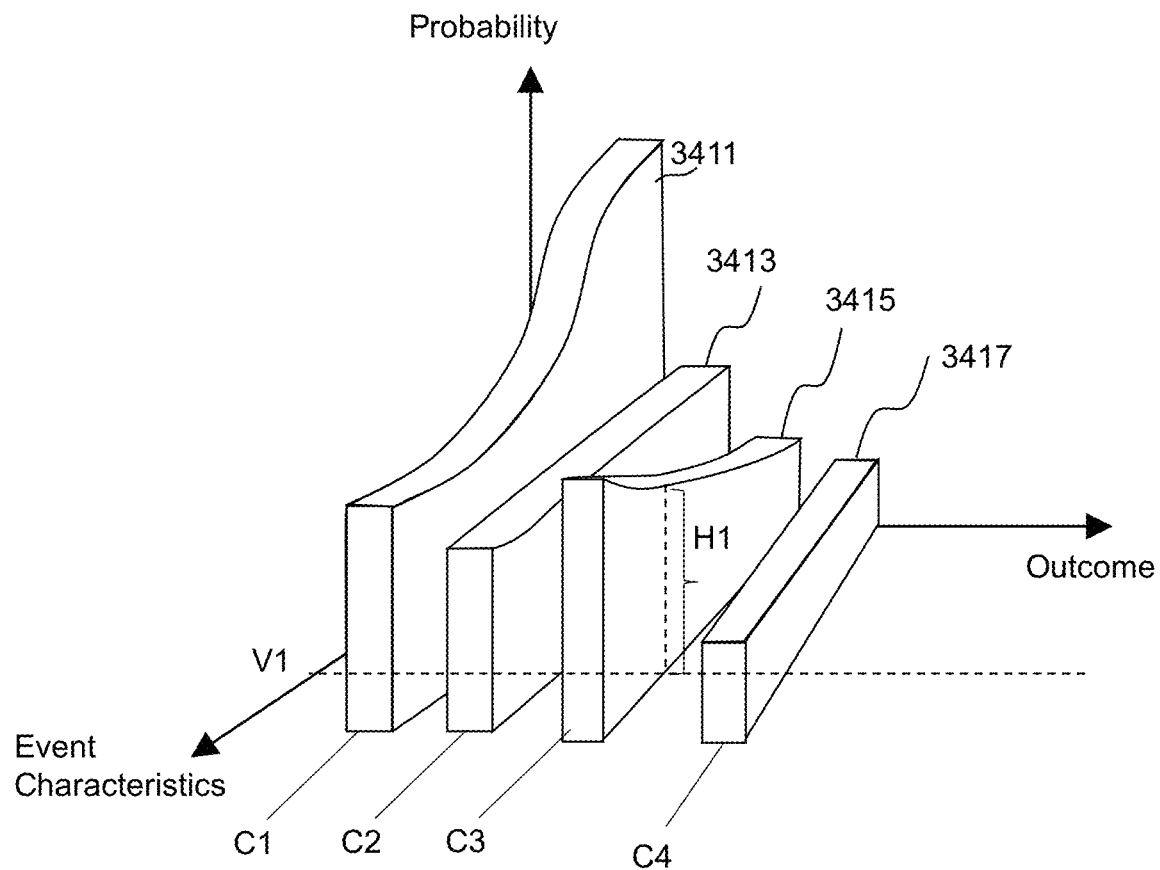
FIG. 34 shows exemplary probability distribution graphs for different events, as a function of event characteristics, consistent with disclosed embodiments.

Additionally or alternatively, using statistical data for surgical procedures that include event "B" and event "C", with event "B" starting after the start of event "C", the probability distribution 3201CB may be determined as shown by bars 3211CB-3217CB corresponding to probability for outcomes C1-C4. It should be noted that other probability distributions (besides distributions 3201B, 3201C, 3201BC, and 3201CB) may be determined using a suitable statistical data depending on various characteristics of events "B", and/or "C" and/or combination of thereof. For instance, an event characteristic may include a duration of time for the event, a starting time for the event, a finishing time for the event, or any other suitable characteristic (e.g., if an event is an incision, an event characteristics may be a length of the incision; if the event is a cardiac arrest, the event characteristics may be blood pressure values during the cardiac arrest; or any other suitable characteristic). An example embodiment of how the probability distribution is affected by an event characteristic is shown in FIG. 34 by plotting heights of bars 3411-3417 corresponding to probability for outcomes C1-C4 in a three-dimensional Cartesian system. As shown in FIG. 34, one axis is a probability for outcomes C1-C4, another axis denotes the outcome (e.g., outcomes C1-C4), and the third axis denotes "Event Characteristics" of an intraoperative event and is represented by a numerical value (herein referred to as the event characteristic value) such as, for example, incision length for intraoperative event being an incision. FIG. 34 shows that bar heights for bars 3411-3417 may change continuously as the event characteristic value changes, while in other examples the event characteristic value may be discrete. For a given event characteristic value (e.g., V1, as shown in FIG. 34) the height value (e.g., H1) for an example bar (e.g., 3415), corresponding to a probability of outcome C3 in case of an event characteristic V1, may be interpolated using nearby height values for bar 3415, when height value H1 is not known for value V1.

Aspects of this disclosure may include determining a predicted outcome based on at least one of a characteristic of the patient, an electronic medical record, or a postoperative surgical report. The patient characteristic may include an age, gender, weight, height, and/or any other information directly or indirectly characterizing the patient (e.g., whether the patient has relatives who can care for the patient may be a characteristic that indirectly influences the predicted outcome of the surgical procedure), to the extent such characteristics may influence the predicted outcome of the surgical procedure. Some other non-limiting examples of patient characteristics are described above. In one example, a similarity measure may be used to identify surgical procedures (for example in the historical data) that are similar to the specific surgical procedure (for example using a k-Nearest Neighbors algorithm, using an exhaustive search algorithm, etc.), and the identified similar surgical procedures may be used to determine the predicted outcome, for example by calculating a statistical function of the outcomes of the identified similar surgical procedures (such as mean, median, mode, and so forth). The similarity measure may be based on at least one of a characteristic of the patient, an electronic medical record, a postoperative surgical report, intraoperative events that occurred in the surgical procedures, durations of phases of the surgical procedures, and so forth.

The electronic medical record (or any other suitable medical record, such as a paper medical record) may contain medical information for the patient (e.g., previous surgical procedures for the patient, previous or current diseases for the patient, allergies for the patient, diseases of patient's parents, diseases of patient's siblings, patient's mental health, or any other medical information about a patient). The medical information may be organized in any suitable manner (e.g., the information may be organized using tables, linked lists, or any other suitable data structure). In some cases, other (non-medical) information related to a patient (e.g., patient's location, diet, religion, race, occupation, fitness record, a marital status, an alcohol or tobacco use, or a previous drug use) may be contained (recorded) in the electronic medical record. In various embodiments, such information in the electronic medical record may be used to determine a predicted outcome for the surgical procedure.

In various embodiments, a postoperative surgical report may further be used to determine the outcome of the surgical procedure. The postoperative surgical report may include any suitable information related to the surgical procedure. For example, the report may include a name of the surgical procedure, patient characteristics, as discussed above, patient's medical history, including the medical report for the patient, other information related to the patient, as discussed above, information about surgical events that happened during the surgical procedure, including information about procedural surgical events, such as actions taken during the surgical procedure, as well as information about adverse or positive surgical events. In an example embodiment, surgical events may include actions such as incisions, suturing, or any other activities, performed by the surgeon. Adverse surgical events may include any events that may negatively influence a surgery and a predicted outcome for a surgical procedure, such as bleeding, rupture of tissues, blood clots, cardiac arrest, or any other adverse surgical eventualities. Positive surgical events may include determining that at least some steps of the surgical procedure may not be necessary. For example, if during a surgical procedure, it is determined that the patient does not have a tumor, removal of the tumor may not be necessary. In various embodiments, the information in the postoperative surgical report may include surgical footage depicting the surgical procedure, audio data, text data, or any other suitable data recorded before, during, or after the surgical procedure.

In various embodiments, determining the predicted outcome based on at least one of a characteristic of a patient, an electronic medical record, or a postoperative surgical report may be achieved by analyzing historical surgical outcomes based on variety of parameters such as patient characteristics, medical history data found in the electronic medical record or various events and event characteristics described in the postoperative surgical report.

In various embodiments, determining the predicted outcome may include using a machine learning model (herein also referred to as an event-based machine-learning model) trained to determine predicted outcomes associated with a specific surgical procedure based on intraoperative events. Additionally, the event-based machine-learning method may be trained to predict surgical outcomes bases on a variety of other parameters (besides intraoperative events) such as patient characteristics, medical history of the patient, characteristics of one or more healthcare professionals administering the surgical procedure or any other suitable parameters.

Figure 35A:
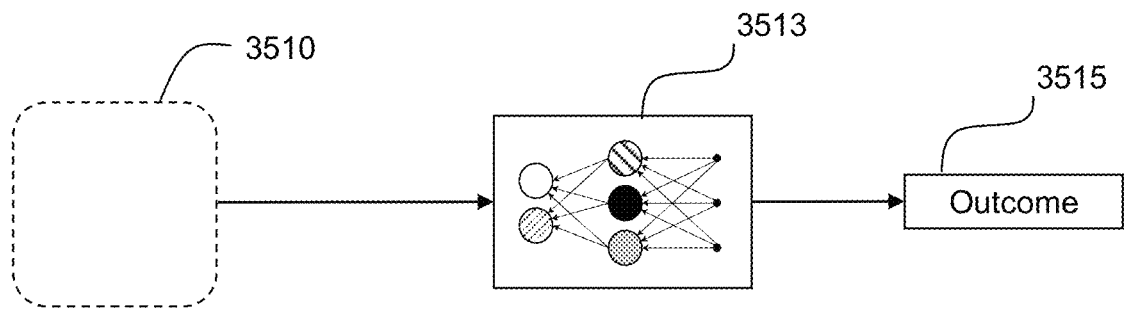
FIG. 35A shows an exemplary machine-learning model, consistent with disclosed embodiments.
Figure 35B:
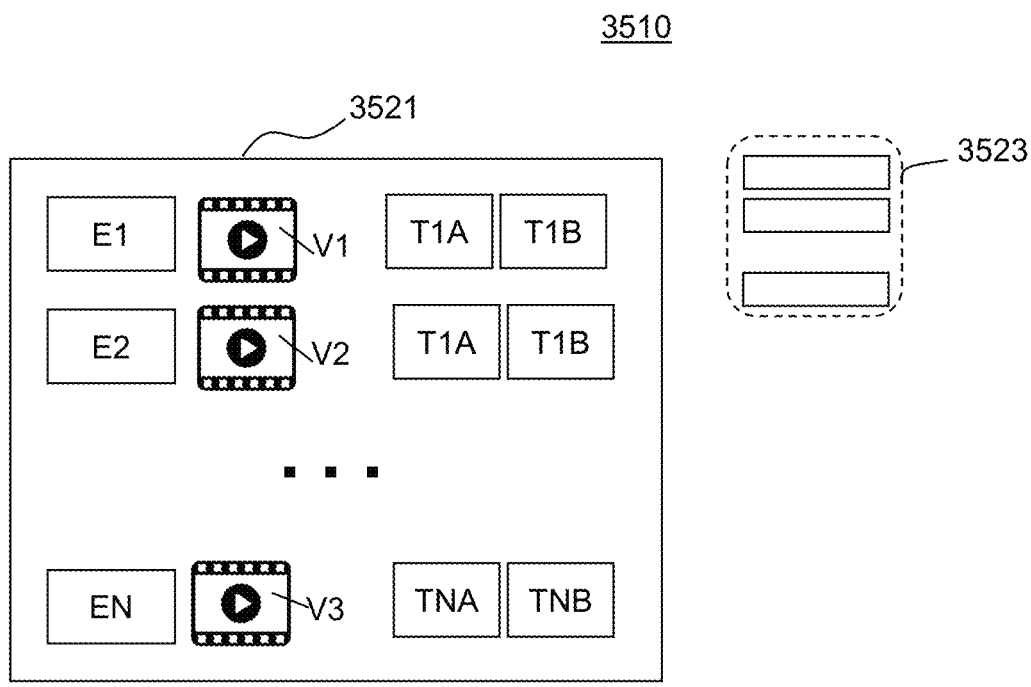
FIG. 35B shows an exemplary input for a machine-learning model, consistent with disclosed embodiments.

FIG. 35A shows an example event-based machine learning model 3513 that takes input 3510 and outputs a predicted outcome for a surgical procedure 3515. Input 3510 may include input parameters 3523, as shown in FIG. 35B, such as patient characteristics and information from a medical record as previously discussed. Further, input 3510 may include information from the postoperative surgical report that may include event data 3521, as shown in FIG. 35B. In an example embodiment, event data 3521 may include a list of events (e.g., events E1-EN), and surgical footage segments V1-VN corresponding to events E1-EN. Further, data 3521 in FIG. 35B may include event starting times T1A-TNA and finishing times T1B-TNB. Surgical footage (e.g., V1) may be a set of frames of a surgical procedure corresponding to an event (e.g., E1). In an example embodiment, for an example surgical procedure, event E1 may be a short event (e.g., incision) for which T1A and T1B may be about the same time; event E2 may be an extended time (e.g., suturing) for which T2A is the time at which the suturing started and T2B is the time at which the suturing ended; and event EN may be a process of administering medications to reverse anesthesia having corresponding starting time TNA and finishing time TNB.

In various embodiments, the event-based machine learning method may be trained using training examples, for example as described above. For example, a training example may be based on historical data. In another example, a training example may include information related to a surgical procedure (for example as described above), together with a label indicating an outcome.

Aspects disclosed embodiments may include determining a predicted outcome using the trained machine-learning model to predict surgical outcomes based on the identified intraoperative event and an identified characteristic of a patient. For instance, an intraoperative event may be "incision," and one of the identified characteristics of a patient may be "65-year-old female." In an example embodiment, identified intraoperative events and one or more identified characteristics of a patient may be used as input data for the trained machine-learning model. For example, input data may be input 3510, as shown in FIG. 35B. In some cases, besides identified intraoperative events and an identified characteristic of a patient, additional input data for the trained machine-learning model may include healthcare professional data, patient medical data, and any other suitable data that has an influence on an outcome of the surgical procedure. The event-based model may be trained, for example as described above, using various training data that may include or be based on historical events. As described above, disclosed embodiments may include using a trained machine-learning model to predict surgical outcomes. In various embodiments, the predicted surgical outcome may be a distribution of probabilities for a different set of outcomes, as shown, for example, by a plot 3201A, as shown in FIG. 33.

Aspects of embodiments for predicting post discharge risk may also include identifying a characteristic of a patient and determining a predicted outcome associated with the surgical procedure based on the identified patient characteristic. The predicted outcome associated with the surgical procedure based on the identified patient characteristic may be determined using a suitable machine-learning model, such as, for example, model 3513, as shown in FIG. 35A.

In some embodiments, an identified patient characteristic may be based on pre-operative patient data (e.g., the pre-operative blood test values, pre-operative vital signals, or any other pre-operative characteristics). Additionally or alternatively, an identified patient characteristic may be based on post-operative patient data (e.g., the post-operative blood test values, post-operative vital signals, post-operative weight, or any other post-operative characteristics).

In various embodiments, identifying the patient characteristic may include using a machine learning model to analyze frames of surgical footage. An example machine-learning model may be an image recognition algorithm, as previously described, for recognizing features within frames of the surgical video footage captured during the surgical procedure. For example, the image recognition algorithm may be used to recognize features such as the size of anatomical structures that are being operated upon, the size of a patient, the estimated age of the patient, gender of the patient, a race of the patient, or any other characteristics related to the patient. The machine-learning model for identifying the patient characteristic may be trained, for example as described above, to identify patient characteristics using training examples of historical surgical procedures (including a related historical surgical video footage) and corresponding historical patient characteristics. The training of a machine-learning method for identifying the patient characteristic may use any suitable approaches, as described above. In various embodiments, training the machine-learning method may use training examples based on historical surgical footage with labels based on output one or more patient characteristics corresponding to the historical surgical footage.

Additionally or alternatively, identifying patient characteristics may be derived from an electronic medical record. For example, the electronic medical record may be read (or parsed) using a suitable computer-based software application, and patient characteristics may be identified from the read (parsed) data. For example, if the electronic record includes "James is a 65-year-old Caucasian male with lung disease," the computer-based software application may identify patient characteristics represented by example records, such as "Age: 65," "Name: James" "Gender: Male," "Medical Condition: Lung Disease," and/or "Race: Caucasian."

Aspects of embodiments for predicting post discharge risk may also include receiving information identifying a realized surgical outcome following the surgical procedure (herein also referred to postoperative information) and updating the machine-learning model by training the machine-learning model using the received information. For example, an online machine learning algorithm and/or a reinforcement machine learning algorithm may be used to update the machine learning model based on the received information. In an example embodiment, receiving the postoperative information may include receiving visual or audio data during a physical examination following the surgical procedure, receiving lab results (e.g., blood test results, urine results, medical imaging data, or any other suitable tests) following the surgical procedure, receiving data related to patient's vital signs (e.g., a pulse of a patient, a blood pressure of the patient, or any other vital signs), and/or receiving notes from a healthcare provider (e.g., a doctor conducting a physical examination of the patient). In some cases, the received postoperative information may be used to determine the realized surgical outcome. For example, the received information may be analyzed by a healthcare provider (e.g., a doctor), and the doctor may identify the realized surgical outcome (e.g., the realized surgical outcome may include a determination by the doctor that the patient does not require any more medical intervention). Alternatively, the received postoperative information may be used by a suitable outcome-determining machine-learning model to determine the realized surgical outcome. In various embodiments, an outcome-determining machine-learning model that takes as input postoperative information may be different than a machine-learning model for predicting an outcome of the surgery based on information obtained during a surgical procedure, and other related information such as patient characteristics, healthcare provider characteristics, or a medical history of the patient, as described above.

In various embodiments, the received information may be used to determine the realized surgical outcome, and the machine-learning model for predicting surgical outcomes based on an identified intraoperative event and an identified patient characteristic may be updated by training the machine-learning method using the received information identifying a realized surgical outcome. The training of a machine-learning method may be used any suitable approaches as described above.

In some embodiments, an output of the machine-learning model for predicting surgical outcomes may be a probability of a predicted outcome. In some cases, the model may be trained by comparing the probability that is output by the model with a corresponding probability of a predicted outcome as inferred from historical surgical data (e.g., historical surgical footage data) of historical surgical procedures. For example, using various historical surgical data, a historical probability of a given outcome of a surgical procedure for a given type of a surgical procedure may be obtained. In some cases, a historical deviation (i.e., a deviation between the historical surgical procedure and a recommended sequence of events for the surgical procedure) may be used to determine how the historical deviation affects changes in the historical probability of a given outcome.

The historical probability value may be compared with a probability value returned by the machine-learning method to determine an error of the method. In various embodiments, if the predicted outcome returned by the machine-learning method is a probability or a probability vector, then the suitable measure may be a difference between the probability and the historical probability or a difference between the probability vector and the historical probability vector. For instance, the probability vector may be used to determine the probability of a predicted outcome for a set of events. For instance, if a set of predicted outcomes includes example outcomes C1-C4, such as "C1: being paralyzed," "C2: being deceased within three months," "C3: in need of blood transfusion within two weeks," "C4: requiring no medical intervention," a probability vector for an outcome vector {C1,C2,C3,C4} may be {p1,p2,p3,p4} with p1-p4 indicating probability of outcomes C1-C4.

Aspects of embodiments for predicting post discharge risk may also include outputting a predicted outcome in a manner associating the predicted outcome with the patient. In some embodiments, a process of outputting may include transmitting the predicted outcome to a receiving party. The receiving party may include one or more healthcare professionals, a patient, a family member, or any other person, organization, or data storage. A process of transmitting may include transmitting the information using any suitable electronic approach (e.g., using wired or wireless communication, as described above) to any suitable electronic device. For example, transmitting the predicted outcome may include transmitting the predicted outcome to a data-receiving device (e.g., a laptop, a smartphone, or any other suitable electronic device) associated with a health care provider. In some cases, transmitting the information may involve mailing (or delivering in person) a physical copy (e.g., a paper copy, a CD-ROM, a hard drive, a DVD, a USB drive, or any other electronic storage device) of documents detailing the predicted outcome. Additionally or alternatively, transmitting the predicted outcome may include transmitting the predicted outcome to at least one of a health insurance provider or a medical malpractice carrier.

In various embodiments, outputting the predicted outcome may be done in a manner that associates the predicted outcome with a patient. For example, a patient's name and/or any other suitable information about the patient may be listed in a document describing a predicted outcome.

In some embodiments, transmitting the predicted outcome may include updating an electronic medical record associated with the patient. A process of updating the electronic medical record may include replacing or modifying any appropriate data in the electronic medical record. For example, updating a medical record may include changing the predicted outcome from "expected to use hands and feet after two weeks of physical therapy" to "expected to be paralyzed for the rest of patient's life."

Aspects of this disclosure may include accessing a data structure containing recommended sequences of surgical events, and identifying at least one specific intraoperative event based on an identification of a deviation between a recommended sequence of events for the surgical procedure identified in the data structure, and an actual sequence of events detected in the accessed frames. A process of accessing a data structure may be performed by any suitable algorithm and/or a machine-learning model configured to identify the deviation, as discussed in this disclosure. For example, the machine-learning model may be used to access the data structure and output deviations between recommended sequences of surgical events and actual events performed during the surgery. For instance, if during an actual incision event, the incision length is shorter than an incision described by a corresponding recommended event, such deviation may be identified by the machine-learning method. The data structure containing a recommended sequence of surgical events may be any suitable data structure described herein, consistent with disclosed embodiments. For example, the data structure may be a relational database having one or more database tables. The data structure may contain a recommended sequence of events and may include names of the events, images corresponding to the events, video data related to the events, or any other suitable data that may describe the events. The data structure may define a recommended sequence of the events by assigning to each event a number associated with an order of the event in the sequence.

In various embodiments, identifying a deviation between a recommended sequence of events for the surgical procedure and an actual sequence of events may include various approaches discussed in this disclosure, for example, as described in connection with FIGS. 26-28, and related description for these figures. In an example embodiment, the events of the surgical procedure may be identified by analyzing the surgical footage of the surgical procedure as previously described. Identifying a deviation between the surgical procedure and the recommended sequence of events may include utilizing a machine-learning approach, as described in this disclosure. Identifying at least one specific intraoperative event based on an identification of the deviation may include identifying at least one actual event detected in the accessed frames that deviates from the recommended sequence of events for the surgical procedure, and such identification may be performed by the machine-learning method for identifying the deviation.

The deviation-based model may be trained using various training data that include historical deviations. In an example embodiment, a historical deviation may be determined by evaluating a deviation for a historical sequence of events of an example historical surgical procedure of a given type (e.g., bronchoscopy) and a corresponding recommended sequence of events for the surgical procedure of the same type. The deviation-based model may be trained using any suitable training process, for example as described above.

In various embodiments, identifying the deviation includes using a machine learning model trained to identify deviations from recommended sequences of events based on historical surgical video footage, historical recommended sequences of events, and information identifying deviations from the historical recommended sequences of events in the historical video footage. Using the machine-learning method for identifying the deviation based on historical surgical video footage, and historical recommended sequences of events are described herein and are not repeated in the interest of brevity.

In various embodiments, identifying the deviation includes comparing frames of a surgical procedure (e.g., frames accessed by any suitable computer-based software application or a healthcare professional for analyzing information within the frames, as discussed above) to reference frames depicting the recommended sequence of events. As previously described, the reference frames may be historical frames captured during historical surgical procedures. In an example embodiment, the video frames and the reference frames depicting the mandatory sequence of events may be synchronized by an event (herein also referred to as a starting event) that may be the same (or substantially similar) to a corresponding starting event of the mandatory (or recommended) sequence of events. In some cases, a frame depicting the beginning of the starting event may be synchronized with a reference frame depicting the starting event of the mandatory (recommended) sequence of events. In some cases, events of the surgical procedure may be first correlated to corresponding reference events of the mandatory sequence, using any suitable approaches described above (e.g., using an image recognition algorithm for recognizing events). After correlating a surgical event with corresponding reference events of the mandatory sequence, a frame depicting the start of the surgical event may be synchronized with a reference frame depicting the start of the corresponding mandatory event.

In various embodiments, identifying a deviation between the specific surgical procedure and the recommended sequence of events for the surgical procedure may be based on at least one of a detected surgical tool in accessed frames of surgical footage, a detected anatomical structure in the accessed frames, or an interaction between the detected surgical tool and the detected anatomical structure. In some cases, identifying the deviation may be based on a detected abnormal fluid leakage situation in the surgical video footage.

For example, if it is determined (e.g., using a machine-learning method, using a visual object detector, using an indication from a healthcare professional, and so forth) that the surgical tool is present in a particular anatomical region, the method may determine that deviation has occurred. In some cases, if the surgical tool is present (as identified in the surgical footage) in a particular anatomical region during a time (or a time interval) of the surgical procedure when it should not be present, the method may determine that the deviation has occurred. Alternatively, in some cases, identifying the deviation may include determining that a surgical tool is not in a particular anatomical region. For example, if during a time (or a time interval) of the surgical procedure, the surgical tool is not present in a particular anatomical region, the method may be configured to determine that the deviation has occurred.

In some cases, when it is determined (e.g., using a machine-learning method, using a visual object detector, using an indication from a healthcare professional, and so forth) that the anatomical structure is present in the surgical footage, it may further be determined that a deviation has occurred. For instance, if the anatomical structure is identified in the surgical footage during a time (or a time interval) of the surgical procedure when it should not be present, the method may determine that the deviation has occurred. Alternatively, in some cases, identifying the deviation may include determining that the anatomical structure is not present in the surgical footage. For example, if during a time (or a time interval) of the surgical procedure, the anatomical structure is not present in the surgical footage, the method may be configured to determine that the deviation has occurred.

Additionally or alternatively, identifying the deviation may include identifying an interaction between a surgical tool and an anatomical structure. A process of identifying the interaction between a surgical tool and an anatomical structure may involve analyzing frames of the surgical procedure to identify the interaction, as described above.

In various embodiments, if the interaction between a surgical tool and an anatomical structure during a surgical procedure is identified and no such interaction is recommended (or expected) for a reference surgical procedure (i.e., the surgical procedure that follows a mandatory (or recommended) sequence of events), then the method may be configured to determine that the deviation has occurred. Alternatively, if the interaction between a surgical tool and an anatomical structure is not identified (e.g., if the interaction is not present during a surgical procedure), and the interaction is recommended for a reference surgical procedure, then the method may be configured to determine that the deviation has occurred. The method may be configured to determine that there is no substantial deviation of a surgical procedure and a reference surgical procedure if an interaction between a surgical tool and an anatomical structure is present (or absent) in both the surgical procedure and the reference surgical procedure.

Aspects of the present disclosure may also involve identifying the deviation based on a detected abnormal fluid leakage situation in the surgical video footage. As described above, the abnormal fluid leakage may include bleeding, urine leakage, bile leakage, lymph leakage, or any other leakage, and may be detected (for example by a corresponding machine-learning model) as described above. For example, if the abnormal fluid leakage is detected (as identified in the surgical footage) in a particular anatomical region during a time (or a time interval) of the surgical procedure when it should not be present, the method may determine that the deviation has occurred. Alternatively, in some cases, identifying the deviation may include determining that the abnormal fluid leakage is not present in a particular anatomical region. For example, if during a time (or a time interval) of the surgical procedure, the abnormal fluid leakage is not present in a particular anatomical region, the method may be configured to determine that the deviation has occurred.

Aspects of disclosed embodiments may include determining at least one action likely to improve a predicted outcome based on accessed frames (e.g., frames of surgical footage), and providing a recommendation based on the determined at least one action. In various embodiments, determining at least one action may include using a suitable machine learning method for accessing and analyzing frames of surgical procedure. In some examples, a machine learning model may be trained using training examples to determine actions likely to improve outcomes of surgical procedures and/or the likely improvements to the outcomes based on information related to the current state of the surgical procedures. An example of such training example may include information related to a state of a particular surgical procedure, together with a label indicating an action likely to improve an outcome of the particular surgical procedure, and/or the likely improvement to the predicted outcome. Such label may be based on an analysis of historical data related to historical surgical procedures, on user input, and so forth. Some non-limiting examples of information related to a current state of a surgical procedure may include images and/or videos of the surgical procedure, information based on an analysis of images and/or videos of the surgical procedure, characteristics of the patient undergoing the surgical procedure, characteristics of a healthcare professional performing at least part of the surgical procedure, characteristics of medical instruments used in the surgical procedure, characteristics of an operating room related to the surgical procedure, intraoperative events occurred in the surgical procedure, current time, durations of surgical phases in the surgical procedure, and so forth. Further, in some examples, the trained machine learning model may be used to analyze information related to a current state of the surgical procedure, and determining the at least one action likely to improve the predicted outcome and/or the likely improvement to the predicted outcome.

Aspects of disclosed embodiments may include providing a recommendation before the particular action is performed. The recommendation may be any suitable electronic notification as described herein and consistent with disclosed embodiments. Alternatively, the recommendation may be any suitable sound signal, visual signal, or any other signal (e.g., tactile signal, such as vibration) that may be transmitted to a healthcare professional (e.g., a surgeon administering a surgical procedure).

Various disclosed embodiments may include forgoing providing a recommendation when a likely improvement to a predicted outcome due to a determined at least one action is below a selected threshold. For example, if a likelihood of improvement is below fifty percent, the recommendation may not be provided. In some cases, an improvement of a first predicted outcome may be offset by an adverse second predicted outcome, and a recommendation for improving a first predicted outcome may not be provided. For example, if a first predicted outcome is identified as "eliminating a rash for a patient" and a second predicted outcome is identified as a "cardiac arrest," then even for a sufficiently high likelihood of improvement of a first predicted outcome (e.g., ninety-nine percent chance of eliminating a rash for a patient), the recommendation may not be provided due to a second outcome of "cardiac arrest" being possible (even if possibility of the second outcome is small, e.g., one percent). Thus, selecting to provide a recommendation or forgoing to provide the recommendation may be based on one or more predicted outcomes. Further, a selected threshold may be based on one or more selected outcomes. For example, if a first outcome is an ability for a person to have a possibility of life for the next twenty years, and a second adverse outcome is a cardiac arrest, the recommendation may still be provided when the possibility of cardiac arrest is sufficiently low (e.g., lower than thirty percent). In some cases, a threshold may be selected based on a characteristic of the patient. For example, if a patient is overweight, a selected threshold for forgoing providing a recommendation for bariatric surgery may be lowered as compared to the same threshold for a less overweight person. In some cases, determining at least one action for improving a predicted outcome may be further based on a characteristic of a patient. For example, if a patient is an elderly person, a bypass procedure may not be recommended, while such a procedure may be recommended for a younger person.

Figure 36:
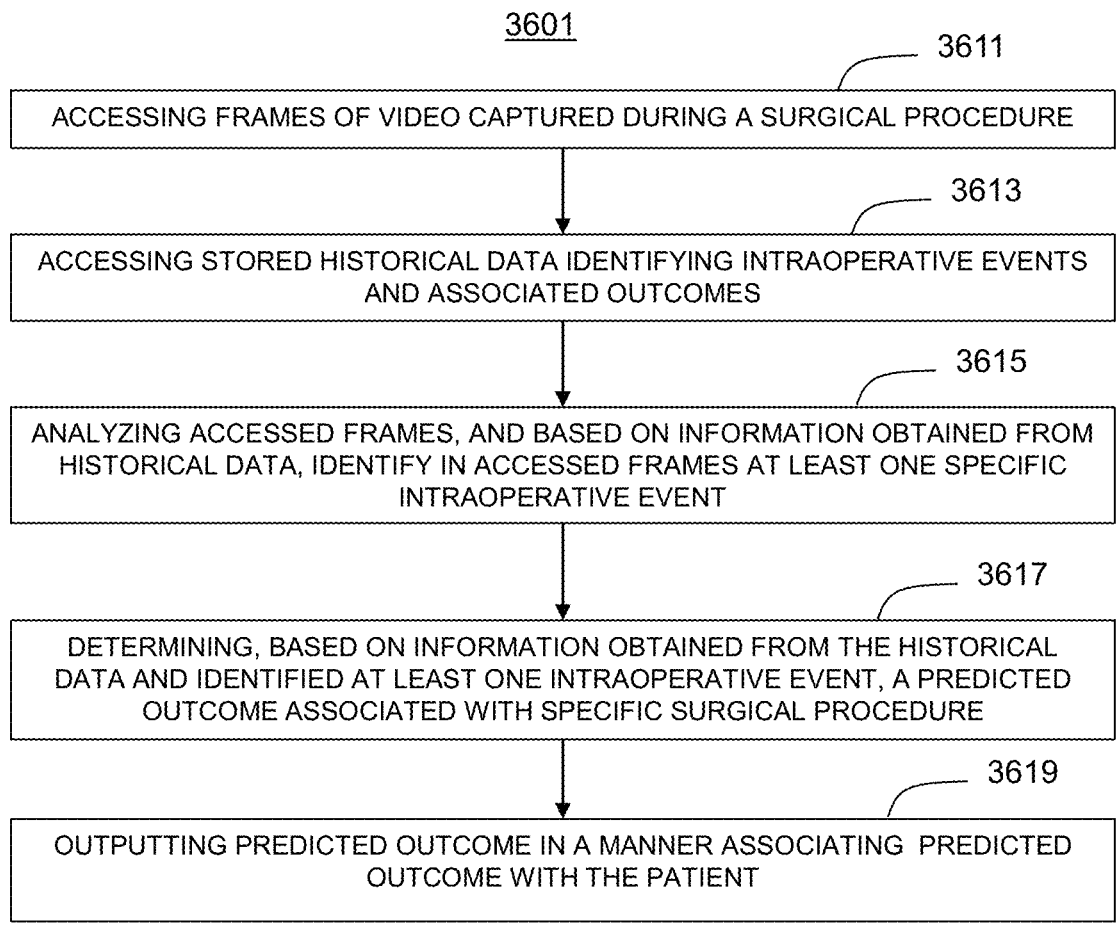
FIG. 36 shows an exemplary process for predicting post discharge risk, consistent with disclosed embodiments.

Aspects of embodiments for predicting post discharge risk are illustrated in FIG. 36 by a process 3601. At step 3611, process 3601 may include accessing frames of video captured during a specific surgical procedure on a patient using any suitable means. For example, accessing may occur via a wired or wireless network, via a machine-learning model, or via any other means for allowing reading/writing data. In some cases, accessing frames may include accessing by a healthcare professional. In such cases, the healthcare professional may use input devices (e.g., keyboard, mouse, or any other input device) for accessing the frames.

At step 3613, process 3601 may include accessing stored historical data identifying intraoperative events and associated outcomes, as described above. At step 3615, process 3601 may include analyzing accessed frames (e.g., frames of surgical footage), and based on information obtained from the historical data, identify in the accessed frames at least one specific intraoperative event. A process of analyzing the accessed frames and identifying in the accessed frames a specific intraoperative event may be performed by a suitable machine-learning model as described above.

At step 3617, process 3601 may include determining, based on information obtained from the historical data and the identified at least one intraoperative event, a predicted outcome associated with the specific surgical procedure, as described above. Process 3601 may conclude with step 3619 for outputting the predicted outcome in a manner associating the predicted outcome with the patient, as previously described.

It should be noted that process 3601 is not limited to steps 3611-3619, and new steps may be added, or some of steps 3611-3619 may be replaced or omitted. For example, step 3613 may be omitted.

As previously discussed, the present disclosure relates to a method and a system for predicting post discharge risk, as well as a non-transitory computer-readable medium that may include instructions that, when executed by at least one processor, cause the at least one processor to execute operations enabling predicting post-discharge risk.

Disclosed embodiments may include any one of the following bullet-pointed features alone or in combination with one or more other bullet-pointed features, whether implemented as a method, by at least one processor, and/or stored as executable instructions on non-transitory computer-readable media:
- accessing at least one video of a surgical procedure
- causing the at least one video to be output for display
- overlaying on the at least one video outputted for display a surgical timeline, wherein the surgical timeline includes markers identifying at least one of a surgical phase, an intraoperative surgical event, and a decision making junction
- enabling a surgeon, while viewing playback of the at least one video to select one or more markers on the surgical timeline, and thereby cause a display of the video to skip to a location associated with the selected marker
- wherein the markers are coded by at least one of a color or a criticality level
- wherein the surgical timeline includes textual information identifying portions of the surgical procedure
- wherein the at least one video includes a compilation of footage from a plurality of surgical procedures, arranged in procedural chronological order
- wherein the compilation of footage depicts complications from the plurality of surgical procedures wherein the one or more markers are associated with the plurality of surgical procedures and are displayed on a common timeline
wherein the one or more markers include a decision making junction marker corresponding to a decision making junction of the surgical procedure
wherein the selection of the decision making junction marker enables the surgeon to view two or more alternative video clips from two or more corresponding other surgical procedures
wherein the two or more video clips present differing conduct
wherein the one or more markers include a decision making junction marker corresponding to a decision making junction of the surgical procedure
wherein the selection of the decision making junction marker causes a display of one or more alternative possible decisions related to the selected decision making junction marker
wherein one or more estimated outcomes associated with the one or more alternative possible decisions are displayed in conjunction with the display of the one or more alternative possible decisions
wherein the one or more estimated outcomes are a result of an analysis of a plurality of videos of past surgical procedures including respective similar decision making junctions
wherein information related to a distribution of past decisions made in respective similar past decision making junctions are displayed in conjunction with the display of the alternative possible decisions
wherein the decision making junction of the surgical procedure is associated with a first patient, and the respective similar past decision making junctions are selected from past surgical procedures associated with patients with similar characteristics to the first patient
wherein the decision making junction of the surgical procedure is associated with a first medical professional, and the respective similar past decision making junctions are selected from past surgical procedures associated with medical professionals with similar characteristics to the first medical professional
wherein the decision making junction of the surgical procedure is associated with a first prior event in the surgical procedure, and the similar past decision making junctions are selected from past surgical procedures including prior events similar to the first prior event
wherein the markers include intraoperative surgical event markers
wherein selection of an intraoperative surgical event marker enables the surgeon to view alternative video clips from differing surgical procedures
wherein the alternative video clips present differing ways in which a selected intraoperative surgical event was handled
wherein the overlay on the video output is displayed before the end of the surgical procedure depicted in the displayed video
wherein the analysis is based on one or more electronic medical records associated with the plurality of videos of past surgical procedures
wherein the respective similar decision making junctions are similar to the decision making junction of the surgical procedure according to a similarity metric
wherein the analysis includes usage of an implementation of a computer vision algorithm
wherein the markers relate to intraoperative surgical events and the selection of an intraoperative surgical event marker enables the surgeon to view alternative video clips from differing surgical procedures
accessing video footage to be indexed, the video footage to be indexed including footage of a particular surgical procedure
analyzing the video footage to identify a video footage location associated with a surgical phase of the particular surgical procedure
generating a phase tag associated with the surgical phase
associating the phase tag with the video footage location
analyzing the video footage to identify an event location of a particular intraoperative surgical event within the surgical phase
associating an event tag with the event location of the particular intraoperative surgical event
storing an event characteristic associated with the particular intraoperative surgical event
associating at least a portion of the video footage of the particular surgical procedure with the phase tag, the event tag, and the event characteristic in a data structure that contains additional video footage of other surgical procedures
wherein the data structure also includes respective phase tags, respective event tags, and respective event characteristics associated with one or more of the other surgical procedures
enabling a user to access the data structure through selection of a selected phase tag, a selected event tag, and a selected event characteristic of video footage for display
performing a lookup in the data structure of surgical video footage matching the at least one selected phase tag, selected event tag, and selected event characteristic to identify a matching subset of stored video footage
causing the matching subset of stored video footage to be displayed to the user, to thereby enable the user to view surgical footage of at least one intraoperative surgical event sharing the selected event characteristic, while omitting playback of video footage lacking the selected event characteristic
wherein enabling the user to view surgical footage of at least one intraoperative surgical event that has the selected event characteristic, while omitting playback of portions of selected surgical events lacking the selected event characteristic, includes sequentially presenting to the user portions of surgical footage of a plurality of intraoperative surgical events sharing the selected event characteristic, while omitting playback of portions of selected surgical events lacking the selected event characteristic
wherein the stored event characteristic includes an adverse outcome of the surgical event
wherein causing the matching subset to be displayed includes enabling the user to view surgical footage of a selected adverse outcome while omitting playback of surgical events lacking the selected adverse outcome
wherein the stored event characteristic includes a surgical technique
wherein causing the matching subset to be displayed includes enabling the user to view surgical footage of a selected surgical technique while omitting playback of surgical footage not associated with the selected surgical technique
wherein the stored event characteristic includes a surgeon skill level wherein causing the matching subset to be displayed includes enabling the user to view footage exhibiting a selected surgeon skill level while omitting playback of footage lacking the selected surgeon skill level wherein the stored event characteristic includes a physical patient characteristic wherein causing the matching subset to be displayed includes enabling the user to view footage exhibiting a selected physical patient characteristic while omitting playback of footage lacking the selected physical patient characteristic wherein the stored event characteristic includes an identity of a specific surgeon wherein causing the matching subset to be displayed includes enabling the user to view footage exhibiting an activity by a selected surgeon while omitting playback of footage lacking activity by the selected surgeon wherein the stored event characteristic includes physiological response wherein causing the matching subset to be displayed includes enabling the user to view footage exhibiting a selected physiological response while omitting playback of footage lacking the selected physiological response wherein analyzing the video footage to identify the video footage location associated with at least one of the surgical event or the surgical phase includes performing computer image analysis on the video footage to identify at least one of a beginning location of the surgical phase for playback or a beginning of a surgical event for playback accessing aggregate data related to a plurality of surgical procedures similar to the particular surgical procedure presenting to the user statistical information associated with the selected event characteristic wherein the accessed video footage includes video footage captured via at least one image sensor located in at least one of a position above an operating table, in a surgical cavity of a patient, within an organ of a patient or within vasculature of a patient wherein identifying the video footage location is based on user input wherein identifying the video footage location includes using computer analysis to analyze frames of the video footage wherein the computer image analysis includes using a neural network model trained using example video frames including previously-identified surgical phases to thereby identify at least one of a video footage location or a phase tag determining the stored event characteristic based on user input determining the stored event characteristic based on a computer analysis of video footage depicting the particular intraoperative surgical event wherein generating the phase tag is based on a computer analysis of video footage depicting the surgical phase wherein identifying a matching subset of stored video footage includes using computer analysis to determine a degree of similarity between the matching subset of stored video and the selected event characteristic accessing particular surgical footage containing a first group of frames associated with at least one intraoperative surgical event and a second group of frames not associated with surgical activity accessing historical data based on historical surgical footage of prior surgical procedures, wherein the historical data includes information that distinguishes portions of surgical footage into frames associated with intraoperative surgical events and frames not associated with surgical activity distinguishing in the particular surgical footage the first group of frames from the second group of frames based on the information of the historical data upon request of a user, presenting to the user an aggregate of the first group of frames of the particular surgical footage, while omitting presentation to the user of the second group of frames wherein the information that distinguishes portions of the historical surgical footage into frames associated with an intraoperative surgical event includes an indicator of at least one of a presence or a movement of a surgical tool wherein the information that distinguishes portions of the historical surgical footage into frames associated with an intraoperative surgical event includes detected tools and anatomical features in associated frames wherein the request of the user includes an indication of at least one type of intraoperative surgical event of interest, and wherein the first group of frames depicts at least one intraoperative surgical event of the at least one type of intraoperative surgical event of interest wherein the request of the user includes a request to view a plurality of intraoperative surgical events in the particular surgical footage, and wherein presenting to the user an aggregate of the first group of frames includes displaying the first group frames in chronological order with chronological frames of the second group omitted wherein the historical data further includes historical surgical outcome data and respective historical cause data wherein the first group of frames includes a cause set of frames and an outcome set of frames wherein the second group of frames includes an intermediate set of frames analyzing the particular surgical footage to identify a surgical outcome and a respective cause of the surgical outcome, the identifying being based on the historical outcome data and respective historical cause data detecting, based on the analyzing, the outcome set of frames in the particular surgical footage, the outcome set of frames being within an outcome phase of the surgical procedure detecting, based on the analyzing, a cause set of frames in the particular surgical footage, the cause set of frames being within a cause phase of the surgical procedure remote in time from the outcome phase wherein the intermediate set of frames is within an intermediate phase interposed between the cause set of frames and the outcome set of frames generating a cause-effect summary of the surgical footage wherein the cause-effect summary includes the cause set of frames and the outcome set of frames and omits the intermediate set of frames wherein the aggregate of the first group of frames presented to the user includes the cause-effect summary wherein the cause phase includes a surgical phase in which the cause occurred wherein the cause set of frames is a subset of the frames in the cause phase wherein the outcome phase includes a surgical phase in which the outcome is observable wherein the outcome set of frames is a subset of frames in the outcome phase using a machine learning model trained to identify surgical outcomes and respective causes of the surgical outcomes using the historical data to analyze the particular surgical footage wherein the particular surgical footage depicts a surgical procedure performed on a patient and captured by at least one image sensor in an operating room exporting the first group of frames for storage in a medical record of the patient generating an index of the at least one intraoperative surgical event, and exporting the first group of frames includes generating a compilation of the first group of frames, the compilation including the index and being configured to enable viewing of the at least one intraoperative surgical event based on a selection of one or more index items wherein the compilation contains a series of frames of differing intraoperative events stored as a continuous video associating the first group of frames with a unique patient identifier and updating a medical record including the unique patient identifier wherein a location of the at least one image sensor is at least one of above an operating table in the operating room or within the patient wherein distinguishing in the particular surgical footage the first group of frames from the second group of frames includes: analyzing the particular surgical footage to detect a medical instrument analyzing the particular surgical footage to detect an anatomical structure analyzing the video to detect a relative movement between the detected medical instrument and the detected anatomical structure distinguishing the first group of frames from the second group of frames based on the relative movement wherein the first group of frames includes surgical activity frames and the second group of frames includes non-surgical activity frames wherein presenting the aggregate thereby enables a surgeon preparing for surgery to omit the non-surgical activity frames during a video review of the abridged presentation wherein distinguishing the first group of frames from the second group of frames is further based on a detected relative position between the medical instrument and the anatomical structure wherein distinguishing the first group of frames from the second group of frames is further based on a detected interaction between the medical instrument and the anatomical structure wherein omitting the non-surgical activity frames includes omitting a majority of frames that capture non-surgical activity accessing a repository of a plurality of sets of surgical video footage reflecting a plurality of surgical procedures performed on differing patients and including intraoperative surgical events, surgical outcomes, patient characteristics, surgeon characteristics, and intraoperative surgical event characteristics enabling a surgeon preparing for a contemplated surgical procedure to input case-specific information corresponding to the contemplated surgical procedure comparing the case-specific information with data associated with the plurality of sets of surgical video footage to identify a group of intraoperative events likely to be encountered during the contemplated surgical procedure using the case-specific information and the identified group of intraoperative events likely to be encountered to identify specific frames in specific sets of the plurality of sets of surgical video footage corresponding to the identified group of intraoperative events wherein the identified specific frames include frames from the plurality of surgical procedures performed on differing patients determining that a first set and a second set of video footage from differing patients contain frames associated with intraoperative events sharing a common characteristic omitting an inclusion of the second set from a compilation to be presented to the surgeon and including the first set in the compilation to be presented to the surgeon enabling the surgeon to view a presentation including the compilation containing frames from the differing surgical procedures performed on differing patients enabling a display of a common surgical timeline including one or more chronological markers corresponding to one or more of the identified specific frames along the presentation wherein enabling the surgeon to view the presentation includes sequentially displaying discrete sets of video footage of the differing surgical procedures performed on differing patients wherein sequentially displaying discrete sets of video footage includes displaying an index of the discrete sets of video footage enabling the surgeon to select one or more of the discrete sets of video footage wherein the index includes a timeline parsing the discrete sets into corresponding surgical phases and textual phase indicators wherein the timeline includes an intraoperative surgical event marker corresponding to an intraoperative surgical event wherein the surgeon is enabled to click on the intraoperative surgical event marker to display at least one frame depicting the corresponding intraoperative surgical event wherein the case-specific information corresponding to the contemplated surgical procedure is received from an external device wherein comparing the case-specific information with data associated with the plurality of sets of surgical video footage includes using an artificial neural network to identify the group of intraoperative events likely to be encountered during the contemplated surgical procedure wherein using the artificial neural network includes providing the case-specific information to the artificial neural network as an input wherein the case-specific information includes a characteristic of a patient associated with the contemplated procedure wherein the characteristic of the patient is received from a medical record of the patient wherein the case-specific information includes information relating to a surgical tool where the information relating to the surgical tool includes at least one of a tool type or a tool model wherein the common characteristic includes a characteristic of the differing patients wherein the common characteristic includes an intraoperative surgical event characteristic of the contemplated surgical procedure wherein determining that a first set and a second set of video footage from differing patients contain frames associated with intraoperative events sharing a common characteristic includes using an implementation of a machine learning model to identify the common characteristic using example video footage to train the machine learning model to determine whether two sets of video footage share the common characteristic wherein implementing the machine learning model includes implementing the trained machine learning model training a machine learning model to generate an index of the repository based on the intraoperative surgical events, the surgical outcomes, the patient characteristics, the surgeon characteristics, and the intraoperative surgical event characteristic generating the index of the repository wherein comparing the case-specific information with data associated with the plurality of sets includes searching the index analyzing frames of the surgical footage to identify in a first set of frames an anatomical structure accessing first historical data, the first historical data being based on an analysis of first frame data captured from a first group of prior surgical procedures analyzing the first set of frames using the first historical data and using the identified anatomical structure to determine a first surgical complexity level associated with the first set of frames analyzing frames of the surgical footage to identify in a second set of frames a medical tool, the anatomical structure, and an interaction between the medical tool and the anatomical structure accessing second historical data, the second historical data being based on an analysis of a second frame data captured from a second group of prior surgical procedures analyzing the second set of frames using the second historical data and using the identified interaction to determine a second surgical complexity level associated with the second set of frames wherein determining the first surgical complexity level further includes identifying in the first set of frames a medical tool wherein determining the second surgical complexity level is based on time elapsed from the first set of frames to the second set of frames wherein at least one of determining the first complexity level or second complexity level is based on a physiological response determining a level of skill demonstrated by a healthcare provider in the surgical footage wherein at least one of determining the first complexity level or second complexity level is based on the determined level of skill demonstrated by the healthcare provider determining that the first surgical complexity level is less than a selected threshold, determining that the second surgical complexity level exceeds the selected threshold, and in response to the determination that the first surgical complexity level is less than the selected threshold and the determination that the second surgical complexity level exceeds the selected threshold, storing the second set of frames in a data structure while omitting the first set of frames from the data structure wherein identifying the anatomical structure in the first set of frames is based on an identification of a medical tool and a first interaction between the medical tool and the anatomical structure tagging the first set of frames with the first surgical complexity level tagging the second set of frames with the second surgical complexity level generating a data structure including the first set of frames with the first tag and the second set of frames with the second tag to enable a surgeon to select the second surgical complexity level, and thereby cause the second set of frames to be displayed, while omitting a display of the first set of frames using a machine learning model trained to identify surgical complexity levels using frame data captured from prior surgical procedures to determine at least one of the first surgical complexity level or the second surgical complexity level wherein determining the second surgical complexity level is based on an event that occurred between the first set of frames and the second set of frames wherein determining at least one of the first surgical complexity level or the second surgical complexity level is based on a condition of the anatomical structure wherein determining at least one of the first surgical complexity level or the second surgical complexity level is based on an analysis of an electronic medical record wherein determining the first surgical complexity level is based on an event that occurred after the first set of frames wherein determining at least one of the first surgical complexity level or the second surgical complexity level is based on a skill level of a surgeon associated with the surgical footage wherein determining the second surgical complexity level is based on an indication that an additional surgeon was called after the first set of frames wherein determining the second surgical complexity level is based on an indication that a particular medicine was administered after the first set of frames wherein the first historical data includes a machine learning model trained using the first frame data captured from the first group of prior surgical procedures wherein the first historical data includes an indication of a statistical relation between a particular anatomical structure and a particular surgical complexity level receiving, from an image sensor positioned in a surgical operating room, visual data tracking an ongoing surgical procedure accessing a data structure containing information based on historical surgical data analyzing the visual data of the ongoing surgical procedure using the data structure to determine an estimated completion time of the ongoing surgical procedure accessing a schedule for the surgical operating room including a scheduled time associated with completion of the ongoing surgical procedure calculating, based on the estimated completion time of the ongoing surgical procedure, whether an expected time of completion is likely to result in variance from the scheduled time associated with the completion outputting a notification upon calculation of the variance, to thereby enable subsequent users of the surgical operating room to adjust their schedules accordingly wherein the notification includes an updated operating room schedule wherein the updated operating room schedule enables a queued healthcare professional to prepare for a subsequent surgical procedure electronically transmitting the notification to a device associated with a subsequent scheduled user of the surgical operating room determining an extent of the variance from the scheduled time associated with the completion in response to a first determined extent, outputting the notification in response to a second determined extent, forgoing outputting the notification determining whether the expected time of completion is likely to result in a delay of at least a selected threshold amount of time from the scheduled time associated with the completion in response to a determination that the expected time of completion is likely to result in a delay of at least the selected threshold amount of time, outputting the notification in response to a determination that the expected time of completion is not likely to result in a delay of at least the selected threshold amount of time, forgoing outputting the notification wherein the determining the estimated completion time is based on one or more stored characteristics associated with a healthcare professional conducting the ongoing surgical procedure updating a historical average time to completion based on determined actual time to complete the ongoing surgical procedure wherein the image sensor is positioned above a patient wherein the image sensor is positioned on a surgical tool wherein analyzing further includes detecting a characteristic event in the received visual data, assessing the information based on historical surgical data to determine an expected time to complete the surgical procedure following an occurrence of the characteristic event in the historical surgical data, and determining the estimated completion time based on the determined expected time to complete using historical visual data to train a machine learning model to detect the characteristic event using historical visual data to train a machine learning model to estimate completion times wherein calculating the estimated completion time includes implementing the trained machine learning model trained using average historical completion times to determine the estimated completion time detecting a medical tool in the visual data wherein calculating the estimated completion time is based on the detected medical tool wherein analyzing further includes detecting an anatomical structure in the visual data wherein calculating the estimated completion time is based on the detected anatomical structure wherein analyzing further includes detecting an interaction between an anatomical structure and a medical tool in the visual data wherein calculating the estimated completion time is based on the detected interaction wherein analyzing further includes determining a skill level of a surgeon in the visual data wherein calculating the estimated completion time is based on the determined skill level accessing video frames captured during a surgical procedure on a patient analyzing the video frames captured during the surgical procedure to identify in the video frames at least one medical instrument, at least one anatomical structure, and at least one interaction between the at least one medical instrument and the at least one anatomical structure accessing a database of reimbursement codes correlated to medical instruments, anatomical structures, and interactions between medical instruments and anatomical structures comparing the identified at least one interaction between the at least one medical instrument and the at least one anatomical structure with information in the database of reimbursement codes to determine at least one reimbursement code associated with the surgical procedure outputting the at least one reimbursement code for use in obtaining an insurance reimbursement for the surgical procedure wherein the at least one reimbursement code outputted includes a plurality of outputted reimbursement codes wherein at least two of the plurality of outputted reimbursement codes are based on differing interactions with a common anatomical structure wherein the at least two outputted reimbursement codes are determined based in part on detection of two differing medical instruments wherein determining the at least one reimbursement code is also based on an analysis of a postoperative surgical report wherein the video frames are captured from an image sensor positioned above the patient wherein the video frames are captured from an image sensor associated with a medical device updating the database by associating the at least one reimbursement code with the surgical procedure generating correlations between processed reimbursement codes and at least one of a plurality of medical instruments in historical video footage, a plurality of anatomical structures in the historical video footage, or a plurality of interactions between medical instruments and anatomical structures in the historical video footage updating the database based on the generated correlations wherein generating correlations includes implementing a statistical model using a machine learning model to detect, in the historical video footage, the at least one plurality of medical instruments, plurality of anatomical structures, or plurality of interactions between medical instruments and anatomical structures analyzing the video frames captured during the surgical procedure to determine a condition of an anatomical structure of the patient determining the at least one reimbursement code associated with the surgical procedure based on the determined condition of the anatomical structure analyzing the video frames captured during the surgical procedure to determine a change in a condition of an anatomical structure of the patient during the surgical procedure determining the at least one reimbursement code associated with the surgical procedure based on the determined change in the condition of the anatomical structure analyzing the video frames captured during the surgical procedure to determine a usage of a particular medical device determining the at least one reimbursement code associated with the surgical procedure based on the determined usage of the particular medical device analyzing the video frames captured during the surgical procedure to determine a type of usage of the particular medical device in response to a first determined type of usage, determining at least a first reimbursement code associated with the surgical procedure in response to a second determined type of usage, determining at least a second reimbursement code associated with the surgical procedure, the at least a first reimbursement code differing from the at least a second reimbursement code receiving a processed reimbursement code associated with the surgical procedure, and updating the database based on the processed reimbursement code wherein the processed reimbursement code differs from a corresponding reimbursement code of the at least one reimbursement codes analyzing the video frames captured during the surgical procedure to determine an amount of a medical supply of a particular type used in the surgical procedure determining the at least one reimbursement code associated with the surgical procedure based on the determined amount receiving an input of an identifier of a patient receiving an input of an identifier of a health care provider receiving an input of surgical footage of a surgical procedure performed on the patient by the health care provider analyzing a plurality of frames of the surgical footage to derive image-based information for populating a post-operative report of the surgical procedure causing the derived image-based information to populate the post-operative report of the surgical procedure analyzing the surgical footage to identify one or more phases of the surgical procedure and to identify a property of at least one phase of the identified phases wherein the derived image-based information is based on the identified at least one phase and the identified property of the at least one phase analyzing the surgical footage to associate a name with the at least one phase wherein the derived image-based information includes the name associated with the at least one phase determining at least a beginning of the at least one phase wherein the derived image-based information is based on the determined beginning associating a time marker with the at least one phase wherein the derived image-based information includes the time marker associated with the at least one phase transmitting data to the health care provider, the transmitted data including the patient identifier and the derived image-based information analyzing the surgical footage to identify at least one recommendation for post-operative treatment providing the identified at least one recommendation wherein the caused populating of the post-operative report of the surgical procedure is configured to enable the health care provider to alter at least part of the derived image-based information in the post-operative report wherein the caused populating of the post-operative report of the surgical procedure is configured to cause at least part of the derived image-based information to be identified in the post-operative report as automatically generated data analyzing the surgical footage to identify a surgical event within the surgical footage and to identify a property of the identified surgical event wherein the derived image-based information is based on the at identified surgical event and the identified property analyzing the surgical footage to determine an event name of the identified surgical event wherein the derived image-based information includes the determined event name associating a time marker with the identified surgical event wherein the derived image-based information includes the time marker providing the derived image-based information in a form enabling updating of an electronic medical record wherein the derived image-based information is based in part on user input wherein the derived image-based information includes a first part associated with a first portion of the surgical procedure and a second part associated with a second portion of the surgical procedure, and further including:

receiving a preliminary post-operative report analyzing the preliminary post-operative report to select a first position and a second position within the preliminary post-operative report, the first position is associated with the first portion of the surgical procedure and the second position is associated with the second portion of the surgical procedure causing the first part of the derived image-based information to be inserted at the selected first position and the second part of the derived image-based information to be inserted at the selected second position analyzing the surgical footage to select at least part of at least one frame of the surgical footage causing the selected at least part of at least one frame of the surgical footage to be included in the post-operative report of the surgical procedure receiving a preliminary post-operative report analyzing the preliminary post-operative report and the surgical footage to select the at least part of at least one frame of the surgical footage receiving a preliminary post-operative report analyzing the preliminary post-operative report and the surgical footage to identify at least one inconsistency between the preliminary post-operative report and the surgical footage providing an indication of the identified at least one inconsistency accessing frames of video captured during a specific surgical procedure accessing stored data identifying a recommended sequence of events for the surgical procedure comparing the accessed frames with the recommended sequence of events to identify an indication of a deviation between the specific surgical procedure and the recommended sequence of events for the surgical procedure determining a name of an intraoperative surgical event associated with the deviation providing a notification of the deviation including the name of the intraoperative surgical event associated with the deviation
wherein identifying the indication of the deviation and providing the notification occurs in real time during the surgical procedure
receiving an indication that a particular action is about to occur in the specific surgical procedure
identifying, using the recommended sequence of events, a preliminary action to the particular action
determining, based on an analysis of the accessed frames, that the identified preliminary action did not yet occurred
in response to the determination that the identified preliminary action did not yet occur identifying the indication of the deviation
wherein the specific surgical procedure is a cholecystectomy
wherein the recommended sequence of events is based on a critical view of safety
wherein the specific surgical procedure is an appendectomy
wherein the specific surgical procedure is a hernia repair
wherein the specific surgical procedure is a hysterectomy
wherein the specific surgical procedure is a radical prostatectomy
wherein the specific surgical procedure is a partial nephrectomy, and the deviation includes neglecting to identify a renal hilum
wherein the specific surgical procedure is a thyroidectomy, and the deviation includes neglecting to identify a recurrent laryngeal nerve
identifying a set of frames associated with the deviation
wherein providing the notification includes displaying the identified set of frames associated with the deviation
wherein the indication that the particular action is about to occur is based on an input from a surgeon performing the specific surgical procedure
wherein the indication that the particular action is about to occur is an entrance of a particular medical instrument to a selected region of interest
wherein identifying the deviation includes determining that a surgical tool is in a particular anatomical region
wherein the specific surgical procedure is a hemicolectomy
wherein the deviation includes neglecting to perform an anastomosis
where identifying the indication of the deviation is based on an elapsed time associated with an intraoperative surgical procedure
receiving video footage of a surgical procedure performed by a surgeon on a patient in an operating room
accessing at least one data structure including image-related data characterizing surgical procedures
analyzing the received video footage using the image-related data to determine an existence of a surgical decision making junction
accessing, in the at least one data structure, a correlation between an outcome and a specific action taken at the decision making junction
based on the determined existence of the decision making junction and the accessed correlation, outputting a recommendation to a user to undertake the specific action
wherein the instructions are configured to cause the at least one processor to execute the operations in real time during the surgical procedure
wherein the user is the surgeon
wherein the decision making junction is determined by an analysis of a plurality of differing historical procedures where differing courses of action occurred following a common surgical situation
wherein the video footage includes images from at least one of an endoscope and an intracorporeal camera
wherein the recommendation includes a recommendation to conduct a medical test
receiving a result of the medical test
based on the determined existence of the decision making junction, the accessed correlation and the received result of the medical test, outputting a second recommendation to the user to undertake a particular action
wherein the specific action includes brining an additional surgeon to the operating room
wherein the decision making junction includes at least one of inappropriate access or exposure, retraction of an anatomical structure, misinterpretation of an anatomical structure or a fluid leak
wherein the recommendation includes a confidence level that a desired surgical outcome will occur if the specific action is taken
wherein the recommendation includes a confidence level that a desired outcome will not occur if the specific action is not taken
wherein the recommendation is based on time elapsed since a particular point in the surgical procedure
wherein the recommendation includes an indication of an undesired surgical outcome likely to occur if the specific action is not undertaken
wherein the recommendation is based on a skill level of the surgeon
wherein the recommendation is based on a surgical event that occurred in the surgical procedure prior to the decision making junction
wherein the specific action includes a plurality of steps
wherein the determination of the existence of the surgical decision making junction is based on at least one of a detected physiological response of an anatomical structure and a motion associated with a surgical tool
receiving a vital sign of the patient and
wherein the recommendation is based on the accessed correlation and the vital sign
wherein the surgeon is a surgical robot and the recommendation is provided in the form of an instruction to the surgical robot
wherein the recommendation is based on a condition of a tissue of the patient
wherein the recommendation of the specific action includes a creation of a stoma
receiving, from at least one image sensor in an operating room, image data of a surgical procedure
analyzing the received image data to determine an identity of an anatomical structure and to determine a condition of the anatomical structure as reflected in the image data
selecting a contact force threshold associated with the anatomical structure, the selected contact force threshold being based on the determined condition of the anatomical structure
receiving an indication of actual contact force on the anatomical structure
comparing the indication of actual contact force with the selected contact force threshold outputting a notification based on a determination that the indication of actual contact force exceeds the selected contact force threshold
wherein the contact force threshold is associated with a tension level
wherein the contact force threshold is associated with a compression level
wherein the actual contact force is associated with a contact between a medical instrument and the anatomical structure
wherein the indication of actual contact force is estimated based on an image analysis of the image data
wherein outputting the notification includes providing a real time warning to a surgeon conducting the surgical procedure
wherein the notification is an instruction to a surgical robot
determining from the image data that the surgical procedure is in a fight mode
wherein the notification is suspended during the fight mode
determining from the image data that the surgeon is operating in a mode ignoring contact force notifications, and suspending at least temporarily, further contact force notifications based on the determination that the surgeon is operating in the mode ignoring contact force notifications
wherein selecting the contact force threshold is based on a location of contact between the anatomical structure and a medical instrument
wherein selecting the contact force threshold is based on an angle of contact between the anatomical structure and a medical instrument
wherein selecting the contact force threshold includes providing the condition of the anatomical structure to a regression model as an input, and selecting the contact force threshold based on an output of the regression model
wherein selecting the contact force threshold is based on a table of anatomical structures including corresponding contact force thresholds
wherein selecting the contact force threshold is based on actions performed by a surgeon
wherein the indication of actual contact force is received from a surgical tool
wherein the indication of actual contact force is received from a surgical robot
using a machine learning model trained using training examples to determine the condition of the anatomical structure in the image data
using a machine learning model trained using training examples to select the contact force threshold
receiving, from at least one image sensor arranged to capture images of a surgical procedure, image data associated with a first event during the surgical procedure
determining, based on the received image data associated with the first event, a predicted outcome associated with the surgical procedure
receiving, from at least one image sensor arranged to capture images of a surgical procedure, image data associated with a second event during the surgical procedure
determining, based on the received image data associated with the second event, a change in the predicted outcome, causing the predicted outcome to drop below a threshold
accessing a data structure of image-related data based on prior surgical procedures
identifying, based on the accessed image-related data, a recommended remedial action
outputting the recommended remedial action
wherein the recommended remedial action includes a recommendation for a surgeon to take a break from the surgical procedure
wherein the recommended remedial action includes a recommendation to request assistance from another surgeon
wherein the recommended remedial action includes a revision to the surgical procedure
wherein the predicted outcome includes a likelihood of hospital readmission
wherein determining the change in the predicted outcome is based on a magnitude of bleeding
wherein identifying the remedial action is based on an indication that the remedial action is likely to raise the predicted outcome above the threshold
wherein identifying the remedial action includes using a machine learning model trained to identify remedial actions using historical examples of remedial actions and surgical outcomes
wherein determining the predicted outcome includes using a machine learning model trained to determine predicted outcomes based on historical surgical videos and information indicating surgical outcome corresponding to the historical surgical videos
wherein determining the predicted outcome includes identifying an interaction between a surgical tool and an anatomical structure, and determining the predicted outcome based on the identified interaction
wherein determining the predicted outcome is based on a skill level of a surgeon depicted in the image data
determining a skill level of a surgeon depicted in the image data
wherein determining the change in the predicted outcome is based on the skill level
further including, in response to the predicted outcome dropping below a threshold, updating a scheduling record associated with a surgical room related to the surgical procedure
wherein determining the change in the predicted outcome is based on a time elapsed between a particular point in the surgical procedure and the second event
wherein determining the predicted outcome is based on a condition of an anatomical structure depicted in the image data
determining the condition of the anatomical structure
wherein determining the change in the predicted outcome is based on a change of a color of at least part of the anatomical structure
wherein determining the change in the predicted outcome is based on a change of appearance of at least part of the anatomical structure
receiving in real time, intracavitary video of a surgical procedure
analyzing frames of the intracavitary video to determine an abnormal fluid leakage situation in the intracavitary video
instituting a remedial action when the abnormal fluid leakage situation is determined
wherein the fluid includes at least one of blood, bile or urine wherein analyzing includes analyzing the frames of the intracavitary video to identify a blood splash and at least one property of the blood splash wherein a selection of the remedial action depends on the at least one property of the identified blood splash wherein the at least one property is associated with a source of the blood splash wherein the at least one property is associated with an intensity of the blood splash wherein the at least one property is associated with a volume of the blood splash wherein analyzing the frames of the intracavitary video includes determining a property of the abnormal fluid leakage situation wherein a selection of the remedial action depends on the determined property wherein the property is associated with a volume of the fluid leakage wherein the property is associated with a color of the fluid leakage wherein the property is associated with a type of fluid associated with the fluid leakage wherein the property is associated with a fluid leakage rate storing the intracavitary video, and, upon determining the abnormal leakage situation, analyzing prior frames of the stored intracavitary video to determine a leakage source wherein instituting the remedial action includes providing a notification of a leakage source wherein determining the leakage source includes identifying a ruptured anatomical organ determining a flow rate associated with the fluid leakage situation wherein instituting the remedial action is based on the flow rate determining a volume of fluid loss associated with the fluid leakage situation wherein instituting the remedial action is based on the volume of fluid loss wherein analyzing frames of intracavitary video to determine an abnormal fluid leakage situation in intracavitary video includes determining whether the determined fluid leakage situation is an abnormal fluid leakage situation, and in response to a determination that the determined fluid leakage situation is an abnormal fluid leakage situation, instituting the remedial action in response to a determination that the determined fluid leakage situation is normal fluid leakage situation, forgoing institution of the remedial action wherein the intracavitary video depicts a surgical robot performing the surgical procedure, and the remedial action includes sending instructions to the robot accessing frames of video captured during a specific surgical procedure on a patient accessing stored historical data identifying intraoperative events and associated outcomes analyzing the accessed frames, and based on information obtained from the historical data, identifying in the accessed frames at least one specific intraoperative event determining, based on information obtained from the historical data and the identified at least one intraoperative event, a predicted outcome associated with the specific surgical procedure outputting the predicted outcome in a manner associating the predicted outcome with the patient wherein identifying the at least one specific intraoperative event is based on at least one of a detected surgical tool in the accessed frames, a detected anatomical structure in the accessed frames, an interaction in the accessed frames between a surgical tool and an anatomical structure, or a detected abnormal fluid leakage situation in the accessed frames wherein a machine learning model is used to identify in the accessed frames the at least one specific intraoperative event, the machine learning model trained using example training data wherein determining the predicted outcome is based on at least one of a characteristic of the patient, an electronic medical record, or a postoperative surgical report wherein a machine learning model is used to determine the predicted outcome associated with the specific surgical procedure based on intraoperative events, the machine learning model trained using training examples wherein determining a predicted outcome includes using the trained machine learning model to predict surgical outcomes based on the identified intraoperative event and an identified characteristic of the patient receiving information identifying a realized surgical outcome following the surgical procedure and updating the machine learning model by training the machine learning model using the received information identifying a characteristic of the patient wherein the predicted outcome is also determined based on the identified patient characteristic wherein the patient characteristic is derived from an electronic medical record wherein identifying the patient characteristic includes using a machine learning model to analyze the accessed frames, the machine learning model being trained to identify patient characteristics using training examples of historical surgical procedures and corresponding historical patient characteristics wherein the predicted outcome includes at least one of a post-discharge mishap, a post-discharge adverse event, a post-discharge complication, or an estimate of a risk of readmission accessing a data structure containing recommended sequences of surgical events wherein identifying the at least one specific intraoperative event is based on an identification of a deviation between a recommended sequence of events for the surgical procedure identified in the data structure, and an actual sequence of events detected in the accessed frames wherein the identification of the deviation is based on at least one of a detected surgical tool in the accessed frames, a detected anatomical structure in the accessed frames, or an interaction in the accessed frames between a surgical tool and an anatomical structure wherein the identification of the deviation includes using a machine learning model trained to identify deviations from recommended sequences of events based on historical surgical video footage, historical recommended sequences of events, and information identifying deviations from the historical recommended sequences of events in the historical video footage wherein identifying the deviation includes comparing the accessed frames to reference frames depicting the recommended sequence of events wherein outputting the predicted outcome includes updating an electronic medical record associated with the patient wherein outputting the predicted outcome includes transmitting the predicted outcome to a data-receiving device associated with a health care provider determining at least one action likely to improve the predicted outcome based on the accessed frames providing a recommendation based on the determined at least one action Systems and methods disclosed herein involve unconventional improvements over conventional approaches. Descriptions of the disclosed embodiments are not exhaustive and are not limited to the precise forms or embodiments disclosed. Modifications and adaptations of the embodiments will be apparent from consideration of the specification and practice of the disclosed embodiments. Additionally, the disclosed embodiments are not limited to the examples discussed herein.

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments. For example, the described implementations include hardware and software, but systems and methods consistent with the present disclosure may be implemented as hardware alone.

Computer programs based on the written description and methods of this specification are within the skill of a software developer. The various functions, scripts, programs, or modules may be created using a variety of programming techniques. For example, programs, scripts, functions, program sections or program modules may be designed in or by means of languages, including JAVASCRIPT, C, C++, JAVA, PHP, PYTHON, RUBY, PERL, BASH, or other programming or scripting languages. One or more of such software sections or modules may be integrated into a computer system, non-transitory computer readable media, or existing communications software. The programs, modules, or code may also be implemented or replicated as firmware or circuit logic.

Moreover, while illustrative embodiments have been described herein, the scope may include any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods may be modified in any manner, including by reordering steps or inserting or deleting steps. It is intended, therefore, that the specification and examples be considered as exemplary only, with a true scope and spirit being indicated by the following claims and their full scope of equivalents.

What is claimed is:

1. A non-transitory computer readable medium containing instructions that, when executed by at least one processor, cause the at least one processor to execute operations enabling automatically populating a post-operative report of a surgical procedure, the operations comprising:

receiving an input of an identifier of a patient;
receiving an input of an identifier of a health care provider;
receiving an input of surgical footage of a surgical procedure performed on the patient by the health care provider;
transforming at least part of the surgical footage using at least one convolution to obtain transformed data;
using the transformed data, analyzing a plurality of frames of the surgical footage to identify a medical instrument, an anatomical structure and a relative movement between the identified medical instrument and the anatomical structure;
deriving image-based information for populating a post-operative report of the surgical procedure, based on the relative movement between the identified medical instrument and the anatomical structure; and
causing the derived image-based information to populate the post-operative report of the surgical procedure.

2. The non-transitory computer readable medium of claim 1, wherein the operations further comprise analyzing the surgical footage to identify one or more phases of the surgical procedure and to identify a decision making junction based on a property of at least one phase of the identified phases; and wherein the derived image-based information is based on the identified at least one phase and the identified decision making junction.

3. The non-transitory computer readable medium of claim 2, wherein the operations further comprise analyzing the surgical footage to identify a name and a duration associated with the at least one phase; and wherein the derived image-based information includes the name and the duration associated with the at least one phase.

4. The non-transitory computer readable medium of claim 2, wherein the operations further comprise determining at least a beginning of the at least one phase; and wherein the derived image-based information is based on the determined beginning.

5. The non-transitory computer readable medium of claim 2, wherein the operations further comprise associating a time marker with the at least one phase; and wherein the derived image-based information includes the time marker associated with the at least one phase.

6. The non-transitory computer readable medium of claim 1, wherein the operations further comprise transmitting data to the health care provider, the transmitted data including the patient identifier and the derived image-based information.

7. The non-transitory computer readable medium of claim 1, wherein the operations further comprise analyzing the surgical footage to identify at least one recommendation for post-operative treatment of the patient; and providing the identified at least one recommendation.

8. The non-transitory computer readable medium of claim 1, wherein the caused populating of the post-operative report of the surgical procedure is configured to enable the health care provider to alter at least part of the derived image-based information in the post-operative report.

9. The non-transitory computer readable medium of claim 1, wherein the caused populating of the post-operative report of the surgical procedure is configured to cause at least part of the derived image-based information to be identified in the post-operative report as automatically generated data.

10. The non-transitory computer readable medium of claim 1, wherein the operations further comprise: analyzing the surgical footage to identify a surgical event within the surgical footage and to identify a property of the identified surgical event; and wherein the derived image-based information is based on the identified surgical event and the identified property.

11. The non-transitory computer readable medium of claim 10, wherein the operations further comprise analyzing the surgical footage to determine an event name of the identified surgical event; and wherein the derived image-based information includes the determined event name.

12. The non-transitory computer readable medium of claim 10, wherein the operations further comprise associating a time marker with the identified surgical event; and wherein the derived image-based information includes the time marker.

13. The non-transitory computer readable medium of claim 1, wherein the operations further comprise providing the derived image-based information in a form enabling updating of an electronic medical record.

14. The non-transitory computer readable medium of claim 1, wherein the derived image-based information is based in part on user input.

15. The non-transitory computer readable medium of claim 1, wherein the derived image-based information includes first data obtained using a first set of sensors located on a medical device and second data obtained using a second set of sensors not located on the medical device, and wherein the first data is used to identify a surgical event and the second data is used to identify a beginning and an end of a surgical phase.

16. The non-transitory computer readable medium of claim 1, wherein the operations further comprise analyzing the surgical footage to select at least part of at least one frame of the surgical footage; and causing the selected at least part of at least one frame of the surgical footage to be included in the post-operative report of the surgical procedure.

17. The non-transitory computer readable medium of claim 16, wherein the operations further comprise:
receiving a preliminary post-operative report; and
analyzing the preliminary post-operative report and the surgical footage to select the at least part of at least one frame of the surgical footage.

18. The non-transitory computer readable medium of claim 1, wherein the operations further comprise:
receiving a preliminary post-operative report;
analyzing the preliminary post-operative report and the surgical footage to identify at least one inconsistency between the preliminary post-operative report and the surgical footage; and
providing an indication of the identified at least one inconsistency.

19. A computer-implemented method of populating a post-operative report of a surgical procedure, the method comprising:
receiving an input of an identifier of a patient;
receiving an input of an identifier of a health care provider;
receiving an input of surgical footage of a surgical procedure performed on the patient by the health care provider;
transforming at least part of the surgical footage using at least one convolution to obtain transformed data;
using the transformed data, analyzing a plurality of frames of the surgical footage to identify a medical instrument, an anatomical structure and a relative movement between the identified medical instrument and the anatomical structure;
deriving image-based information for populating a post-operative report of the surgical procedure, based on the relative movement between the identified medical instrument and the anatomical structure; and
causing the derived image-based information to populate a post-operative report of the surgical procedure.

20. A system for automatically populating a post-operative report of a surgical procedure, the system configured to:
receive an input of an identifier of a patient;
receive an input of an identifier of a health care provider;
receive an input of surgical footage of a surgical procedure performed on the patient by the health care provider;
transforming at least part of the surgical footage using at least one convolution to obtain transformed data;
using the transformed data, analyze a plurality of frames of the surgical footage to identify a medical instrument, an anatomical structure and a relative movement between the identified medical instrument and the anatomical structure;
derive image-based information for populating a post-operative report of the surgical procedure, based on the relative movement between the identified medical instrument and the anatomical structure; and
cause the derived image-based information to populate a post-operative report of the surgical procedure.

* * * * *